(12) United States Patent
Gharagozloo et al.

(10) Patent No.: US 6,864,261 B2
(45) Date of Patent: Mar. 8, 2005

(54) THERAPEUTIC AGENTS USEFUL FOR TREATING PAIN

(75) Inventors: Parviz Gharagozloo, Pennington, NJ (US); Khondaker Islam, Langhorne, PA (US); Donald J. Kyle, Newtown, PA (US); Qun Sun, Princeton, NJ (US); Laykea Tafesse, Robinsville, NJ (US); John William Frank Whitehead, Newtown, PA (US); Ji Yang, Princeton Junction, NJ (US); Xiaoming Zhou, Plainsboro, NJ (US)

(73) Assignee: Euro-Celtique S.A. (LU)

( * ) Notice: Subject to any disclaimer, the term of this patent is extended or adjusted under 35 U.S.C. 154(b) by 40 days.

(21) Appl. No.: 10/429,078

(22) Filed: May 2, 2003

(65) Prior Publication Data

US 2004/0053914 A1 Mar. 18, 2004

Related U.S. Application Data

(60) Provisional application No. 60/376,803, filed on May 2, 2002, and provisional application No. 60/460,218, filed on Apr. 3, 2003.

(51) Int. Cl.$^7$ .................... A61K 31/496; C07D 401/04
(52) U.S. Cl. .................... 514/253.01; 544/360; 544/364
(58) Field of Search .............................. 544/360, 364; 514/253.01

(56) References Cited

U.S. PATENT DOCUMENTS

| | | | |
|---|---|---|---|
| 5,039,680 A | 8/1991 | Imperato et al. | 514/304 |
| 5,075,341 A | 12/1991 | Mendelson et al. | 514/282 |
| 5,198,459 A | 3/1993 | Imperato et al. | 514/397 |
| 5,232,934 A | 8/1993 | Downs | 514/345 |
| 5,556,837 A | 9/1996 | Nestler et al. | 514/21 |
| 5,556,838 A | 9/1996 | Mayer et al. | 514/25 |
| 5,574,052 A | 11/1996 | Rose et al. | 514/343 |
| 5,762,925 A | 6/1998 | Sagen | 424/93.7 |
| 5,922,872 A | 7/1999 | Cook et al. | 544/368 |
| 6,109,269 A | 8/2000 | Rise et al. | 128/898 |
| 6,204,284 B1 | 3/2001 | Beer et al. | 514/412 |

FOREIGN PATENT DOCUMENTS

| | | |
|---|---|---|
| WO | WO 99/37304 | 7/1999 |
| WO | WO 02/08221 A2 | 1/2002 |
| WO | WO 02/16318 A1 | 2/2002 |
| WO | WO 02/072536 A1 | 9/2002 |
| WO | WO 02/076946 A3 | 10/2002 |
| WO | WO 02/076946 A2 | 10/2002 |

OTHER PUBLICATIONS

Berkow et al., "The Merck Manual of Medical Information," pp. 345–350, 1997.
Berkow et al., "The Merck Manual of Medical Information," pp. 352–355, 1997.
Berkow et al., "The Merck Manual of Medical Information," pp. 496–500, 1997.
Berkow et al., "The Merck Manual of Medical Information," pp. 528–530, 1997.
Berkow et al., "The Merck Manual of Medical Information," pp. 530–532, 1997.
Berkow et al., "The Merck Manual of Medical Information," pp. 631–634, 1997.
Berkow et al., "The Merck Manual of Medical Information," pp. 525–526, 1997.
Chiamulera et al., "Reinforcing and Locomotor Stimulant Effects of Cocaine are Absent in mGluR5 Null Mutant Rice," Nature Neuroscience 4(9):873–874(2001).
Cooke, "Glycopyrrolate in Bladder Dysfunction," SA Medical Journal, 63:3 (1983).
Di Marzo et al., "Endovanilloid Signaling in Pain," Current Opinion in Neurobiology 12:372–379 (2002).
Dogrul et al., Peripheral and Spinal Antihyperalgesic activity of SIB–1757, a Metabotropic glutamate receptor (mGLUR$_5$) Antagonist, in Experimental Neuropathic Pain in Rats, Neuroscience Letters 292(2):115–118 (2000).
Foley, "Pain" Cecil Textbook of Medicine, pp. 100–107 (1996).

(List continued on next page.)

Primary Examiner—Johann Richter
Assistant Examiner—Ebenezer Sackey
(74) Attorney, Agent, or Firm—Jones Day

(57) ABSTRACT

A compound of formula

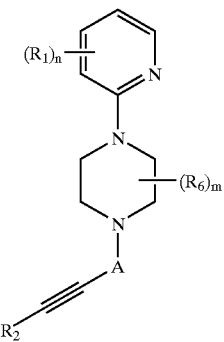

(wherein A, $R_1$, $R_2$, $R_6$, m and n are disclosed herein) or a pharmaceutically acceptable salt thereof (a "Piperazine Compound"); pharmaceutical compositions comprising a Piperazine Compound; and methods for treating pain, urinary incontinence (UI), an addictive disorder, Parkinson's disease, parkinsonism, anxiety, epilepsy, stroke, a seizure, a pruritic condition, psychosis, a cognitive disorder, a memory deficit, restricted brain function, Huntington's chorea, amyotrophic lateral sclerosis (ALS), dementia, retinopathy, a muscle spasm, a migraine, vomiting, dyskinesia and depression in an animal comprising administering to an animal in need thereof an effective amount of a Piperazine Compound are disclosed.

77 Claims, 1 Drawing Sheet

OTHER PUBLICATIONS

Figure 1:
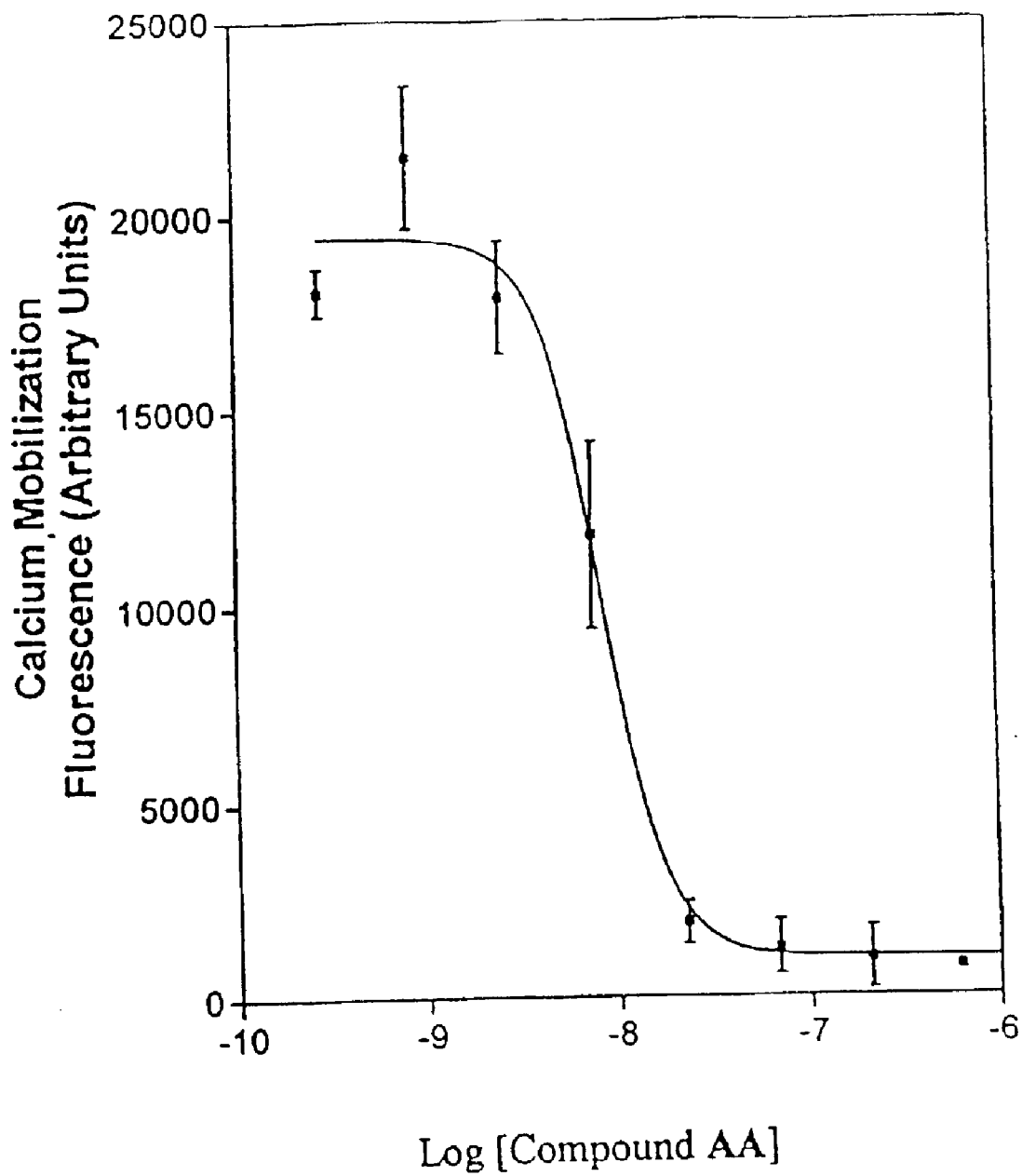

Fundytus et al, "Antisense Oligonucleotide Knockdown of mGluR$_1$ Alleviates Hyperalgesia and Allodynia Associated with Chronic Inflammation," Pharmacology, Biochemistry & Behavior 73:401–410 (2002).

Fundytus et al., "In vivo Antinociceptive activity of Anti–Rat mGluR$_1$ and mGluR$_5$ Antibodies in Rats," NeuroReport 9:731–735 (1998).

Fundytus et al., "Knockdown of Spinal Metabotropic Glutamate Receptor 1 (mGluR$_1$) Alleviates Pain and Restores Opioid Efficacy after Nerve Injury in Rats," British Journal of Pharmacology 132:354–367 (2001).

Fundytus et al., "Effect of Activity at Metabotropic, as well as Ionotropic (NMDA), Glutamate Receptors on Morphine Dependence," British Journal of Pharmacology 113:1215–20 (1994).

Fundytus, "Glutamate Receptors and Nociception Implications for the Drug–Treatment of Pain," CNS Drugs 15:29–58, (2001).

Goodman and Gillman's The Pharmaceutical Basis of Therapeutics 506, 901–915 (L. Brunton, author; J. Hardman and L. Limbird eds., 9$^{th}$ ed. 1996).

Herzog et al., "Urinary Incontinenece: Medical and Psychosocial Aspects," Annu. Rev. Gerontol. Geriatr. 9:74–119, (1989).

Jhamandas et al., "Spinal Amino Acid Release and Precipitated Withdrawal in Rats Chronically Infused with Spinal Morphine," The Journal of Neuroscience 16(8):2758–66 (Apr. 15, 1996).

Levin et al., "Direct Measurement of the Anticholinergic Activity of a Series of Pharmacological Compounds on the Canine and Rabbit Urinary Bladder," The Journal of Urology, 128:396–398 (1982).

Mirakur et al., "Glycopyrrolate: Pharmacology and Clinical use," Anaesthesia 38:1195–1204 (1983).

Ossowska et al., "Blockade of the Metabotropic Glutamate Receptor Subtype 5 (mGluR5) produces antiparkinsonian–Like Effects in Rats," Neuropharmacology 41:413–420 (2001).

Resnick, "Urinary Incontinence," Lancet 346:94–99 (1995).

Sharif et al., "Attenuation of Morphine Tolerance after Antisense Oligonucleotide Knock–Down of Spinal mGluR1, " British Journal of Pharmacology 136:865–72 (2002).

Spooren et al., "Novel Allosteric Antagonists Shed Light on Receptors and CNS Disorders," Trends in Pharmacological Sciences, 22(7):331–337 (2001).

Tatarczynska et al., Potential anxiolytic– and Antidepressant–Like Effects of MPEP, a Potent, Selective and Systemically Active mGlu5 Receptor Antagonist, British Journal of Pharmacology 132(7):1423–1430 (2001).

Walker et al., "Metabotropic Glutamate Receptor Subtype 5 (mGlu5) and Nociceptive Function. I. Selective Blockade of mGlu5 Receptors in Models of Acute, Persistent and Chronic Pain," Neuropharmacology 40:1–9 (2001).

Wein, "Pharmacology of Incontinence," Urologic Clinics of North America, 22(3):557–577 (1995).

Bartho et al., "Involvement of Capsaicin–Sensitive Neurones in Hyperalgesia and Enhanced Opioid Antinociception in Inflammation," Naunyn–Schmiedeberg's Archives of Pharmacology, 342:666–670 (1990).

D'Amour et al., "A Method for Determining Loss of Pain Sensation," J. Pharmacol. Exp. Ther. 72:74–79 (1941).

Hargreaves et al., "A New and Sensitive Method for Measuring Thermal Nociception in Cutaneous Hyperalgesia," Pain 32(1):77–88 (1988).

Kim, "An Experimental Model for Peripheral Neuropathy Produced by Segmental Spinal Nerve Ligation in the Rat," Pain 50(3):355–363 (1992).

Masu et al., "," Nature, 349:760–765 (1991).

Miller et al., "," The Journal of Neuroscience 15(9):6103–6109 (1995).

Schlaeger et al., "," New Dev. Appl. Anim. Cell Techn., Proc. ESACT Meet., 15$^{th}$ (1998), 105–112 and 117–120.

Seltzer et al., "A Novel Behavioral Model of Neuropathic Pain Disorders Produced in Rats by Partial Sciatic Nerve Injury," Pain 43:205–218 (1990).

Stein, "Unilateral Inflammation of the Hindpaw in Rats as a Model of Prolonged Noxious Stimulation: Alterations in Behavior and Nociceptive Thresholds," Pharmacology Biochemistry and Behavior 31:451–455 (1988).

Treit, "Animal Models for the Study of Anti–Anxiety Agents: A Review," Neuroscience & Biobehavioral Reviews 9(2):203–222 (1985).

THERAPEUTIC AGENTS USEFUL FOR TREATING PAIN

This application claims the benefit of U.S. provisional application No. 60/376,803, filed May 2, 2002, and U.S. provisional application No. 60/460,218, filed Apr. 3, 2003, the disclosure of each provisional application being incorporated by reference herein in its entirety.

1. FIELD OF THE INVENTION

The present invention relates to Piperazine Compounds, compositions comprising a Piperazine Compound and methods for treating or preventing a condition such as pain, urinary incontinence (UI), an addictive disorder, Parkinson's disease, parkinsonism, anxiety, epilepsy, stroke, a seizure, a pruritic condition, psychosis, a cognitive disorder, a memory deficit, restricted brain function, Huntington's chorea, amyotrophic lateral sclerosis (ALS), dementia, retinopathy, a muscle spasm, a migraine, vomiting, dyskinesia or depression comprising administering to the animal in an animal in need thereof an effective amount of a Piperazine Compound.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, *Pain, in Cecil Textbook of Medicine* 100–107 (J. C. Bennett and F. Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or cental nervous system and is maintained by aberrant somatosensory processing. There is a large body of evidence relating activity at both Group I mGluRs (mGluR1 and mGluR5) (M. E. Fundytus, *CNS Drugs* 15:29–58 (2001)) and vaniloid receptors (VR1) (V. Di Marzo et al., *Current Opinion in Neurobiology* 12:372–379 (2002)) to pain processing. Inhibiting mGluR1 or mGluR5 reduces pain, as shown by in vivo treatment with antibodies selective for either mGluR1 or mGluR5, where neuropathic pain in rats was attenuated (M. E. Fundytus et al., *NeuroReport* 9:731–735 (1998)). It has also been shown that antisense oligonucleotide knockdown of mGluR1 alleviates both neuropathic and inflammatory pain (M. E. Fundytus et al., *British Journal of Pharmacology* 132:354–367 (2001); M. E. Fundytus et al., *Pharmacology, Biochemsitry & Behavior* 73:401–410 (2002)). Small molecule antagonists for mGluR5-attenuated pain in in vivo animal models are disclosed in, e.g., K. Walker et al., *Neuropharmacology* 40: 1–9 (2000) and A. Dogrul et al., *Neuroscience Letters* 292:115–118 (2000)).

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g. gabapentin, carbamazepine, valproic acid, topiramate, phenytoin), NMDA antagonists (e.g. ketamine, dextromethorphan), topical lidocaine (for post-herpetic neuralgia), and tricyclic antidepressants (e.g. fluoxetine, sertraline and amitriptyline).

UI is uncontrollable urination, generally caused by bladder-detrusor-muscle instability. UI affects people of all ages and levels of physical health, both in health care settings and in the community at large. At present, UI afflicts 15–30% of elderly people living at home, one-third of those living in acute-care settings, and at least one-half of those living in long-term care institutions (R. M. Resnick, *Lancet* 346:94 (1995)). Persons having UI are predisposed to also having urinary-tract infections, pressure ulcers, perineal rashes and urosepsis. Psychosocially, UI is associated with embarrassment, social stigmatization, depression and a risk of institutionalization (Herzo et al., *Annu. Rev. Gerontol. Geriatr.* 9:74 (1989)). Economically, the costs of UI are great; in the United States alone, health-care costs associated with UI are over $15 billion per annum.

Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity. For example, anticholinergics such as propantheline bromide and glycopyrrolate, and combinations of smooth-muscle relaxants such as a combination of racemic oxybutynin and dicyclomine or an anticholinergic, have been used to treat UI (See, e.g., A. J. Wein, *Urol. Clin. N. Am.* 22:557–577 (1995); Levin et al., *J. Urol.* 128:396–398 (1982); Cooke et al., *S. Afr. Med. J.* 63:3 (1983); R. K. Mirakhur et al., *Anaesthesia* 38:1195–1204 (1983)). These drugs are not effective, however, in all patients having uninhibited bladder contractions. Administration of anticholinergic medications represent the mainstay of this type of treatment.

None of the existing commercial drug treatments for UI, however, has achieved complete success in all classes of UI patients, nor has treatment occurred without significant adverse side effects. For example, drowsiness, dry mouth, constipation, blurred vision, headaches, tachycardia, and cardiac arrhythmia, which are related to the anticholinergic activity of traditional anti-UI drugs, can occur frequently and adversely affect patient compliance. Yet despite the prevalence of unwanted anticholinergic effects in many patients, anticholinergic drugs are currently prescribed for patients having UI. *The Merck Manual of Medical Information* 631–634 (R. Berkow ed., 1997).

Many drugs can cause physical and/or psychological addiction. The most well known types of these drugs include opiates, such as heroin, opium, and morphine; sympathomimetics, including cocaine and amphetamines; sedative-hypnotics, including alcohol, benzodiazepines and barbiturates; and nicotine, which has effects similar to opioids and sympathomimetics. Drug addiction is characterized by a craving or compulsion for taking the drug and an inability to limit its intake. Additionally, drug dependence is associated with drug tolerance, the loss of effect of the drug following repeated administration, and withdrawal, the appearance of physical and behavioral symptoms when the drug is not consumed. Sensitization occurs if repeated administration of a drug leads to an increased response to each dose. Tolerance, sensitization, and withdrawal are phenomena evidencing a change in the central nervous system resulting from continued use of the drug. This change can motivate the addicted individual to continue consuming the drug despite serious social, legal, physical and/or professional consequences. (See, e.g., U.S. Pat. No. 6,109,269 to Rise et al.).

Certain pharmaceutical agents have been administered for treating addiction. U.S. Pat. No. 5,556,838 to Mayer et al. discloses the use of nontoxic NMDA-blocking agents co-administered with an addictive substance to prevent the development of tolerance or withdrawal symptoms. U.S. Pat. No. 5,574,052 to Rose et al. discloses co-administration of an addictive substance with an antagonist to partially block the pharmacological effects of the substance. U.S. Pat. No. 5,075,341 to Mendelson et al. discloses the use of a mixed opiate agonist/antagonist to treat cocaine and opiate addiction. U.S. Pat. No. 5,232,934 to Downs discloses administration of 3-phenoxypyridine to treat addiction. U.S. Pat. Nos. 5,039,680 and 5,198,459 to Imperato et al. disclose using a serotonin antagonist to treat chemical addiction. U.S. Pat. No. 5,556,837 to Nestler et. al. discloses infusing BDNF or NT-4 growth factors to inhibit or reverse neurological adaptive changes that correlate with behavioral changes in an addicted individual. U.S. Pat. No. 5,762,925 to Sagan discloses implanting encapsulated adrenal medullary cells into an animal's central nervous system to inhibit the development of opioid intolerance. U.S. Pat. No. 6,204,284 to Beer et al. discloses racemic (±)-1-(3,4-dichlorophenyl)-3-azabicyclo[3.1.0]hexane for use in the prevention or relief of a withdrawal syndrome resulting from addiction to drugs and for the treatment of chemical dependencies. Glutamate release is enhanced during opioid withdrawal (K. Jhamandas et al., *Journal of Neurosience* 16:2758–2766 (1996)). Recent evidence suggests a role for Group I mGluRs in opioid tolerance and dependence. An interaction between opioids and mGluRs was demonstrated when it was shown that an antagonist at Group I mGluRs significantly attenuated withdrawal symptoms in opioid-dependent rats (M. E. Fundytus et al., *British Journal of Pharmacology* 113:1215–1220 (1994)). More recent results show that antisense oligonucleotide knockdown of mGluR1 reduces protein kinase C activity (M. E. Fundytus et al., *British Journal of Pharmacology* 132:354–367 (2001)), which may be associated in the development of opioid tolerance and dependence (see also M. E. Fundytus, *CNS Drugs* 15:29–58, (2001)). Very recently, it has been shown that antisense oligonucleotide knockdown of mGluR1 attenuates the development of opioid tolerance (R. N. Sharif et al., *British Journal of Pharmacology* 136:865–872 (2002)). Selective antagonists of the mGluR5 receptor have also been shown to exert anti-dependence activity in vivo (C. Chiamulera et al., *Nature Neuroscience* 4:873–874 (2001)).

Parkinson's disease is a clinical syndrome comprising bradykinesia (slowness and poverty of movement), muscular rigidity, resting tremor (which usually abates during voluntary movement), and an impairment of postural balance leading to disturbance of gait and falling. The features of Parkinson's disease are a loss of pigmented, dopaminergic neurons of the substantia nigra pars compacta and the appearance of intracellular inclusions known as Lewy bodies (*Goodman and Gillman's The Pharmaceutical Basis of Therapeutics* 506 (9$^{th}$ ed. 1996)). Without treatment, Parkinson's disease progresses to a rigid akinetic state in which patients are incapable of caring for themselves. Death frequently results from complications of immobility, including aspiration pneumonia or pulmonary embolism. Drugs commonly used for the treatment of Parkinson's disease include carbidopa/levodopa, pergolide, bromocriptine, selegiline, amantadine, and trihexyphenidyl hydrochloride. There remains, however, a need for drugs useful for the treatment of Parkinson's disease and having an improved therapeutic profile.

Anxiety is a fear, apprehension, or dread of impending danger often accompanied by restlessness, tension, tachycardia, and dyspnea. Other symptoms commonly associated with anxiety include depression, especially accompanied with dysthymic disorder (chronic "neurotic" depression); panic disorder; agoraphobia and other specific phobias; eating disorders; and many personality disorders. Often anxiety is unattached to a clearly identified treatable primary illness. If a primary illness is found, however, it can be desirable to deal with the anxiety at the same time as the primary illness.

Currently, benzodiazepines are the most commonly used anti-anxiety agents for generalized anxiety disorder. Benzodiazepines, however, carry the risk of producing impairment of cognition and skilled motor functions, particularly in the elderly, which can result in confusion, delerium, and falls with fractures. Sedatives are also commonly prescribed for treating anxiety. The azapirones, such as buspirone, are also used to treat moderate anxiety. The azapirones, however, are less useful for treating severe anxiety accompanied with panic attacks. Antagonists of the mGluR5 receptor have also been shown to exert anxiolytic and anti-depressant activity in in vivo animal models (E. Tatarczynska et al., *Br. J. Pharmacol.* 132(7):1423–1430 (2001) and P. J. M. Will et al., *Trends in Pharmacological Sciences* 22(7):331–37 (2001)).

Epilepsy is a disorder characterized by the tendency to have recurring seizures. The etiology commonly consists of lesions in some part of the cortex, such as a tumor; developmental malformation; or damage due to trauma or stroke. In some cases the etiology is genetic. An epileptic seizure can be triggered by repetitive sounds, flashing lights, video games, or touching certain parts of the body. Epilepsy is typically treated with anti-seizure drugs. In epilepsy cases, where anti-seizure drugs are ineffective, and the defect in the brain is isolated to a small area of the brain, surgical removal of that part of the brain can be helpful in alleviating the seizures. In patients who have several sources for the seizures or who have seizures that spread quickly to all parts of the brain, surgical removal of the nerve fibers that connect the two sides of the brain can be helpful.

A seizure is the result of abnormal electrical discharge in the brain. The discharge can involve a small area of the brain and lead to the person only noticing an odd taste or smell or it can involve a large area of the brain and lead to convulsions, i.e., a seizure that causes jerking and spasms of the muscles throughout the body. Convulsions can also result in brief attacks of altered consciousness and loss of consciousness, muscle control, or bladder control. A seizure is often preceded by an aura, i.e., unusual sensation of smell, taste, or vision or an intense feeling that a seizure is about to begin. A seizure typically lasts for about 2 to 5 minutes. When the seizure ends the person can have headache, sore muscles, unusual sensations, confusion, and profound fatigue (postictal state). Usually the person cannot remember what happened during the seizure.

Examples of drugs for treating a seizure and epilepsy include carbamazepine, ethosuximide, gabapentin, lamotrigine, phenobarbital, phenytoin, primidone, valproic acid, trimethadione, benzodiazepines, γ-vinyl GABA, acetazolamide, and felbamate. Anti-seizure drugs, however, can have side effects such as drowsiness; hyperactivity; hallucinations; inability to concentrate; central and peripheral nervous system toxicity, such as nystagmus, ataxia, diplopia, and vertigo; gingival hyperplasia; gastrointestinal disturbances such as nausea, vomiting, epigastric pain, and anorexia; endocrine effects such as inhibition of antidiuretic hormone, hyperglycemia, glycosuria, osteomalacia; and hypersensitivity such as scarlatiniform rash, morbilliform rash, Stevens-Johnson syndrome, systemic lupus erythematosus, and hepatic necrosis; and hematological reactions such as red-cell aplasia, agranulocytosis, thrombocytopenia, aplastic anemia, and megaloblastic anemia. *The Merck Manual of Medical Information* 345–350 (R. Berkow ed., 1997).

A stroke or cerebrovascular accident, is the death of brain tissue (cerebral infarction) resulting from the lack of blood flow and insufficient oxygen to the brain. A stroke can be either ischemic or hemorrhagic. In an ischemic stroke, blood supply to the brain is cut off because of atherosclerosis or a blood clot that has blocked a blood vessel. In a hemorrhagic stroke, a blood vessel bursts preventing normal blood flow and allowing blood to leak into an area of the brain and destroying it. Most strokes develop rapidly and cause brain damage within minutes. In some cases, however, strokes can continue to worsen for several hours or days. Symptoms of strokes vary depending on what part of the brain is effected. Symptoms include loss or abnormal sensations in an arm or leg or one side of the body, weakness or paralysis of an arm or leg or one side of the body, partial loss of vison or hearing, double vision, dizziness, slurred speech, difficulty in thinking of the appropriate word or saying it, inability to recognize parts of the body, unusual movements, loss of bladder control, imbalance, and falling, and fainting. The symptoms can be permanent and can be associated with coma or stupor. Strokes can cause edema or swelling of the brain which can further damage brain tissue. For persons suffering from a stroke, intensive rehabilitation can help overcome the disability caused by impairment of brain tissue. Rehabilitation trains other parts of the brain to assume the tasks previously performed by the damaged part.

Examples of drugs for treating strokes include anticoagulants such as heparin, drugs that break up clots such as streptokinase or tissue plasminogen activator, and drugs that reduce swelling such as mannitol or corticosteroids. *The Merck Manual of Medical Information* 352–355 (R. Berkow ed., 1997).

Pruritus is an unpleasant sensation that prompts scratching. Pruritus can be attributed to dry skin, scabies, dermatitis, herpetiformis, atopic dermatitis, pruritus vulvae et ani, malaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, or fiberglass dermatitis. Conventionally, pruritus is treated by phototherapy with ultraviolet B or PUVA or with therapeutic agents such as naltrexone, nalmefene, danazol, and tricyclic antidepressants.

Selective antagonists of the metabotropic glutamate receptor 5 ("mGluR5") have been shown to exert analgesic activity in in vivo animal models (K. Walker et al., *europharmacology* 40:1–9 (2000) and A. Dogrul et al., *Neuroscience Letters*, 292(2):115–118 (2000)).

Selective antagonists of the mGluR5 receptor have also been shown to exert anti-Parkinson activity in vivo (K. J. Ossowska et al., *Neuropharmacology* 41(4):413–20 (2001) and P. J. M. Will et al., *Trends in Pharmacological Sciences* 22(7):331–37 (2001)).

Selective antagonists of the mGluR5 receptor have also been shown to exert anti-dependence activity in vivo (C. Chiamulera et al., *Nature Neuroscience* 4(9):873–74 (2001)).

International Publication No. WO 99/37304 by Rohne-Poulenc Rorer Pharmaceuticals, Inc. discloses oxoazaheterocyclic compounds useful for inhibiting factorXa.

There remains, however, a clear need in the art for new drugs useful for treating or preventing pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia or depression.

Citation of any reference in Section 2 of this application is not to be construed as an admission that such reference is prior art to the present application.

3. SUMMARY OF THE INVENTION

The present invention encompasses compounds having the formula (I):

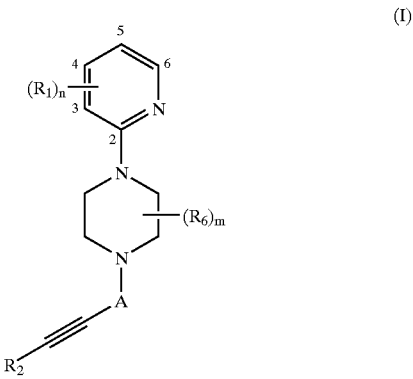

and pharmaceutically acceptable salts thereof, wherein:

A is —C(O)—, —C(S)—, —CH($C_1$–$C_4$ alkyl)-, —C($C_1$–$C_4$ alkyl)($C_1$–$C_4$ alkyl)-, —CH(phenyl)- or —C(phenyl)$_2$-, each phenyl independently being unsubstituted or substituted with one or more $R_7$ groups;

each $R_1$ is independently —H, —($C_1$–$C_3$)alkyl, —O($C_1$–$C_3$ alkyl), -halo, —OCF$_3$, —NO$_2$, —OH, —CN, —S(O)$_2$R$_4$, —C(O)OR$_4$, —OC(O)R$_4$, —NH$_2$ or —NHR$_4$;

$R_2$ is —($C_1$–$C_{10}$)alkyl, —($C_2$–$C_{10}$)alkenyl, —($C_2$–$C_{10}$)alkynyl, —($C_3$–$C_{10}$)cycloalkyl, —($C_8$–$C_{14}$)bicycloalkyl, —($C_8$–$C_{14}$)tricycloalkyl, —($C_5$–$C_{10}$)cycloalkenyl, —($C_8$–$C_{14}$)bicycloalkenyl, —($C_8$–$C_{14}$)tricycloalkenyl, -(3- to 7-membered)heterocycle or -(7- to 10-membered)bicycloheterocycle, each of which is unsubstituted or substituted with one or more $R_3$ groups, or $R_2$ is -phenyl, -naphthyl or —($C_{14}$)aryl, each of which is unsubstituted or substituted with one or more $R_5$ groups, or $R_2$ is -(5- to 10-membered)heteroaryl, which is unsubstituted or substituted with one or more $R_5$' groups;

each $R_3$ is independently —CN, —OH, -halo, —N$_3$, —NO$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each $R_4$ is independently —H, —($C_1$–$C_6$)alkyl, —($C_2$–$C_6$)alkenyl, —($C_2$–$C_6$)alkynyl, —($C_3$–$C_8$)cycloalkyl, —($C_5$–$C_8$)cycloalkenyl, -phenyl, -(3- to 5-membered)heterocycle, —C(halo)$_3$ or —CH(halo)$_2$;

each $R_5$ is independently —($C_1$–$C_6$)alkyl, —O($C_1$–$C_6$) alkyl, —($C_2$–$C_6$)alkenyl, —($C_2$–$C_6$)alkynyl, —($C_3$–$C_8$)cycloalkyl, —($C_5$–$C_8$)cycloalkenyl, -phenyl, —($C_3$–$C_5$)heterocycle, —C(halo)$_3$, —OC(halo)$_3$, —CH(halo)$_2$, —OCH(halo)$_2$, —CN, —OH, -halo, —N$_3$, —NO$_2$, —N($R_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each $R_5'$ is independently —($C_1$–$C_6$)alkyl, —O($C_1$–$C_6$) alkyl, —($C_2$–$C_6$)alkenyl, —($C_2$–$C_6$)alkynyl, —($C_3$–$C_8$)cycloalkyl, —($C_5$–$C_8$)cycloalkenyl, -phenyl, —($C_3$–$C_5$)heterocycle, —C(halo)$_3$, —OC(halo)$_3$, —CH(halo)$_2$, —OCH(halo)$_2$, —CN, —OH, -halo, —N$_3$, —NO$_2$, —N($R_4$)$_2$, —CH=NR$_4$, —NR$_4$OH, —COR$_4$, —C(O)OR$_4$, —OC(O)R$_4$, —OC(O)OR$_4$, —SR$_4$, —S(O)R$_4$ or —S(O)$_2$R$_4$;

each $R_6$ is independently —($C_1$–$C_3$ alkyl), —CH$_2$OH, —OH, -halo, —NO$_2$, —CN or —NH$_2$;

each $R_7$ is independently —($C_1$–$C_6$)alkyl, —O($C_1$–$C_6$) alkyl, halo, —C(halo)$_3$ or —OC(halo)$_3$;

m is 0, 1 or 2; and n is an integer from 1–4.

The present invention also encompasses compounds having the formula (I), and pharmaceutically acceptable salts thereof, wherein:

A is —C(O)—, —C(S)—, —CH$_2$—, —CH($C_1$–$C_4$ alkyl)-, —C($C_1$–$C_4$ alkyl)($C_1$–$C_4$ alkyl)-, —CH(phenyl)- or —C(phenyl)$_2$-, each phenyl independently being unsubstituted or substituted with one or more $R_7$ groups;

each $R_1$ is independently —H, —($C_1$–$C_3$)alkyl, —O($C_1$–$C_3$ alkyl), -halo, —OCF$_3$, —NO$_2$, —OH, —CN, —S(O)$_2$R$_4$, —C(O)OR$_4$, —OC(O)R$_4$, —NH$_2$ or —NHR$_4$;

$R_2$ is —($C_1$–$C_{10}$)alkyl, —($C_2$–$C_{10}$)alkenyl, —($C_2$–$C_{10}$) alkynyl, —($C_3$–$C_{10}$)cycloalkyl, —($C_8$–$C_{14}$)bicycloalkyl, —($C_8$–$C_{14}$)tricycloalkyl, —($C_5$–$C_{10}$) cycloalkenyl, —($C_8$–$C_{14}$)bicycloalkenyl or —($C_8$–$C_{14}$)tricycloalkenyl, each of which is unsubstituted or substituted with one or more $R_3$ groups, or $R_2$ is -phenyl, -naphthyl or —($C_{14}$)aryl, each of which is unsubstituted or substituted with one or more $R_5$ groups;

each $R_3$ is independently —CN, —OH, -halo, —N$_3$, —NO$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each $R_4$ is independently —H, —($C_1$–$C_6$)alkyl, —($C_2$–$C_6$)alkenyl, —($C_2$–$C_6$)alkynyl, —($C_3$–$C_8$) cycloalkyl, —($C_5$–$C_8$)cycloalkenyl, -phenyl, -(3- to 5-membered)heterocycle, —C(halo)$_3$ or —CH(halo)$_2$;

each $R_5$ is independently —($C_1$–$C_6$)alkyl, —O($C_1$–$C_6$) alkyl, —($C_2$–$C_6$)alkenyl, —($C_2$–$C_6$)alkynyl, —($C_3$–$C_8$)cycloalkyl, —($C_5$–$C_8$)cycloalkenyl, -phenyl, —($C_3$–$C_5$)heterocycle, —C(halo)$_3$, —OC(halo)$_3$, —CH(halo)$_2$, —OCH(halo)$_2$, —CN, —OH, -halo, —N$_3$, —NO$_2$, —N($R_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each $R_6$ is independently —($C_1$–$C_3$ alkyl), —CH$_2$OH, —OH, -halo, —NO$_2$, —CN or —NH$_2$;

each $R_7$ is independently —($C_1$–$C_6$)alkyl, —O($C_1$–$C_6$) alkyl, halo, —C(halo)$_3$ or —OC(halo)$_3$;

m is 0, 1 or 2; and n is an integer from 1–4.

The present invention also encompasses compounds having the formula (I), and pharmaceutically acceptable salts thereof, wherein:

A is —C(O)—, —C(S)—, —CH($C_1$–$C_4$ alkyl)- or —C($C_1$–$C_4$ alkyl)($C_1$–$C_4$ alkyl)-;

each $R_1$ is independently —($C_1$–$C_3$)alkyl, -halo, —NO$_2$, —OH, or —CN;

m is 0 or 1;

n is an integer from 1–4;

$R_2$ is —($C_1$–$C_{10}$)alkyl, —($C_2$–$C_{10}$)alkenyl, —($C_2$–$C_{10}$) alkynyl, —($C_3$–$C_{10}$)cycloalkyl, —($C_8$–$C_{14}$) bicycloalkyl, —($C_8$–$C_{14}$)tricycloalkyl, —($C_5$–$C_{10}$) cycloalkenyl, —($C_8$–$C_{14}$)bicycloalkenyl, —($C_8$–$C_{14}$) tricycloalkenyl, -(3- to 7-membered)heterocycle, or -(7- to 10-membered)bicycloheterocycle, each of which is unsubstituted or substituted with one or more $R_3$ groups, or $R_2$ is -phenyl, -naphthyl or —($C_{14}$)aryl, each of which is unsubstituted or substituted with one or more $R_5$ groups, or $R_2$ is -(5- to 10-membered)heteroaryl which is unsubstituted or substituted with one or more $R_5'$ groups;

each $R_3$ is independently —CN, —OH, -halo, —N$_3$, —NO$_2$, —N($R_4$)$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each $R_4$ is independently —H, —($C_1$–$C_6$)alkyl, —($C_2$–$C_6$)alkenyl, —($C_2$–$C_6$)alkynyl, —($C_3$–$C_8$) cycloalkyl, —($C_5$–$C_8$)cycloalkenyl, -phenyl, -(3- to 5-membered)heterocycle, —C(halo)$_3$ or —CH(halo)$_2$;

each $R_5$ is independently —($C_1$–$C_6$)alkyl, —($C_2$–$C_6$)alkenyl, —($C_2$–$C_6$)alkynyl, —($C_3$–$C_8$)cycloalkyl, —($C_5$–$C_8$)cycloalkenyl, -phenyl, -(3- to 5-membered) heterocycle, —C(halo)$_3$, —CH(halo)$_2$, —CN, —OH, -halo, —N$_3$, —NO$_2$, —N($R_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$, or —S(O)$_2$R$_4$;

each $R_5'$ is independently —($C_1$–$C_6$)alkyl, —($C_2$–$C_6$)alkenyl, —($C_2$–$C_6$)alkynyl, —($C_3$–$C_8$)cycloalkyl, —($C_5$–$C_8$)cycloalkenyl, -phenyl, -(3- to 5-membered) heterocycle, —C(halo)$_3$, —CH(halo)$_2$, —CN, —OH, -halo, —N$_3$, —NO$_2$, —N($R_4$)$_2$, —CH=NR$_4$, —NR$_4$OH, —COR$_4$, —C(O)OR$_4$, —OC(O)R$_4$, —OC(O)OR$_4$, —SR$_4$, —S(O)R$_4$, or —S(O)$_2$R$_4$; and each $R_6$ is —($C_1$–$C_3$)alkyl.

The present invention also encompasses compounds having the formula (I), and pharmaceutically acceptable salts thereof, wherein:

A is —C(O)—, —C(S)—, —CH$_2$—, —CH($C_1$–$C_4$ alkyl)- or —C($C_1$–$C_4$ alkyl)($C_1$–$C_4$ alkyl)-;

each $R_1$ is independently —($C_1$–$C_3$)alkyl, -halo, —NO$_2$, —OH or —CN;

m is 0 or 1;

n is an integer from 1–4;

$R_2$ is —($C_1$–$C_{10}$)alkyl, —($C_2$–$C_{10}$)alkenyl, —($C_2$–$C_{10}$) alkynyl, —($C_3$–$C_{10}$)cycloalkyl, —($C_8$–$C_{14}$)bicycloalkyl, —($C_8$–$C_{14}$)tricycloalkyl, —($C_5$–$C_{10}$) cycloalkenyl, —($C_8$–$C_{14}$)bicycloalkenyl or —($C_8$–$C_{14}$)tricycloalkenyl, each of which is unsubstituted or substituted with one or more $R_3$ groups, or $R_2$ is -phenyl, -naphthyl or —($C_{14}$)aryl, each of which is unsubstituted or substituted with one or more $R_5$ groups;

each $R_3$ is independently —CN, —OH, -halo, —N$_3$, —NO$_2$, —N($R_4$)$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$, or —S(O)$_2$R$_4$;

each $R_4$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$ or —CH(halo)$_2$;

each $R_5$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —CN, —OH, -halo, —$N_3$, —$NO_2$, —N($R_4$)$_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$, or —S(O)$_2R_4$; and each $R_6$ is —($C_1$-$C_3$)alkyl.

The present invention also encompasses compounds having the formula (Ia):

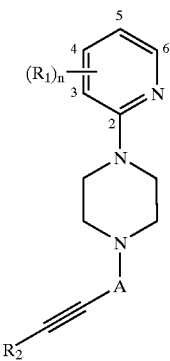

(Ia)

and pharmaceutically acceptable salts thereof, wherein:

A is —C(O)—, —C(S)—, —CH($C_1$-$C_4$ alkyl)- or —C($C_1$-$C_4$ alkyl)($C_1$-$C_4$ alkyl)-;

each $R_1$ is independently —($C_1$-$C_3$)alkyl, -halo, —$NO_2$, —OH or —CN;

n is an integer from 1–4;

$R_2$ is —($C_1$-$C_{10}$)alkyl, —($C_2$-$C_{10}$)alkenyl, —($C_2$-$C_{10}$) alkynyl, —($C_3$-$C_{10}$)cycloalkyl, —($C_8$-$C_{14}$) bicycloalkyl, —($C_8$-$C_{14}$)tricycloalkyl, —($C_5$-$C_{10}$) cycloalkenyl, —($C_8$-$C_{14}$)bicycloalkenyl, —($C_8$-$C_{14}$) tricycloalkenyl, -(3- to 7-membered)heterocycle or -(7- to 10-membered)bicycloheterocycle, each of which is unsubstituted or substituted with one or more $R_3$ groups, or $R_2$ is -phenyl, -naphthyl or —($C_{14}$)aryl, each of which is unsubstituted or substituted with one or more $R_5$ groups, or $R_2$ is -(5- to 10-membered)heteroaryl which is unsubstituted or substituted with one or more $R_5'$ groups;

each $R_3$ is independently —CN, —OH, -halo, —$N_3$, —$NO_2$, —N($R_4$)$_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —($C_1$-$C_6$)alkyl, —($C_2$-$C_6$)alkenyl, —($C_2$-$C_6$)alkynyl, —($C_3$-$C_8$) cycloalkyl, —($C_5$-$C_8$)cycloalkenyl, -phenyl, -(3- to 5-membered)heterocycle, —C(halo)$_3$ or —CH(halo)$_2$; and each $R_5$ is independently —($C_1$-$C_6$)alkyl, —($C_2$-$C_6$) alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —CN, —OH, -halo, —$N_3$, —$NO_2$, —N($R_4$)$_2$, —CH=$NR_4$, —$NR_4$OH, —$OR_4$, —$COR_4$, —C(O)$OR_4$, —OC(O) $R_4$, —OC(O)$OR_4$, —$SR_4$, —S(O)$R_4$, or —S(O)$_2R_4$; and each $R_5'$ is independently —($C_1$-$C_6$)alkyl, —($C_2$-$C_6$) alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —CN, —OH, -halo, —$N_3$, —$NO_2$, —N($R_4$)$_2$, —CH=$NR_4$, —$NR_4$OH, —$COR_4$, —C(O)$OR_4$, —OC(O)$R_4$, —OC(O)$OR_4$, —$SR_4$, —S(O)$R_4$ or —S(O)$_2R_4$.

The present invention also encompasses compounds having the formula (Ia), and pharmaceutically acceptable salts thereof, wherein:

A is —C(O)—, —C(S)—, —$CH_2$—, —CH($C_1$-$C_4$ alkyl)- or —C($C_1$-$C_4$ alkyl)($C_1$-$C_4$ alkyl)-;

each $R_1$ is independently —($C_1$-$C_3$)alkyl, -halo, —$NO_2$, —OH or —CN;

n is an integer from 1–4;

$R_2$ is —($C_1$-$C_{10}$)alkyl, —($C_2$-$C_{10}$)alkenyl, —($C_2$-$C_{10}$) alkynyl, —($C_3$-$C_{10}$)cycloalkyl, —($C_8$-$C_{14}$) bicycloalkyl, —($C_8$-$C_{14}$)tricycloalkyl, —($C_5$-$C_{10}$) cycloalkenyl, —($C_8$-$C_{14}$)bicycloalkenyl or —($C_8$-$C_{14}$)tricycloalkenyl, each of which is unsubstituted or substituted with one or more $R_3$ groups, or $R_2$ is -phenyl, -naphthyl or —($C_{14}$)aryl, each of which is unsubstituted or substituted with one or more $R_5$ groups;

each $R_3$ is independently —CN, —OH, -halo, —$N_3$, —$NO_2$, —N($R_4$)$_2$, =$NR_4$, —CH=$NR_4$, —$NR_4$OH, —$OR_4$, —$COR_4$, —C(O)$OR_4$, —OC(O)$R_4$, —OC(O) $OR_4$, —$SR_4$, —S(O)$R_4$ or —S(O)$_2R_4$;

each $R_4$ is independently —H, —($C_1$-$C_6$)alkyl, —($C_2$-$C_6$)alkenyl, —($C_2$-$C_6$)alkynyl, —($C_3$-$C_8$) cycloalkyl, —($C_5$-$C_8$)cycloalkenyl, -phenyl, -(3- to 5-membered)heterocycle, —C(halo)$_3$ or —CH(halo)$_2$; and each $R_5$ is independently —($C_1$-$C_6$)alkyl, —($C_2$-$C_6$) alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —CN, —OH, -halo, —$N_3$, —$NO_2$, —N($R_4$)$_2$, —CH=$NR_4$, —$NR_4$OH, —$OR_4$, —$COR_4$, —C(O)$OR_4$, —OC(O) $R_4$, —OC(O)$OR_4$, —$SR_4$, —S(O)$R_4$ or —S(O)$_2R_4$.

A compound of formula (I), (Ia) or a pharmaceutically acceptable salt thereof (a "Piperazine Compound") is useful for treating or preventing pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia or depression (each being a "Condition") in an animal.

The invention also relates to compositions comprising an effective amount of a Piperazine Compound and a pharmaceutically acceptable carrier or excipient. The compositions are useful for treating or preventing a Condition.

The invention further relates to methods for treating a Condition, comprising administering to an animal in need thereof an effective amount of a Piperazine Compound.

The invention further relates to methods for preventing a Condition, comprising administering to an animal in need thereof an effective amount of a Piperazine Compound.

The invention still further relates to methods for inhibiting mGluR5 function in a cell, comprising contacting a cell capable of expressing mGluR5 with an effective amount of a Piperazine Compound.

The invention still further relates to methods for inhibiting metabotropic glutamate receptor 1 ("mGluR1") function in a cell, comprising contacting a cell capable of expressing mGluR1 with an effective amount of a Piperazine Compound.

The invention still further relates to a method for preparing a composition comprising the step of admixing a Piperazine Compound and a pharmaceutically acceptable carrier or excipient.

The invention still further relates to a kit comprising a container containing an effective amount of a Piperazine Compound. The invention also relates to a kit comprising a container containing an effective amount of a Piperazine Compound and instructions for using the Piperazine Compound to treat or prevent a Condition.

The present invention may be understood more fully by reference to the following detailed description, figure and illustrative examples, which are intended to exemplify non-limiting embodiments of the invention.

4. BRIEF DESCRIPTION OF THE DRAWINGS

FIG. 1 is a plot of calcium mobilization as measured by calcium fluoresence against log [Piperazine Compound AA] for the dose dependent inhibition of glutamate induced calcium mobilization in rat astrocytes in the presence of 10 μM glutamate.

5. DETAILED DESCRIPTION OF THE INVENTION

5.1 Compounds of Formula (I)

The present invention encompasses compounds of Formula (I):

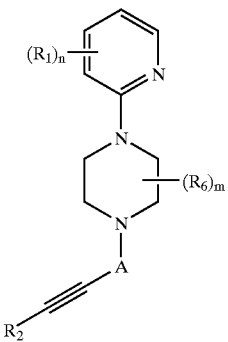

(I)

and pharmaceutically acceptable salts thereof, wherein:

A is —C(O)—, —C(S)—, —CH($C_1$-$C_4$ alkyl)-, —C($C_1$-$C_4$ alkyl)($C_1$-$C_4$ alkyl)-, —CH(phenyl)- or —C(phenyl)$_2$-, each phenyl independently being unsubstituted or substituted with one or more $R_7$ groups;

each $R_1$ is independently —H, —($C_1$-$C_3$)alkyl, —O($C_1$-$C_3$ alkyl), -halo, —CF$_3$, —OCF$_3$, —NO$_2$, —OH, —CN, —S(O)$_2$R$_4$, —C(O)OR$_4$, —OC(O)R$_4$, —NH$_2$, —NHR$_4$ or —N(R$_4$)$_2$;

R$_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle or -(7- to 10-membered)bicycloheterocycle, each of which is unsubstituted or substituted with one or more R$_3$ groups, or R$_2$ is -phenyl, -naphthyl, —($C_{14}$)aryl or -(5- to 10-membered)heteroaryl, each of which is unsubstituted or substituted with one or more R$_5$ groups;

each R$_3$ is independently —CN, —OH, -halo, —N$_3$, —NO$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_4$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$ or —CH(halo)$_2$;

each R$_5$ is independently —($C_1$-$C_6$)alkyl, —O($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_3$-$C_5$)heterocycle, —C(halo)$_3$, —OC(halo)$_3$, —CH(halo)$_2$, —OCH(halo)$_2$, —CN, —OH, -halo, —N$_3$, —NO$_2$, —N(R$_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_6$ is independently —($C_1$-$C_3$ alkyl), —CH$_2$OH, —OH, -halo, —NO$_2$, —CN or —NH$_2$;

each R$_7$ is independently —($C_1$-$C_6$)alkyl, —O($C_1$-$C_6$) alkyl, halo, —C(halo)$_3$ or —OC(halo)$_3$;

m is 0, 1 or 2; and n is an integer from 0–4.

In another embodiment, the present invention also encompasses compounds having the formula (I), and pharmaceutically acceptable salts thereof, wherein:

A is —C(O)—, —C(S)—, —CH($C_1$-$C_4$ alkyl)-, —C($C_1$-$C_4$ alkyl)($C_1$-$C_4$ alkyl)-, —CH(phenyl)- or —C(phenyl)$_2$-, each phenyl independently being unsubstituted or substituted with one or more $R_7$ groups, each $R_1$ is independently —H, —($C_1$-$C_3$)alkyl, —O($C_1$-$C_3$ alkyl), -halo, —OCF$_3$, —NO$_2$, —OH, —CN, —S(O)$_2$R$_4$, —C(O)OR$_4$, —OC(O)R$_4$, —NH$_2$ or —NHR$_4$;

R$_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle or -(7- to 10-membered)bicycloheterocycle, each of which is unsubstituted or substituted with one or more R$_3$ groups, or R$_2$ is -phenyl, -naphthyl or —($C_{14}$)aryl, each of which is unsubstituted or substituted with one or more R$_5$ groups, or R$_2$ is -(5- to 10-membered)heteroaryl, which is unsubstituted or substituted with one or more R$_5$' groups;

each R$_3$ is independently —CN, —OH, -halo, —N$_3$, —NO$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_4$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$ or —CH(halo)$_2$;

each R$_5$ is independently —($C_1$-$C_6$)alkyl, —O($C_1$-$C_6$) alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_3$-$C_5$)heterocycle, —C(halo)$_3$, —OC(halo)$_3$, —CH(halo)$_2$, —OCH(halo)$_2$, —CN, —OH, -halo, —N$_3$, —NO$_2$, —N(R$_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_5$' is independently —($C_1$-$C_6$)alkyl, —O($C_1$-$C_6$) alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_3$-$C_5$)heterocycle, —C(halo)$_3$, —OC(halo)$_3$, —CH(halo)$_2$, —OCH(halo)$_2$, —CN, —OH, -halo, —N$_3$, —NO$_2$, —N(R$_4$)$_2$, —CH=NR$_4$, —NR$_4$OH, —COR$_4$, —C(O)OR$_4$, —OC(O)R$_4$, —OC(O)OR$_4$, —SR$_4$, —S(O)R$_4$ or —S(O)$_2$R$_4$;

each R$_6$ is independently —(C$_1$-C$_3$ alkyl), —CH$_2$OH, —OH, -halo, —NO$_2$, —CN or —NH$_2$;

each R$_7$ is independently —(C$_1$-C$_6$)alkyl, —O(C$_1$-C$_6$)alkyl, halo, —C(halo)$_3$ or —OC(halo)$_3$;

m is 0, 1 or 2; and n is an integer from 1–4.

The present invention also encompasses compounds having the formula (I), and pharmaceutically acceptable salts thereof, wherein:

A is —C(O)—, —C(S)—, —CH$_2$—, —CH(C$_1$-C$_4$ alkyl)-, —C(C$_1$-C$_4$ alkyl)(C$_1$-C$_4$ alkyl)-, —CH(phenyl)- or —C(phenyl)$_2$-, each phenyl independently being unsubstituted or substituted with one or more R$_7$ groups;

each R$_1$ is independently —H, —(C$_1$-C$_3$)alkyl, —O(C$_1$-C$_3$ alkyl), -halo, —CF$_3$, —OCF$_3$, —NO$_2$, —OH, —CN, —S(O)$_2$R$_4$, —C(O)OR$_4$, —OC(O)R$_4$, —NH$_2$, —NHR$_4$ or —N(R$_4$)$_2$;

R$_2$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl or —(C$_8$-C$_{14}$)tricycloalkenyl, each of which is unsubstituted or substituted with one or more R$_3$ groups, or R$_2$ is -phenyl, -naphthyl or —(C$_{14}$)aryl, each of which is unsubstituted or substituted with one or more R$_5$ groups;

each R$_3$ is independently —CN, —OH, -halo, —N$_3$, —NO$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_4$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$ or —CH(halo)$_2$;

each R$_5$ is independently —(C$_1$-C$_6$)alkyl, —O(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —OC(halo)$_3$, —CH(halo)$_2$, —OCH(halo)$_2$, —CN, —OH, -halo, —N$_3$, —NO$_2$, —N(R$_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_6$ is independently —(C$_1$-C$_3$ alkyl), —CH$_2$OH, —OH, -halo, —NO$_2$, —CN or —NH$_2$;

each R$_7$ is independently —(C$_1$-C$_6$)alkyl, —O(C$_1$-C$_6$)alkyl, halo, —C(halo)$_3$ or —OC(halo)$_3$;

m is 0, 1 or 2; and n is an integer from 0–4.

In another embodiment, the present invention also encompasses compounds having the formula (I), and pharmaceutically acceptable salts thereof, wherein:

A is —C(O)—, —C(S)—, —CH$_2$—, —CH(C$_1$-C$_4$ alkyl)-, —C(C$_1$-C$_4$ alkyl)(C$_1$-C$_4$ alkyl)-, —CH(phenyl)- or —C(phenyl)$_2$-, each phenyl independently being unsubstituted or substituted with one or more R$_7$ groups;

each R$_1$ is independently —H, —(C$_1$-C$_3$)alkyl, —O(C$_1$-C$_3$ alkyl), -halo, —OCF$_3$, —NO$_2$, —OH, —CN, —S(O)$_2$R$_4$, —C(O)OR$_4$, —OC(O)R$_4$, —NH$_2$ or —NHR$_4$;

R$_2$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl or —(C$_8$-C$_{14}$)tricycloalkenyl, each of which is unsubstituted or substituted with one or more R$_3$ groups, or -phenyl, -naphthyl or —(C$_{14}$)aryl, each of which is unsubstituted or substituted with one or more R$_5$ groups;

each R$_3$ is independently —CN, —OH, -halo, —N$_3$, —NO$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_4$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$ or —CH(halo)$_2$;

each R$_5$ is independently —(C$_1$-C$_6$)alkyl, —O(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —OC(halo)$_3$, —CH(halo)$_2$, —OCH(halo)$_2$, —CN, —OH, -halo, —N$_3$, —NO$_2$, —N(R$_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_6$ is independently —(C$_1$-C$_3$ alkyl), —CH$_2$OH, —OH, -halo, —NO$_2$, —CN or —NH$_2$;

each R$_7$ is independently —(C$_1$-C$_6$)alkyl, —O(C$_1$-C$_6$)alkyl, halo, —C(halo)$_3$ or —OC(halo)$_3$;

m is 0, 1 or 2; and n is an integer from 1–4.

The present invention also encompasses compounds having the formula (I), and pharmaceutically acceptable salts thereof, wherein:

A is —C(O)—, —C(S)—, —CH(C$_1$-C$_4$ alkyl)- or —C(C$_1$-C$_4$ alkyl)(C$_1$-C$_4$ alkyl)-;

each R$_1$ is independently —(C$_1$-C$_3$)alkyl, -halo, —NO$_2$, —OH, or —CN;

m is 0 or 1;

n is an integer from 1–4;

R$_2$ is —H, —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_3$ groups, or R$_2$ is -phenyl, -naphthyl, —(C$_{14}$)aryl or -(5- to 10-membered)heteroaryl, each of which is unsubstituted or substituted with one or more R$_5$ groups;

each R$_3$ is independently —CN, —OH, -halo, —N$_3$, —NO$_2$, —N(R$_4$)$_2$, =NR$_4$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$;

each R$_4$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$ or —CH(halo)$_2$;

each R$_5$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CN, —OH, -halo, —N$_3$, —NO$_2$, —N(R$_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$, or —S(O)$_2$R$_4$; and each $R_6$ is —$(C_1-C_3)$alkyl.

In another embodiment, the present invention also encompasses compounds having the formula (I), and pharmaceutically acceptable salts thereof, wherein:

A is —C(O)—, —C(S)—, —CH($C_1-C_4$ alkyl)- or —C($C_1-C_4$ alkyl)($C_1-C_4$ alkyl)-;

each $R_1$ is independently —$(C_1-C_3)$alkyl, -halo, —$NO_2$, —OH, or —CN;

m is 0 or 1;

n is an integer from 1–4;

$R_2$ is —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_3$ groups, or $R_2$ is -phenyl, -naphthyl or —$(C_{14})$aryl, each of which is unsubstituted or substituted with one or more $R_5$ groups, or $R_2$ is -(5- to 10-membered)heteroaryl which is unsubstituted or substituted with one or more $R_5'$ groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$ or —CH(halo)$_2$;

each $R_5$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$, or —S(O)$_2R_4$;

each $R_5'$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$COR_4$, —C(O)$OR_4$, —OC(O)$R_4$, —OC(O)$OR_4$, —$SR_4$, —S(O)$R_4$, or —S(O)$_2R_4$; and each $R_6$ is —$(C_1-C_3)$alkyl.

In another embodiment A is —C(O)—.

In another embodiment, n is 1; $R_1$ is substituted at the 3-position of the pyridyl ring and is —$CH_3$, -halo, —$NO_2$, —OH or —CN; and $R_2$ is -phenyl, -naphthyl or —$(C_{14})$aryl, each which is unsubstituted or substituted with one or more $R_5$ groups.

In another embodiment, n is 1; $R_1$ is substituted at the 3-position of the pyridyl ring and is —$CH_3$, -halo, —$NO_2$, —OH or —CN; and $R_2$ is -(5- to 10-membered)heteroaryl, which is unsubstituted or substituted with one or more $R_5'$ groups.

In another embodiment, n is 1; $R_1$ is substituted at the 3-position of the pyridyl ring and is —$CH_3$, -halo, —$NO_2$, —OH or —CN; and $R_2$ is —$(C_1-C_{10})$alkyl, which is unsubstituted or substituted with one or more $R_3$ groups.

In another embodiment A is —C(O)—; n is 1; $R_1$ is substituted at the 3-position of the pyridyl ring and is —$CH_3$, -halo, —$NO_2$, —OH, or —CN; and $R_2$ is -phenyl, -naphthyl, —$(C_{14})$aryl or -(5- to 10-membered)heteroaryl, each which is unsubstituted or substituted with one or more $R_5$ groups.

In another embodiment A is —C(O)—; n is 1; $R_1$ is —$NO_2$ and substituted at the 3-position of the pyridyl ring; and $R_2$ is phenyl, which is unsubstituted or substituted with one or more $R_5$ groups.

In another embodiment A is —C(O)—, n is 1, $R_1$ is —$NO_2$ and substituted at the 3-position of the pyridyl ring, and $R_2$ is unsubstituted phenyl.

In another embodiment A is —C(O)—, n is 1, $R_1$ is —$CH_3$, and $R_2$ is unsubstituted phenyl.

In another embodiment A is —C(O)—; n is 1; $R_1$ is —$NO_2$, -halo or —CN, each of which is substituted at the 3-position of the pyridyl ring; and $R_2$ is unsubstituted phenyl.

In another embodiment m is 0.

In another embodiment m is 1.

In another embodiment each $R_6$ is —$CH_3$.

The present invention also encompasses compounds having the formula (I), and pharmaceutically acceptable salts thereof, wherein:

A is —C(O)—, —C(S)—, —$CH_2$—, —CH($C_1-C_4$ alkyl)- or —C($C_1-C_4$ alkyl)($C_1-C_4$ alkyl)-;

each $R_1$ is independently —$(C_1-C_3)$alkyl, -halo, —$NO_2$, —OH or —CN;

m is 0 or 1;

n is an integer from 1–4;

$R_2$ is —H, —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl or —$(C_8-C_{14})$tricycloalkenyl, each of which is unsubstituted or substituted with one or more $R_3$ groups, or $R_2$ is -phenyl, -naphthyl or —$(C_{14})$aryl, each of which is unsubstituted or substituted with one or more $R_5$ groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$, or —S(O)$_2R_4$;

each $R_4$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —C(halo)$_3$ or —CH(halo)$_2$;

each $R_5$ is independently —$(C_1-C_6)$alkyl, —$(C_2-C_6)$alkenyl, —$(C_2-C_6)$alkynyl —$(C_3-C_8)$cycloalkyl, —$(C_5-C_8)$cycloalkenyl, -phenyl, —$(C_3-C_5)$heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$, or —S(O)$_2R_4$; and each $R_6$ is —$(C_1-C_3)$alkyl.

In another embodiment, the present invention also encompasses compounds having the formula (I), and pharmaceutically acceptable salts thereof, wherein:

A is —C(O)—, —C(S)—, —$CH_2$—, —CH($C_1-C_4$ alkyl)- or —C($C_1-C_4$ alkyl)($C_1-C_4$ alkyl)-;

each $R_1$ is independently —$(C_1-C_3)$alkyl, -halo, —$NO_2$, —OH or —CN;

m is 0 or 1;

n is an integer from 1–4;

$R_2$ is —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl or —($C_8$–$C_{14}$)tricycloalkenyl, each of which is unsubstituted or substituted with one or more $R_3$ groups, or $R_2$ is -phenyl, -naphthyl or —($C_{14}$)aryl, each of which is unsubstituted or substituted with one or more $R_5$ groups;

each $R_3$ is independently —CN, —OH, -halo, —$N_3$, —$NO_2$, —N($R_4$)$_2$, =N$R_4$, —CH=N$R_4$, —$NR_4$OH, —O$R_4$, —CO$R_4$, —C(O)O$R_4$, —OC(O)$R_4$, —OC(O)O$R_4$, —S$R_4$, —S(O)$R_4$, or —S(O)$_2R_4$;

each $R_4$ is independently —H, —($C_1$–$C_6$)alkyl, —($C_2$–$C_6$)alkenyl, —($C_2$–$C_6$)alkynyl, —($C_3$–$C_8$)cycloalkyl, —($C_5$–$C_8$)cycloalkenyl, -phenyl, -(3- to 5-membered)heterocycle, —C(halo)$_3$ or —CH(halo)$_2$;

each $R_5$ is independently —($C_1$–$C_6$)alkyl, —($C_2$–$C_6$)alkenyl, —($C_2$–$C_6$)alkynyl, —($C_3$–$C_8$)cycloalkyl, —($C_5$–$C_8$)cycloalkenyl, -phenyl, -(3- to 5-membered) heterocycle, —C(halo)$_3$, —CH(halo)$_2$, —CN, —OH, -halo, —$N_3$, —$NO_2$, —N($R_4$)$_2$, —CH=N$R_4$, —$NR_4$OH, —O$R_4$, —CO$R_4$, —C(O)O$R_4$, —OC(O)$R_4$, —OC(O)O$R_4$, —S$R_4$, —S(O)$R_4$, or —S(O)$_2R_4$; and each $R_6$ is —($C_1$–$C_3$)alkyl.

In another embodiment A is —$CH_2$—, n is 1, $R_1$ is —$NO_2$ and substituted at the 3-position of the pyridyl ring, and $R_2$ is unsubstituted phenyl.

In another embodiment A is —$CH_2$—, n is 2, an $R_1$ group is an —$NO_2$ substituted at the 3-position of the pyridyl ring and the other $R_1$ group is a —OH substituted at the 6-position of the pyridyl ring, and $R_2$ is unsubstituted phenyl.

In another embodiment A is —$CH_2$—, n is 1, $R_1$ is —CN and substituted at the 3-position of the pyridyl ring, and $R_2$ is unsubstituted phenyl.

In another embodiment A is —$CH_2$—, n is 1, $R_1$ is —Cl and substituted at the 3-position of the pyridyl ring, and $R_2$ is unsubstituted phenyl.

In another embodiment m is 0.

In another embodiment m is 1.

In another embodiment each $R_6$ is —$CH_3$.

In the Piperazine Compounds of Formula (I), each $R_6$ can be on any carbon of the piperazine ring. In one embodiment, the Piperazine Compounds have only one $R_6$ group, and that $R_6$ group is attached to a carbon atom adjacent to the nitrogen atom attached to the pyridinyl group. In another embodiment, the Piperazine Compound has only one $R_6$ group, and that $R_6$ group is attached to a carbon atom adjacent to the nitrogen atom attached to the A group.

In another embodiment, two $R_6$ groups are on a single atom of the piperazine ring. In another embodiment, an $R_6$ group is attached to a carbon atom adjacent to the nitrogen atom attached to the pyridinyl group and another $R_6$ group is attached to a carbon atom adjacent to the nitrogen atom attached to the A group.

In another embodiment, the Piperazine Compound has two $R_6$ groups, each being attached to a different carbon atom adjacent to a nitrogen atom attached to the pyridinyl group. In another embodiment, the Piperazine Compound has two $R_6$ groups, each being attached to a different carbon atom adjacent to a nitrogen atom attached to the A group.

In one embodiment, wherein the Piperazine Compound has one or two $R_6$ groups, the carbon atom to which an $R_6$ group is attached has the (R) configuration. In another embodiment, wherein the Piperazine Compound has one or two $R_6$ groups, the carbon atom to which the $R_6$ group is attached has the (S) configuration. In another embodiment, the Piperazine Compound has one or two $R_6$ groups, and at least one of the carbon atoms to which an $R_6$ group is attached has the (R) configuration. In another embodiment, the Piperazine Compound has one or two $R_6$ groups, and at least one of the carbon atoms to which an $R_6$ group is attached has the (S) configuration.

In another embodiment, the Piperazine Compound has one or two $R_6$ groups, an $R_6$ group is attached to a carbon atom adjacent to a nitrogen atom attached to the pyridinyl group, and the carbon to which the $R_6$ group is attached is in the (R) configuration. In another embodiment, the Piperazine Compound has one or two $R_6$ groups, an $R_6$ group is attached to a carbon atom adjacent to a nitrogen attached to the pyridinyl group, the carbon to which the $R_6$ group is attached is in the (R) configuration, and $R_6$ is —($C_1$–$C_3$) alkyl. In another embodiment, the Piperazine Compound has one or two $R_6$ groups, an $R_6$ group is attached to a carbon atom adjacent to a nitrogen attached to the pyridinyl group, the carbon to which the $R_6$ group is attached is in the (R) configuration, and $R_6$ is —$CH_3$. In another embodiment, the Piperazine Compound has one or two $R_6$ groups, an $R_6$ group is attached to a carbon atom adjacent to a nitrogen attached to the pyridinyl group, the carbon to which the $R_6$ group is attached is in the (R) configuration, and $R_6$ is —$CH_2$OH. In another embodiment, the Piperazine Compound has one or two $R_6$ groups, an $R_6$ group is attached to a carbon atom adjacent to a nitrogen attached to the pyridinyl group, the carbon to which the $R_6$ group is attached is in the (R) configuration, and $R_6$ is —$CH_2CH_3$.

In another embodiment, the Piperazine Compound has one or two $R_6$ groups, an $R_6$ group is attached to a carbon atom adjacent to a nitrogen atom attached to the A group, and the carbon to which the $R_6$ group is attached is in the (R) configuration. In another embodiment, the Piperazine Compound has one or two $R_6$ groups, an $R_6$ group is attached to a carbon atom adjacent to a nitrogen attached to the A group, the carbon to which the $R_6$ group is attached is in the (R) configuration, and $R_6$ is —($C_1$–$C_3$)alkyl. In another embodiment, the Piperazine Compound has one or two $R_6$ groups, an $R_6$ group is attached to a carbon atom adjacent to a nitrogen attached to the A group, the carbon to which the $R_6$ group is attached is in the (R) configuration, and $R_6$ is —$CH_3$. In another embodiment, the Piperazine Compound has one or two $R_6$ groups, an $R_6$ group is attached to a carbon atom adjacent to a nitrogen attached to the A group, the carbon to which the $R_6$ group is attached is in the (R) configuration, and $R_6$ is —$CH_2$OH. In another embodiment, the Piperazine Compound has one or two $R_6$ groups, an $R_6$ group is attached to a carbon atom adjacent to a nitrogen attached to the A group, the carbon to which the $R_6$ group is attached is in the (R) configuration, and $R_6$ is —$CH_2CH_3$.

In another embodiment, the Piperazine Compound has one or two $R_6$ groups, an $R_6$ group is attached to a carbon atom adjacent to a nitrogen attached to the pyridinyl group, and the carbon to which the $R_6$ group is attached is in the (S) configuration. In another embodiment, the Piperazine Compound has one or two $R_6$ groups, an $R_6$ group is attached to a carbon atom adjacent to a nitrogen attached to the pyridinyl group, the carbon to which the $R_6$ group is attached is in the (S) configuration, and $R_6$ is —($C_1$–$C_3$) alkyl. In another embodiment, the Piperazine Compound has one or two $R_6$ groups, an $R_6$ group is attached to a carbon atom adjacent to a nitrogen attached to the pyridinyl group, the carbon to which the $R_6$ group is attached is in the (S) configuration, and $R_6$ is —$CH_3$. In another embodiment, the Piperazine Compound has one or two $R_6$ groups, an $R_6$ group is attached to a carbon atom adjacent to a nitrogen attached to the pyridinyl group, the carbon to which the $R_6$ group is attached is in the (S) configuration, and $R_6$ is —$CH_2OH$. In another embodiment, the Piperazine Compound has one or two $R_6$ groups, an $R_6$ group is attached to a carbon atom adjacent to a nitrogen attached to the pyridinyl group, the carbon to which the $R_6$ group is attached is in the (S) configuration, and $R_6$ is —$CH_2CH_3$.

In another embodiment, the Piperazine Compound has one or two $R_6$ groups, an $R_6$ group is attached to a carbon atom adjacent to a nitrogen atom attached to the A group, and the carbon to which the $R_6$ group is attached is in the (S) configuration. In another embodiment, the Piperazine Compound has one or two $R_6$ groups, an $R_6$ group is attached to a carbon atom adjacent to a nitrogen attached to the A group, the carbon to which the $R_6$ group is attached is in the (S) configuration, and $R_6$ is —$(C_1-C_3)$alkyl. In another embodiment, the Piperazine Compound has one or two $R_6$ groups, an $R_6$ group is attached to a carbon atom adjacent to a nitrogen attached to the A group, the carbon to which the $R_6$ group is attached is in the (S) configuration, and $R_6$ is —$CH_3$. In another embodiment, the Piperazine Compound has one or two $R_6$ groups, an $R_6$ group is attached to a carbon atom adjacent to a nitrogen attached to the A group, the carbon to which the $R_6$ group is attached is in the (S) configuration, and $R_6$ is —$CH_2OH$. In another embodiment, the Piperazine Compound has one or two $R_6$ groups, an $R_6$ group is attached to a carbon atom adjacent to a nitrogen attached to the A group, the carbon to which the $R_6$ group is attached is in the (S) configuration, and $R_6$ is —$CH_2CH_3$.

In another embodiment, the Piperazine Compound has only one $R_6$ group, the $R_6$ group is attached to a carbon atom adjacent to a nitrogen atom attached to the pyridinyl group, and the carbon to which the $R_6$ group is attached is in the (R) configuration. In another embodiment, the Piperazine Compound has only one $R_6$ group, the $R_6$ group is attached to a carbon atom adjacent to a nitrogen attached to the pyridinyl group, the carbon to which the $R_6$ group is attached is in the (R) configuration, and $R_6$ is —$(C_1-C_3)$alkyl. In another embodiment, the Piperazine Compound has only one $R_6$ group, the $R_6$ group is attached to a carbon atom adjacent to a nitrogen attached to the pyridinyl group, the carbon to which the $R_6$ group is attached is in the (R) configuration, and $R_6$ is —$CH_3$. In another embodiment, the Piperazine Compound has only one $R_6$ group, the $R_6$ group is attached to a carbon atom adjacent to a nitrogen attached to the pyridinyl group, the carbon to which the $R_6$ group is attached is in the (R) configuration, and $R_6$ is —$CH_2OH$. In another embodiment, the Piperazine Compound has only one $R_6$ group, the $R_6$ group is attached to a carbon atom adjacent to a nitrogen attached to the pyridinyl group, the carbon to which the $R_6$ group is attached is in the (R) configuration, and $R_6$ is —$CH_2CH_3$.

In another embodiment, the Piperazine Compound has only one $R_6$ group, the $R_6$ group is attached to a carbon atom adjacent to a nitrogen atom attached to the A group, and the carbon to which the $R_6$ group is attached is in the (R) configuration. In another embodiment, the Piperazine Compound has only one $R_6$ group, the $R_6$ group is attached to a carbon atom adjacent to a nitrogen attached to the A group, the carbon to which the $R_6$ group is attached is in the (R) configuration, and $R_6$ is —$(C_1-C_3)$alkyl. In another embodiment, the Piperazine Compound has only one $R_6$ group, the $R_6$ group is attached to a carbon atom adjacent to a nitrogen attached to the A group, the carbon to which the $R_6$ group is attached is in the (R) configuration, and $R_6$ is —$CH_3$. In another embodiment, the Piperazine Compound has only one $R_6$ group, the $R_6$ group is attached to a carbon atom adjacent to a nitrogen attached to the A group, the carbon to which the $R_6$ group is attached is in the (R) configuration, and $R_6$ is —$CH_2OH$. In another embodiment, the Piperazine Compound has only one $R_6$ group, the $R_6$ group is attached to a carbon atom adjacent to a nitrogen attached to the A group, the carbon to which the $R_6$ group is attached is in the (R) configuration, and $R_6$ is —$CH_2CH_3$.

In another embodiment, the Piperazine Compound has only one $R_6$ group, the $R_6$ group is attached to a carbon atom adjacent to a nitrogen atom attached to the pyridinyl group, and the carbon to which the $R_6$ group is attached is in the (S) configuration. In another embodiment, the Piperazine Compound has only one $R_6$ group, the $R_6$ group is attached to a carbon atom adjacent to a nitrogen attached to the pyridinyl group, the carbon to which the $R_6$ group is attached is in the (S) configuration, and $R_6$ is —$(C_1-C_3)$alkyl. In another embodiment, the Piperazine Compound has only one $R_6$ group, the $R_6$ group is attached to a carbon atom adjacent to a nitrogen attached to the pyridinyl group, the carbon to which the $R_6$ group is attached is in the (S) configuration, and $R_6$ is —$CH_3$. In another embodiment, the Piperazine Compound has only one $R_6$ group, the $R_6$ group is attached to a carbon atom adjacent to a nitrogen attached to the pyridinyl group, the carbon to which the $R_6$ group is attached is in the (S) configuration, and $R_6$ is —$CH_2OH$. In another embodiment, the Piperazine Compound has only one $R_6$ group, the $R_6$ group is attached to a carbon atom adjacent to a nitrogen attached to the pyridinyl group, the carbon to which the $R_6$ group is attached is in the (S) configuration, and $R_6$ is —$CH_2CH_3$.

In another embodiment, the Piperazine Compound has only one $R_6$ group, the $R_6$ group is attached to a carbon atom adjacent to a nitrogen atom attached to the A group, and the carbon to which the $R_6$ group is attached is in the (S) configuration. In another embodiment, the Piperazine Compound has only one $R_6$ group, the $R_6$ group is attached to a carbon atom adjacent to a nitrogen attached to the A group, the carbon to which the $R_6$ group is attached is in the (S) configuration, and $R_6$ is —$(C_1-C_3)$alkyl. In another embodiment, the Piperazine Compound has only one $R_6$ group, the $R_6$ group is attached to a carbon atom adjacent to a nitrogen attached to the A group, the carbon to which the $R_6$ group is attached is in the (S) configuration, and $R_6$ is —$CH_3$. In another embodiment, the Piperazine Compound has only one $R_6$ group, the $R_6$ group is attached to a carbon atom adjacent to a nitrogen attached to the A group, the carbon to which the $R_6$ group is attached is in the (S) configuration, and $R_6$ is —$CH_2OH$. In another embodiment, the Piperazine Compound has only one $R_6$ group, the $R_6$ group is attached to a carbon atom adjacent to a nitrogen attached to the A group, the carbon to which the $R_6$ group is attached is in the (R) configuration, and $R_6$ is —$CH_2CH_3$.

In another embodiment, the $R_6$ group is attached to a carbon atom adjacent to a nitrogen attached to the A group. In another embodiment, the $R_6$ group is attached to a carbon atom adjacent to a nitrogen attached to the A group and the $R_6$ group is a —$CH_3$. In another embodiment, the $R_6$ group is attached to a carbon atom adjacent to a nitrogen attached to the A group and the $R_6$ group is a —$CH_2CH_3$. In another embodiment, the $R_6$ group is attached to a carbon atom adjacent to a nitrogen attached to the A group and the carbon to which the $R_6$ group is attached is in the (R) configuration. In another embodiment, the $R_6$ group is attached to a carbon atom adjacent to a nitrogen attached to the A group, the carbon to which the $R_6$ group is attached is in the (R)

configuration, and the $R_6$ group is a —$CH_3$. In another embodiment, the $R_6$ group is attached to a carbon atom adjacent to a nitrogen attached to the A group, the carbon to which the $R_6$ group is attached is in the (R) configuration, and the $R_6$ group is a —$CH_2CH_3$.

In another embodiment A is —C(O)—; n is 2; an $R_1$ is substituted at the 4-position of the pyridinyl ring (denoted hereinafter for convenience as "$R_1''''$") and is —$CH_3$, —$OCH_3$ or -halo; the other $R_1$ is substituted at the 6-position of the pyridinyl ring (denoted hereinafter for convenience as "$R_1''''$") and is —H or —$CH_3$; $R_2$ is -phenyl or -pyridyl, each which is unsubstituted or substituted with one or more $R_5$ or $R_5'$ groups, as described above, and $R_6$ is —H, —$CH_3$ or —$CH_2OH$ and is attached to a carbon atom adjacent to the nitrogen atom attached to the A group.

In another embodiment A is —C(O)—; n is 2; $R_1'$ is —$CH_3$, —$OCH_3$ or —Cl; $R_1'''$ is —H or —$CH_3$; $R_2$ is -phenyl or -pyridyl, each which is unsubstituted or substituted with one or more $R_5$ or $R_5'$ groups, as described above; and $R_6$ is —H, —$CH_3$ or —$CH_2OH$ and is attached to a carbon atom adjacent to the nitrogen atom attached to the A group.

In another embodiment A is —C(O)—; n is 2; $R_1'$ is —$CH_3$, —$OCH_3$ or -halo; $R_1'''$ is —H or —$CH_3$; $R_2$ is -phenyl or -pyridyl, each which is unsubstituted or substituted with one or more $R_5$ or $R_5'$ groups, as described above, selected from -halo and —$CH_3$; and $R_6$ is —H, —$CH_3$ or —$CH_2OH$ and is attached to a carbon atom adjacent to the nitrogen atom attached to the A group.

In another embodiment A is —C(O)—; n is 2; $R_1'$ is —$CH_3$, —$OCH_3$ or —Cl; $R_1'''$ is —H or —$CH_3$; $R_2$ is -phenyl or -pyridyl, each which is unsubstituted or substituted with one or more $R_5$ or $R_5'$ groups, as described above, selected from —F, —Cl and —$CH_3$; and $R_6$ is —H, —$CH_3$ or —$CH_2OH$ and is attached to a carbon atom adjacent to the nitrogen atom attached to the A group.

In another embodiment A is —C(O)—; n is 2; $R_1'$ is —$CH_3$, —$OCH_3$ or —Cl; $R_1'''$ is —H or —$CH_3$; $R_2$ is -phenyl which is unsubstituted or substituted with one $R_5$ group that is para to the phenyl group's point of attachment to the triple bond and is selected from —F and —$OCH_3$; and $R_6$ is —H, —$CH_3$ or —$CH_2OH$ and is attached to a carbon atom adjacent to the nitrogen atom attached to the A group.

In another embodiment A is —C(O)—; n is 2; $R_1'$ is —$CH_3$, —$OCH_3$ or —Cl; $R_1'''$ is —H or —$CH_3$; $R_2$ is -pyridyl which is attached at its 2-position and is unsubstituted or substituted with one $R_5'$ group at the 5-position of the -pyridyl group's point of attachment to the triple bond and is selected from —F, —Cl and —$CH_3$; and $R_6$ is —H, —$CH_3$ or —$CH_2OH$ and is attached to a carbon atom adjacent to the nitrogen atom attached to the A group.

In another embodiment A is —C(O)—; n is 2; $R_1'$ is —$CH_3$, —$OCH_3$ or —Cl; $R_1'''$ is —H or —$CH_3$; $R_2$ is -pyridyl which is attached at its 3-position and is unsubstituted or substituted with one $R_5'$ group at the 6-position of the -pyridyl group's point of attachment to the triple bond and is selected from —F, —Cl and —$CH_3$; and $R_6$ is —H, —$CH_3$ or —$CH_2OH$ and is attached to a carbon atom adjacent to the nitrogen atom attached to the A group.

5.2 Compounds of Formula (Ia)

The present invention also encompasses compounds of Formula (Ia):

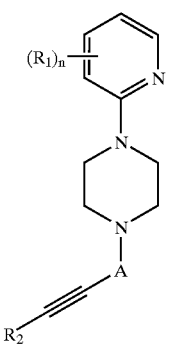

(Ia)

and pharmaceutically acceptable salts thereof, wherein:

A is —C(O)—, —C(S)—, —CH($C_1$-$C_4$ alkyl)- or —C(($C_1$-$C_4$ alkyl)($C_1$-$C_4$ alkyl)-;

each $R_1$ is independently —($C_1$-$C_3$)alkyl, -halo, —$NO_2$, —OH or —CN;

n is an integer from 1–4;

$R_2$ is —H, —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle or -(7- to 10-membered)bicycloheterocycle, each of which is unsubstituted or substituted with one or more $R_3$ groups, or $R_2$ is -phenyl, -naphthyl, —($C_{14}$)aryl or -(5- to 10-membered)heteroaryl, each of which is unsubstituted or substituted with one or more $R_5$ groups;

each $R_3$ is independently —CN, —OH, -halo, —$N_3$, —$NO_2$, —N($R_4$)$_2$, =$NR_4$, —CH=$NR_4$, —$NR_4OH$, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$ or —CH(halo)$_2$; and each $R_5$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —CN, —OH, -halo, —$N_3$, —$NO_2$, —N($R_4$)$_2$, —CH=$NR_4$, —$NR_4OH$, —$OR_4$, —$COR_4$, —C(O)$OR_4$, —OC(O)$R_4$, —OC(O)$OR_4$, —$SR_4$, —S(O)$R_4$ or —S(O)$_2R_4$.

In another embodiment, the present invention also encompasses compounds having the formula (Ia), and pharmaceutically acceptable salts thereof, wherein:

A is —C(O)—, —C(S)—, —CH($C_1$-$C_4$ alkyl)- or —C(($C_1$-$C_4$ alkyl)($C_1$-$C_4$ alkyl)-;

each $R_1$ is independently —($C_1$-$C_3$)alkyl, -halo, —$NO_2$, —OH or —CN;

n is an integer from 1–4;

$R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle or -(7- to 10-membered)bicycloheterocycle, each of which is unsubstituted or substituted with one or more $R_3$ groups, or $R_2$ is -phenyl, -naphthyl or —$(C_{14})$aryl, each of which is unsubstituted or substituted with one or more $R_5$ groups, or $R_2$ is -(5- to 10-membered)heteroaryl which is unsubstituted or substituted with one or more $R_5'$ groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$ or —CH(halo)$_2$;

each $R_5$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$; and each $R_5'$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$COR_4$, —C(O)$OR_4$, —OC(O)$R_4$, —OC(O)$OR_4$, —$SR_4$, —S(O)$R_4$ or —S(O)$_2R_4$.

In another embodiment A is —C(O)—.

In another embodiment A is —C(O)—; n is 1; $R_1$ is substituted at the 3-position of the pyridyl ring and is —$CH_3$, -halo, —$NO_2$, —OH, or —CN; and $R_2$ is -phenyl, -naphthyl, —$(C_{14})$aryl or -(5- to 10-membered)heteroaryl, each which is unsubstituted or substituted with one or more $R_5$ groups.

In another embodiment A is —C(O)—; n is 1; $R_1$ is —$NO_2$ and substituted at the 3-position of the pyridyl ring; and $R_2$ is phenyl, which is unsubstituted or substituted with one or more $R_5$ groups.

In another embodiment A is —C(O)—, n is 1, $R_1$ is —$NO_2$ and substituted at the 3-position of the pyridyl ring, and $R_2$ is unsubstituted phenyl.

In another embodiment A is —C(O)—, n is 1, $R_1$ is —$CH_3$, and $R_2$ is unsubstituted phenyl.

In another embodiment A is —C(O)—; n is 1; $R_1$ is —$NO_2$, -halo or —CN, each of which is substituted at the 3-position of the pyridyl ring; and $R_2$ is unsubstituted phenyl.

The present invention also encompasses compounds having the formula (Ia), and pharmaceutically acceptable salts thereof, wherein:

A is —C(O)—, —C(S)—, —$CH_2$—, —CH($C_1-C_4$ alkyl)- or —C($C_1-C_4$ alkyl)($C_1-C_4$ alkyl)-;

each $R_1$ is independently —$(C_1-C_3)$alkyl, -halo, —$NO_2$, —OH or —CN;

n is an integer from 1–4;

$R_2$ is —H, —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl or —$(C_8-C_{14})$tricycloalkenyl, each of which is unsubstituted or substituted with one or more $R_3$ groups, or $R_2$ is -phenyl, -naphthyl or —$(C_{14})$aryl, each of which is unsubstituted or substituted with one or more $R_5$ groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$ or —CH(halo)$_2$; and each $R_5$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$.

In another embodiment, the present invention also encompasses compounds having the formula (Ia), and pharmaceutically acceptable salts thereof, wherein:

A is —C(O)—, —C(S)—, —$CH_2$—, —CH($C_1-C_4$ alkyl)- or —C($C_1-C_4$ alkyl)($C_1-C_4$ alkyl)-;

each $R_1$ is independently —$(C_1-C_3)$alkyl, -halo, —$NO_2$, —OH or —CN;

n is an integer from 1–4;

$R_2$ is —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl or —$(C_8-C_{14})$tricycloalkenyl, each of which is unsubstituted or substituted with one or more $R_3$ groups, or $R_2$ is -phenyl, -naphthyl or —$(C_{14})$aryl, each of which is unsubstituted or substituted with one or more $R_5$ groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$ or —CH(halo)$_2$; and each $R_5$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$.

In another embodiment A is —$CH_2$—, n is 1, $R_1$ is —$NO_2$ and substituted at the 3-position of the pyridyl ring, and $R_2$ is unsubstituted phenyl.

In another embodiment A is —$CH_2$—, n is 2, $R_1$ is an —$NO_2$ substituted at the 3-position of the pyridyl ring, $R_1'''$ is a —OH and $R_2$ is unsubstituted phenyl.

In another embodiment A is —$CH_2$—, n is 1, $R_1$ is —CN and substituted at the 3-position of the pyridyl ring, and $R_2$ is unsubstituted phenyl.

In another embodiment A is —$CH_2$—, n is 1, $R_1$ is —Cl and substituted at the 3-position of the pyridyl ring, and $R_2$ is unsubstituted phenyl.

Illustrative compounds of formulas (I) and (Ia) have the structure:

Compound AA
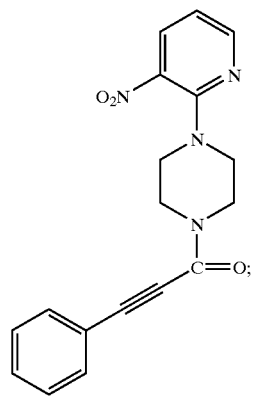
Compound AB
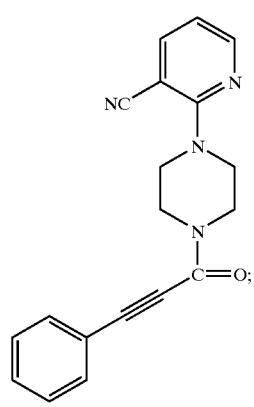
Compound AC
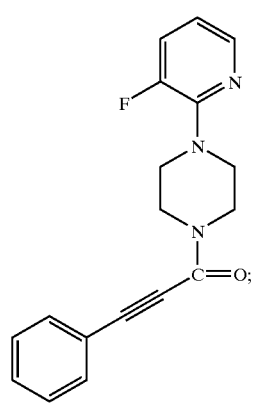
Compound AD
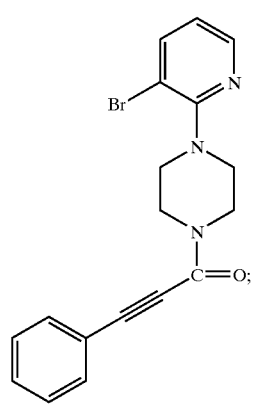
Compound AE
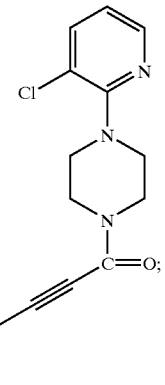
Compound AF
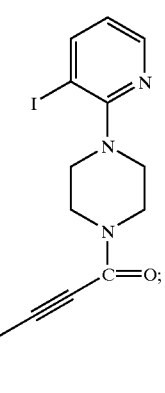
Compound AG
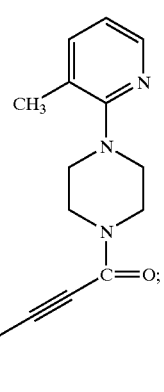
Compound AH
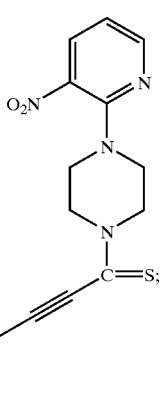

Compound AI

Compound AJ

Compound AK

Compound AL

Compound AM

Compound AN

Compound AO

Compound AP

Compound AQ
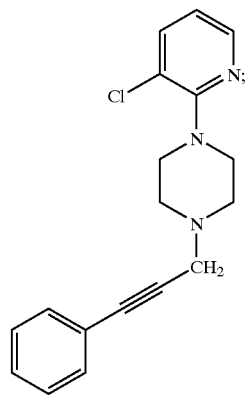
Compound AR
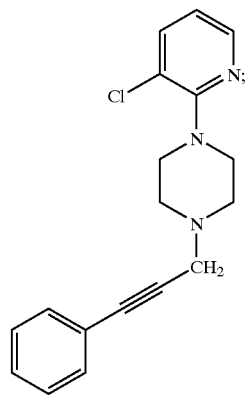
Compound AS
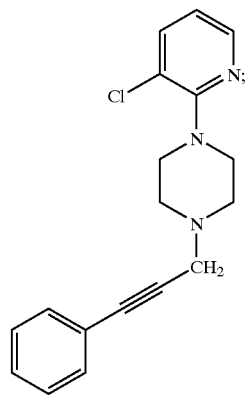
Compound AT
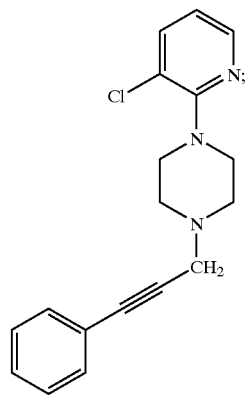
Compound AU
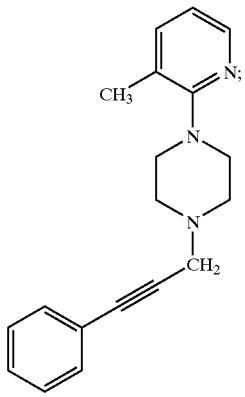
Compound AV
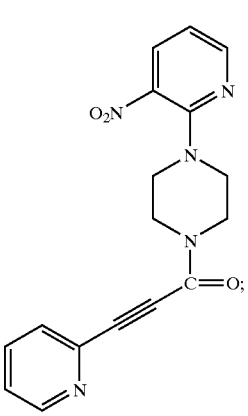
Compound AW
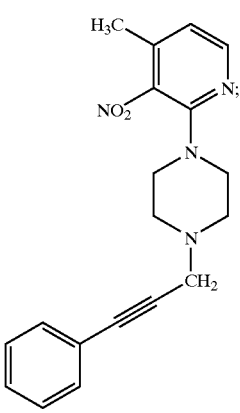
Compound AX
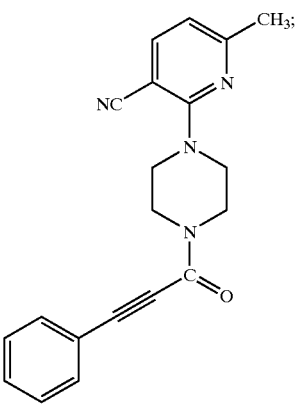

Compound AY
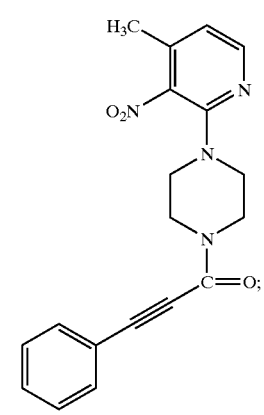
Compound AZ
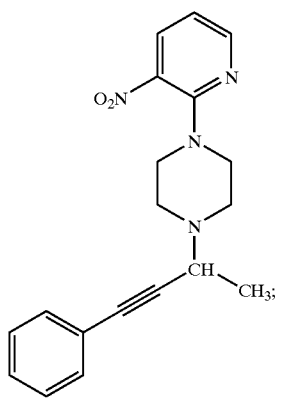
Compound BA
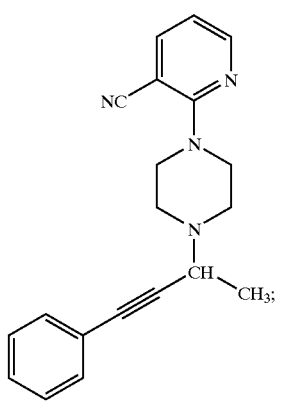
Compound BB
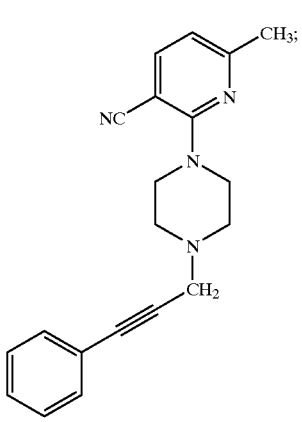
Compound BC
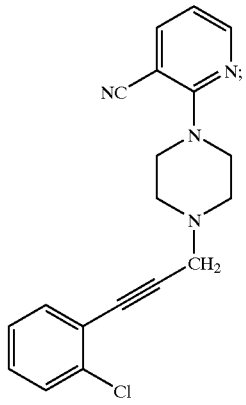
Compound BD
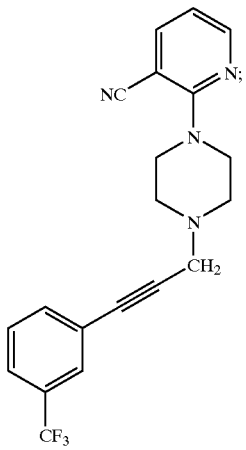
Compound BE
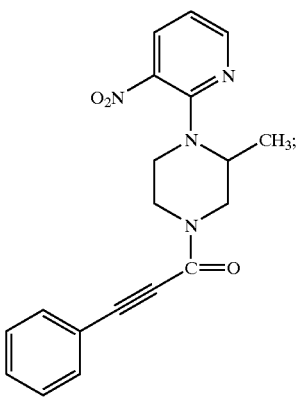
Compound BF
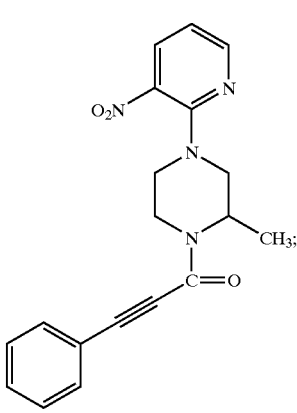

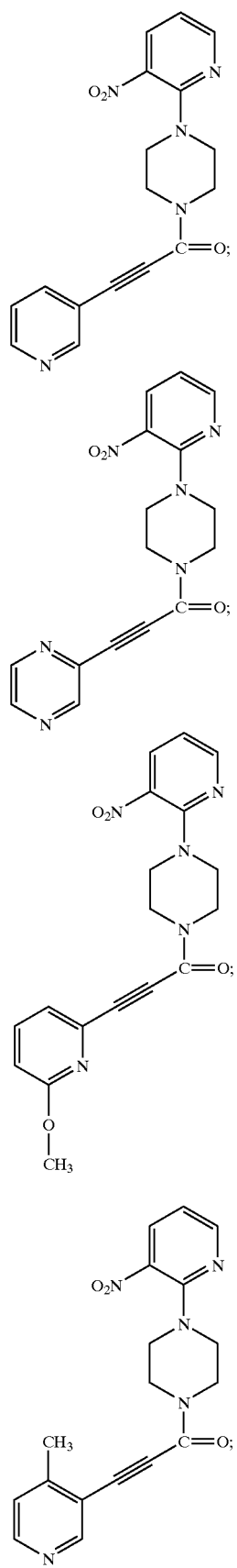

Compound BO
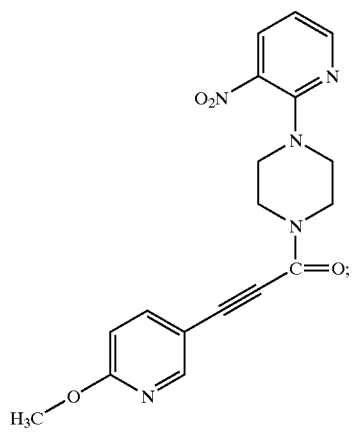
Compound BP
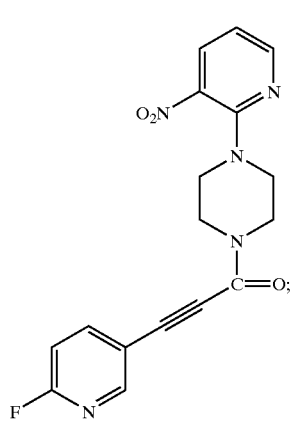
Compound BQ
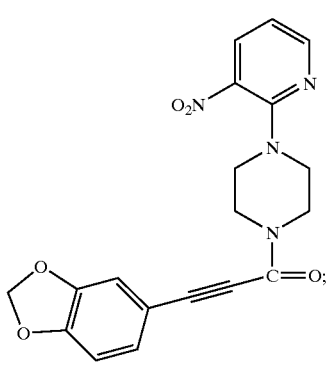
Compound BR
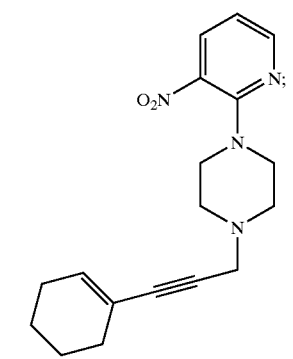
Compound BS
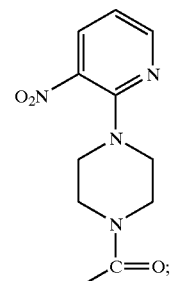
Compound BT
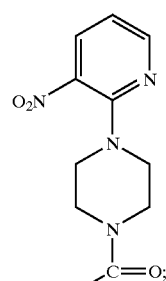
Compound BU
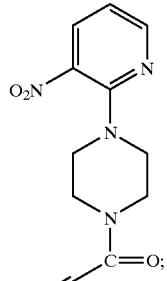
Compound BV
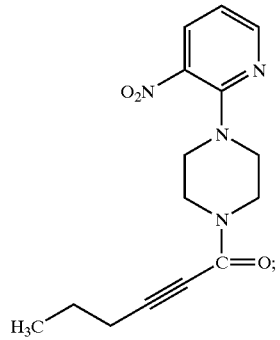

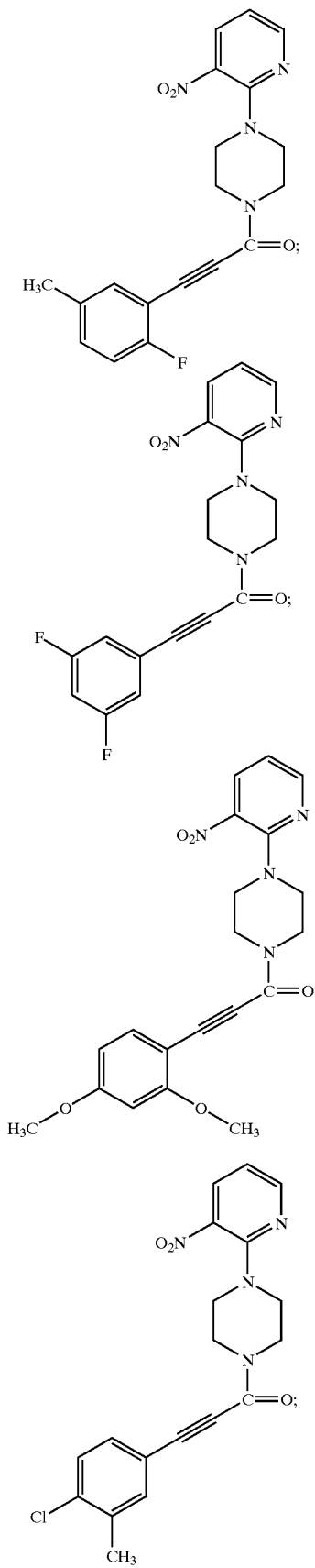
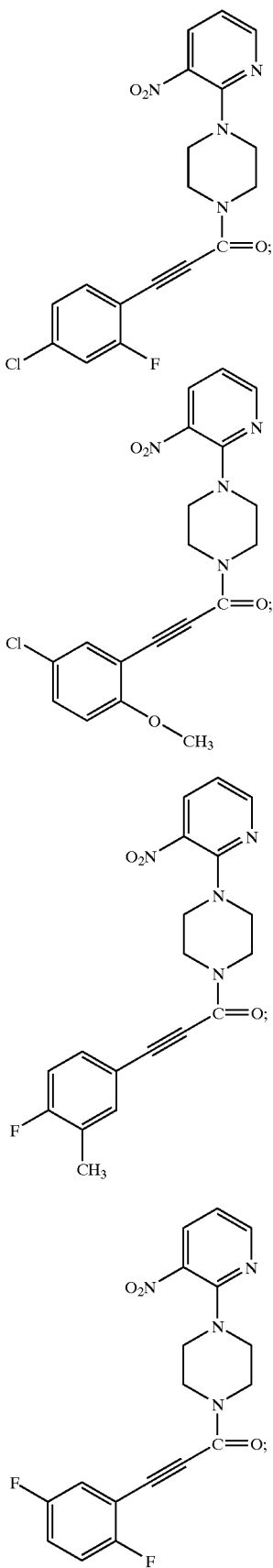

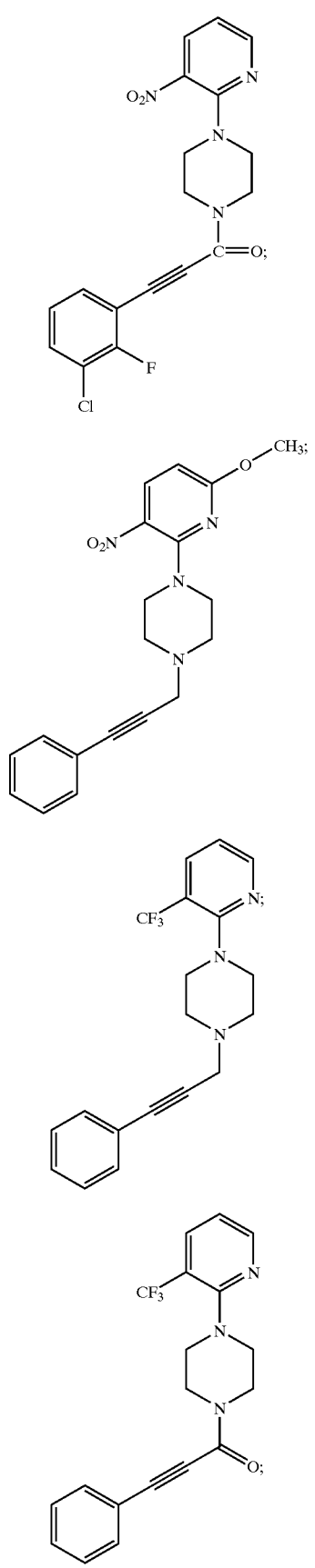
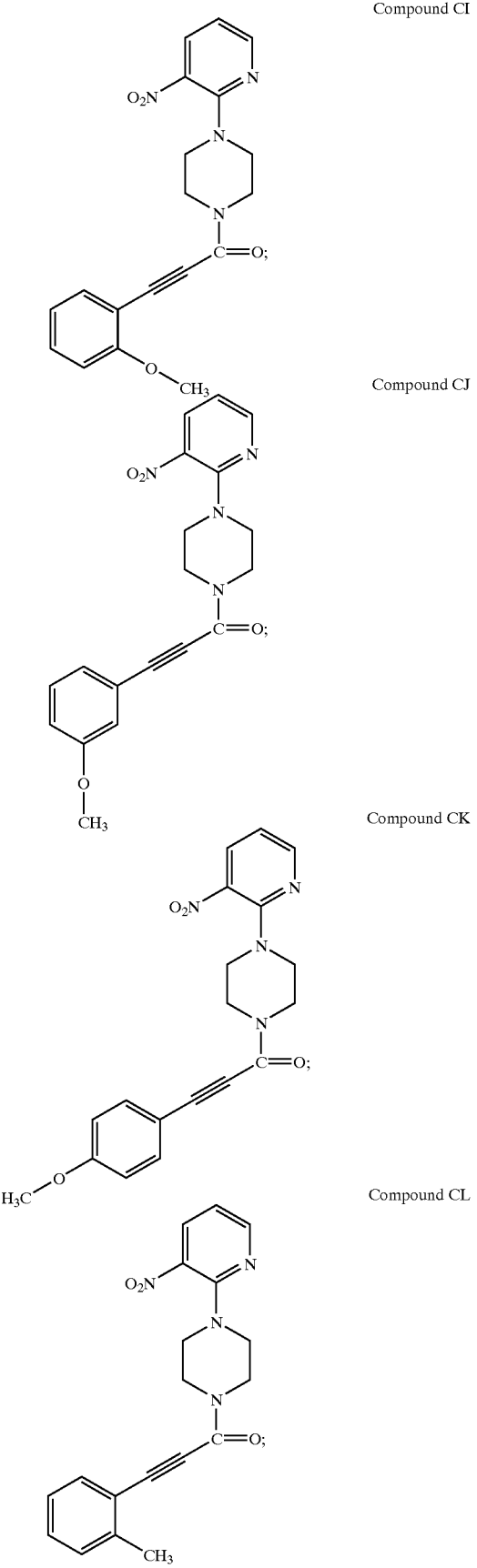

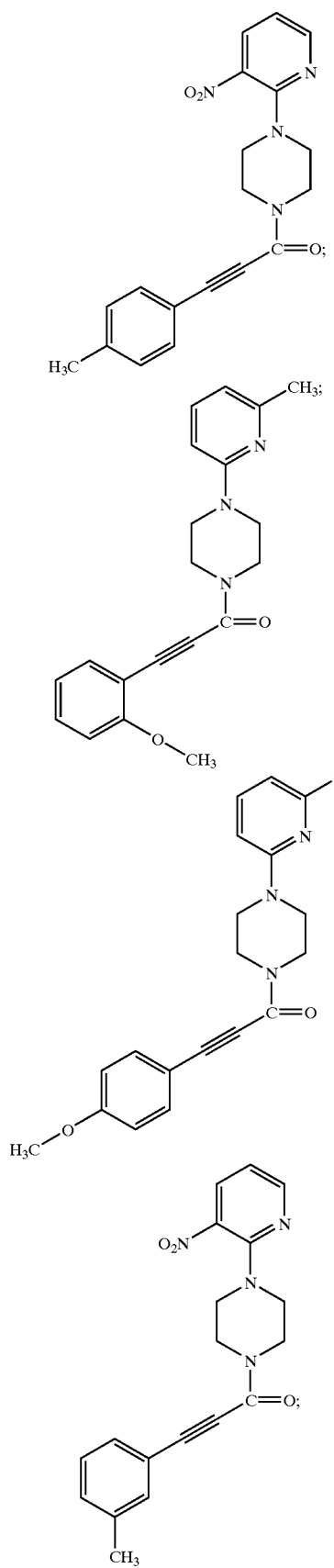
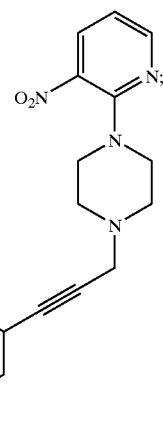
Compound CM
Compound CN
Compound CO
Compound CP
Compound CS
Compound CT
Compound CU
Compound CV Compound CW Compound CX Compound CY Compound CZ Compound DA Compound DB Compound DC Compound DD -continued
Compound DE
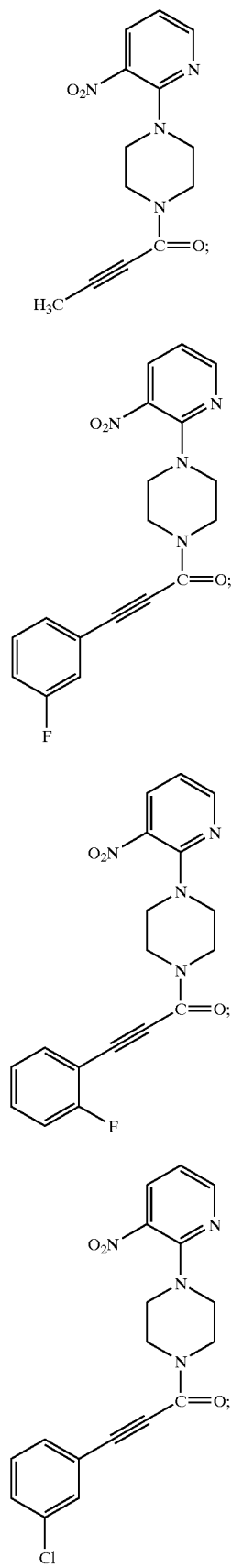
Compound DF
Compound DG
Compound DH
-continued
Compound DI
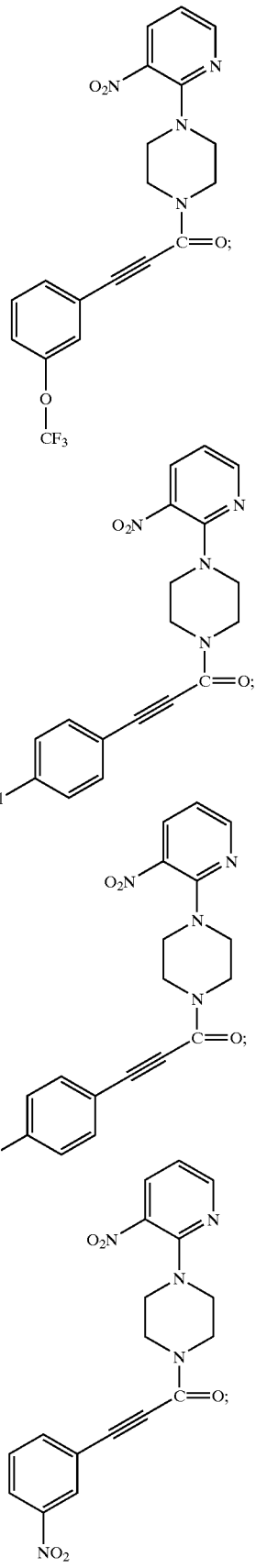
Compound DJ
Compound DK
Compound DL Compound DM
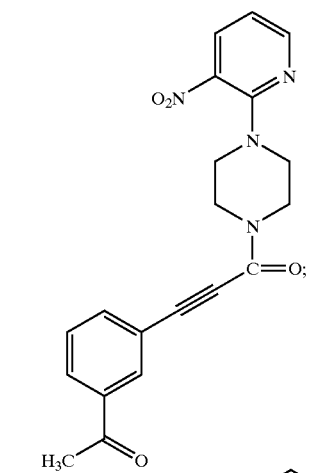
Compound DN
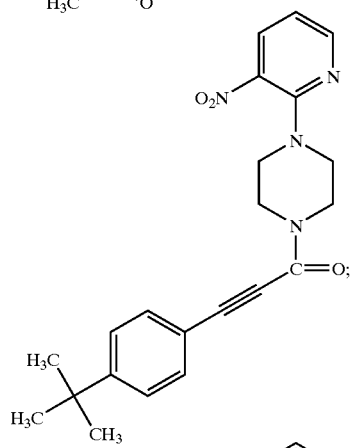
Compound DO
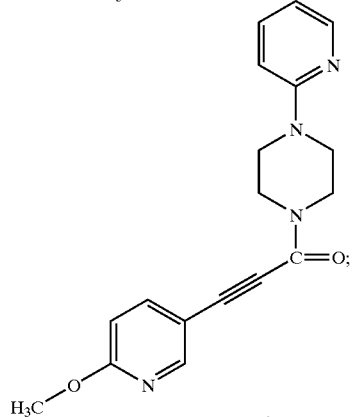
Compound DP
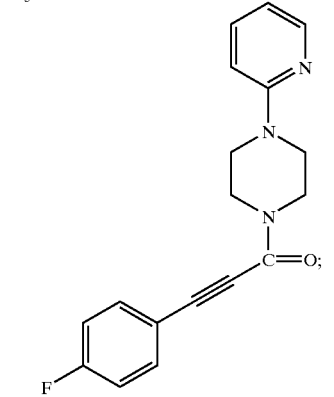
Compound DQ
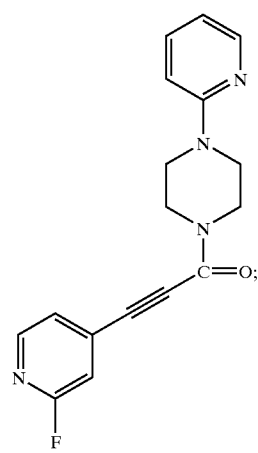
Compound DR
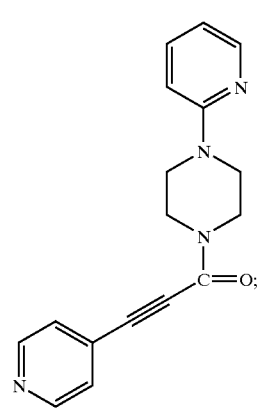
Compound DS
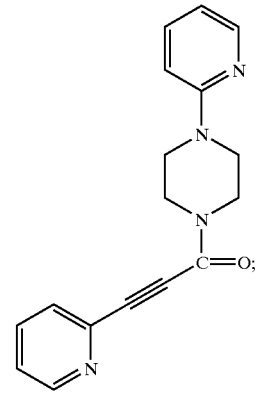
Compound DT
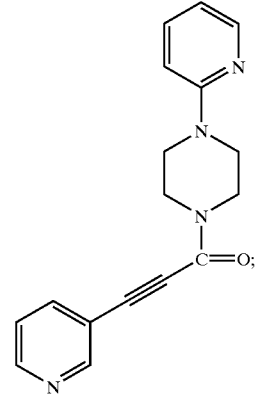

-continued

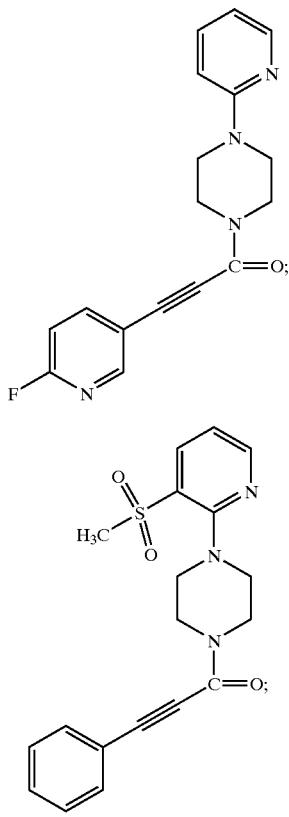

and pharmaceutically acceptable salts thereof.

Other illustrative compounds of formulas (I) and (Ia) are listed below in Table 1:

TABLE 1

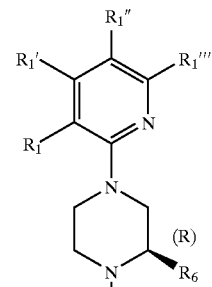

(IIa)

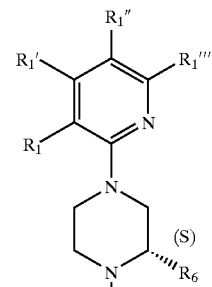

(IIb)

and pharmaceutically acceptable salts thereof, where:

| Compound | | $R_6$ | $R_1$ | $R_1'$ | $R_1''$ | $R_1'''$ | Y | Z |
|---|---|---|---|---|---|---|---|---|
| 100 | (IIa) | —H | —H | —H | —H | —H | —C(H)— | —C(H)— |
| 101 | (IIa) | —H | —H | —H | —H | —H | —C(H)— | —N— |
| 102 | (IIa) | —H | —H | —H | —H | —H | —N— | —C(H)— |
| 103 | (IIa) | —H | —H | —H | —H | —CH$_3$ | —C(H)— | —C(H)— |
| 104 | (IIa) | —H | —H | —H | —H | —CH$_3$ | —C(H)— | —N— |
| 105 | (IIa) | —H | —H | —H | —H | —CH$_3$ | —N— | —C(H)— |
| 106 | (IIa) | —H | —H | —H | —H | —OCH$_3$ | —C(H)— | —C(H)— |
| 107 | (IIa) | —H | —H | —H | —H | —OCH$_3$ | —C(H)— | —N— |
| 108 | (IIa) | —H | —H | —H | —H | —OCH$_3$ | —N— | —C(H)— |
| 109 | (IIa) | —H | —H | —H | —H | —OCF$_3$ | —C(H)— | —C(H)— |
| 110 | (IIa) | —H | —H | —H | —H | —OCF$_3$ | —C(H)— | —N— |
| 111 | (IIa) | —H | —H | —H | —H | —OCF$_3$ | —N— | —C(H)— |
| 112 | (IIa) | —H | —H | —H | —H | —F | —C(H)— | —C(H)— |
| 113 | (IIa) | —H | —H | —H | —H | —F | —C(H)— | —N— |
| 114 | (IIa) | —H | —H | —H | —H | —F | —N— | —C(H)— |
| 115 | (IIa) | —H | —H | —H | —CH$_3$ | —H | —C(H)— | —C(H)— |
| 116 | (IIa) | —H | —H | —H | —CH$_3$ | —H | —C(H)— | —N— |
| 117 | (IIa) | —H | —H | —H | —CH$_3$ | —H | —N— | —C(H)— |
| 118 | (IIa) | —H | —H | —H | —CH$_3$ | —CH$_3$ | —C(H)— | —C(H)— |
| 119 | (IIa) | —H | —H | —H | —CH$_3$ | —CH$_3$ | —C(H)— | —N— |
| 120 | (IIa) | —H | —H | —H | —CH$_3$ | —CH$_3$ | —N— | —C(H)— |
| 121 | (IIa) | —H | —H | —H | —CH$_3$ | —OCH$_3$ | —C(H)— | —C(H)— |

-continued

| Compound | | R$_6$ | R$_1$ | R$_1$' | R$_1$'' | R$_1$''' | Y | Z |
|---|---|---|---|---|---|---|---|---|
| 122 | (IIa) | —H | —H | —H | —CH$_3$ | —OCH$_3$ | —C(H)— | —N— |
| 123 | (IIa) | —H | —H | —H | —CH$_3$ | —OCH$_3$ | —N— | —C(H)— |
| 124 | (IIa) | —H | —H | —H | —CH$_3$ | —OCF$_3$ | —C(H)— | —C(H)— |
| 125 | (IIa) | —H | —H | —H | —CH$_3$ | —OCF$_3$ | —C(H)— | —N— |
| 126 | (IIa) | —H | —H | —H | —CH$_3$ | —OCF$_3$ | —N— | —C(H)— |
| 127 | (IIa) | —H | —H | —H | —CH$_3$ | —F | —C(H)— | —C(H)— |
| 128 | (IIa) | —H | —H | —H | —CH$_3$ | —F | —C(H)— | —N— |
| 129 | (IIa) | —H | —H | —H | —CH$_3$ | —F | —N— | —C(H)— |
| 130 | (IIa) | —H | —H | —H | —OCH$_3$ | —H | —C(H)— | —C(H)— |
| 131 | (IIa) | —H | —H | —H | —OCH$_3$ | —H | —C(H)— | —N— |
| 132 | (IIa) | —H | —H | —H | —OCH$_3$ | —H | —N— | —C(H)— |
| 133 | (IIa) | —H | —H | —H | —OCH$_3$ | —CH$_3$ | —C(H)— | —C(H)— |
| 134 | (IIa) | —H | —H | —H | —OCH$_3$ | —CH$_3$ | —C(H)— | —N— |
| 135 | (IIa) | —H | —H | —H | —OCH$_3$ | —CH$_3$ | —N— | —C(H)— |
| 136 | (IIa) | —H | —H | —H | —OCH$_3$ | —OCH$_3$ | —C(H)— | —C(H)— |
| 137 | (IIa) | —H | —H | —H | —OCH$_3$ | —OCH$_3$ | —C(H)— | —N— |
| 138 | (IIa) | —H | —H | —H | —OCH$_3$ | —OCH$_3$ | —N— | —C(H)— |
| 139 | (IIa) | —H | —H | —H | —OCH$_3$ | —OCF$_3$ | —C(H)— | —C(H)— |
| 140 | (IIa) | —H | —H | —H | —OCH$_3$ | —OCF$_3$ | —C(H)— | —N— |
| 141 | (IIa) | —H | —H | —H | —OCH$_3$ | —OCF$_3$ | —N— | —C(H)— |
| 142 | (IIa) | —H | —H | —H | —OCH$_3$ | —F | —C(H)— | —C(H)— |
| 143 | (IIa) | —H | —H | —H | —OCH$_3$ | —F | —C(H)— | —N— |
| 144 | (IIa) | —H | —H | —H | —OCH$_3$ | —F | —N— | —C(H)— |
| 145 | (IIa) | —H | —H | —H | —NO$_2$ | —H | —C(H)— | —C(H)— |
| 146 | (IIa) | —H | —H | —H | —NO$_2$ | —H | —C(H)— | —N— |
| 147 | (IIa) | —H | —H | —H | —NO$_2$ | —H | —N— | —C(H)— |
| 148 | (IIa) | —H | —H | —H | —NO$_2$ | —CH$_3$ | —C(H)— | —C(H)— |
| 149 | (IIa) | —H | —H | —H | —NO$_2$ | —CH$_3$ | —C(H)— | —N— |
| 150 | (IIa) | —H | —H | —H | —NO$_2$ | —CH$_3$ | —N— | —C(H)— |
| 151 | (IIa) | —H | —H | —H | —NO$_2$ | —OCH$_3$ | —C(H)— | —C(H)— |
| 152 | (IIa) | —H | —H | —H | —NO$_2$ | —OCH$_3$ | —C(H)— | —N— |
| 153 | (IIa) | —H | —H | —H | —NO$_2$ | —OCH$_3$ | —N— | —C(H)— |
| 154 | (IIa) | —H | —H | —H | —NO$_2$ | —OCF$_3$ | —C(H)— | —C(H)— |
| 155 | (IIa) | —H | —H | —H | —NO$_2$ | —OCF$_3$ | —C(H)— | —N— |
| 156 | (IIa) | —H | —H | —H | —NO$_2$ | —OCF$_3$ | —N— | —C(H)— |
| 157 | (IIa) | —H | —H | —H | —NO$_2$ | —F | —C(H)— | —C(H)— |
| 158 | (IIa) | —H | —H | —H | —NO$_2$ | —F | —C(H)— | —N— |
| 159 | (IIa) | —H | —H | —H | —NO$_2$ | —F | —N— | —C(H)— |
| 160 | (IIa) | —H | —H | —CH$_3$ | —H | —H | —C(H)— | —C(H)— |
| 161 | (IIa) | —H | —H | —CH$_3$ | —H | —H | —C(H)— | —N— |
| 162 | (IIa) | —H | —H | —CH$_3$ | —H | —H | —N— | —C(H)— |
| 163 | (IIa) | —H | —H | —CH$_3$ | —H | —CH$_3$ | —C(H)— | —C(H)— |
| 164 | (IIa) | —H | —H | —CH$_3$ | —H | —CH$_3$ | —C(H)— | —N— |
| 165 | (IIa) | —H | —H | —CH$_3$ | —H | —CH$_3$ | —N— | —C(H)— |
| 166 | (IIa) | —H | —H | —CH$_3$ | —H | —OCH$_3$ | —C(H)— | —C(H)— |
| 167 | (IIa) | —H | —H | —CH$_3$ | —H | —OCH$_3$ | —C(H)— | —N— |
| 168 | (IIa) | —H | —H | —CH$_3$ | —H | —OCH$_3$ | —N— | —C(H)— |
| 169 | (IIa) | —H | —H | —CH$_3$ | —H | —OCF$_3$ | —C(H)— | —C(H)— |
| 170 | (IIa) | —H | —H | —CH$_3$ | —H | —OCF$_3$ | —C(H)— | —N— |
| 171 | (IIa) | —H | —H | —CH$_3$ | —H | —OCF$_3$ | —N— | —C(H)— |
| 172 | (IIa) | —H | —H | —CH$_3$ | —H | —F | —C(H)— | —C(H)— |
| 173 | (IIa) | —H | —H | —CH$_3$ | —H | —F | —C(H)— | —N— |
| 174 | (IIa) | —H | —H | —CH$_3$ | —H | —F | —N— | —C(H)— |
| 175 | (IIa) | —H | —H | —CH$_3$ | —CH$_3$ | —H | —C(H)— | —C(H)— |
| 176 | (IIa) | —H | —H | —CH$_3$ | —CH$_3$ | —H | —C(H)— | —N— |
| 177 | (IIa) | —H | —H | —CH$_3$ | —CH$_3$ | —H | —N— | —C(H)— |
| 178 | (IIa) | —H | —H | —CH$_3$ | —CH$_3$ | —CH$_3$ | —C(H)— | —C(H)— |
| 179 | (IIa) | —H | —H | —CH$_3$ | —CH$_3$ | —CH$_3$ | —C(H)— | —N— |
| 180 | (IIa) | —H | —H | —CH$_3$ | —CH$_3$ | —CH$_3$ | —N— | —C(H)— |
| 181 | (IIa) | —H | —H | —CH$_3$ | —CH$_3$ | —OCH$_3$ | —C(H)— | —C(H)— |
| 182 | (IIa) | —H | —H | —CH$_3$ | —CH$_3$ | —OCH$_3$ | —C(H)— | —N— |
| 183 | (IIa) | —H | —H | —CH$_3$ | —CH$_3$ | —OCH$_3$ | —N— | —C(H)— |
| 184 | (IIa) | —H | —H | —CH$_3$ | —CH$_3$ | —OCF$_3$ | —C(H)— | —C(H)— |
| 185 | (IIa) | —H | —H | —CH$_3$ | —CH$_3$ | —OCF$_3$ | —C(H)— | —N— |
| 186 | (IIa) | —H | —H | —CH$_3$ | —CH$_3$ | —OCF$_3$ | —N— | —C(H)— |
| 187 | (IIa) | —H | —H | —CH$_3$ | —CH$_3$ | —F | —C(H)— | —C(H)— |
| 188 | (IIa) | —H | —H | —CH$_3$ | —CH$_3$ | —F | —C(H)— | —N— |
| 189 | (IIa) | —H | —H | —CH$_3$ | —CH$_3$ | —F | —N— | —C(H)— |
| 190 | (IIa) | —H | —H | —CH$_3$ | —OCH$_3$ | —H | —C(H)— | —C(H)— |
| 191 | (IIa) | —H | —H | —CH$_3$ | —OCH$_3$ | —H | —C(H)— | —N— |
| 192 | (IIa) | —H | —H | —CH$_3$ | —OCH$_3$ | —H | —N— | —C(H)— |
| 193 | (IIa) | —H | —H | —CH$_3$ | —OCH$_3$ | —CH$_3$ | —C(H)— | —C(H)— |
| 194 | (IIa) | —H | —H | —CH$_3$ | —OCH$_3$ | —CH$_3$ | —C(H)— | —N— |
| 195 | (IIa) | —H | —H | —CH$_3$ | —OCH$_3$ | —CH$_3$ | —N— | —C(H)— |
| 196 | (IIa) | —H | —H | —CH$_3$ | —OCH$_3$ | —OCH$_3$ | —C(H)— | —C(H)— |
| 197 | (IIa) | —H | —H | —CH$_3$ | —OCH$_3$ | —OCH$_3$ | —C(H)— | —N— |
| 198 | (IIa) | —H | —H | —CH$_3$ | —OCH$_3$ | —OCH$_3$ | —N— | —C(H)— |

-continued

| Compound | | $R_6$ | $R_1$ | $R_1{}'$ | $R_1{}''$ | $R_1{}'''$ | Y | Z |
|---|---|---|---|---|---|---|---|---|
| 199 | (IIa) | —H | —H | —CH₃ | —OCH₃ | —OCF₃ | —C(H)— | —C(H)— |
| 200 | (IIa) | —H | —H | —CH₃ | —OCH₃ | —OCF₃ | —C(H)— | —N— |
| 201 | (IIa) | —H | —H | —CH₃ | —OCH₃ | —OCF₃ | —N— | —C(H)— |
| 202 | (IIa) | —H | —H | —CH₃ | —OCH₃ | —F | —C(H)— | —C(H)— |
| 203 | (IIa) | —H | —H | —CH₃ | —OCH₃ | —F | —C(H)— | —N— |
| 204 | (IIa) | —H | —H | —CH₃ | —OCH₃ | —F | —N— | —C(H)— |
| 205 | (IIa) | —H | —H | —CH₃ | —NO₂ | —H | —C(H)— | —C(H)— |
| 206 | (IIa) | —H | —H | —CH₃ | —NO₂ | —H | —C(H)— | —N— |
| 207 | (IIa) | —H | —H | —CH₃ | —NO₂ | —H | —N— | —C(H)— |
| 208 | (IIa) | —H | —H | —CH₃ | —NO₂ | —CH₃ | —C(H)— | —C(H)— |
| 209 | (IIa) | —H | —H | —CH₃ | —NO₂ | —CH₃ | —C(H)— | —N— |
| 210 | (IIa) | —H | —H | —CH₃ | —NO₂ | —CH₃ | —N— | —C(H)— |
| 211 | (IIa) | —H | —H | —CH₃ | —NO₂ | —OCH₃ | —C(H)— | —C(H)— |
| 212 | (IIa) | —H | —H | —CH₃ | —NO₂ | —OCH₃ | —C(H)— | —N— |
| 213 | (IIa) | —H | —H | —CH₃ | —NO₂ | —OCH₃ | —N— | —C(H)— |
| 214 | (IIa) | —H | —H | —CH₃ | —NO₂ | —OCF₃ | —C(H)— | —C(H)— |
| 215 | (IIa) | —H | —H | —CH₃ | —NO₂ | —OCF₃ | —C(H)— | —N— |
| 216 | (IIa) | —H | —H | —CH₃ | —NO₂ | —OCF₃ | —N— | —C(H)— |
| 217 | (IIa) | —H | —H | —CH₃ | —NO₂ | —F | —C(H)— | —C(H)— |
| 218 | (IIa) | —H | —H | —CH₃ | —NO₂ | —F | —C(H)— | —N— |
| 219 | (IIa) | —H | —H | —CH₃ | —NO₂ | —F | —N— | —C(H)— |
| 220 | (IIa) | —H | —H | —OCH₃ | —H | —H | —C(H)— | —C(H)— |
| 221 | (IIa) | —H | —H | —OCH₃ | —H | —H | —C(H)— | —N— |
| 222 | (IIa) | —H | —H | —OCH₃ | —H | —H | —N— | —C(H)— |
| 223 | (IIa) | —H | —H | —OCH₃ | —H | —CH₃ | —C(H)— | —C(H)— |
| 224 | (IIa) | —H | —H | —OCH₃ | —H | —CH₃ | —C(H)— | —N— |
| 225 | (IIa) | —H | —H | —OCH₃ | —H | —CH₃ | —N— | —C(H)— |
| 226 | (IIa) | —H | —H | —OCH₃ | —H | —OCH₃ | —C(H)— | —C(H)— |
| 227 | (IIa) | —H | —H | —OCH₃ | —H | —OCH₃ | —C(H)— | —N— |
| 228 | (IIa) | —H | —H | —OCH₃ | —H | —OCH₃ | —N— | —C(H)— |
| 229 | (IIa) | —H | —H | —OCH₃ | —H | —OCF₃ | —C(H)— | —C(H)— |
| 230 | (IIa) | —H | —H | —OCH₃ | —H | —OCF₃ | —C(H)— | —N— |
| 231 | (IIa) | —H | —H | —OCH₃ | —H | —OCF₃ | —N— | —C(H)— |
| 232 | (IIa) | —H | —H | —OCH₃ | —H | —F | —C(H)— | —C(H)— |
| 233 | (IIa) | —H | —H | —OCH₃ | —H | —F | —C(H)— | —N— |
| 234 | (IIa) | —H | —H | —OCH₃ | —H | —F | —N— | —C(H)— |
| 235 | (IIa) | —H | —H | —OCH₃ | —CH₃ | —H | —C(H)— | —C(H)— |
| 236 | (IIa) | —H | —H | —OCH₃ | —CH₃ | —H | —C(H)— | —N— |
| 237 | (IIa) | —H | —H | —OCH₃ | —CH₃ | —H | —N— | —C(H)— |
| 238 | (IIa) | —H | —H | —OCH₃ | —CH₃ | —CH₃ | —C(H)— | —C(H)— |
| 239 | (IIa) | —H | —H | —OCH₃ | —CH₃ | —CH₃ | —C(H)— | —N— |
| 240 | (IIa) | —H | —H | —OCH₃ | —CH₃ | —CH₃ | —N— | —C(H)— |
| 241 | (IIa) | —H | —H | —OCH₃ | —CH₃ | —OCH₃ | —C(H)— | —C(H)— |
| 242 | (IIa) | —H | —H | —OCH₃ | —CH₃ | —OCH₃ | —C(H)— | —N— |
| 243 | (IIa) | —H | —H | —OCH₃ | —CH₃ | —OCH₃ | —N— | —C(H)— |
| 244 | (IIa) | —H | —H | —OCH₃ | —CH₃ | —OCF₃ | —C(H)— | —C(H)— |
| 245 | (IIa) | —H | —H | —OCH₃ | —CH₃ | —OCF₃ | —C(H)— | —N— |
| 246 | (IIa) | —H | —H | —OCH₃ | —CH₃ | —OCF₃ | —N— | —C(H)— |
| 247 | (IIa) | —H | —H | —OCH₃ | —CH₃ | —F | —C(H)— | —C(H)— |
| 248 | (IIa) | —H | —H | —OCH₃ | —CH₃ | —F | —C(H)— | —N— |
| 249 | (IIa) | —H | —H | —OCH₃ | —CH₃ | —F | —N— | —C(H)— |
| 250 | (IIa) | —H | —H | —OCH₃ | —OCH₃ | —H | —C(H)— | —C(H)— |
| 251 | (IIa) | —H | —H | —OCH₃ | —OCH₃ | —H | —C(H)— | —N— |
| 252 | (IIa) | —H | —H | —OCH₃ | —OCH₃ | —H | —N— | —C(H)— |
| 253 | (IIa) | —H | —H | —OCH₃ | —OCH₃ | —CH₃ | —C(H)— | —C(H)— |
| 254 | (IIa) | —H | —H | —OCH₃ | —OCH₃ | —CH₃ | —C(H)— | —N— |
| 255 | (IIa) | —H | —H | —OCH₃ | —OCH₃ | —CH₃ | —N— | —C(H)— |
| 256 | (IIa) | —H | —H | —OCH₃ | —OCH₃ | —OCH₃ | —C(H)— | —C(H)— |
| 257 | (IIa) | —H | —H | —OCH₃ | —OCH₃ | —OCH₃ | —C(H)— | —N— |
| 258 | (IIa) | —H | —H | —OCH₃ | —OCH₃ | —OCH₃ | —N— | —C(H)— |
| 259 | (IIa) | —H | —H | —OCH₃ | —OCH₃ | —OCF₃ | —C(H)— | —C(H)— |
| 260 | (IIa) | —H | —H | —OCH₃ | —OCH₃ | —OCF₃ | —C(H)— | —N— |
| 261 | (IIa) | —H | —H | —OCH₃ | —OCH₃ | —OCF₃ | —N— | —C(H)— |
| 262 | (IIa) | —H | —H | —OCH₃ | —OCH₃ | —F | —C(H)— | —C(H)— |
| 263 | (IIa) | —H | —H | —OCH₃ | —OCH₃ | —F | —C(H)— | —N— |
| 264 | (IIa) | —H | —H | —OCH₃ | —OCH₃ | —F | —N— | —C(H)— |
| 265 | (IIa) | —H | —H | —OCH₃ | —NO₂ | —H | —C(H)— | —C(H)— |
| 266 | (IIa) | —H | —H | —OCH₃ | —NO₂ | —H | —C(H)— | —N— |
| 267 | (IIa) | —H | —H | —OCH₃ | —NO₂ | —H | —N— | —C(H)— |
| 268 | (IIa) | —H | —H | —OCH₃ | —NO₂ | —CH₃ | —C(H)— | —C(H)— |
| 269 | (IIa) | —H | —H | —OCH₃ | —NO₂ | —CH₃ | —C(H)— | —N— |
| 270 | (IIa) | —H | —H | —OCH₃ | —NO₂ | —CH₃ | —N— | —C(H)— |
| 271 | (IIa) | —H | —H | —OCH₃ | —NO₂ | —OCH₃ | —C(H)— | —C(H)— |
| 272 | (IIa) | —H | —H | —OCH₃ | —NO₂ | —OCH₃ | —C(H)— | —N— |
| 273 | (IIa) | —H | —H | —OCH₃ | —NO₂ | —OCH₃ | —N— | —C(H)— |
| 274 | (IIa) | —H | —H | —OCH₃ | —NO₂ | —OCF₃ | —C(H)— | —C(H)— |
| 275 | (IIa) | —H | —H | —OCH₃ | —NO₂ | —OCF₃ | —C(H)— | —N— |

| Compound | | $R_6$ | $R_1$ | $R_1{}'$ | $R_1{}''$ | $R_1{}'''$ | Y | Z |
|---|---|---|---|---|---|---|---|---|
| 276 | (IIa) | —H | —H | —OCH$_3$ | —NO$_2$ | —OCF$_3$ | —N— | —C(H)— |
| 277 | (IIa) | —H | —H | —OCH$_3$ | —NO$_2$ | —F | —C(H)— | —C(H)— |
| 278 | (IIa) | —H | —H | —OCH$_3$ | —NO$_2$ | —F | —C(H)— | —N— |
| 279 | (IIa) | —H | —H | —OCH$_3$ | —NO$_2$ | —F | —N— | —C(H)— |
| 280 | (IIa) | —H | —NO$_2$ | —H | —H | —H | —C(H)— | —C(H)— |
| 281 | (IIa) | —H | —NO$_2$ | —H | —H | —H | —C(H)— | —N— |
| 282 | (IIa) | —H | —NO$_2$ | —H | —H | —H | —N— | —C(H)— |
| 283 | (IIa) | —H | —NO$_2$ | —H | —H | —CH$_3$ | —C(H)— | —C(H)— |
| 284 | (IIa) | —H | —NO$_2$ | —H | —H | —CH$_3$ | —C(H)— | —N— |
| 285 | (IIa) | —H | —NO$_2$ | —H | —H | —CH$_3$ | —N— | —C(H)— |
| 286 | (IIa) | —H | —NO$_2$ | —H | —H | —OCH$_3$ | —C(H)— | —C(H)— |
| 287 | (IIa) | —H | —NO$_2$ | —H | —H | —OCH$_3$ | —C(H)— | —N— |
| 288 | (IIa) | —H | —NO$_2$ | —H | —H | —OCH$_3$ | —N— | —C(H)— |
| 289 | (IIa) | —H | —NO$_2$ | —H | —H | —OCF$_3$ | —C(H)— | —C(H)— |
| 290 | (IIa) | —H | —NO$_2$ | —H | —H | —OCF$_3$ | —C(H)— | —N— |
| 291 | (IIa) | —H | —NO$_2$ | —H | —H | —OCF$_3$ | —N— | —C(H)— |
| 292 | (IIa) | —H | —NO$_2$ | —H | —H | —F | —C(H)— | —C(H)— |
| 293 | (IIa) | —H | —NO$_2$ | —H | —H | —F | —C(H)— | —N— |
| 294 | (IIa) | —H | —NO$_2$ | —H | —H | —F | —N— | —C(H)— |
| 295 | (IIa) | —H | —NO$_2$ | —H | —CH$_3$ | —H | —C(H)— | —C(H)— |
| 296 | (IIa) | —H | —NO$_2$ | —H | —CH$_3$ | —H | —C(H)— | —N— |
| 297 | (IIa) | —H | —NO$_2$ | —H | —CH$_3$ | —H | —N— | —C(H)— |
| 298 | (IIa) | —H | —NO$_2$ | —H | —CH$_3$ | —CH$_3$ | —C(H)— | —C(H)— |
| 299 | (IIa) | —H | —NO$_2$ | —H | —CH$_3$ | —CH$_3$ | —C(H)— | —N— |
| 300 | (IIa) | —H | —NO$_2$ | —H | —CH$_3$ | —CH$_3$ | —N— | —C(H)— |
| 301 | (IIa) | —H | —NO$_2$ | —H | —CH$_3$ | —OCH$_3$ | —C(H)— | —C(H)— |
| 302 | (IIa) | —H | —NO$_2$ | —H | —CH$_3$ | —OCH$_3$ | —C(H)— | —N— |
| 303 | (IIa) | —H | —NO$_2$ | —H | —CH$_3$ | —OCH$_3$ | —N— | —C(H)— |
| 304 | (IIa) | —H | —NO$_2$ | —H | —CH$_3$ | —OCF$_3$ | —C(H)— | —C(H)— |
| 305 | (IIa) | —H | —NO$_2$ | —H | —CH$_3$ | —OCF$_3$ | —C(H)— | —N— |
| 306 | (IIa) | —H | —NO$_2$ | —H | —CH$_3$ | —OCF$_3$ | —N— | —C(H)— |
| 307 | (IIa) | —H | —NO$_2$ | —H | —CH$_3$ | —F | —C(H)— | —C(H)— |
| 308 | (IIa) | —H | —NO$_2$ | —H | —CH$_3$ | —F | —C(H)— | —N— |
| 309 | (IIa) | —H | —NO$_2$ | —H | —CH$_3$ | —F | —N— | —C(H)— |
| 310 | (IIa) | —H | —NO$_2$ | —H | —OCH$_3$ | —H | —C(H)— | —C(H)— |
| 311 | (IIa) | —H | —NO$_2$ | —H | —OCH$_3$ | —H | —C(H)— | —N— |
| 312 | (IIa) | —H | —NO$_2$ | —H | —OCH$_3$ | —H | —N— | —C(H)— |
| 313 | (IIa) | —H | —NO$_2$ | —H | —OCH$_3$ | —CH$_3$ | —C(H)— | —C(H)— |
| 314 | (IIa) | —H | —NO$_2$ | —H | —OCH$_3$ | —CH$_3$ | —C(H)— | —N— |
| 315 | (IIa) | —H | —NO$_2$ | —H | —OCH$_3$ | —CH$_3$ | —N— | —C(H)— |
| 316 | (IIa) | —H | —NO$_2$ | —H | —OCH$_3$ | —OCH$_3$ | —C(H)— | —C(H)— |
| 317 | (IIa) | —H | —NO$_2$ | —H | —OCH$_3$ | —OCH$_3$ | —C(H)— | —N— |
| 318 | (IIa) | —H | —NO$_2$ | —H | —OCH$_3$ | —OCH$_3$ | —N— | —C(H)— |
| 319 | (IIa) | —H | —NO$_2$ | —H | —OCH$_3$ | —OCF$_3$ | —C(H)— | —C(H)— |
| 320 | (IIa) | —H | —NO$_2$ | —H | —OCH$_3$ | —OCF$_3$ | —C(H)— | —N— |
| 321 | (IIa) | —H | —NO$_2$ | —H | —OCH$_3$ | —OCF$_3$ | —N— | —C(H)— |
| 322 | (IIa) | —H | —NO$_2$ | —H | —OCH$_3$ | —F | —C(H)— | —C(H)— |
| 323 | (IIa) | —H | —NO$_2$ | —H | —OCH$_3$ | —F | —C(H)— | —N— |
| 324 | (IIa) | —H | —NO$_2$ | —H | —OCH$_3$ | —F | —N— | —C(H)— |
| 325 | (IIa) | —H | —NO$_2$ | —H | —NO$_2$ | —H | —C(H)— | —C(H)— |
| 326 | (IIa) | —H | —NO$_2$ | —H | —NO$_2$ | —H | —C(H)— | —N— |
| 327 | (IIa) | —H | —NO$_2$ | —H | —NO$_2$ | —H | —N— | —C(H)— |
| 328 | (IIa) | —H | —NO$_2$ | —H | —NO$_2$ | —CH$_3$ | —C(H)— | —C(H)— |
| 329 | (IIa) | —H | —NO$_2$ | —H | —NO$_2$ | —CH$_3$ | —C(H)— | —N— |
| 330 | (IIa) | —H | —NO$_2$ | —H | —NO$_2$ | —CH$_3$ | —N— | —C(H)— |
| 331 | (IIa) | —H | —NO$_2$ | —H | —NO$_2$ | —OCH$_3$ | —C(H)— | —C(H)— |
| 332 | (IIa) | —H | —NO$_2$ | —H | —NO$_2$ | —OCH$_3$ | —C(H)— | —N— |
| 333 | (IIa) | —H | —NO$_2$ | —H | —NO$_2$ | —OCH$_3$ | —N— | —C(H)— |
| 334 | (IIa) | —H | —NO$_2$ | —H | —NO$_2$ | —OCF$_3$ | —C(H)— | —C(H)— |
| 335 | (IIa) | —H | —NO$_2$ | —H | —NO$_2$ | —OCF$_3$ | —C(H)— | —N— |
| 336 | (IIa) | —H | —NO$_2$ | —H | —NO$_2$ | —OCF$_3$ | —N— | —C(H)— |
| 337 | (IIa) | —H | —NO$_2$ | —H | —NO$_2$ | —F | —C(H)— | —C(H)— |
| 338 | (IIa) | —H | —NO$_2$ | —H | —NO$_2$ | —F | —C(H)— | —N— |
| 339 | (IIa) | —H | —NO$_2$ | —H | —NO$_2$ | —F | —N— | —C(H)— |
| 340 | (IIa) | —H | —NO$_2$ | —CH$_3$ | —H | —H | —C(H)— | —C(H)— |
| 341 | (IIa) | —H | —NO$_2$ | —CH$_3$ | —H | —H | —C(H)— | —N— |
| 342 | (IIa) | —H | —NO$_2$ | —CH$_3$ | —H | —H | —N— | —C(H)— |
| 343 | (IIa) | —H | —NO$_2$ | —CH$_3$ | —H | —CH$_3$ | —C(H)— | —C(H)— |
| 344 | (IIa) | —H | —NO$_2$ | —CH$_3$ | —H | —CH$_3$ | —C(H)— | —N— |
| 345 | (IIa) | —H | —NO$_2$ | —CH$_3$ | —H | —CH$_3$ | —N— | —C(H)— |
| 346 | (IIa) | —H | —NO$_2$ | —CH$_3$ | —H | —OCH$_3$ | —C(H)— | —C(H)— |
| 347 | (IIa) | —H | —NO$_2$ | —CH$_3$ | —H | —OCH$_3$ | —C(H)— | —N— |
| 348 | (IIa) | —H | —NO$_2$ | —CH$_3$ | —H | —OCH$_3$ | —N— | —C(H)— |
| 349 | (IIa) | —H | —NO$_2$ | —CH$_3$ | —H | —OCF$_3$ | —C(H)— | —C(H)— |
| 350 | (IIa) | —H | —NO$_2$ | —CH$_3$ | —H | —OCF$_3$ | —C(H)— | —N— |
| 351 | (IIa) | —H | —NO$_2$ | —CH$_3$ | —H | —OCF$_3$ | —N— | —C(H)— |
| 352 | (IIa) | —H | —NO$_2$ | —CH$_3$ | —H | —F | —C(H)— | —C(H)— |

-continued

| Compound | | R$_6$ | R$_1$ | R$_1$' | R$_1$'' | R$_1$''' | Y | Z |
|---|---|---|---|---|---|---|---|---|
| 353 | (IIa) | —H | —NO$_2$ | —CH$_3$ | —H | —F | —C(H)— | —N— |
| 354 | (IIa) | —H | —NO$_2$ | —CH$_3$ | —H | —F | —N— | —C(H)— |
| 355 | (IIa) | —H | —NO$_2$ | —CH$_3$ | —CH$_3$ | —H | —C(H)— | —C(H)— |
| 356 | (IIa) | —H | —NO$_2$ | —CH$_3$ | —CH$_3$ | —H | —C(H)— | —N— |
| 357 | (IIa) | —H | —NO$_2$ | —CH$_3$ | —CH$_3$ | —H | —N— | —C(H)— |
| 358 | (IIa) | —H | —NO$_2$ | —CH$_3$ | —CH$_3$ | —CH$_3$ | —C(H)— | —C(H)— |
| 359 | (IIa) | —H | —NO$_2$ | —CH$_3$ | —CH$_3$ | —CH$_3$ | —C(H)— | —N— |
| 360 | (IIa) | —H | —NO$_2$ | —CH$_3$ | —CH$_3$ | —CH$_3$ | —N— | —C(H)— |
| 361 | (IIa) | —H | —NO$_2$ | —CH$_3$ | —CH$_3$ | —OCH$_3$ | —C(H)— | —C(H)— |
| 362 | (IIa) | —H | —NO$_2$ | —CH$_3$ | —CH$_3$ | —OCH$_3$ | —C(H)— | —N— |
| 363 | (IIa) | —H | —NO$_2$ | —CH$_3$ | —CH$_3$ | —OCH$_3$ | —N— | —C(H)— |
| 364 | (IIa) | —H | —NO$_2$ | —CH$_3$ | —CH$_3$ | —OCF$_3$ | —C(H)— | —C(H)— |
| 365 | (IIa) | —H | —NO$_2$ | —CH$_3$ | —CH$_3$ | —OCF$_3$ | —C(H)— | —N— |
| 366 | (IIa) | —H | —NO$_2$ | —CH$_3$ | —CH$_3$ | —OCF$_3$ | —N— | —C(H)— |
| 367 | (IIa) | —H | —NO$_2$ | —CH$_3$ | —CH$_3$ | —F | —C(H)— | —C(H)— |
| 368 | (IIa) | —H | —NO$_2$ | —CH$_3$ | —CH$_3$ | —F | —C(H)— | —N— |
| 369 | (IIa) | —H | —NO$_2$ | —CH$_3$ | —CH$_3$ | —F | —N— | —C(H)— |
| 370 | (IIa) | —H | —NO$_2$ | —CH$_3$ | —OCH$_3$ | —H | —C(H)— | —C(H)— |
| 371 | (IIa) | —H | —NO$_2$ | —CH$_3$ | —OCH$_3$ | —H | —C(H)— | —N— |
| 372 | (IIa) | —H | —NO$_2$ | —CH$_3$ | —OCH$_3$ | —H | —N— | —C(H)— |
| 373 | (IIa) | —H | —NO$_2$ | —CH$_3$ | —OCH$_3$ | —CH$_3$ | —C(H)— | —C(H)— |
| 374 | (IIa) | —H | —NO$_2$ | —CH$_3$ | —OCH$_3$ | —CH$_3$ | —C(H)— | —N— |
| 375 | (IIa) | —H | —NO$_2$ | —CH$_3$ | —OCH$_3$ | —CH$_3$ | —N— | —C(H)— |
| 376 | (IIa) | —H | —NO$_2$ | —CH$_3$ | —OCH$_3$ | —OCH$_3$ | —C(H)— | —C(H)— |
| 377 | (IIa) | —H | —NO$_2$ | —CH$_3$ | —OCH$_3$ | —OCH$_3$ | —C(H)— | —N— |
| 378 | (IIa) | —H | —NO$_2$ | —CH$_3$ | —OCH$_3$ | —OCH$_3$ | —N— | —C(H)— |
| 379 | (IIa) | —H | —NO$_2$ | —CH$_3$ | —OCH$_3$ | —OCF$_3$ | —C(H)— | —C(H)— |
| 380 | (IIa) | —H | —NO$_2$ | —CH$_3$ | —OCH$_3$ | —OCF$_3$ | —C(H)— | —N— |
| 381 | (IIa) | —H | —NO$_2$ | —CH$_3$ | —OCH$_3$ | —OCF$_3$ | —N— | —C(H)— |
| 382 | (IIa) | —H | —NO$_2$ | —CH$_3$ | —OCH$_3$ | —F | —C(H)— | —C(H)— |
| 383 | (IIa) | —H | —NO$_2$ | —CH$_3$ | —OCH$_3$ | —F | —C(H)— | —N— |
| 384 | (IIa) | —H | —NO$_2$ | —CH$_3$ | —OCH$_3$ | —F | —N— | —C(H)— |
| 385 | (IIa) | —H | —NO$_2$ | —CH$_3$ | —NO$_2$ | —H | —C(H)— | —C(H)— |
| 386 | (IIa) | —H | —NO$_2$ | —CH$_3$ | —NO$_2$ | —H | —C(H)— | —N— |
| 387 | (IIa) | —H | —NO$_2$ | —CH$_3$ | —NO$_2$ | —H | —N— | —C(H)— |
| 388 | (IIa) | —H | —NO$_2$ | —CH$_3$ | —NO$_2$ | —CH$_3$ | —C(H)— | —C(H)— |
| 389 | (IIa) | —H | —NO$_2$ | —CH$_3$ | —NO$_2$ | —CH$_3$ | —C(H)— | —N— |
| 390 | (IIa) | —H | —NO$_2$ | —CH$_3$ | —NO$_2$ | —CH$_3$ | —N— | —C(H)— |
| 391 | (IIa) | —H | —NO$_2$ | —CH$_3$ | —NO$_2$ | —OCH$_3$ | —C(H)— | —C(H)— |
| 392 | (IIa) | —H | —NO$_2$ | —CH$_3$ | —NO$_2$ | —OCH$_3$ | —C(H)— | —N— |
| 393 | (IIa) | —H | —NO$_2$ | —CH$_3$ | —NO$_2$ | —OCH$_3$ | —N— | —C(H)— |
| 394 | (IIa) | —H | —NO$_2$ | —CH$_3$ | —NO$_2$ | —OCF$_3$ | —C(H)— | —C(H)— |
| 395 | (IIa) | —H | —NO$_2$ | —CH$_3$ | —NO$_2$ | —OCF$_3$ | —C(H)— | —N— |
| 396 | (IIa) | —H | —NO$_2$ | —CH$_3$ | —NO$_2$ | —OCF$_3$ | —N— | —C(H)— |
| 397 | (IIa) | —H | —NO$_2$ | —CH$_3$ | —NO$_2$ | —F | —C(H)— | —C(H)— |
| 398 | (IIa) | —H | —NO$_2$ | —CH$_3$ | —NO$_2$ | —F | —C(H)— | —N— |
| 399 | (IIa) | —H | —NO$_2$ | —CH$_3$ | —NO$_2$ | —F | —N— | —C(H)— |
| 400 | (IIa) | —H | —NO$_2$ | —OCH$_3$ | —H | —H | —C(H)— | —C(H)— |
| 401 | (IIa) | —H | —NO$_2$ | —OCH$_3$ | —H | —H | —C(H)— | —N— |
| 402 | (IIa) | —H | —NO$_2$ | —OCH$_3$ | —H | —H | —N— | —C(H)— |
| 403 | (IIa) | —H | —NO$_2$ | —OCH$_3$ | —H | —CH$_3$ | —C(H)— | —C(H)— |
| 404 | (IIa) | —H | —NO$_2$ | —OCH$_3$ | —H | —CH$_3$ | —C(H)— | —N— |
| 405 | (IIa) | —H | —NO$_2$ | —OCH$_3$ | —H | —CH$_3$ | —N— | —C(H)— |
| 406 | (IIa) | —H | —NO$_2$ | —OCH$_3$ | —H | —OCH$_3$ | —C(H)— | —C(H)— |
| 407 | (IIa) | —H | —NO$_2$ | —OCH$_3$ | —H | —OCH$_3$ | —C(H)— | —N— |
| 408 | (IIa) | —H | —NO$_2$ | —OCH$_3$ | —H | —OCH$_3$ | —N— | —C(H)— |
| 409 | (IIa) | —H | —NO$_2$ | —OCH$_3$ | —H | —OCF$_3$ | —C(H)— | —C(H)— |
| 410 | (IIa) | —H | —NO$_2$ | —OCH$_3$ | —H | —OCF$_3$ | —C(H)— | —N— |
| 411 | (IIa) | —H | —NO$_2$ | —OCH$_3$ | —H | —OCF$_3$ | —N— | —C(H)— |
| 412 | (IIa) | —H | —NO$_2$ | —OCH$_3$ | —H | —F | —C(H)— | —C(H)— |
| 413 | (IIa) | —H | —NO$_2$ | —OCH$_3$ | —H | —F | —C(H)— | —N— |
| 414 | (IIa) | —H | —NO$_2$ | —OCH$_3$ | —H | —F | —N— | —C(H)— |
| 415 | (IIa) | —H | —NO$_2$ | —OCH$_3$ | —CH$_3$ | —H | —C(H)— | —C(H)— |
| 416 | (IIa) | —H | —NO$_2$ | —OCH$_3$ | —CH$_3$ | —H | —C(H)— | —N— |
| 417 | (IIa) | —H | —NO$_2$ | —OCH$_3$ | —CH$_3$ | —H | —N— | —C(H)— |
| 418 | (IIa) | —H | —NO$_2$ | —OCH$_3$ | —CH$_3$ | —CH$_3$ | —C(H)— | —C(H)— |
| 419 | (IIa) | —H | —NO$_2$ | —OCH$_3$ | —CH$_3$ | —CH$_3$ | —C(H)— | —N— |
| 420 | (IIa) | —H | —NO$_2$ | —OCH$_3$ | —CH$_3$ | —CH$_3$ | —N— | —C(H)— |
| 421 | (IIa) | —H | —NO$_2$ | —OCH$_3$ | —CH$_3$ | —OCH$_3$ | —C(H)— | —C(H)— |
| 422 | (IIa) | —H | —NO$_2$ | —OCH$_3$ | —CH$_3$ | —OCH$_3$ | —C(H)— | —N— |
| 423 | (IIa) | —H | —NO$_2$ | —OCH$_3$ | —CH$_3$ | —OCH$_3$ | —N— | —C(H)— |
| 424 | (IIa) | —H | —NO$_2$ | —OCH$_3$ | —CH$_3$ | —OCF$_3$ | —C(H)— | —C(H)— |
| 425 | (IIa) | —H | —NO$_2$ | —OCH$_3$ | —CH$_3$ | —OCF$_3$ | —C(H)— | —N— |
| 426 | (IIa) | —H | —NO$_2$ | —OCH$_3$ | —CH$_3$ | —OCF$_3$ | —N— | —C(H)— |
| 427 | (IIa) | —H | —NO$_2$ | —OCH$_3$ | —CH$_3$ | —F | —C(H)— | —C(H)— |
| 428 | (IIa) | —H | —NO$_2$ | —OCH$_3$ | —CH$_3$ | —F | —C(H)— | —N— |
| 429 | (IIa) | —H | —NO$_2$ | —OCH$_3$ | —CH$_3$ | —F | —N— | —C(H)— |

-continued

| Compound | | R$_6$ | R$_1$ | R$_1$' | R$_1$" | R$_1$'" | Y | Z |
|---|---|---|---|---|---|---|---|---|
| 430 | (IIa) | —H | —NO$_2$ | —OCH$_3$ | —OCH$_3$ | —H | —C(H)— | —C(H)— |
| 431 | (IIa) | —H | —NO$_2$ | —OCH$_3$ | —OCH$_3$ | —H | —C(H)— | —N— |
| 432 | (IIa) | —H | —NO$_2$ | —OCH$_3$ | —OCH$_3$ | —H | —N— | —C(H)— |
| 433 | (IIa) | —H | —NO$_2$ | —OCH$_3$ | —OCH$_3$ | —CH$_3$ | —C(H)— | —C(H)— |
| 434 | (IIa) | —H | —NO$_2$ | —OCH$_3$ | —OCH$_3$ | —CH$_3$ | —C(H)— | —N— |
| 435 | (IIa) | —H | —NO$_2$ | —OCH$_3$ | —OCH$_3$ | —CH$_3$ | —N— | —C(H)— |
| 436 | (IIa) | —H | —NO$_2$ | —OCH$_3$ | —OCH$_3$ | —OCH$_3$ | —C(H)— | —C(H)— |
| 437 | (IIa) | —H | —NO$_2$ | —OCH$_3$ | —OCH$_3$ | —OCH$_3$ | —C(H)— | —N— |
| 438 | (IIa) | —H | —NO$_2$ | —OCH$_3$ | —OCH$_3$ | —OCH$_3$ | —N— | —C(H)— |
| 439 | (IIa) | —H | —NO$_2$ | —OCH$_3$ | —OCH$_3$ | —OCF$_3$ | —C(H)— | —C(H)— |
| 440 | (IIa) | —H | —NO$_2$ | —OCH$_3$ | —OCH$_3$ | —OCF$_3$ | —C(H)— | —N— |
| 441 | (IIa) | —H | —NO$_2$ | —OCH$_3$ | —OCH$_3$ | —OCF$_3$ | —N— | —C(H)— |
| 442 | (IIa) | —H | —NO$_2$ | —OCH$_3$ | —OCH$_3$ | —F | —C(H)— | —C(H)— |
| 443 | (IIa) | —H | —NO$_2$ | —OCH$_3$ | —OCH$_3$ | —F | —C(H)— | —N— |
| 444 | (IIa) | —H | —NO$_2$ | —OCH$_3$ | —OCH$_3$ | —F | —N— | —C(H)— |
| 445 | (IIa) | —H | —NO$_2$ | —OCH$_3$ | —NO$_2$ | —H | —C(H)— | —C(H)— |
| 446 | (IIa) | —H | —NO$_2$ | —OCH$_3$ | —NO$_2$ | —H | —C(H)— | —N— |
| 447 | (IIa) | —H | —NO$_2$ | —OCH$_3$ | —NO$_2$ | —H | —N— | —C(H)— |
| 448 | (IIa) | —H | —NO$_2$ | —OCH$_3$ | —NO$_2$ | —CH$_3$ | —C(H)— | —C(H)— |
| 449 | (IIa) | —H | —NO$_2$ | —OCH$_3$ | —NO$_2$ | —CH$_3$ | —C(H)— | —N— |
| 450 | (IIa) | —H | —NO$_2$ | —OCH$_3$ | —NO$_2$ | —CH$_3$ | —N— | —C(H)— |
| 451 | (IIa) | —H | —NO$_2$ | —OCH$_3$ | —NO$_2$ | —OCH$_3$ | —C(H)— | —C(H)— |
| 452 | (IIa) | —H | —NO$_2$ | —OCH$_3$ | —NO$_2$ | —OCH$_3$ | —C(H)— | —N— |
| 453 | (IIa) | —H | —NO$_2$ | —OCH$_3$ | —NO$_2$ | —OCH$_3$ | —N— | —C(H)— |
| 454 | (IIa) | —H | —NO$_2$ | —OCH$_3$ | —NO$_2$ | —OCF$_3$ | —C(H)— | —C(H)— |
| 455 | (IIa) | —H | —NO$_2$ | —OCH$_3$ | —NO$_2$ | —OCF$_3$ | —C(H)— | —N— |
| 456 | (IIa) | —H | —NO$_2$ | —OCH$_3$ | —NO$_2$ | —OCF$_3$ | —N— | —C(H)— |
| 457 | (IIa) | —H | —NO$_2$ | —OCH$_3$ | —NO$_2$ | —F | —C(H)— | —C(H)— |
| 458 | (IIa) | —H | —NO$_2$ | —OCH$_3$ | —NO$_2$ | —F | —C(H)— | —N— |
| 459 | (IIa) | —H | —NO$_2$ | —OCH$_3$ | —NO$_2$ | —F | —N— | —C(H)— |
| 460 | (IIa) | —H | —OCH$_3$ | —H | —H | —H | —C(H)— | —C(H)— |
| 461 | (IIa) | —H | —OCH$_3$ | —H | —H | —H | —C(H)— | —N— |
| 462 | (IIa) | —H | —OCH$_3$ | —H | —H | —H | —N— | —C(H)— |
| 463 | (IIa) | —H | —OCH$_3$ | —H | —H | —CH$_3$ | —C(H)— | —C(H)— |
| 464 | (IIa) | —H | —OCH$_3$ | —H | —H | —CH$_3$ | —C(H)— | —N— |
| 465 | (IIa) | —H | —OCH$_3$ | —H | —H | —CH$_3$ | —N— | —C(H)— |
| 466 | (IIa) | —H | —OCH$_3$ | —H | —H | —OCH$_3$ | —C(H)— | —C(H)— |
| 467 | (IIa) | —H | —OCH$_3$ | —H | —H | —OCH$_3$ | —C(H)— | —N— |
| 468 | (IIa) | —H | —OCH$_3$ | —H | —H | —OCH$_3$ | —N— | —C(H)— |
| 469 | (IIa) | —H | —OCH$_3$ | —H | —H | —OCF$_3$ | —C(H)— | —C(H)— |
| 470 | (IIa) | —H | —OCH$_3$ | —H | —H | —OCF$_3$ | —C(H)— | —N— |
| 471 | (IIa) | —H | —OCH$_3$ | —H | —H | —OCF$_3$ | —N— | —C(H)— |
| 472 | (IIa) | —H | —OCH$_3$ | —H | —H | —F | —C(H)— | —C(H)— |
| 473 | (IIa) | —H | —OCH$_3$ | —H | —H | —F | —C(H)— | —N— |
| 474 | (IIa) | —H | —OCH$_3$ | —H | —H | —F | —N— | —C(H)— |
| 475 | (IIa) | —H | —OCH$_3$ | —H | —CH$_3$ | —H | —C(H)— | —C(H)— |
| 476 | (IIa) | —H | —OCH$_3$ | —H | —CH$_3$ | —H | —C(H)— | —N— |
| 477 | (IIa) | —H | —OCH$_3$ | —H | —CH$_3$ | —H | —N— | —C(H)— |
| 478 | (IIa) | —H | —OCH$_3$ | —H | —CH$_3$ | —CH$_3$ | —C(H)— | —C(H)— |
| 479 | (IIa) | —H | —OCH$_3$ | —H | —CH$_3$ | —CH$_3$ | —C(H)— | —N— |
| 480 | (IIa) | —H | —OCH$_3$ | —H | —CH$_3$ | —CH$_3$ | —N— | —C(H)— |
| 481 | (IIa) | —H | —OCH$_3$ | —H | —CH$_3$ | —OCH$_3$ | —C(H)— | —C(H)— |
| 482 | (IIa) | —H | —OCH$_3$ | —H | —CH$_3$ | —OCH$_3$ | —C(H)— | —N— |
| 483 | (IIa) | —H | —OCH$_3$ | —H | —CH$_3$ | —OCH$_3$ | —N— | —C(H)— |
| 484 | (IIa) | —H | —OCH$_3$ | —H | —CH$_3$ | —OCF$_3$ | —C(H)— | —C(H)— |
| 485 | (IIa) | —H | —OCH$_3$ | —H | —CH$_3$ | —OCF$_3$ | —C(H)— | —N— |
| 486 | (IIa) | —H | —OCH$_3$ | —H | —CH$_3$ | —OCF$_3$ | —N— | —C(H)— |
| 487 | (IIa) | —H | —OCH$_3$ | —H | —CH$_3$ | —F | —C(H)— | —C(H)— |
| 488 | (IIa) | —H | —OCH$_3$ | —H | —CH$_3$ | —F | —C(H)— | —N— |
| 489 | (IIa) | —H | —OCH$_3$ | —H | —CH$_3$ | —F | —N— | —C(H)— |
| 490 | (IIa) | —H | —OCH$_3$ | —H | —OCH$_3$ | —H | —C(H)— | —C(H)— |
| 491 | (IIa) | —H | —OCH$_3$ | —H | —OCH$_3$ | —H | —C(H)— | —N— |
| 492 | (IIa) | —H | —OCH$_3$ | —H | —OCH$_3$ | —H | —N— | —C(H)— |
| 493 | (IIa) | —H | —OCH$_3$ | —H | —OCH$_3$ | —CH$_3$ | —C(H)— | —C(H)— |
| 494 | (IIa) | —H | —OCH$_3$ | —H | —OCH$_3$ | —CH$_3$ | —C(H)— | —N— |
| 495 | (IIa) | —H | —OCH$_3$ | —H | —OCH$_3$ | —CH$_3$ | —N— | —C(H)— |
| 496 | (IIa) | —H | —OCH$_3$ | —H | —OCH$_3$ | —OCH$_3$ | —C(H)— | —C(H)— |
| 497 | (IIa) | —H | —OCH$_3$ | —H | —OCH$_3$ | —OCH$_3$ | —C(H)— | —N— |
| 498 | (IIa) | —H | —OCH$_3$ | —H | —OCH$_3$ | —OCH$_3$ | —N— | —C(H)— |
| 499 | (IIa) | —H | —OCH$_3$ | —H | —OCH$_3$ | —OCF$_3$ | —C(H)— | —C(H)— |
| 500 | (IIa) | —H | —OCH$_3$ | —H | —OCH$_3$ | —OCF$_3$ | —C(H)— | —N— |
| 501 | (IIa) | —H | —OCH$_3$ | —H | —OCH$_3$ | —OCF$_3$ | —N— | —C(H)— |
| 502 | (IIa) | —H | —OCH$_3$ | —H | —OCH$_3$ | —F | —C(H)— | —C(H)— |
| 503 | (IIa) | —H | —OCH$_3$ | —H | —OCH$_3$ | —F | —C(H)— | —N— |
| 504 | (IIa) | —H | —OCH$_3$ | —H | —OCH$_3$ | —F | —N— | —C(H)— |
| 505 | (IIa) | —H | —OCH$_3$ | —H | —NO$_2$ | —H | —C(H)— | —C(H)— |
| 506 | (IIa) | —H | —OCH$_3$ | —H | —NO$_2$ | —H | —C(H)— | —N— |

-continued

| Compound | | $R_6$ | $R_1$ | $R_1'$ | $R_1''$ | $R_1'''$ | Y | Z |
|---|---|---|---|---|---|---|---|---|
| 507 | (IIa) | —H | —OCH$_3$ | —H | —NO$_2$ | —H | —N— | —C(H)— |
| 508 | (IIa) | —H | —OCH$_3$ | —H | —NO$_2$ | —CH$_3$ | —C(H)— | —C(H)— |
| 509 | (IIa) | —H | —OCH$_3$ | —H | —NO$_2$ | —CH$_3$ | —C(H)— | —N— |
| 510 | (IIa) | —H | —OCH$_3$ | —H | —NO$_2$ | —CH$_3$ | —N— | —C(H)— |
| 511 | (IIa) | —H | —OCH$_3$ | —H | —NO$_2$ | —OCH$_3$ | —C(H)— | —C(H)— |
| 512 | (IIa) | —H | —OCH$_3$ | —H | —NO$_2$ | —OCH$_3$ | —C(H)— | —N— |
| 513 | (IIa) | —H | —OCH$_3$ | —H | —NO$_2$ | —OCH$_3$ | —N— | —C(H)— |
| 514 | (IIa) | —H | —OCH$_3$ | —H | —NO$_2$ | —OCF$_3$ | —C(H)— | —C(H)— |
| 515 | (IIa) | —H | —OCH$_3$ | —H | —NO$_2$ | —OCF$_3$ | —C(H)— | —N— |
| 516 | (IIa) | —H | —OCH$_3$ | —H | —NO$_2$ | —OCF$_3$ | —N— | —C(H)— |
| 517 | (IIa) | —H | —OCH$_3$ | —H | —NO$_2$ | —F | —C(H)— | —C(H)— |
| 518 | (IIa) | —H | —OCH$_3$ | —H | —NO$_2$ | —F | —C(H)— | —N— |
| 519 | (IIa) | —H | —OCH$_3$ | —H | —NO$_2$ | —F | —N— | —C(H)— |
| 520 | (IIa) | —H | —OCH$_3$ | —CH$_3$ | —H | —H | —C(H)— | —C(H)— |
| 521 | (IIa) | —H | —OCH$_3$ | —CH$_3$ | —H | —H | —C(H)— | —N— |
| 522 | (IIa) | —H | —OCH$_3$ | —CH$_3$ | —H | —H | —N— | —C(H)— |
| 523 | (IIa) | —H | —OCH$_3$ | —CH$_3$ | —H | —CH$_3$ | —C(H)— | —C(H)— |
| 524 | (IIa) | —H | —OCH$_3$ | —CH$_3$ | —H | —CH$_3$ | —C(H)— | —N— |
| 525 | (IIa) | —H | —OCH$_3$ | —CH$_3$ | —H | —CH$_3$ | —N— | —C(H)— |
| 526 | (IIa) | —H | —OCH$_3$ | —CH$_3$ | —H | —OCH$_3$ | —C(H)— | —C(H)— |
| 527 | (IIa) | —H | —OCH$_3$ | —CH$_3$ | —H | —OCH$_3$ | —C(H)— | —N— |
| 528 | (IIa) | —H | —OCH$_3$ | —CH$_3$ | —H | —OCH$_3$ | —N— | —C(H)— |
| 529 | (IIa) | —H | —OCH$_3$ | —CH$_3$ | —H | —OCF$_3$ | —C(H)— | —C(H)— |
| 530 | (IIa) | —H | —OCH$_3$ | —CH$_3$ | —H | —OCF$_3$ | —C(H)— | —N— |
| 531 | (IIa) | —H | —OCH$_3$ | —CH$_3$ | —H | —OCF$_3$ | —N— | —C(H)— |
| 532 | (IIa) | —H | —OCH$_3$ | —CH$_3$ | —H | —F | —C(H)— | —C(H)— |
| 533 | (IIa) | —H | —OCH$_3$ | —CH$_3$ | —H | —F | —C(H)— | —N— |
| 534 | (IIa) | —H | —OCH$_3$ | —CH$_3$ | —H | —F | —N— | —C(H)— |
| 535 | (IIa) | —H | —OCH$_3$ | —CH$_3$ | —CH$_3$ | —H | —C(H)— | —C(H)— |
| 536 | (IIa) | —H | —OCH$_3$ | —CH$_3$ | —CH$_3$ | —H | —C(H)— | —N— |
| 537 | (IIa) | —H | —OCH$_3$ | —CH$_3$ | —CH$_3$ | —H | —N— | —C(H)— |
| 538 | (IIa) | —H | —OCH$_3$ | —CH$_3$ | —CH$_3$ | —CH$_3$ | —C(H)— | —C(H)— |
| 539 | (IIa) | —H | —OCH$_3$ | —CH$_3$ | —CH$_3$ | —CH$_3$ | —C(H)— | —N— |
| 540 | (IIa) | —H | —OCH$_3$ | —CH$_3$ | —CH$_3$ | —CH$_3$ | —N— | —C(H)— |
| 541 | (IIa) | —H | —OCH$_3$ | —CH$_3$ | —CH$_3$ | —OCH$_3$ | —C(H)— | —C(H)— |
| 542 | (IIa) | —H | —OCH$_3$ | —CH$_3$ | —CH$_3$ | —OCH$_3$ | —C(H)— | —N— |
| 543 | (IIa) | —H | —OCH$_3$ | —CH$_3$ | —CH$_3$ | —OCH$_3$ | —N— | —C(H)— |
| 544 | (IIa) | —H | —OCH$_3$ | —CH$_3$ | —CH$_3$ | —OCF$_3$ | —C(H)— | —C(H)— |
| 545 | (IIa) | —H | —OCH$_3$ | —CH$_3$ | —CH$_3$ | —OCF$_3$ | —C(H)— | —N— |
| 546 | (IIa) | —H | —OCH$_3$ | —CH$_3$ | —CH$_3$ | —OCF$_3$ | —N— | —C(H)— |
| 547 | (IIa) | —H | —OCH$_3$ | —CH$_3$ | —CH$_3$ | —F | —C(H)— | —C(H)— |
| 548 | (IIa) | —H | —OCH$_3$ | —CH$_3$ | —CH$_3$ | —F | —C(H)— | —N— |
| 549 | (IIa) | —H | —OCH$_3$ | —CH$_3$ | —CH$_3$ | —F | —N— | —C(H)— |
| 550 | (IIa) | —H | —OCH$_3$ | —CH$_3$ | —OCH$_3$ | —H | —C(H)— | —C(H)— |
| 551 | (IIa) | —H | —OCH$_3$ | —CH$_3$ | —OCH$_3$ | —H | —C(H)— | —N— |
| 552 | (IIa) | —H | —OCH$_3$ | —CH$_3$ | —OCH$_3$ | —H | —N— | —C(H)— |
| 553 | (IIa) | —H | —OCH$_3$ | —CH$_3$ | —OCH$_3$ | —CH$_3$ | —C(H)— | —C(H)— |
| 554 | (IIa) | —H | —OCH$_3$ | —CH$_3$ | —OCH$_3$ | —CH$_3$ | —C(H)— | —N— |
| 555 | (IIa) | —H | —OCH$_3$ | —CH$_3$ | —OCH$_3$ | —CH$_3$ | —N— | —C(H)— |
| 556 | (IIa) | —H | —OCH$_3$ | —CH$_3$ | —OCH$_3$ | —OCH$_3$ | —C(H)— | —C(H)— |
| 557 | (IIa) | —H | —OCH$_3$ | —CH$_3$ | —OCH$_3$ | —OCH$_3$ | —C(H)— | —N— |
| 558 | (IIa) | —H | —OCH$_3$ | —CH$_3$ | —OCH$_3$ | —OCH$_3$ | —N— | —C(H)— |
| 559 | (IIa) | —H | —OCH$_3$ | —CH$_3$ | —OCH$_3$ | —OCF$_3$ | —C(H)— | —C(H)— |
| 560 | (IIa) | —H | —OCH$_3$ | —CH$_3$ | —OCH$_3$ | —OCF$_3$ | —C(H)— | —N— |
| 561 | (IIa) | —H | —OCH$_3$ | —CH$_3$ | —OCH$_3$ | —OCF$_3$ | —N— | —C(H)— |
| 562 | (IIa) | —H | —OCH$_3$ | —CH$_3$ | —OCH$_3$ | —F | —C(H)— | —C(H)— |
| 563 | (IIa) | —H | —OCH$_3$ | —CH$_3$ | —OCH$_3$ | —F | —C(H)— | —N— |
| 564 | (IIa) | —H | —OCH$_3$ | —CH$_3$ | —OCH$_3$ | —F | —N— | —C(H)— |
| 565 | (IIa) | —H | —OCH$_3$ | —CH$_3$ | —NO$_2$ | —H | —C(H)— | —C(H)— |
| 566 | (IIa) | —H | —OCH$_3$ | —CH$_3$ | —NO$_2$ | —H | —C(H)— | —N— |
| 567 | (IIa) | —H | —OCH$_3$ | —CH$_3$ | —NO$_2$ | —H | —N— | —C(H)— |
| 568 | (IIa) | —H | —OCH$_3$ | —CH$_3$ | —NO$_2$ | —CH$_3$ | —C(H)— | —C(H)— |
| 569 | (IIa) | —H | —OCH$_3$ | —CH$_3$ | —NO$_2$ | —CH$_3$ | —C(H)— | —N— |
| 570 | (IIa) | —H | —OCH$_3$ | —CH$_3$ | —NO$_2$ | —CH$_3$ | —N— | —C(H)— |
| 571 | (IIa) | —H | —OCH$_3$ | —CH$_3$ | —NO$_2$ | —OCH$_3$ | —C(H)— | —C(H)— |
| 572 | (IIa) | —H | —OCH$_3$ | —CH$_3$ | —NO$_2$ | —OCH$_3$ | —C(H)— | —N— |
| 573 | (IIa) | —H | —OCH$_3$ | —CH$_3$ | —NO$_2$ | —OCH$_3$ | —N— | —C(H)— |
| 574 | (IIa) | —H | —OCH$_3$ | —CH$_3$ | —NO$_2$ | —OCF$_3$ | —C(H)— | —C(H)— |
| 575 | (IIa) | —H | —OCH$_3$ | —CH$_3$ | —NO$_2$ | —OCF$_3$ | —C(H)— | —N— |
| 576 | (IIa) | —H | —OCH$_3$ | —CH$_3$ | —NO$_2$ | —OCF$_3$ | —N— | —C(H)— |
| 577 | (IIa) | —H | —OCH$_3$ | —CH$_3$ | —NO$_2$ | —F | —C(H)— | —C(H)— |
| 578 | (IIa) | —H | —OCH$_3$ | —CH$_3$ | —NO$_2$ | —F | —C(H)— | —N— |
| 579 | (IIa) | —H | —OCH$_3$ | —CH$_3$ | —NO$_2$ | —F | —N— | —C(H)— |
| 580 | (IIa) | —H | —OCH$_3$ | —OCH$_3$ | —H | —H | —C(H)— | —C(H)— |
| 581 | (IIa) | —H | —OCH$_3$ | —OCH$_3$ | —H | —H | —C(H)— | —N— |
| 582 | (IIa) | —H | —OCH$_3$ | —OCH$_3$ | —H | —H | —N— | —C(H)— |
| 583 | (IIa) | —H | —OCH$_3$ | —OCH$_3$ | —H | —CH$_3$ | —C(H)— | —C(H)— |

-continued

| Compound | | R$_6$ | R$_1$ | R$_1'$ | R$_1''$ | R$_1'''$ | Y | Z |
|---|---|---|---|---|---|---|---|---|
| 584 | (IIa) | —H | —OCH$_3$ | —OCH$_3$ | —H | —CH$_3$ | —C(H)— | —N— |
| 585 | (IIa) | —H | —OCH$_3$ | —OCH$_3$ | —H | —CH$_3$ | —N— | —C(H)— |
| 586 | (IIa) | —H | —OCH$_3$ | —OCH$_3$ | —H | —OCH$_3$ | —C(H)— | —C(H)— |
| 587 | (IIa) | —H | —OCH$_3$ | —OCH$_3$ | —H | —OCH$_3$ | —C(H)— | —N— |
| 588 | (IIa) | —H | —OCH$_3$ | —OCH$_3$ | —H | —OCH$_3$ | —N— | —C(H)— |
| 589 | (IIa) | —H | —OCH$_3$ | —OCH$_3$ | —H | —OCF$_3$ | —C(H)— | —C(H)— |
| 590 | (IIa) | —H | —OCH$_3$ | —OCH$_3$ | —H | —OCF$_3$ | —C(H)— | —N— |
| 591 | (IIa) | —H | —OCH$_3$ | —OCH$_3$ | —H | —OCF$_3$ | —N— | —C(H)— |
| 592 | (IIa) | —H | —OCH$_3$ | —OCH$_3$ | —H | —F | —C(H)— | —C(H)— |
| 593 | (IIa) | —H | —OCH$_3$ | —OCH$_3$ | —H | —F | —C(H)— | —N— |
| 594 | (IIa) | —H | —OCH$_3$ | —OCH$_3$ | —H | —F | —N— | —C(H)— |
| 595 | (IIa) | —H | —OCH$_3$ | —OCH$_3$ | —CH$_3$ | —H | —C(H)— | —C(H)— |
| 596 | (IIa) | —H | —OCH$_3$ | —OCH$_3$ | —CH$_3$ | —H | —C(H)— | —N— |
| 597 | (IIa) | —H | —OCH$_3$ | —OCH$_3$ | —CH$_3$ | —H | —N— | —C(H)— |
| 598 | (IIa) | —H | —OCH$_3$ | —OCH$_3$ | —CH$_3$ | —CH$_3$ | —C(H)— | —C(H)— |
| 599 | (IIa) | —H | —OCH$_3$ | —OCH$_3$ | —CH$_3$ | —CH$_3$ | —C(H)— | —N— |
| 600 | (IIa) | —H | —OCH$_3$ | —OCH$_3$ | —CH$_3$ | —CH$_3$ | —N— | —C(H)— |
| 601 | (IIa) | —H | —OCH$_3$ | —OCH$_3$ | —CH$_3$ | —OCH$_3$ | —C(H)— | —C(H)— |
| 602 | (IIa) | —H | —OCH$_3$ | —OCH$_3$ | —CH$_3$ | —OCH$_3$ | —C(H)— | —N— |
| 603 | (IIa) | —H | —OCH$_3$ | —OCH$_3$ | —CH$_3$ | —OCH$_3$ | —N— | —C(H)— |
| 604 | (IIa) | —H | —OCH$_3$ | —OCH$_3$ | —CH$_3$ | —OCF$_3$ | —C(H)— | —C(H)— |
| 605 | (IIa) | —H | —OCH$_3$ | —OCH$_3$ | —CH$_3$ | —OCF$_3$ | —C(H)— | —N— |
| 606 | (IIa) | —H | —OCH$_3$ | —OCH$_3$ | —CH$_3$ | —OCF$_3$ | —N— | —C(H)— |
| 607 | (IIa) | —H | —OCH$_3$ | —OCH$_3$ | —CH$_3$ | —F | —C(H)— | —C(H)— |
| 608 | (IIa) | —H | —OCH$_3$ | —OCH$_3$ | —CH$_3$ | —F | —C(H)— | —N— |
| 609 | (IIa) | —H | —OCH$_3$ | —OCH$_3$ | —CH$_3$ | —F | —N— | —C(H)— |
| 610 | (IIa) | —H | —OCH$_3$ | —OCH$_3$ | —OCH$_3$ | —H | —C(H)— | —C(H)— |
| 611 | (IIa) | —H | —OCH$_3$ | —OCH$_3$ | —OCH$_3$ | —H | —C(H)— | —N— |
| 612 | (IIa) | —H | —OCH$_3$ | —OCH$_3$ | —OCH$_3$ | —H | —N— | —C(H)— |
| 613 | (IIa) | —H | —OCH$_3$ | —OCH$_3$ | —OCH$_3$ | —CH$_3$ | —C(H)— | —C(H)— |
| 614 | (IIa) | —H | —OCH$_3$ | —OCH$_3$ | —OCH$_3$ | —CH$_3$ | —C(H)— | —N— |
| 615 | (IIa) | —H | —OCH$_3$ | —OCH$_3$ | —OCH$_3$ | —CH$_3$ | —N— | —C(H)— |
| 616 | (IIa) | —H | —OCH$_3$ | —OCH$_3$ | —OCH$_3$ | —OCH$_3$ | —C(H)— | —C(H)— |
| 617 | (IIa) | —H | —OCH$_3$ | —OCH$_3$ | —OCH$_3$ | —OCH$_3$ | —C(H)— | —N— |
| 618 | (IIa) | —H | —OCH$_3$ | —OCH$_3$ | —OCH$_3$ | —OCH$_3$ | —N— | —C(H)— |
| 619 | (IIa) | —H | —OCH$_3$ | —OCH$_3$ | —OCH$_3$ | —OCF$_3$ | —C(H)— | —C(H)— |
| 620 | (IIa) | —H | —OCH$_3$ | —OCH$_3$ | —OCH$_3$ | —OCF$_3$ | —C(H)— | —N— |
| 621 | (IIa) | —H | —OCH$_3$ | —OCH$_3$ | —OCH$_3$ | —OCF$_3$ | —N— | —C(H)— |
| 622 | (IIa) | —H | —OCH$_3$ | —OCH$_3$ | —OCH$_3$ | —F | —C(H)— | —C(H)— |
| 623 | (IIa) | —H | —OCH$_3$ | —OCH$_3$ | —OCH$_3$ | —F | —C(H)— | —N— |
| 624 | (IIa) | —H | —OCH$_3$ | —OCH$_3$ | —OCH$_3$ | —F | —N— | —C(H)— |
| 625 | (IIa) | —H | —OCH$_3$ | —OCH$_3$ | —NO$_2$ | —H | —C(H)— | —C(H)— |
| 626 | (IIa) | —H | —OCH$_3$ | —OCH$_3$ | —NO$_2$ | —H | —C(H)— | —N— |
| 627 | (IIa) | —H | —OCH$_3$ | —OCH$_3$ | —NO$_2$ | —H | —N— | —C(H)— |
| 628 | (IIa) | —H | —OCH$_3$ | —OCH$_3$ | —NO$_2$ | —CH$_3$ | —C(H)— | —C(H)— |
| 629 | (IIa) | —H | —OCH$_3$ | —OCH$_3$ | —NO$_2$ | —CH$_3$ | —C(H)— | —N— |
| 630 | (IIa) | —H | —OCH$_3$ | —OCH$_3$ | —NO$_2$ | —CH$_3$ | —N— | —C(H)— |
| 631 | (IIa) | —H | —OCH$_3$ | —OCH$_3$ | —NO$_2$ | —OCH$_3$ | —C(H)— | —C(H)— |
| 632 | (IIa) | —H | —OCH$_3$ | —OCH$_3$ | —NO$_2$ | —OCH$_3$ | —C(H)— | —N— |
| 633 | (IIa) | —H | —OCH$_3$ | —OCH$_3$ | —NO$_2$ | —OCH$_3$ | —N— | —C(H)— |
| 634 | (IIa) | —H | —OCH$_3$ | —OCH$_3$ | —NO$_2$ | —OCF$_3$ | —C(H)— | —C(H)— |
| 635 | (IIa) | —H | —OCH$_3$ | —OCH$_3$ | —NO$_2$ | —OCF$_3$ | —C(H)— | —N— |
| 636 | (IIa) | —H | —OCH$_3$ | —OCH$_3$ | —NO$_2$ | —OCF$_3$ | —N— | —C(H)— |
| 637 | (IIa) | —H | —OCH$_3$ | —OCH$_3$ | —NO$_2$ | —F | —C(H)— | —C(H)— |
| 638 | (IIa) | —H | —OCH$_3$ | —OCH$_3$ | —NO$_2$ | —F | —C(H)— | —N— |
| 639 | (IIa) | —H | —OCH$_3$ | —OCH$_3$ | —NO$_2$ | —F | —N— | —C(H)— |
| 640 | (IIa) or (IIb) | —CH$_3$ | —H | —H | —H | —H | —C(H)— | —C(H)— |
| 641 | (IIa) or (IIb) | —CH$_3$ | —H | —H | —H | —H | —C(H)— | —N— |
| 642 | (IIa) or (IIb) | —CH$_3$ | —H | —H | —H | —H | —N— | —C(H)— |
| 643 | (IIa) or (IIb) | —CH$_3$ | —H | —H | —H | —CH$_3$ | —C(H)— | —C(H)— |
| 644 | (IIa) or (IIb) | —CH$_3$ | —H | —H | —H | —CH$_3$ | —C(H)— | —N— |
| 645 | (IIa) or (IIb) | —CH$_3$ | —H | —H | —H | —CH$_3$ | —N— | —C(H)— |
| 646 | (IIa) or (IIb) | —CH$_3$ | —H | —H | —H | —OCH$_3$ | —C(H)— | —C(H)— |
| 647 | (IIa) or (IIb) | —CH$_3$ | —H | —H | —H | —OCH$_3$ | —C(H)— | —N— |
| 648 | (IIa) or (IIb) | —CH$_3$ | —H | —H | —H | —OCH$_3$ | —N— | —C(H)— |
| 649 | (IIa) or (IIb) | —CH$_3$ | —H | —H | —H | —OCF$_3$ | —C(H)— | —C(H)— |
| 650 | (IIa) or (IIb) | —CH$_3$ | —H | —H | —H | —OCF$_3$ | —C(H)— | —N— |
| 651 | (IIa) or (IIb) | —CH$_3$ | —H | —H | —H | —OCF$_3$ | —N— | —C(H)— |
| 652 | (IIa) or (IIb) | —CH$_3$ | —H | —H | —H | —F | —C(H)— | —C(H)— |
| 653 | (IIa) or (IIb) | —CH$_3$ | —H | —H | —H | —F | —C(H)— | —N— |
| 654 | (IIa) or (IIb) | —CH$_3$ | —H | —H | —H | —F | —N— | —C(H)— |
| 655 | (IIa) or (IIb) | —CH$_3$ | —H | —H | —CH$_3$ | —H | —C(H)— | —C(H)— |
| 656 | (IIa) or (IIb) | —CH$_3$ | —H | —H | —CH$_3$ | —H | —C(H)— | —N— |
| 657 | (IIa) or (IIb) | —CH$_3$ | —H | —H | —CH$_3$ | —H | —N— | —C(H)— |
| 658 | (IIa) or (IIb) | —CH$_3$ | —H | —H | —CH$_3$ | —CH$_3$ | —C(H)— | —C(H)— |
| 659 | (IIa) or (IIb) | —CH$_3$ | —H | —H | —CH$_3$ | —CH$_3$ | —C(H)— | —N— |
| 660 | (IIa) or (IIb) | —CH$_3$ | —H | —H | —CH$_3$ | —CH$_3$ | —N— | —C(H)— |

-continued

| Compound | | R₆ | R₁ | R₁' | R₁" | R₁'" | Y | Z |
|---|---|---|---|---|---|---|---|---|
| 661 | (IIa) or (IIb) | —CH₃ | —H | —H | —CH₃ | —OCH₃ | —C(H)— | —C(H)— |
| 662 | (IIa) or (IIb) | —CH₃ | —H | —H | —CH₃ | —OCH₃ | —C(H)— | —N— |
| 663 | (IIa) or (IIb) | —CH₃ | —H | —H | —CH₃ | —OCH₃ | —N— | —C(H)— |
| 664 | (IIa) or (IIb) | —CH₃ | —H | —H | —CH₃ | —OCF₃ | —C(H)— | —C(H)— |
| 665 | (IIa) or (IIb) | —CH₃ | —H | —H | —CH₃ | —OCF₃ | —C(H)— | —N— |
| 666 | (IIa) or (IIb) | —CH₃ | —H | —H | —CH₃ | —OCF₃ | —N— | —C(H)— |
| 667 | (IIa) or (IIb) | —CH₃ | —H | —H | —CH₃ | —F | —C(H)— | —C(H)— |
| 668 | (IIa) or (IIb) | —CH₃ | —H | —H | —CH₃ | —F | —C(H)— | —N— |
| 669 | (IIa) or (IIb) | —CH₃ | —H | —H | —CH₃ | —F | —N— | —C(H)— |
| 670 | (IIa) or (IIb) | —CH₃ | —H | —H | —OCH₃ | —H | —C(H)— | —C(H)— |
| 671 | (IIa) or (IIb) | —CH₃ | —H | —H | —OCH₃ | —H | —C(H)— | —N— |
| 672 | (IIa) or (IIb) | —CH₃ | —H | —H | —OCH₃ | —H | —N— | —C(H)— |
| 673 | (IIa) or (IIb) | —CH₃ | —H | —H | —OCH₃ | —CH₃ | —C(H)— | —C(H)— |
| 674 | (IIa) or (IIb) | —CH₃ | —H | —H | —OCH₃ | —CH₃ | —C(H)— | —N— |
| 675 | (IIa) or (IIb) | —CH₃ | —H | —H | —OCH₃ | —CH₃ | —N— | —C(H)— |
| 676 | (IIa) or (IIb) | —CH₃ | —H | —H | —OCH₃ | —OCH₃ | —C(H)— | —C(H)— |
| 677 | (IIa) or (IIb) | —CH₃ | —H | —H | —OCH₃ | —OCH₃ | —C(H)— | —N— |
| 678 | (IIa) or (IIb) | —CH₃ | —H | —H | —OCH₃ | —OCH₃ | —N— | —C(H)— |
| 679 | (IIa) or (IIb) | —CH₃ | —H | —H | —OCH₃ | —OCF₃ | —C(H)— | —C(H)— |
| 680 | (IIa) or (IIb) | —CH₃ | —H | —H | —OCH₃ | —OCF₃ | —C(H)— | —N— |
| 681 | (IIa) or (IIb) | —CH₃ | —H | —H | —OCH₃ | —OCF₃ | —N— | —C(H)— |
| 682 | (IIa) or (IIb) | —CH₃ | —H | —H | —OCH₃ | —F | —C(H)— | —C(H)— |
| 683 | (IIa) or (IIb) | —CH₃ | —H | —H | —OCH₃ | —F | —C(H)— | —N— |
| 684 | (IIa) or (IIb) | —CH₃ | —H | —H | —OCH₃ | —F | —N— | —C(H)— |
| 685 | (IIa) or (IIb) | —CH₃ | —H | —H | —NO₂ | —H | —C(H)— | —C(H)— |
| 686 | (IIa) or (IIb) | —CH₃ | —H | —H | —NO₂ | —H | —C(H)— | —N— |
| 687 | (IIa) or (IIb) | —CH₃ | —H | —H | —NO₂ | —H | —N— | —C(H)— |
| 688 | (IIa) or (IIb) | —CH₃ | —H | —H | —NO₂ | —CH₃ | —C(H)— | —C(H)— |
| 689 | (IIa) or (IIb) | —CH₃ | —H | —H | —NO₂ | —CH₃ | —C(H)— | —N— |
| 690 | (IIa) or (IIb) | —CH₃ | —H | —H | —NO₂ | —CH₃ | —N— | —C(H)— |
| 691 | (IIa) or (IIb) | —CH₃ | —H | —H | —NO₂ | —OCH₃ | —C(H)— | —C(H)— |
| 692 | (IIa) or (IIb) | —CH₃ | —H | —H | —NO₂ | —OCH₃ | —C(H)— | —N— |
| 693 | (IIa) or (IIb) | —CH₃ | —H | —H | —NO₂ | —OCH₃ | —N— | —C(H)— |
| 694 | (IIa) or (IIb) | —CH₃ | —H | —H | —NO₂ | —OCF₃ | —C(H)— | —C(H)— |
| 695 | (IIa) or (IIb) | —CH₃ | —H | —H | —NO₂ | —OCF₃ | —C(H)— | —N— |
| 696 | (IIa) or (IIb) | —CH₃ | —H | —H | —NO₂ | —OCF₃ | —N— | —C(H)— |
| 697 | (IIa) or (IIb) | —CH₃ | —H | —H | —NO₂ | —F | —C(H)— | —C(H)— |
| 698 | (IIa) or (IIb) | —CH₃ | —H | —H | —NO₂ | —F | —C(H)— | —N— |
| 699 | (IIa) or (IIb) | —CH₃ | —H | —H | —NO₂ | —F | —N— | —C(H)— |
| 700 | (IIa) or (IIb) | —CH₃ | —H | —CH₃ | —H | —H | —C(H)— | —C(H)— |
| 701 | (IIa) or (IIb) | —CH₃ | —H | —CH₃ | —H | —H | —C(H)— | —N— |
| 702 | (IIa) or (IIb) | —CH₃ | —H | —CH₃ | —H | —H | —N— | —C(H)— |
| 703 | (IIa) or (IIb) | —CH₃ | —H | —CH₃ | —H | —CH₃ | —C(H)— | —C(H)— |
| 704 | (IIa) or (IIb) | —CH₃ | —H | —CH₃ | —H | —CH₃ | —C(H)— | —N— |
| 705 | (IIa) or (IIb) | —CH₃ | —H | —CH₃ | —H | —CH₃ | —N— | —C(H)— |
| 706 | (IIa) or (IIb) | —CH₃ | —H | —CH₃ | —H | —OCH₃ | —C(H)— | —C(H)— |
| 707 | (IIa) or (IIb) | —CH₃ | —H | —CH₃ | —H | —OCH₃ | —C(H)— | —N— |
| 708 | (IIa) or (IIb) | —CH₃ | —H | —CH₃ | —H | —OCH₃ | —N— | —C(H)— |
| 709 | (IIa) or (IIb) | —CH₃ | —H | —CH₃ | —H | —OCF₃ | —C(H)— | —C(H)— |
| 710 | (IIa) or (IIb) | —CH₃ | —H | —CH₃ | —H | —OCF₃ | —C(H)— | —N— |
| 711 | (IIa) or (IIb) | —CH₃ | —H | —CH₃ | —H | —OCF₃ | —N— | —C(H)— |
| 712 | (IIa) or (IIb) | —CH₃ | —H | —CH₃ | —H | —F | —C(H)— | —C(H)— |
| 713 | (IIa) or (IIb) | —CH₃ | —H | —CH₃ | —H | —F | —C(H)— | —N— |
| 714 | (IIa) or (IIb) | —CH₃ | —H | —CH₃ | —H | —F | —N— | —C(H)— |
| 715 | (IIa) or (IIb) | —CH₃ | —H | —CH₃ | —CH₃ | —H | —C(H)— | —C(H)— |
| 716 | (IIa) or (IIb) | —CH₃ | —H | —CH₃ | —CH₃ | —H | —C(H)— | —N— |
| 717 | (IIa) or (IIb) | —CH₃ | —H | —CH₃ | —CH₃ | —H | —N— | —C(H)— |
| 718 | (IIa) or (IIb) | —CH₃ | —H | —CH₃ | —CH₃ | —CH₃ | —C(H)— | —C(H)— |
| 719 | (IIa) or (IIb) | —CH₃ | —H | —CH₃ | —CH₃ | —CH₃ | —C(H)— | —N— |
| 720 | (IIa) or (IIb) | —CH₃ | —H | —CH₃ | —CH₃ | —CH₃ | —N— | —C(H)— |
| 721 | (IIa) or (IIb) | —CH₃ | —H | —CH₃ | —CH₃ | —OCH₃ | —C(H)— | —C(H)— |
| 722 | (IIa) or (IIb) | —CH₃ | —H | —CH₃ | —CH₃ | —OCH₃ | —C(H)— | —N— |
| 723 | (IIa) or (IIb) | —CH₃ | —H | —CH₃ | —CH₃ | —OCH₃ | —N— | —C(H)— |
| 724 | (IIa) or (IIb) | —CH₃ | —H | —CH₃ | —CH₃ | —OCF₃ | —C(H)— | —C(H)— |
| 725 | (IIa) or (IIb) | —CH₃ | —H | —CH₃ | —CH₃ | —OCF₃ | —C(H)— | —N— |
| 726 | (IIa) or (IIb) | —CH₃ | —H | —CH₃ | —CH₃ | —OCF₃ | —N— | —C(H)— |
| 727 | (IIa) or (IIb) | —CH₃ | —H | —CH₃ | —CH₃ | —F | —C(H)— | —C(H)— |
| 728 | (IIa) or (IIb) | —CH₃ | —H | —CH₃ | —CH₃ | —F | —C(H)— | —N— |
| 729 | (IIa) or (IIb) | —CH₃ | —H | —CH₃ | —CH₃ | —F | —N— | —C(H)— |
| 730 | (IIa) or (IIb) | —CH₃ | —H | —CH₃ | —OCH₃ | —H | —C(H)— | —C(H)— |
| 731 | (IIa) or (IIb) | —CH₃ | —H | —CH₃ | —OCH₃ | —H | —C(H)— | —N— |
| 732 | (IIa) or (IIb) | —CH₃ | —H | —CH₃ | —OCH₃ | —H | —N— | —C(H)— |
| 733 | (IIa) or (IIb) | —CH₃ | —H | —CH₃ | —OCH₃ | —CH₃ | —C(H)— | —C(H)— |
| 734 | (IIa) or (IIb) | —CH₃ | —H | —CH₃ | —OCH₃ | —CH₃ | —C(H)— | —N— |
| 735 | (IIa) or (IIb) | —CH₃ | —H | —CH₃ | —OCH₃ | —CH₃ | —N— | —C(H)— |
| 736 | (IIa) or (IIb) | —CH₃ | —H | —CH₃ | —OCH₃ | —OCH₃ | —C(H)— | —C(H)— |
| 737 | (IIa) or (IIb) | —CH₃ | —H | —CH₃ | —OCH₃ | —OCH₃ | —C(H)— | —N— |

-continued

| Compound | | $R_6$ | $R_1$ | $R_1'$ | $R_1''$ | $R_1'''$ | Y | Z |
|---|---|---|---|---|---|---|---|---|
| 738 | (IIa) or (IIb) | —CH$_3$ | —H | —CH$_3$ | —OCH$_3$ | —OCH$_3$ | —N— | —C(H)— |
| 739 | (IIa) or (IIb) | —CH$_3$ | —H | —CH$_3$ | —OCH$_3$ | —OCF$_3$ | —C(H)— | —C(H)— |
| 740 | (IIa) or (IIb) | —CH$_3$ | —H | —CH$_3$ | —OCH$_3$ | —OCF$_3$ | —C(H)— | —N— |
| 741 | (IIa) or (IIb) | —CH$_3$ | —H | —CH$_3$ | —OCH$_3$ | —OCF$_3$ | —N— | —C(H)— |
| 742 | (IIa) or (IIb) | —CH$_3$ | —H | —CH$_3$ | —OCH$_3$ | —F | —C(H)— | —C(H)— |
| 743 | (IIa) or (IIb) | —CH$_3$ | —H | —CH$_3$ | —OCH$_3$ | —F | —C(H)— | —N— |
| 744 | (IIa) or (IIb) | —CH$_3$ | —H | —CH$_3$ | —OCH$_3$ | —F | —N— | —C(H)— |
| 745 | (IIa) or (IIb) | —CH$_3$ | —H | —CH$_3$ | —NO$_2$ | —H | —C(H)— | —C(H)— |
| 746 | (IIa) or (IIb) | —CH$_3$ | —H | —CH$_3$ | —NO$_2$ | —H | —C(H)— | —N— |
| 747 | (IIa) or (IIb) | —CH$_3$ | —H | —CH$_3$ | —NO$_2$ | —H | —N— | —C(H)— |
| 748 | (IIa) or (IIb) | —CH$_3$ | —H | —CH$_3$ | —NO$_2$ | —CH$_3$ | —C(H)— | —C(H)— |
| 749 | (IIa) or (IIb) | —CH$_3$ | —H | —CH$_3$ | —NO$_2$ | —CH$_3$ | —C(H)— | —N— |
| 750 | (IIa) or (IIb) | —CH$_3$ | —H | —CH$_3$ | —NO$_2$ | —CH$_3$ | —N— | —C(H)— |
| 751 | (IIa) or (IIb) | —CH$_3$ | —H | —CH$_3$ | —NO$_2$ | —OCH$_3$ | —C(H)— | —C(H)— |
| 752 | (IIa) or (IIb) | —CH$_3$ | —H | —CH$_3$ | —NO$_2$ | —OCH$_3$ | —C(H)— | —N— |
| 753 | (IIa) or (IIb) | —CH$_3$ | —H | —CH$_3$ | —NO$_2$ | —OCH$_3$ | —N— | —C(H)— |
| 754 | (IIa) or (IIb) | —CH$_3$ | —H | —CH$_3$ | —NO$_2$ | —OCF$_3$ | —C(H)— | —C(H)— |
| 755 | (IIa) or (IIb) | —CH$_3$ | —H | —CH$_3$ | —NO$_2$ | —OCF$_3$ | —C(H)— | —N— |
| 756 | (IIa) or (IIb) | —CH$_3$ | —H | —CH$_3$ | —NO$_2$ | —OCF$_3$ | —N— | —C(H)— |
| 757 | (IIa) or (IIb) | —CH$_3$ | —H | —CH$_3$ | —NO$_2$ | —F | —C(H)— | —C(H)— |
| 758 | (IIa) or (IIb) | —CH$_3$ | —H | —CH$_3$ | —NO$_2$ | —F | —C(H)— | —N— |
| 759 | (IIa) or (IIb) | —CH$_3$ | —H | —CH$_3$ | —NO$_2$ | —F | —N— | —C(H)— |
| 760 | (IIa) or (IIb) | —CH$_3$ | —H | —OCH$_3$ | —H | —H | —C(H)— | —C(H)— |
| 761 | (IIa) or (IIb) | —CH$_3$ | —H | —OCH$_3$ | —H | —H | —C(H)— | —N— |
| 762 | (IIa) or (IIb) | —CH$_3$ | —H | —OCH$_3$ | —H | —H | —N— | —C(H)— |
| 763 | (IIa) or (IIb) | —CH$_3$ | —H | —OCH$_3$ | —H | —CH$_3$ | —C(H)— | —C(H)— |
| 764 | (IIa) or (IIb) | —CH$_3$ | —H | —OCH$_3$ | —H | —CH$_3$ | —C(H)— | —N— |
| 765 | (IIa) or (IIb) | —CH$_3$ | —H | —OCH$_3$ | —H | —CH$_3$ | —N— | —C(H)— |
| 766 | (IIa) or (IIb) | —CH$_3$ | —H | —OCH$_3$ | —H | —OCH$_3$ | —C(H)— | —C(H)— |
| 767 | (IIa) or (IIb) | —CH$_3$ | —H | —OCH$_3$ | —H | —OCH$_3$ | —C(H)— | —N— |
| 768 | (IIa) or (IIb) | —CH$_3$ | —H | —OCH$_3$ | —H | —OCH$_3$ | —N— | —C(H)— |
| 769 | (IIa) or (IIb) | —CH$_3$ | —H | —OCH$_3$ | —H | —OCF$_3$ | —C(H)— | —C(H)— |
| 770 | (IIa) or (IIb) | —CH$_3$ | —H | —OCH$_3$ | —H | —OCF$_3$ | —C(H)— | —N— |
| 771 | (IIa) or (IIb) | —CH$_3$ | —H | —OCH$_3$ | —H | —OCF$_3$ | —N— | —C(H)— |
| 772 | (IIa) or (IIb) | —CH$_3$ | —H | —OCH$_3$ | —H | —F | —C(H)— | —C(H)— |
| 773 | (IIa) or (IIb) | —CH$_3$ | —H | —OCH$_3$ | —H | —F | —C(H)— | —N— |
| 774 | (IIa) or (IIb) | —CH$_3$ | —H | —OCH$_3$ | —H | —F | —N— | —C(H)— |
| 775 | (IIa) or (IIb) | —CH$_3$ | —H | —OCH$_3$ | —CH$_3$ | —H | —C(H)— | —C(H)— |
| 776 | (IIa) or (IIb) | —CH$_3$ | —H | —OCH$_3$ | —CH$_3$ | —H | —C(H)— | —N— |
| 777 | (IIa) or (IIb) | —CH$_3$ | —H | —OCH$_3$ | —CH$_3$ | —H | —N— | —C(H)— |
| 778 | (IIa) or (IIb) | —CH$_3$ | —H | —OCH$_3$ | —CH$_3$ | —CH$_3$ | —C(H)— | —C(H)— |
| 779 | (IIa) or (IIb) | —CH$_3$ | —H | —OCH$_3$ | —CH$_3$ | —CH$_3$ | —C(H)— | —N— |
| 780 | (IIa) or (IIb) | —CH$_3$ | —H | —OCH$_3$ | —CH$_3$ | —CH$_3$ | —N— | —C(H)— |
| 781 | (IIa) or (IIb) | —CH$_3$ | —H | —OCH$_3$ | —CH$_3$ | —OCH$_3$ | —C(H)— | —C(H)— |
| 782 | (IIa) or (IIb) | —CH$_3$ | —H | —OCH$_3$ | —CH$_3$ | —OCH$_3$ | —C(H)— | —N— |
| 783 | (IIa) or (IIb) | —CH$_3$ | —H | —OCH$_3$ | —CH$_3$ | —OCH$_3$ | —N— | —C(H)— |
| 784 | (IIa) or (IIb) | —CH$_3$ | —H | —OCH$_3$ | —CH$_3$ | —OCF$_3$ | —C(H)— | —C(H)— |
| 785 | (IIa) or (IIb) | —CH$_3$ | —H | —OCH$_3$ | —CH$_3$ | —OCF$_3$ | —C(H)— | —N— |
| 786 | (IIa) or (IIb) | —CH$_3$ | —H | —OCH$_3$ | —CH$_3$ | —OCF$_3$ | —N— | —C(H)— |
| 787 | (IIa) or (IIb) | —CH$_3$ | —H | —OCH$_3$ | —CH$_3$ | —F | —C(H)— | —C(H)— |
| 788 | (IIa) or (IIb) | —CH$_3$ | —H | —OCH$_3$ | —CH$_3$ | —F | —C(H)— | —N— |
| 789 | (IIa) or (IIb) | —CH$_3$ | —H | —OCH$_3$ | —CH$_3$ | —F | —N— | —C(H)— |
| 790 | (IIa) or (IIb) | —CH$_3$ | —H | —OCH$_3$ | —OCH$_3$ | —H | —C(H)— | —C(H)— |
| 791 | (IIa) or (IIb) | —CH$_3$ | —H | —OCH$_3$ | —OCH$_3$ | —H | —C(H)— | —N— |
| 792 | (IIa) or (IIb) | —CH$_3$ | —H | —OCH$_3$ | —OCH$_3$ | —H | —N— | —C(H)— |
| 793 | (IIa) or (IIb) | —CH$_3$ | —H | —OCH$_3$ | —OCH$_3$ | —CH$_3$ | —C(H)— | —C(H)— |
| 794 | (IIa) or (IIb) | —CH$_3$ | —H | —OCH$_3$ | —OCH$_3$ | —CH$_3$ | —C(H)— | —N— |
| 795 | (IIa) or (IIb) | —CH$_3$ | —H | —OCH$_3$ | —OCH$_3$ | —CH$_3$ | —N— | —C(H)— |
| 796 | (IIa) or (IIb) | —CH$_3$ | —H | —OCH$_3$ | —OCH$_3$ | —OCH$_3$ | —C(H)— | —C(H)— |
| 797 | (IIa) or (IIb) | —CH$_3$ | —H | —OCH$_3$ | —OCH$_3$ | —OCH$_3$ | —C(H)— | —N— |
| 798 | (IIa) or (IIb) | —CH$_3$ | —H | —OCH$_3$ | —OCH$_3$ | —OCH$_3$ | —N— | —C(H)— |
| 799 | (IIa) or (IIb) | —CH$_3$ | —H | —OCH$_3$ | —OCH$_3$ | —OCF$_3$ | —C(H)— | —C(H)— |
| 800 | (IIa) or (IIb) | —CH$_3$ | —H | —OCH$_3$ | —OCH$_3$ | —OCF$_3$ | —C(H)— | —N— |
| 801 | (IIa) or (IIb) | —CH$_3$ | —H | —OCH$_3$ | —OCH$_3$ | —OCF$_3$ | —N— | —C(H)— |
| 802 | (IIa) or (IIb) | —CH$_3$ | —H | —OCH$_3$ | —OCH$_3$ | —F | —C(H)— | —C(H)— |
| 803 | (IIa) or (IIb) | —CH$_3$ | —H | —OCH$_3$ | —OCH$_3$ | —F | —C(H)— | —N— |
| 804 | (IIa) or (IIb) | —CH$_3$ | —H | —OCH$_3$ | —OCH$_3$ | —F | —N— | —C(H)— |
| 805 | (IIa) or (IIb) | —CH$_3$ | —H | —OCH$_3$ | —NO$_2$ | —H | —C(H)— | —C(H)— |
| 806 | (IIa) or (IIb) | —CH$_3$ | —H | —OCH$_3$ | —NO$_2$ | —H | —C(H)— | —N— |
| 807 | (IIa) or (IIb) | —CH$_3$ | —H | —OCH$_3$ | —NO$_2$ | —H | —N— | —C(H)— |
| 808 | (IIa) or (IIb) | —CH$_3$ | —H | —OCH$_3$ | —NO$_2$ | —CH$_3$ | —C(H)— | —C(H)— |
| 809 | (IIa) or (IIb) | —CH$_3$ | —H | —OCH$_3$ | —NO$_2$ | —CH$_3$ | —C(H)— | —N— |
| 810 | (IIa) or (IIb) | —CH$_3$ | —H | —OCH$_3$ | —NO$_2$ | —CH$_3$ | —N— | —C(H)— |
| 811 | (IIa) or (IIb) | —CH$_3$ | —H | —OCH$_3$ | —NO$_2$ | —OCH$_3$ | —C(H)— | —C(H)— |
| 812 | (IIa) or (IIb) | —CH$_3$ | —H | —OCH$_3$ | —NO$_2$ | —OCH$_3$ | —C(H)— | —N— |
| 813 | (IIa) or (IIb) | —CH$_3$ | —H | —OCH$_3$ | —NO$_2$ | —OCH$_3$ | —N— | —C(H)— |
| 814 | (IIa) or (IIb) | —CH$_3$ | —H | —OCH$_3$ | —NO$_2$ | —OCF$_3$ | —C(H)— | —C(H)— |

-continued

| Compound | | $R_6$ | $R_1$ | $R_1'$ | $R_1''$ | $R_1'''$ | Y | Z |
|---|---|---|---|---|---|---|---|---|
| 815 | (IIa) or (IIb) | —CH₃ | —H | —OCH₃ | —NO₂ | —OCF₃ | —C(H)— | —N— |
| 816 | (IIa) or (IIb) | —CH₃ | —H | —OCH₃ | —NO₂ | —OCF₃ | —N— | —C(H)— |
| 817 | (IIa) or (IIb) | —CH₃ | —H | —OCH₃ | —NO₂ | —F | —C(H)— | —C(H)— |
| 818 | (IIa) or (IIb) | —CH₃ | —H | —OCH₃ | —NO₂ | —F | —C(H)— | —N— |
| 819 | (IIa) or (IIb) | —CH₃ | —H | —OCH₃ | —NO₂ | —F | —N— | —C(H)— |
| 820 | (IIa) or (IIb) | —CH₃ | —NO₂ | —H | —H | —H | —C(H)— | —C(H)— |
| 821 | (IIa) or (IIb) | —CH₃ | —NO₂ | —H | —H | —H | —C(H)— | —N— |
| 822 | (IIa) or (IIb) | —CH₃ | —NO₂ | —H | —H | —H | —N— | —C(H)— |
| 823 | (IIa) or (IIb) | —CH₃ | —NO₂ | —H | —H | —CH₃ | —C(H)— | —C(H)— |
| 824 | (IIa) or (IIb) | —CH₃ | —NO₂ | —H | —H | —CH₃ | —C(H)— | —N— |
| 825 | (IIa) or (IIb) | —CH₃ | —NO₂ | —H | —H | —CH₃ | —N— | —C(H)— |
| 826 | (IIa) or (IIb) | —CH₃ | —NO₂ | —H | —H | —OCH₃ | —C(H)— | —C(H)— |
| 827 | (IIa) or (IIb) | —CH₃ | —NO₂ | —H | —H | —OCH₃ | —C(H)— | —N— |
| 828 | (IIa) or (IIb) | —CH₃ | —NO₂ | —H | —H | —OCH₃ | —N— | —C(H)— |
| 829 | (IIa) or (IIb) | —CH₃ | —NO₂ | —H | —H | —OCF₃ | —C(H)— | —C(H)— |
| 830 | (IIa) or (IIb) | —CH₃ | —NO₂ | —H | —H | —OCF₃ | —C(H)— | —N— |
| 831 | (IIa) or (IIb) | —CH₃ | —NO₂ | —H | —H | —OCF₃ | —N— | —C(H)— |
| 832 | (IIa) or (IIb) | —CH₃ | —NO₂ | —H | —H | —F | —C(H)— | —C(H)— |
| 833 | (IIa) or (IIb) | —CH₃ | —NO₂ | —H | —H | —F | —C(H)— | —N— |
| 834 | (IIa) or (IIb) | —CH₃ | —NO₂ | —H | —H | —F | —N— | —C(H)— |
| 835 | (IIa) or (IIb) | —CH₃ | —NO₂ | —H | —CH₃ | —H | —C(H)— | —C(H)— |
| 836 | (IIa) or (IIb) | —CH₃ | —NO₂ | —H | —CH₃ | —H | —C(H)— | —N— |
| 837 | (IIa) or (IIb) | —CH₃ | —NO₂ | —H | —CH₃ | —H | —N— | —C(H)— |
| 838 | (IIa) or (IIb) | —CH₃ | —NO₂ | —H | —CH₃ | —CH₃ | —C(H)— | —C(H)— |
| 839 | (IIa) or (IIb) | —CH₃ | —NO₂ | —H | —CH₃ | —CH₃ | —C(H)— | —N— |
| 840 | (IIa) or (IIb) | —CH₃ | —NO₂ | —H | —CH₃ | —CH₃ | —N— | —C(H)— |
| 841 | (IIa) or (IIb) | —CH₃ | —NO₂ | —H | —CH₃ | —OCH₃ | —C(H)— | —C(H)— |
| 842 | (IIa) or (IIb) | —CH₃ | —NO₂ | —H | —CH₃ | —OCH₃ | —C(H)— | —N— |
| 843 | (IIa) or (IIb) | —CH₃ | —NO₂ | —H | —CH₃ | —OCH₃ | —N— | —C(H)— |
| 844 | (IIa) or (IIb) | —CH₃ | —NO₂ | —H | —CH₃ | —OCF₃ | —C(H)— | —C(H)— |
| 845 | (IIa) or (IIb) | —CH₃ | —NO₂ | —H | —CH₃ | —OCF₃ | —C(H)— | —N— |
| 846 | (IIa) or (IIb) | —CH₃ | —NO₂ | —H | —CH₃ | —OCF₃ | —N— | —C(H)— |
| 847 | (IIa) or (IIb) | —CH₃ | —NO₂ | —H | —CH₃ | —F | —C(H)— | —C(H)— |
| 848 | (IIa) or (IIb) | —CH₃ | —NO₂ | —H | —CH₃ | —F | —C(H)— | —N— |
| 849 | (IIa) or (IIb) | —CH₃ | —NO₂ | —H | —CH₃ | —F | —N— | —C(H)— |
| 850 | (IIa) or (IIb) | —CH₃ | —NO₂ | —H | —OCH₃ | —H | —C(H)— | —C(H)— |
| 851 | (IIa) or (IIb) | —CH₃ | —NO₂ | —H | —OCH₃ | —H | —C(H)— | —N— |
| 852 | (IIa) or (IIb) | —CH₃ | —NO₂ | —H | —OCH₃ | —H | —N— | —C(H)— |
| 853 | (IIa) or (IIb) | —CH₃ | —NO₂ | —H | —OCH₃ | —CH₃ | —C(H)— | —C(H)— |
| 854 | (IIa) or (IIb) | —CH₃ | —NO₂ | —H | —OCH₃ | —CH₃ | —C(H)— | —N— |
| 855 | (IIa) or (IIb) | —CH₃ | —NO₂ | —H | —OCH₃ | —CH₃ | —N— | —C(H)— |
| 856 | (IIa) or (IIb) | —CH₃ | —NO₂ | —H | —OCH₃ | —OCH₃ | —C(H)— | —C(H)— |
| 857 | (IIa) or (IIb) | —CH₃ | —NO₂ | —H | —OCH₃ | —OCH₃ | —C(H)— | —N— |
| 858 | (IIa) or (IIb) | —CH₃ | —NO₂ | —H | —OCH₃ | —OCH₃ | —N— | —C(H)— |
| 859 | (IIa) or (IIb) | —CH₃ | —NO₂ | —H | —OCH₃ | —OCF₃ | —C(H)— | —C(H)— |
| 860 | (IIa) or (IIb) | —CH₃ | —NO₂ | —H | —OCH₃ | —OCF₃ | —C(H)— | —N— |
| 861 | (IIa) or (IIb) | —CH₃ | —NO₂ | —H | —OCH₃ | —OCF₃ | —N— | —C(H)— |
| 862 | (IIa) or (IIb) | —CH₃ | —NO₂ | —H | —OCH₃ | —F | —C(H)— | —C(H)— |
| 863 | (IIa) or (IIb) | —CH₃ | —NO₂ | —H | —OCH₃ | —F | —C(H)— | —N— |
| 864 | (IIa) or (IIb) | —CH₃ | —NO₂ | —H | —OCH₃ | —F | —N— | —C(H)— |
| 865 | (IIa) or (IIb) | —CH₃ | —NO₂ | —H | —NO₂ | —H | —C(H)— | —C(H)— |
| 866 | (IIa) or (IIb) | —CH₃ | —NO₂ | —H | —NO₂ | —H | —C(H)— | —N— |
| 867 | (IIa) or (IIb) | —CH₃ | —NO₂ | —H | —NO₂ | —H | —N— | —C(H)— |
| 868 | (IIa) or (IIb) | —CH₃ | —NO₂ | —H | —NO₂ | —CH₃ | —C(H)— | —C(H)— |
| 869 | (IIa) or (IIb) | —CH₃ | —NO₂ | —H | —NO₂ | —CH₃ | —C(H)— | —N— |
| 870 | (IIa) or (IIb) | —CH₃ | —NO₂ | —H | —NO₂ | —CH₃ | —N— | —C(H)— |
| 871 | (IIa) or (IIb) | —CH₃ | —NO₂ | —H | —NO₂ | —OCH₃ | —C(H)— | —C(H)— |
| 872 | (IIa) or (IIb) | —CH₃ | —NO₂ | —H | —NO₂ | —OCH₃ | —C(H)— | —N— |
| 873 | (IIa) or (IIb) | —CH₃ | —NO₂ | —H | —NO₂ | —OCH₃ | —N— | —C(H)— |
| 874 | (IIa) or (IIb) | —CH₃ | —NO₂ | —H | —NO₂ | —OCF₃ | —C(H)— | —C(H)— |
| 875 | (IIa) or (IIb) | —CH₃ | —NO₂ | —H | —NO₂ | —OCF₃ | —C(H)— | —N— |
| 876 | (IIa) or (IIb) | —CH₃ | —NO₂ | —H | —NO₂ | —OCF₃ | —N— | —C(H)— |
| 877 | (IIa) or (IIb) | —CH₃ | —NO₂ | —H | —NO₂ | —F | —C(H)— | —C(H)— |
| 878 | (IIa) or (IIb) | —CH₃ | —NO₂ | —H | —NO₂ | —F | —C(H)— | —N— |
| 879 | (IIa) or (IIb) | —CH₃ | —NO₂ | —H | —NO₂ | —F | —N— | —C(H)— |
| 880 | (IIa) or (IIb) | —CH₃ | —NO₂ | —CH₃ | —H | —H | —C(H)— | —C(H)— |
| 881 | (IIa) or (IIb) | —CH₃ | —NO₂ | —CH₃ | —H | —H | —C(H)— | —N— |
| 882 | (IIa) or (IIb) | —CH₃ | —NO₂ | —CH₃ | —H | —H | —N— | —C(H)— |
| 883 | (IIa) or (IIb) | —CH₃ | —NO₂ | —CH₃ | —H | —CH₃ | —C(H)— | —C(H)— |
| 884 | (IIa) or (IIb) | —CH₃ | —NO₂ | —CH₃ | —H | —CH₃ | —C(H)— | —N— |
| 885 | (IIa) or (IIb) | —CH₃ | —NO₂ | —CH₃ | —H | —CH₃ | —N— | —C(H)— |
| 886 | (IIa) or (IIb) | —CH₃ | —NO₂ | —CH₃ | —H | —OCH₃ | —C(H)— | —C(H)— |
| 887 | (IIa) or (IIb) | —CH₃ | —NO₂ | —CH₃ | —H | —OCH₃ | —C(H)— | —N— |
| 888 | (IIa) or (IIb) | —CH₃ | —NO₂ | —CH₃ | —H | —OCH₃ | —N— | —C(H)— |
| 889 | (IIa) or (IIb) | —CH₃ | —NO₂ | —CH₃ | —H | —OCF₃ | —C(H)— | —C(H)— |
| 890 | (IIa) or (IIb) | —CH₃ | —NO₂ | —CH₃ | —H | —OCF₃ | —C(H)— | —N— |
| 891 | (IIa) or (IIb) | —CH₃ | —NO₂ | —CH₃ | —H | —OCF₃ | —N— | —C(H)— |

-continued

| Compound | | $R_6$ | $R_1$ | $R_1'$ | $R_1''$ | $R_1'''$ | Y | Z |
|---|---|---|---|---|---|---|---|---|
| 892 | (IIa) or (IIb) | —CH₃ | —NO₂ | —CH₃ | —H | —F | —C(H)— | —C(H)— |
| 893 | (IIa) or (IIb) | —CH₃ | —NO₂ | —CH₃ | —H | —F | —C(H)— | —N— |
| 894 | (IIa) or (IIb) | —CH₃ | —NO₂ | —CH₃ | —H | —F | —N— | —C(H)— |
| 895 | (IIa) or (IIb) | —CH₃ | —NO₂ | —CH₃ | —CH₃ | —H | —C(H)— | —C(H)— |
| 896 | (IIa) or (IIb) | —CH₃ | —NO₂ | —CH₃ | —CH₃ | —H | —C(H)— | —N— |
| 897 | (IIa) or (IIb) | —CH₃ | —NO₂ | —CH₃ | —CH₃ | —H | —N— | —C(H)— |
| 898 | (IIa) or (IIb) | —CH₃ | —NO₂ | —CH₃ | —CH₃ | —CH₃ | —C(H)— | —C(H)— |
| 899 | (IIa) or (IIb) | —CH₃ | —NO₂ | —CH₃ | —CH₃ | —CH₃ | —C(H)— | —N— |
| 900 | (IIa) or (IIb) | —CH₃ | —NO₂ | —CH₃ | —CH₃ | —CH₃ | —N— | —C(H)— |
| 901 | (IIa) or (IIb) | —CH₃ | —NO₂ | —CH₃ | —CH₃ | —OCH₃ | —C(H)— | —C(H)— |
| 902 | (IIa) or (IIb) | —CH₃ | —NO₂ | —CH₃ | —CH₃ | —OCH₃ | —C(H)— | —N— |
| 903 | (IIa) or (IIb) | —CH₃ | —NO₂ | —CH₃ | —CH₃ | —OCH₃ | —N— | —C(H)— |
| 904 | (IIa) or (IIb) | —CH₃ | —NO₂ | —CH₃ | —CH₃ | —OCF₃ | —C(H)— | —C(H)— |
| 905 | (IIa) or (IIb) | —CH₃ | —NO₂ | —CH₃ | —CH₃ | —OCF₃ | —C(H)— | —N— |
| 906 | (IIa) or (IIb) | —CH₃ | —NO₂ | —CH₃ | —CH₃ | —OCF₃ | —N— | —C(H)— |
| 907 | (IIa) or (IIb) | —CH₃ | —NO₂ | —CH₃ | —CH₃ | —F | —C(H)— | —C(H)— |
| 908 | (IIa) or (IIb) | —CH₃ | —NO₂ | —CH₃ | —CH₃ | —F | —C(H)— | —N— |
| 909 | (IIa) or (IIb) | —CH₃ | —NO₂ | —CH₃ | —CH₃ | —F | —N— | —C(H)— |
| 910 | (IIa) or (IIb) | —CH₃ | —NO₂ | —CH₃ | —OCH₃ | —H | —C(H)— | —C(H)— |
| 911 | (IIa) or (IIb) | —CH₃ | —NO₂ | —CH₃ | —OCH₃ | —H | —C(H)— | —N— |
| 912 | (IIa) or (IIb) | —CH₃ | —NO₂ | —CH₃ | —OCH₃ | —H | —N— | —C(H)— |
| 913 | (IIa) or (IIb) | —CH₃ | —NO₂ | —CH₃ | —OCH₃ | —CH₃ | —C(H)— | —C(H)— |
| 914 | (IIa) or (IIb) | —CH₃ | —NO₂ | —CH₃ | —OCH₃ | —CH₃ | —C(H)— | —N— |
| 915 | (IIa) or (IIb) | —CH₃ | —NO₂ | —CH₃ | —OCH₃ | —CH₃ | —N— | —C(H)— |
| 916 | (IIa) or (IIb) | —CH₃ | —NO₂ | —CH₃ | —OCH₃ | —OCH₃ | —C(H)— | —C(H)— |
| 917 | (IIa) or (IIb) | —CH₃ | —NO₂ | —CH₃ | —OCH₃ | —OCH₃ | —C(H)— | —N— |
| 918 | (IIa) or (IIb) | —CH₃ | —NO₂ | —CH₃ | —OCH₃ | —OCH₃ | —N— | —C(H)— |
| 919 | (IIa) or (IIb) | —CH₃ | —NO₂ | —CH₃ | —OCH₃ | —OCF₃ | —C(H)— | —C(H)— |
| 920 | (IIa) or (IIb) | —CH₃ | —NO₂ | —CH₃ | —OCH₃ | —OCF₃ | —C(H)— | —N— |
| 921 | (IIa) or (IIb) | —CH₃ | —NO₂ | —CH₃ | —OCH₃ | —OCF₃ | —N— | —C(H)— |
| 922 | (IIa) or (IIb) | —CH₃ | —NO₂ | —CH₃ | —OCH₃ | —F | —C(H)— | —C(H)— |
| 923 | (IIa) or (IIb) | —CH₃ | —NO₂ | —CH₃ | —OCH₃ | —F | —C(H)— | —N— |
| 924 | (IIa) or (IIb) | —CH₃ | —NO₂ | —CH₃ | —OCH₃ | —F | —N— | —C(H)— |
| 925 | (IIa) or (IIb) | —CH₃ | —NO₂ | —CH₃ | —NO₂ | —H | —C(H)— | —C(H)— |
| 926 | (IIa) or (IIb) | —CH₃ | —NO₂ | —CH₃ | —NO₂ | —H | —C(H)— | —N— |
| 927 | (IIa) or (IIb) | —CH₃ | —NO₂ | —CH₃ | —NO₂ | —H | —N— | —C(H)— |
| 928 | (IIa) or (IIb) | —CH₃ | —NO₂ | —CH₃ | —NO₂ | —CH₃ | —C(H)— | —C(H)— |
| 929 | (IIa) or (IIb) | —CH₃ | —NO₂ | —CH₃ | —NO₂ | —CH₃ | —C(H)— | —N— |
| 930 | (IIa) or (IIb) | —CH₃ | —NO₂ | —CH₃ | —NO₂ | —CH₃ | —N— | —C(H)— |
| 931 | (IIa) or (IIb) | —CH₃ | —NO₂ | —CH₃ | —NO₂ | —OCH₃ | —C(H)— | —C(H)— |
| 932 | (IIa) or (IIb) | —CH₃ | —NO₂ | —CH₃ | —NO₂ | —OCH₃ | —C(H)— | —N— |
| 933 | (IIa) or (IIb) | —CH₃ | —NO₂ | —CH₃ | —NO₂ | —OCH₃ | —N— | —C(H)— |
| 934 | (IIa) or (IIb) | —CH₃ | —NO₂ | —CH₃ | —NO₂ | —OCF₃ | —C(H)— | —C(H)— |
| 935 | (IIa) or (IIb) | —CH₃ | —NO₂ | —CH₃ | —NO₂ | —OCF₃ | —C(H)— | —N— |
| 936 | (IIa) or (IIb) | —CH₃ | —NO₂ | —CH₃ | —NO₂ | —OCF₃ | —N— | —C(H)— |
| 937 | (IIa) or (IIb) | —CH₃ | —NO₂ | —CH₃ | —NO₂ | —F | —C(H)— | —C(H)— |
| 938 | (IIa) or (IIb) | —CH₃ | —NO₂ | —CH₃ | —NO₂ | —F | —C(H)— | —N— |
| 939 | (IIa) or (IIb) | —CH₃ | —NO₂ | —CH₃ | —NO₂ | —F | —N— | —C(H)— |
| 940 | (IIa) or (IIb) | —CH₃ | —NO₂ | —OCH₃ | —H | —H | —C(H)— | —C(H)— |
| 941 | (IIa) or (IIb) | —CH₃ | —NO₂ | —OCH₃ | —H | —H | —C(H)— | —N— |
| 942 | (IIa) or (IIb) | —CH₃ | —NO₂ | —OCH₃ | —H | —H | —N— | —C(H)— |
| 943 | (IIa) or (IIb) | —CH₃ | —NO₂ | —OCH₃ | —H | —CH₃ | —C(H)— | —C(H)— |
| 944 | (IIa) or (IIb) | —CH₃ | —NO₂ | —OCH₃ | —H | —CH₃ | —C(H)— | —N— |
| 945 | (IIa) or (IIb) | —CH₃ | —NO₂ | —OCH₃ | —H | —CH₃ | —N— | —C(H)— |
| 946 | (IIa) or (IIb) | —CH₃ | —NO₂ | —OCH₃ | —H | —OCH₃ | —C(H)— | —C(H)— |
| 947 | (IIa) or (IIb) | —CH₃ | —NO₂ | —OCH₃ | —H | —OCH₃ | —C(H)— | —N— |
| 948 | (IIa) or (IIb) | —CH₃ | —NO₂ | —OCH₃ | —H | —OCH₃ | —N— | —C(H)— |
| 949 | (IIa) or (IIb) | —CH₃ | —NO₂ | —OCH₃ | —H | —OCF₃ | —C(H)— | —C(H)— |
| 950 | (IIa) or (IIb) | —CH₃ | —NO₂ | —OCH₃ | —H | —OCF₃ | —C(H)— | —N— |
| 951 | (IIa) or (IIb) | —CH₃ | —NO₂ | —OCH₃ | —H | —OCF₃ | —N— | —C(H)— |
| 952 | (IIa) or (IIb) | —CH₃ | —NO₂ | —OCH₃ | —H | —F | —C(H)— | —C(H)— |
| 953 | (IIa) or (IIb) | —CH₃ | —NO₂ | —OCH₃ | —H | —F | —C(H)— | —N— |
| 954 | (IIa) or (IIb) | —CH₃ | —NO₂ | —OCH₃ | —H | —F | —N— | —C(H)— |
| 955 | (IIa) or (IIb) | —CH₃ | —NO₂ | —OCH₃ | —CH₃ | —H | —C(H)— | —C(H)— |
| 956 | (IIa) or (IIb) | —CH₃ | —NO₂ | —OCH₃ | —CH₃ | —H | —C(H)— | —N— |
| 957 | (IIa) or (IIb) | —CH₃ | —NO₂ | —OCH₃ | —CH₃ | —H | —N— | —C(H)— |
| 958 | (IIa) or (IIb) | —CH₃ | —NO₂ | —OCH₃ | —CH₃ | —CH₃ | —C(H)— | —C(H)— |
| 959 | (IIa) or (IIb) | —CH₃ | —NO₂ | —OCH₃ | —CH₃ | —CH₃ | —C(H)— | —N— |
| 960 | (IIa) or (IIb) | —CH₃ | —NO₂ | —OCH₃ | —CH₃ | —CH₃ | —N— | —C(H)— |
| 961 | (IIa) or (IIb) | —CH₃ | —NO₂ | —OCH₃ | —CH₃ | —OCH₃ | —C(H)— | —C(H)— |
| 962 | (IIa) or (IIb) | —CH₃ | —NO₂ | —OCH₃ | —CH₃ | —OCH₃ | —C(H)— | —N— |
| 963 | (IIa) or (IIb) | —CH₃ | —NO₂ | —OCH₃ | —CH₃ | —OCH₃ | —N— | —C(H)— |
| 964 | (IIa) or (IIb) | —CH₃ | —NO₂ | —OCH₃ | —CH₃ | —OCF₃ | —C(H)— | —C(H)— |
| 965 | (IIa) or (IIb) | —CH₃ | —NO₂ | —OCH₃ | —CH₃ | —OCF₃ | —C(H)— | —N— |
| 966 | (IIa) or (IIb) | —CH₃ | —NO₂ | —OCH₃ | —CH₃ | —OCF₃ | —N— | —C(H)— |
| 967 | (IIa) or (IIb) | —CH₃ | —NO₂ | —OCH₃ | —CH₃ | —F | —C(H)— | —C(H)— |
| 968 | (IIa) or (IIb) | —CH₃ | —NO₂ | —OCH₃ | —CH₃ | —F | —C(H)— | —N— |

-continued

| Compound | $R_6$ | $R_1$ | $R_1'$ | $R_1''$ | $R_1'''$ | Y | Z |
|---|---|---|---|---|---|---|---|
| 969 (IIa) or (IIb) | —CH$_3$ | —NO$_2$ | —OCH$_3$ | —CH$_3$ | —F | —N— | —C(H)— |
| 970 (IIa) or (IIb) | —CH$_3$ | —NO$_2$ | —OCH$_3$ | —OCH$_3$ | —H | —C(H)— | —C(H)— |
| 971 (IIa) or (IIb) | —CH$_3$ | —NO$_2$ | —OCH$_3$ | —OCH$_3$ | —H | —C(H)— | —N— |
| 972 (IIa) or (IIb) | —CH$_3$ | —NO$_2$ | —OCH$_3$ | —OCH$_3$ | —H | —N— | —C(H)— |
| 973 (IIa) or (IIb) | —CH$_3$ | —NO$_2$ | —OCH$_3$ | —OCH$_3$ | —CH$_3$ | —C(H)— | —C(H)— |
| 974 (IIa) or (IIb) | —CH$_3$ | —NO$_2$ | —OCH$_3$ | —OCH$_3$ | —CH$_3$ | —C(H)— | —N— |
| 975 (IIa) or (IIb) | —CH$_3$ | —NO$_2$ | —OCH$_3$ | —OCH$_3$ | —CH$_3$ | —N— | —C(H)— |
| 976 (IIa) or (IIb) | —CH$_3$ | —NO$_2$ | —OCH$_3$ | —OCH$_3$ | —OCH$_3$ | —C(H)— | —C(H)— |
| 977 (IIa) or (IIb) | —CH$_3$ | —NO$_2$ | —OCH$_3$ | —OCH$_3$ | —OCH$_3$ | —C(H)— | —N— |
| 978 (IIa) or (IIb) | —CH$_3$ | —NO$_2$ | —OCH$_3$ | —OCH$_3$ | —OCH$_3$ | —N— | —C(H)— |
| 979 (IIa) or (IIb) | —CH$_3$ | —NO$_2$ | —OCH$_3$ | —OCH$_3$ | —OCF$_3$ | —C(H)— | —C(H)— |
| 980 (IIa) or (IIb) | —CH$_3$ | —NO$_2$ | —OCH$_3$ | —OCH$_3$ | —OCF$_3$ | —C(H)— | —N— |
| 981 (IIa) or (IIb) | —CH$_3$ | —NO$_2$ | —OCH$_3$ | —OCH$_3$ | —OCF$_3$ | —N— | —C(H)— |
| 982 (IIa) or (IIb) | —CH$_3$ | —NO$_2$ | —OCH$_3$ | —OCH$_3$ | —F | —C(H)— | —C(H)— |
| 983 (IIa) or (IIb) | —CH$_3$ | —NO$_2$ | —OCH$_3$ | —OCH$_3$ | —F | —C(H)— | —N— |
| 984 (IIa) or (IIb) | —CH$_3$ | —NO$_2$ | —OCH$_3$ | —OCH$_3$ | —F | —N— | —C(H)— |
| 985 (IIa) or (IIb) | —CH$_3$ | —NO$_2$ | —OCH$_3$ | —NO$_2$ | —H | —C(H)— | —C(H)— |
| 986 (IIa) or (IIb) | —CH$_3$ | —NO$_2$ | —OCH$_3$ | —NO$_2$ | —H | —C(H)— | —N— |
| 987 (IIa) or (IIb) | —CH$_3$ | —NO$_2$ | —OCH$_3$ | —NO$_2$ | —H | —N— | —C(H)— |
| 988 (IIa) or (IIb) | —CH$_3$ | —NO$_2$ | —OCH$_3$ | —NO$_2$ | —CH$_3$ | —C(H)— | —C(H)— |
| 989 (IIa) or (IIb) | —CH$_3$ | —NO$_2$ | —OCH$_3$ | —NO$_2$ | —CH$_3$ | —C(H)— | —N— |
| 990 (IIa) or (IIb) | —CH$_3$ | —NO$_2$ | —OCH$_3$ | —NO$_2$ | —CH$_3$ | —N— | —C(H)— |
| 991 (IIa) or (IIb) | —CH$_3$ | —NO$_2$ | —OCH$_3$ | —NO$_2$ | —OCH$_3$ | —C(H)— | —C(H)— |
| 992 (IIa) or (IIb) | —CH$_3$ | —NO$_2$ | —OCH$_3$ | —NO$_2$ | —OCH$_3$ | —C(H)— | —N— |
| 993 (IIa) or (IIb) | —CH$_3$ | —NO$_2$ | —OCH$_3$ | —NO$_2$ | —OCH$_3$ | —N— | —C(H)— |
| 994 (IIa) or (IIb) | —CH$_3$ | —NO$_2$ | —OCH$_3$ | —NO$_2$ | —OCF$_3$ | —C(H)— | —C(H)— |
| 995 (IIa) or (IIb) | —CH$_3$ | —NO$_2$ | —OCH$_3$ | —NO$_2$ | —OCF$_3$ | —C(H)— | —N— |
| 996 (IIa) or (IIb) | —CH$_3$ | —NO$_2$ | —OCH$_3$ | —NO$_2$ | —OCF$_3$ | —N— | —C(H)— |
| 997 (IIa) or (IIb) | —CH$_3$ | —NO$_2$ | —OCH$_3$ | —NO$_2$ | —F | —C(H)— | —C(H)— |
| 998 (IIa) or (IIb) | —CH$_3$ | —NO$_2$ | —OCH$_3$ | —NO$_2$ | —F | —C(H)— | —N— |
| 999 (IIa) or (IIb) | —CH$_3$ | —NO$_2$ | —OCH$_3$ | —NO$_2$ | —F | —N— | —C(H)— |
| 1000 (IIa) or (IIb) | —CH$_3$ | —OCH$_3$ | —H | —H | —H | —C(H)— | —C(H)— |
| 1001 (IIa) or (IIb) | —CH$_3$ | —OCH$_3$ | —H | —H | —H | —C(H)— | —N— |
| 1002 (IIa) or (IIb) | —CH$_3$ | —OCH$_3$ | —H | —H | —H | —N— | —C(H)— |
| 1003 (IIa) or (IIb) | —CH$_3$ | —OCH$_3$ | —H | —H | —CH$_3$ | —C(H)— | —C(H)— |
| 1004 (IIa) or (IIb) | —CH$_3$ | —OCH$_3$ | —H | —H | —CH$_3$ | —C(H)— | —N— |
| 1005 (IIa) or (IIb) | —CH$_3$ | —OCH$_3$ | —H | —H | —CH$_3$ | —N— | —C(H)— |
| 1006 (IIa) or (IIb) | —CH$_3$ | —OCH$_3$ | —H | —H | —OCH$_3$ | —C(H)— | —C(H)— |
| 1007 (IIa) or (IIb) | —CH$_3$ | —OCH$_3$ | —H | —H | —OCH$_3$ | —C(H)— | —N— |
| 1008 (IIa) or (IIb) | —CH$_3$ | —OCH$_3$ | —H | —H | —OCH$_3$ | —N— | —C(H)— |
| 1009 (IIa) or (IIb) | —CH$_3$ | —OCH$_3$ | —H | —H | —OCF$_3$ | —C(H)— | —C(H)— |
| 1010 (IIa) or (IIb) | —CH$_3$ | —OCH$_3$ | —H | —H | —OCF$_3$ | —C(H)— | —N— |
| 1011 (IIa) or (IIb) | —CH$_3$ | —OCH$_3$ | —H | —H | —OCF$_3$ | —N— | —C(H)— |
| 1012 (IIa) or (IIb) | —CH$_3$ | —OCH$_3$ | —H | —H | —F | —C(H)— | —C(H)— |
| 1013 (IIa) or (IIb) | —CH$_3$ | —OCH$_3$ | —H | —H | —F | —C(H)— | —N— |
| 1014 (IIa) or (IIb) | —CH$_3$ | —OCH$_3$ | —H | —H | —F | —N— | —C(H)— |
| 1015 (IIa) or (IIb) | —CH$_3$ | —OCH$_3$ | —H | —CH$_3$ | —H | —C(H)— | —C(H)— |
| 1016 (IIa) or (IIb) | —CH$_3$ | —OCH$_3$ | —H | —CH$_3$ | —H | —C(H)— | —N— |
| 1017 (IIa) or (IIb) | —CH$_3$ | —OCH$_3$ | —H | —CH$_3$ | —H | —N— | —C(H)— |
| 1018 (IIa) or (IIb) | —CH$_3$ | —OCH$_3$ | —H | —CH$_3$ | —CH$_3$ | —C(H)— | —C(H)— |
| 1019 (IIa) or (IIb) | —CH$_3$ | —OCH$_3$ | —H | —CH$_3$ | —CH$_3$ | —C(H)— | —N— |
| 1020 (IIa) or (IIb) | —CH$_3$ | —OCH$_3$ | —H | —CH$_3$ | —CH$_3$ | —N— | —C(H)— |
| 1021 (IIa) or (IIb) | —CH$_3$ | —OCH$_3$ | —H | —CH$_3$ | —OCH$_3$ | —C(H)— | —C(H)— |
| 1022 (IIa) or (IIb) | —CH$_3$ | —OCH$_3$ | —H | —CH$_3$ | —OCH$_3$ | —C(H)— | —N— |
| 1023 (IIa) or (IIb) | —CH$_3$ | —OCH$_3$ | —H | —CH$_3$ | —OCH$_3$ | —N— | —C(H)— |
| 1024 (IIa) or (IIb) | —CH$_3$ | —OCH$_3$ | —H | —CH$_3$ | —OCF$_3$ | —C(H)— | —C(H)— |
| 1025 (IIa) or (IIb) | —CH$_3$ | —OCH$_3$ | —H | —CH$_3$ | —OCF$_3$ | —C(H)— | —N— |
| 1026 (IIa) or (IIb) | —CH$_3$ | —OCH$_3$ | —H | —CH$_3$ | —OCF$_3$ | —N— | —C(H)— |
| 1027 (IIa) or (IIb) | —CH$_3$ | —OCH$_3$ | —H | —CH$_3$ | —F | —C(H)— | —C(H)— |
| 1028 (IIa) or (IIb) | —CH$_3$ | —OCH$_3$ | —H | —CH$_3$ | —F | —C(H)— | —N— |
| 1029 (IIa) or (IIb) | —CH$_3$ | —OCH$_3$ | —H | —CH$_3$ | —F | —N— | —C(H)— |
| 1030 (IIa) or (IIb) | —CH$_3$ | —OCH$_3$ | —H | —OCH$_3$ | —H | —C(H)— | —C(H)— |
| 1031 (IIa) or (IIb) | —CH$_3$ | —OCH$_3$ | —H | —OCH$_3$ | —H | —C(H)— | —N— |
| 1032 (IIa) or (IIb) | —CH$_3$ | —OCH$_3$ | —H | —OCH$_3$ | —H | —N— | —C(H)— |
| 1033 (IIa) or (IIb) | —CH$_3$ | —OCH$_3$ | —H | —OCH$_3$ | —CH$_3$ | —C(H)— | —C(H)— |
| 1034 (IIa) or (IIb) | —CH$_3$ | —OCH$_3$ | —H | —OCH$_3$ | —CH$_3$ | —C(H)— | —N— |
| 1035 (IIa) or (IIb) | —CH$_3$ | —OCH$_3$ | —H | —OCH$_3$ | —CH$_3$ | —N— | —C(H)— |
| 1036 (IIa) or (IIb) | —CH$_3$ | —OCH$_3$ | —H | —OCH$_3$ | —OCH$_3$ | —C(H)— | —C(H)— |
| 1037 (IIa) or (IIb) | —CH$_3$ | —OCH$_3$ | —H | —OCH$_3$ | —OCH$_3$ | —C(H)— | —N— |
| 1038 (IIa) or (IIb) | —CH$_3$ | —OCH$_3$ | —H | —OCH$_3$ | —OCH$_3$ | —N— | —C(H)— |
| 1039 (IIa) or (IIb) | —CH$_3$ | —OCH$_3$ | —H | —OCH$_3$ | —OCF$_3$ | —C(H)— | —C(H)— |
| 1040 (IIa) or (IIb) | —CH$_3$ | —OCH$_3$ | —H | —OCH$_3$ | —OCF$_3$ | —C(H)— | —N— |
| 1041 (IIa) or (IIb) | —CH$_3$ | —OCH$_3$ | —H | —OCH$_3$ | —OCF$_3$ | —N— | —C(H)— |
| 1042 (IIa) or (IIb) | —CH$_3$ | —OCH$_3$ | —H | —OCH$_3$ | —F | —C(H)— | —C(H)— |
| 1043 (IIa) or (IIb) | —CH$_3$ | —OCH$_3$ | —H | —OCH$_3$ | —F | —C(H)— | —N— |
| 1044 (IIa) or (IIb) | —CH$_3$ | —OCH$_3$ | —H | —OCH$_3$ | —F | —N— | —C(H)— |
| 1045 (IIa) or (IIb) | —CH$_3$ | —OCH$_3$ | —H | —NO$_2$ | —H | —C(H)— | —C(H)— |

-continued

| Compound | | $R_6$ | $R_1$ | $R_1'$ | $R_1''$ | $R_1'''$ | Y | Z |
|---|---|---|---|---|---|---|---|---|
| 1046 | (IIa) or (IIb) | —CH₃ | —OCH₃ | —H | —NO₂ | —H | —C(H)— | —N— |
| 1047 | (IIa) or (IIb) | —CH₃ | —OCH₃ | —H | —NO₂ | —H | —N— | —C(H)— |
| 1048 | (IIa) or (IIb) | —CH₃ | —OCH₃ | —H | —NO₂ | —CH₃ | —C(H)— | —C(H)— |
| 1049 | (IIa) or (IIb) | —CH₃ | —OCH₃ | —H | —NO₂ | —CH₃ | —C(H)— | —N— |
| 1050 | (IIa) or (IIb) | —CH₃ | —OCH₃ | —H | —NO₂ | —CH₃ | —N— | —C(H)— |
| 1051 | (IIa) or (IIb) | —CH₃ | —OCH₃ | —H | —NO₂ | —OCH₃ | —C(H)— | —C(H)— |
| 1052 | (IIa) or (IIb) | —CH₃ | —OCH₃ | —H | —NO₂ | —OCH₃ | —C(H)— | —N— |
| 1053 | (IIa) or (IIb) | —CH₃ | —OCH₃ | —H | —NO₂ | —OCH₃ | —N— | —C(H)— |
| 1054 | (IIa) or (IIb) | —CH₃ | —OCH₃ | —H | —NO₂ | —OCF₃ | —C(H)— | —C(H)— |
| 1055 | (IIa) or (IIb) | —CH₃ | —OCH₃ | —H | —NO₂ | —OCF₃ | —C(H)— | —N— |
| 1056 | (IIa) or (IIb) | —CH₃ | —OCH₃ | —H | —NO₂ | —OCF₃ | —N— | —C(H)— |
| 1057 | (IIa) or (IIb) | —CH₃ | —OCH₃ | —H | —NO₂ | —F | —C(H)— | —C(H)— |
| 1058 | (IIa) or (IIb) | —CH₃ | —OCH₃ | —H | —NO₂ | —F | —C(H)— | —N— |
| 1059 | (IIa) or (IIb) | —CH₃ | —OCH₃ | —H | —NO₂ | —F | —N— | —C(H)— |
| 1060 | (IIa) or (IIb) | —CH₃ | —OCH₃ | —CH₃ | —H | —H | —C(H)— | —C(H)— |
| 1061 | (IIa) or (IIb) | —CH₃ | —OCH₃ | —CH₃ | —H | —H | —C(H)— | —N— |
| 1062 | (IIa) or (IIb) | —CH₃ | —OCH₃ | —CH₃ | —H | —H | —N— | —C(H)— |
| 1063 | (IIa) or (IIb) | —CH₃ | —OCH₃ | —CH₃ | —H | —CH₃ | —C(H)— | —C(H)— |
| 1064 | (IIa) or (IIb) | —CH₃ | —OCH₃ | —CH₃ | —H | —CH₃ | —C(H)— | —N— |
| 1065 | (IIa) or (IIb) | —CH₃ | —OCH₃ | —CH₃ | —H | —CH₃ | —N— | —C(H)— |
| 1066 | (IIa) or (IIb) | —CH₃ | —OCH₃ | —CH₃ | —H | —OCH₃ | —C(H)— | —C(H)— |
| 1067 | (IIa) or (IIb) | —CH₃ | —OCH₃ | —CH₃ | —H | —OCH₃ | —C(H)— | —N— |
| 1068 | (IIa) or (IIb) | —CH₃ | —OCH₃ | —CH₃ | —H | —OCH₃ | —N— | —C(H)— |
| 1069 | (IIa) or (IIb) | —CH₃ | —OCH₃ | —CH₃ | —H | —OCF₃ | —C(H)— | —C(H)— |
| 1070 | (IIa) or (IIb) | —CH₃ | —OCH₃ | —CH₃ | —H | —OCF₃ | —C(H)— | —N— |
| 1071 | (IIa) or (IIb) | —CH₃ | —OCH₃ | —CH₃ | —H | —OCF₃ | —N— | —C(H)— |
| 1072 | (IIa) or (IIb) | —CH₃ | —OCH₃ | —CH₃ | —H | —F | —C(H)— | —C(H)— |
| 1073 | (IIa) or (IIb) | —CH₃ | —OCH₃ | —CH₃ | —H | —F | —C(H)— | —N— |
| 1074 | (IIa) or (IIb) | —CH₃ | —OCH₃ | —CH₃ | —H | —F | —N— | —C(H)— |
| 1075 | (IIa) or (IIb) | —CH₃ | —OCH₃ | —CH₃ | —CH₃ | —H | —C(H)— | —C(H)— |
| 1076 | (IIa) or (IIb) | —CH₃ | —OCH₃ | —CH₃ | —CH₃ | —H | —C(H)— | —N— |
| 1077 | (IIa) or (IIb) | —CH₃ | —OCH₃ | —CH₃ | —CH₃ | —H | —N— | —C(H)— |
| 1078 | (IIa) or (IIb) | —CH₃ | —OCH₃ | —CH₃ | —CH₃ | —CH₃ | —C(H)— | —C(H)— |
| 1079 | (IIa) or (IIb) | —CH₃ | —OCH₃ | —CH₃ | —CH₃ | —CH₃ | —C(H)— | —N— |
| 1080 | (IIa) or (IIb) | —CH₃ | —OCH₃ | —CH₃ | —CH₃ | —CH₃ | —N— | —C(H)— |
| 1081 | (IIa) or (IIb) | —CH₃ | —OCH₃ | —CH₃ | —CH₃ | —OCH₃ | —C(H)— | —C(H)— |
| 1082 | (IIa) or (IIb) | —CH₃ | —OCH₃ | —CH₃ | —CH₃ | —OCH₃ | —C(H)— | —N— |
| 1083 | (IIa) or (IIb) | —CH₃ | —OCH₃ | —CH₃ | —CH₃ | —OCH₃ | —N— | —C(H)— |
| 1084 | (IIa) or (IIb) | —CH₃ | —OCH₃ | —CH₃ | —CH₃ | —OCF₃ | —C(H)— | —C(H)— |
| 1085 | (IIa) or (IIb) | —CH₃ | —OCH₃ | —CH₃ | —CH₃ | —OCF₃ | —C(H)— | —N— |
| 1086 | (IIa) or (IIb) | —CH₃ | —OCH₃ | —CH₃ | —CH₃ | —OCF₃ | —N— | —C(H)— |
| 1087 | (IIa) or (IIb) | —CH₃ | —OCH₃ | —CH₃ | —CH₃ | —F | —C(H)— | —C(H)— |
| 1088 | (IIa) or (IIb) | —CH₃ | —OCH₃ | —CH₃ | —CH₃ | —F | —C(H)— | —N— |
| 1089 | (IIa) or (IIb) | —CH₃ | —OCH₃ | —CH₃ | —CH₃ | —F | —N— | —C(H)— |
| 1090 | (IIa) or (IIb) | —CH₃ | —OCH₃ | —CH₃ | —OCH₃ | —H | —C(H)— | —C(H)— |
| 1091 | (IIa) or (IIb) | —CH₃ | —OCH₃ | —CH₃ | —OCH₃ | —H | —C(H)— | —N— |
| 1092 | (IIa) or (IIb) | —CH₃ | —OCH₃ | —CH₃ | —OCH₃ | —H | —N— | —C(H)— |
| 1093 | (IIa) or (IIb) | —CH₃ | —OCH₃ | —CH₃ | —OCH₃ | —CH₃ | —C(H)— | —C(H)— |
| 1094 | (IIa) or (IIb) | —CH₃ | —OCH₃ | —CH₃ | —OCH₃ | —CH₃ | —C(H)— | —N— |
| 1095 | (IIa) or (IIb) | —CH₃ | —OCH₃ | —CH₃ | —OCH₃ | —CH₃ | —N— | —C(H)— |
| 1096 | (IIa) or (IIb) | —CH₃ | —OCH₃ | —CH₃ | —OCH₃ | —OCH₃ | —C(H)— | —C(H)— |
| 1097 | (IIa) or (IIb) | —CH₃ | —OCH₃ | —CH₃ | —OCH₃ | —OCH₃ | —C(H)— | —N— |
| 1098 | (IIa) or (IIb) | —CH₃ | —OCH₃ | —CH₃ | —OCH₃ | —OCH₃ | —N— | —C(H)— |
| 1099 | (IIa) or (IIb) | —CH₃ | —OCH₃ | —CH₃ | —OCH₃ | —OCF₃ | —C(H)— | —C(H)— |
| 1100 | (IIa) or (IIb) | —CH₃ | —OCH₃ | —CH₃ | —OCH₃ | —OCF₃ | —C(H)— | —N— |
| 1101 | (IIa) or (IIb) | —CH₃ | —OCH₃ | —CH₃ | —OCH₃ | —OCF₃ | —N— | —C(H)— |
| 1102 | (IIa) or (IIb) | —CH₃ | —OCH₃ | —CH₃ | —OCH₃ | —F | —C(H)— | —C(H)— |
| 1103 | (IIa) or (IIb) | —CH₃ | —OCH₃ | —CH₃ | —OCH₃ | —F | —C(H)— | —N— |
| 1104 | (IIa) or (IIb) | —CH₃ | —OCH₃ | —CH₃ | —OCH₃ | —F | —N— | —C(H)— |
| 1105 | (IIa) or (IIb) | —CH₃ | —OCH₃ | —CH₃ | —NO₂ | —H | —C(H)— | —C(H)— |
| 1106 | (IIa) or (IIb) | —CH₃ | —OCH₃ | —CH₃ | —NO₂ | —H | —C(H)— | —N— |
| 1107 | (IIa) or (IIb) | —CH₃ | —OCH₃ | —CH₃ | —NO₂ | —H | —N— | —C(H)— |
| 1108 | (IIa) or (IIb) | —CH₃ | —OCH₃ | —CH₃ | —NO₂ | —CH₃ | —C(H)— | —C(H)— |
| 1109 | (IIa) or (IIb) | —CH₃ | —OCH₃ | —CH₃ | —NO₂ | —CH₃ | —C(H)— | —N— |
| 1110 | (IIa) or (IIb) | —CH₃ | —OCH₃ | —CH₃ | —NO₂ | —CH₃ | —N— | —C(H)— |
| 1111 | (IIa) or (IIb) | —CH₃ | —OCH₃ | —CH₃ | —NO₂ | —OCH₃ | —C(H)— | —C(H)— |
| 1112 | (IIa) or (IIb) | —CH₃ | —OCH₃ | —CH₃ | —NO₂ | —OCH₃ | —C(H)— | —N— |
| 1113 | (IIa) or (IIb) | —CH₃ | —OCH₃ | —CH₃ | —NO₂ | —OCH₃ | —N— | —C(H)— |
| 1114 | (IIa) or (IIb) | —CH₃ | —OCH₃ | —CH₃ | —NO₂ | —OCF₃ | —C(H)— | —C(H)— |
| 1115 | (IIa) or (IIb) | —CH₃ | —OCH₃ | —CH₃ | —NO₂ | —OCF₃ | —C(H)— | —N— |
| 1116 | (IIa) or (IIb) | —CH₃ | —OCH₃ | —CH₃ | —NO₂ | —OCF₃ | —N— | —C(H)— |
| 1117 | (IIa) or (IIb) | —CH₃ | —OCH₃ | —CH₃ | —NO₂ | —F | —C(H)— | —C(H)— |
| 1118 | (IIa) or (IIb) | —CH₃ | —OCH₃ | —CH₃ | —NO₂ | —F | —C(H)— | —N— |
| 1119 | (IIa) or (IIb) | —CH₃ | —OCH₃ | —CH₃ | —NO₂ | —F | —N— | —C(H)— |
| 1120 | (IIa) or (IIb) | —CH₃ | —OCH₃ | —OCH₃ | —H | —H | —C(H)— | —C(H)— |
| 1121 | (IIa) or (IIb) | —CH₃ | —OCH₃ | —OCH₃ | —H | —H | —C(H)— | —N— |
| 1122 | (IIa) or (IIb) | —CH₃ | —OCH₃ | —OCH₃ | —H | —H | —N— | —C(H)— |

-continued

| Compound | R$_6$ | R$_1$ | R$_1$' | R$_1$" | R$_1$''' | Y | Z |
| --- | --- | --- | --- | --- | --- | --- | --- |
| 1123 (IIa) or (IIb) | —CH$_3$ | —OCH$_3$ | —OCH$_3$ | —H | —CH$_3$ | —C(H)— | —C(H)— |
| 1124 (IIa) or (IIb) | —CH$_3$ | —OCH$_3$ | —OCH$_3$ | —H | —CH$_3$ | —C(H)— | —N— |
| 1125 (IIa) or (IIb) | —CH$_3$ | —OCH$_3$ | —OCH$_3$ | —H | —CH$_3$ | —N— | —C(H)— |
| 1126 (IIa) or (IIb) | —CH$_3$ | —OCH$_3$ | —OCH$_3$ | —H | —OCH$_3$ | —C(H)— | —C(H)— |
| 1127 (IIa) or (IIb) | —CH$_3$ | —OCH$_3$ | —OCH$_3$ | —H | —OCH$_3$ | —C(H)— | —N— |
| 1128 (IIa) or (IIb) | —CH$_3$ | —OCH$_3$ | —OCH$_3$ | —H | —OCH$_3$ | —N— | —C(H)— |
| 1129 (IIa) or (IIb) | —CH$_3$ | —OCH$_3$ | —OCH$_3$ | —H | —OCF$_3$ | —C(H)— | —C(H)— |
| 1130 (IIa) or (IIb) | —CH$_3$ | —OCH$_3$ | —OCH$_3$ | —H | —OCF$_3$ | —C(H)— | —N— |
| 1131 (IIa) or (IIb) | —CH$_3$ | —OCH$_3$ | —OCH$_3$ | —H | —OCF$_3$ | —N— | —C(H)— |
| 1132 (IIa) or (IIb) | —CH$_3$ | —OCH$_3$ | —OCH$_3$ | —H | —F | —C(H)— | —C(H)— |
| 1133 (IIa) or (IIb) | —CH$_3$ | —OCH$_3$ | —OCH$_3$ | —H | —F | —C(H)— | —N— |
| 1134 (IIa) or (IIb) | —CH$_3$ | —OCH$_3$ | —OCH$_3$ | —H | —F | —N— | —C(H)— |
| 1135 (IIa) or (IIb) | —CH$_3$ | —OCH$_3$ | —OCH$_3$ | —CH$_3$ | —H | —C(H)— | —C(H)— |
| 1136 (IIa) or (IIb) | —CH$_3$ | —OCH$_3$ | —OCH$_3$ | —CH$_3$ | —H | —C(H)— | —N— |
| 1137 (IIa) or (IIb) | —CH$_3$ | —OCH$_3$ | —OCH$_3$ | —CH$_3$ | —H | —N— | —C(H)— |
| 1138 (IIa) or (IIb) | —CH$_3$ | —OCH$_3$ | —OCH$_3$ | —CH$_3$ | —CH$_3$ | —C(H)— | —C(H)— |
| 1139 (IIa) or (IIb) | —CH$_3$ | —OCH$_3$ | —OCH$_3$ | —CH$_3$ | —CH$_3$ | —C(H)— | —N— |
| 1140 (IIa) or (IIb) | —CH$_3$ | —OCH$_3$ | —OCH$_3$ | —CH$_3$ | —CH$_3$ | —N— | —C(H)— |
| 1141 (IIa) or (IIb) | —CH$_3$ | —OCH$_3$ | —OCH$_3$ | —CH$_3$ | —OCH$_3$ | —C(H)— | —C(H)— |
| 1142 (IIa) or (IIb) | —CH$_3$ | —OCH$_3$ | —OCH$_3$ | —CH$_3$ | —OCH$_3$ | —C(H)— | —N— |
| 1143 (IIa) or (IIb) | —CH$_3$ | —OCH$_3$ | —OCH$_3$ | —CH$_3$ | —OCH$_3$ | —N— | —C(H)— |
| 1144 (IIa) or (IIb) | —CH$_3$ | —OCH$_3$ | —OCH$_3$ | —CH$_3$ | —OCF$_3$ | —C(H)— | —C(H)— |
| 1145 (IIa) or (IIb) | —CH$_3$ | —OCH$_3$ | —OCH$_3$ | —CH$_3$ | —OCF$_3$ | —C(H)— | —N— |
| 1146 (IIa) or (IIb) | —CH$_3$ | —OCH$_3$ | —OCH$_3$ | —CH$_3$ | —OCF$_3$ | —N— | —C(H)— |
| 1147 (IIa) or (IIb) | —CH$_3$ | —OCH$_3$ | —OCH$_3$ | —CH$_3$ | —F | —C(H)— | —C(H)— |
| 1148 (IIa) or (IIb) | —CH$_3$ | —OCH$_3$ | —OCH$_3$ | —CH$_3$ | —F | —C(H)— | —N— |
| 1149 (IIa) or (IIb) | —CH$_3$ | —OCH$_3$ | —OCH$_3$ | —CH$_3$ | —F | —N— | —C(H)— |
| 1150 (IIa) or (IIb) | —CH$_3$ | —OCH$_3$ | —OCH$_3$ | —OCH$_3$ | —H | —C(H)— | —C(H)— |
| 1151 (IIa) or (IIb) | —CH$_3$ | —OCH$_3$ | —OCH$_3$ | —OCH$_3$ | —H | —C(H)— | —N— |
| 1152 (IIa) or (IIb) | —CH$_3$ | —OCH$_3$ | —OCH$_3$ | —OCH$_3$ | —H | —N— | —C(H)— |
| 1153 (IIa) or (IIb) | —CH$_3$ | —OCH$_3$ | —OCH$_3$ | —OCH$_3$ | —CH$_3$ | —C(H)— | —C(H)— |
| 1154 (IIa) or (IIb) | —CH$_3$ | —OCH$_3$ | —OCH$_3$ | —OCH$_3$ | —CH$_3$ | —C(H)— | —N— |
| 1155 (IIa) or (IIb) | —CH$_3$ | —OCH$_3$ | —OCH$_3$ | —OCH$_3$ | —CH$_3$ | —N— | —C(H)— |
| 1156 (IIa) or (IIb) | —CH$_3$ | —OCH$_3$ | —OCH$_3$ | —OCH$_3$ | —OCH$_3$ | —C(H)— | —C(H)— |
| 1157 (IIa) or (IIb) | —CH$_3$ | —OCH$_3$ | —OCH$_3$ | —OCH$_3$ | —OCH$_3$ | —C(H)— | —N— |
| 1158 (IIa) or (IIb) | —CH$_3$ | —OCH$_3$ | —OCH$_3$ | —OCH$_3$ | —OCH$_3$ | —N— | —C(H)— |
| 1159 (IIa) or (IIb) | —CH$_3$ | —OCH$_3$ | —OCH$_3$ | —OCH$_3$ | —OCF$_3$ | —C(H)— | —C(H)— |
| 1160 (IIa) or (IIb) | —CH$_3$ | —OCH$_3$ | —OCH$_3$ | —OCH$_3$ | —OCF$_3$ | —C(H)— | —N— |
| 1161 (IIa) or (IIb) | —CH$_3$ | —OCH$_3$ | —OCH$_3$ | —OCH$_3$ | —OCF$_3$ | —N— | —C(H)— |
| 1162 (IIa) or (IIb) | —CH$_3$ | —OCH$_3$ | —OCH$_3$ | —OCH$_3$ | —F | —C(H)— | —C(H)— |
| 1163 (IIa) or (IIb) | —CH$_3$ | —OCH$_3$ | —OCH$_3$ | —OCH$_3$ | —F | —C(H)— | —N— |
| 1164 (IIa) or (IIb) | —CH$_3$ | —OCH$_3$ | —OCH$_3$ | —OCH$_3$ | —F | —N— | —C(H)— |
| 1165 (IIa) or (IIb) | —CH$_3$ | —OCH$_3$ | —OCH$_3$ | —NO$_2$ | —H | —C(H)— | —C(H)— |
| 1166 (IIa) or (IIb) | —CH$_3$ | —OCH$_3$ | —OCH$_3$ | —NO$_2$ | —H | —C(H)— | —N— |
| 1167 (IIa) or (IIb) | —CH$_3$ | —OCH$_3$ | —OCH$_3$ | —NO$_2$ | —H | —N— | —C(H)— |
| 1168 (IIa) or (IIb) | —CH$_3$ | —OCH$_3$ | —OCH$_3$ | —NO$_2$ | —CH$_3$ | —C(H)— | —C(H)— |
| 1169 (IIa) or (IIb) | —CH$_3$ | —OCH$_3$ | —OCH$_3$ | —NO$_2$ | —CH$_3$ | —C(H)— | —N— |
| 1170 (IIa) or (IIb) | —CH$_3$ | —OCH$_3$ | —OCH$_3$ | —NO$_2$ | —CH$_3$ | —N— | —C(H)— |
| 1171 (IIa) or (IIb) | —CH$_3$ | —OCH$_3$ | —OCH$_3$ | —NO$_2$ | —OCH$_3$ | —C(H)— | —C(H)— |
| 1172 (IIa) or (IIb) | —CH$_3$ | —OCH$_3$ | —OCH$_3$ | —NO$_2$ | —OCH$_3$ | —C(H)— | —N— |
| 1173 (IIa) or (IIb) | —CH$_3$ | —OCH$_3$ | —OCH$_3$ | —NO$_2$ | —OCH$_3$ | —N— | —C(H)— |
| 1174 (IIa) or (IIb) | —CH$_3$ | —OCH$_3$ | —OCH$_3$ | —NO$_2$ | —OCF$_3$ | —C(H)— | —C(H)— |
| 1175 (IIa) or (IIb) | —CH$_3$ | —OCH$_3$ | —OCH$_3$ | —NO$_2$ | —OCF$_3$ | —C(H)— | —N— |
| 1176 (IIa) or (IIb) | —CH$_3$ | —OCH$_3$ | —OCH$_3$ | —NO$_2$ | —OCF$_3$ | —N— | —C(H)— |
| 1177 (IIa) or (IIb) | —CH$_3$ | —OCH$_3$ | —OCH$_3$ | —NO$_2$ | —F | —C(H)— | —C(H)— |
| 1178 (IIa) or (IIb) | —CH$_3$ | —OCH$_3$ | —OCH$_3$ | —NO$_2$ | —F | —C(H)— | —N— |
| 1179 (IIa) or (IIb) | —CH$_3$ | —OCH$_3$ | —OCH$_3$ | —NO$_2$ | —F | —N— | —C(H)— |
| 1180 (IIa) or (IIb) | —CH$_2$OH | —H | —H | —H | —H | —C(H)— | —C(H)— |
| 1181 (IIa) or (IIb) | —CH$_2$OH | —H | —H | —H | —H | —C(H)— | —N— |
| 1182 (IIa) or (IIb) | —CH$_2$OH | —H | —H | —H | —H | —N— | —C(H)— |
| 1183 (IIa) or (IIb) | —CH$_2$OH | —H | —H | —H | —CH$_3$ | —C(H)— | —C(H)— |
| 1184 (IIa) or (IIb) | —CH$_2$OH | —H | —H | —H | —CH$_3$ | —C(H)— | —N— |
| 1185 (IIa) or (IIb) | —CH$_2$OH | —H | —H | —H | —CH$_3$ | —N— | —C(H)— |
| 1186 (IIa) or (IIb) | —CH$_2$OH | —H | —H | —H | —OCH$_3$ | —C(H)— | —C(H)— |
| 1187 (IIa) or (IIb) | —CH$_2$OH | —H | —H | —H | —OCH$_3$ | —C(H)— | —N— |
| 1188 (IIa) or (IIb) | —CH$_2$OH | —H | —H | —H | —OCH$_3$ | —N— | —C(H)— |
| 1189 (IIa) or (IIb) | —CH$_2$OH | —H | —H | —H | —OCF$_3$ | —C(H)— | —C(H)— |
| 1190 (IIa) or (IIb) | —CH$_2$OH | —H | —H | —H | —OCF$_3$ | —C(H)— | —N— |
| 1191 (IIa) or (IIb) | —CH$_2$OH | —H | —H | —H | —OCF$_3$ | —N— | —C(H)— |
| 1192 (IIa) or (IIb) | —CH$_2$OH | —H | —H | —H | —F | —C(H)— | —C(H)— |
| 1193 (IIa) or (IIb) | —CH$_2$OH | —H | —H | —H | —F | —C(H)— | —N— |
| 1194 (IIa) or (IIb) | —CH$_2$OH | —H | —H | —H | —F | —N— | —C(H)— |
| 1195 (IIa) or (IIb) | —CH$_2$OH | —H | —H | —CH$_3$ | —H | —C(H)— | —C(H)— |
| 1196 (IIa) or (IIb) | —CH$_2$OH | —H | —H | —CH$_3$ | —H | —C(H)— | —N— |
| 1197 (IIa) or (IIb) | —CH$_2$OH | —H | —H | —CH$_3$ | —H | —N— | —C(H)— |
| 1198 (IIa) or (IIb) | —CH$_2$OH | —H | —H | —CH$_3$ | —CH$_3$ | —C(H)— | —C(H)— |
| 1199 (IIa) or (IIb) | —CH$_2$OH | —H | —H | —CH$_3$ | —CH$_3$ | —C(H)— | —N— |

-continued

| Compound | | $R_6$ | $R_1$ | $R_1'$ | $R_1''$ | $R_1'''$ | Y | Z |
|---|---|---|---|---|---|---|---|---|
| 1200 | (IIa) or (IIb) | —CH₂OH | —H | —H | —CH₃ | —CH₃ | —N— | —C(H)— |
| 1201 | (IIa) or (IIb) | —CH₂OH | —H | —H | —CH₃ | —OCH₃ | —C(H)— | —C(H)— |
| 1202 | (IIa) or (IIb) | —CH₂OH | —H | —H | —CH₃ | —OCH₃ | —C(H)— | —N— |
| 1203 | (IIa) or (IIb) | —CH₂OH | —H | —H | —CH₃ | —OCH₃ | —N— | —C(H)— |
| 1204 | (IIa) or (IIb) | —CH₂OH | —H | —H | —CH₃ | —OCF₃ | —C(H)— | —C(H)— |
| 1205 | (IIa) or (IIb) | —CH₂OH | —H | —H | —CH₃ | —OCF₃ | —C(H)— | —N— |
| 1206 | (IIa) or (IIb) | —CH₂OH | —H | —H | —CH₃ | —OCF₃ | —N— | —C(H)— |
| 1207 | (IIa) or (IIb) | —CH₂OH | —H | —H | —CH₃ | —F | —C(H)— | —C(H)— |
| 1208 | (IIa) or (IIb) | —CH₂OH | —H | —H | —CH₃ | —F | —C(H)— | —N— |
| 1209 | (IIa) or (IIb) | —CH₂OH | —H | —H | —CH₃ | —F | —N— | —C(H)— |
| 1210 | (IIa) or (IIb) | —CH₂OH | —H | —H | —OCH₃ | —H | —C(H)— | —C(H)— |
| 1211 | (IIa) or (IIb) | —CH₂OH | —H | —H | —OCH₃ | —H | —C(H)— | —N— |
| 1212 | (IIa) or (IIb) | —CH₂OH | —H | —H | —OCH₃ | —H | —N— | —C(H)— |
| 1213 | (IIa) or (IIb) | —CH₂OH | —H | —H | —OCH₃ | —CH₃ | —C(H)— | —C(H)— |
| 1214 | (IIa) or (IIb) | —CH₂OH | —H | —H | —OCH₃ | —CH₃ | —C(H)— | —N— |
| 1215 | (IIa) or (IIb) | —CH₂OH | —H | —H | —OCH₃ | —CH₃ | —N— | —C(H)— |
| 1216 | (IIa) or (IIb) | —CH₂OH | —H | —H | —OCH₃ | —OCH₃ | —C(H)— | —C(H)— |
| 1217 | (IIa) or (IIb) | —CH₂OH | —H | —H | —OCH₃ | —OCH₃ | —C(H)— | —N— |
| 1218 | (IIa) or (IIb) | —CH₂OH | —H | —H | —OCH₃ | —OCH₃ | —N— | —C(H)— |
| 1219 | (IIa) or (IIb) | —CH₂OH | —H | —H | —OCH₃ | —OCF₃ | —C(H)— | —C(H)— |
| 1220 | (IIa) or (IIb) | —CH₂OH | —H | —H | —OCH₃ | —OCF₃ | —C(H)— | —N— |
| 1221 | (IIa) or (IIb) | —CH₂OH | —H | —H | —OCH₃ | —OCF₃ | —N— | —C(H)— |
| 1222 | (IIa) or (IIb) | —CH₂OH | —H | —H | —OCH₃ | —F | —C(H)— | —C(H)— |
| 1223 | (IIa) or (IIb) | —CH₂OH | —H | —H | —OCH₃ | —F | —C(H)— | —N— |
| 1224 | (IIa) or (IIb) | —CH₂OH | —H | —H | —OCH₃ | —F | —N— | —C(H)— |
| 1225 | (IIa) or (IIb) | —CH₂OH | —H | —H | —NO₂ | —H | —C(H)— | —C(H)— |
| 1226 | (IIa) or (IIb) | —CH₂OH | —H | —H | —NO₂ | —H | —C(H)— | —N— |
| 1227 | (IIa) or (IIb) | —CH₂OH | —H | —H | —NO₂ | —H | —N— | —C(H)— |
| 1228 | (IIa) or (IIb) | —CH₂OH | —H | —H | —NO₂ | —CH₃ | —C(H)— | —C(H)— |
| 1229 | (IIa) or (IIb) | —CH₂OH | —H | —H | —NO₂ | —CH₃ | —C(H)— | —N— |
| 1230 | (IIa) or (IIb) | —CH₂OH | —H | —H | —NO₂ | —CH₃ | —N— | —C(H)— |
| 1231 | (IIa) or (IIb) | —CH₂OH | —H | —H | —NO₂ | —OCH₃ | —C(H)— | —C(H)— |
| 1232 | (IIa) or (IIb) | —CH₂OH | —H | —H | —NO₂ | —OCH₃ | —C(H)— | —N— |
| 1233 | (IIa) or (IIb) | —CH₂OH | —H | —H | —NO₂ | —OCH₃ | —N— | —C(H)— |
| 1234 | (IIa) or (IIb) | —CH₂OH | —H | —H | —NO₂ | —OCF₃ | —C(H)— | —C(H)— |
| 1235 | (IIa) or (IIb) | —CH₂OH | —H | —H | —NO₂ | —OCF₃ | —C(H)— | —N— |
| 1236 | (IIa) or (IIb) | —CH₂OH | —H | —H | —NO₂ | —OCF₃ | —N— | —C(H)— |
| 1237 | (IIa) or (IIb) | —CH₂OH | —H | —H | —NO₂ | —F | —C(H)— | —C(H)— |
| 1238 | (IIa) or (IIb) | —CH₂OH | —H | —H | —NO₂ | —F | —C(H)— | —N— |
| 1239 | (IIa) or (IIb) | —CH₂OH | —H | —H | —NO₂ | —F | —N— | —C(H)— |
| 1240 | (IIa) or (IIb) | —CH₂OH | —H | —CH₃ | —H | —H | —C(H)— | —C(H)— |
| 1241 | (IIa) or (IIb) | —CH₂OH | —H | —CH₃ | —H | —H | —C(H)— | —N— |
| 1242 | (IIa) or (IIb) | —CH₂OH | —H | —CH₃ | —H | —H | —N— | —C(H)— |
| 1243 | (IIa) or (IIb) | —CH₂OH | —H | —CH₃ | —H | —CH₃ | —C(H)— | —C(H)— |
| 1244 | (IIa) or (IIb) | —CH₂OH | —H | —CH₃ | —H | —CH₃ | —C(H)— | —N— |
| 1245 | (IIa) or (IIb) | —CH₂OH | —H | —CH₃ | —H | —CH₃ | —N— | —C(H)— |
| 1246 | (IIa) or (IIb) | —CH₂OH | —H | —CH₃ | —H | —OCH₃ | —C(H)— | —C(H)— |
| 1247 | (IIa) or (IIb) | —CH₂OH | —H | —CH₃ | —H | —OCH₃ | —C(H)— | —N— |
| 1248 | (IIa) or (IIb) | —CH₂OH | —H | —CH₃ | —H | —OCH₃ | —N— | —C(H)— |
| 1249 | (IIa) or (IIb) | —CH₂OH | —H | —CH₃ | —H | —OCF₃ | —C(H)— | —C(H)— |
| 1250 | (IIa) or (IIb) | —CH₂OH | —H | —CH₃ | —H | —OCF₃ | —C(H)— | —N— |
| 1251 | (IIa) or (IIb) | —CH₂OH | —H | —CH₃ | —H | —OCF₃ | —N— | —C(H)— |
| 1252 | (IIa) or (IIb) | —CH₂OH | —H | —CH₃ | —H | —F | —C(H)— | —C(H)— |
| 1253 | (IIa) or (IIb) | —CH₂OH | —H | —CH₃ | —H | —F | —C(H)— | —N— |
| 1254 | (IIa) or (IIb) | —CH₂OH | —H | —CH₃ | —H | —F | —N— | —C(H)— |
| 1255 | (IIa) or (IIb) | —CH₂OH | —H | —CH₃ | —CH₃ | —H | —C(H)— | —C(H)— |
| 1256 | (IIa) or (IIb) | —CH₂OH | —H | —CH₃ | —CH₃ | —H | —C(H)— | —N— |
| 1257 | (IIa) or (IIb) | —CH₂OH | —H | —CH₃ | —CH₃ | —H | —N— | —C(H)— |
| 1258 | (IIa) or (IIb) | —CH₂OH | —H | —CH₃ | —CH₃ | —CH₃ | —C(H)— | —C(H)— |
| 1259 | (IIa) or (IIb) | —CH₂OH | —H | —CH₃ | —CH₃ | —CH₃ | —C(H)— | —N— |
| 1260 | (IIa) or (IIb) | —CH₂OH | —H | —CH₃ | —CH₃ | —CH₃ | —N— | —C(H)— |
| 1261 | (IIa) or (IIb) | —CH₂OH | —H | —CH₃ | —CH₃ | —OCH₃ | —C(H)— | —C(H)— |
| 1262 | (IIa) or (IIb) | —CH₂OH | —H | —CH₃ | —CH₃ | —OCH₃ | —C(H)— | —N— |
| 1263 | (IIa) or (IIb) | —CH₂OH | —H | —CH₃ | —CH₃ | —OCH₃ | —N— | —C(H)— |
| 1264 | (IIa) or (IIb) | —CH₂OH | —H | —CH₃ | —CH₃ | —OCF₃ | —C(H)— | —C(H)— |
| 1265 | (IIa) or (IIb) | —CH₂OH | —H | —CH₃ | —CH₃ | —OCF₃ | —C(H)— | —N— |
| 1266 | (IIa) or (IIb) | —CH₂OH | —H | —CH₃ | —CH₃ | —OCF₃ | —N— | —C(H)— |
| 1267 | (IIa) or (IIb) | —CH₂OH | —H | —CH₃ | —CH₃ | —F | —C(H)— | —C(H)— |
| 1268 | (IIa) or (IIb) | —CH₂OH | —H | —CH₃ | —CH₃ | —F | —C(H)— | —N— |
| 1269 | (IIa) or (IIb) | —CH₂OH | —H | —CH₃ | —CH₃ | —F | —N— | —C(H)— |
| 1270 | (IIa) or (IIb) | —CH₂OH | —H | —CH₃ | —OCH₃ | —H | —C(H)— | —C(H)— |
| 1271 | (IIa) or (IIb) | —CH₂OH | —H | —CH₃ | —OCH₃ | —H | —C(H)— | —N— |
| 1272 | (IIa) or (IIb) | —CH₂OH | —H | —CH₃ | —OCH₃ | —H | —N— | —C(H)— |
| 1273 | (IIa) or (IIb) | —CH₂OH | —H | —CH₃ | —OCH₃ | —CH₃ | —C(H)— | —C(H)— |
| 1274 | (IIa) or (IIb) | —CH₂OH | —H | —CH₃ | —OCH₃ | —CH₃ | —C(H)— | —N— |
| 1275 | (IIa) or (IIb) | —CH₂OH | —H | —CH₃ | —OCH₃ | —CH₃ | —N— | —C(H)— |
| 1276 | (IIa) or (IIb) | —CH₂OH | —H | —CH₃ | —OCH₃ | —OCH₃ | —C(H)— | —C(H)— |

-continued

| Compound | R₆ | R₁ | R₁' | R₁'' | R₁''' | Y | Z |
|---|---|---|---|---|---|---|---|
| 1277 (IIa) or (IIb) | —CH₂OH | —H | —CH₃ | —OCH₃ | —OCH₃ | —C(H)— | —N— |
| 1278 (IIa) or (IIb) | —CH₂OH | —H | —CH₃ | —OCH₃ | —OCH₃ | —N— | —C(H)— |
| 1279 (IIa) or (IIb) | —CH₂OH | —H | —CH₃ | —OCH₃ | —OCF₃ | —C(H)— | —C(H)— |
| 1280 (IIa) or (IIb) | —CH₂OH | —H | —CH₃ | —OCH₃ | —OCF₃ | —C(H)— | —N— |
| 1281 (IIa) or (IIb) | —CH₂OH | —H | —CH₃ | —OCH₃ | —OCF₃ | —N— | —C(H)— |
| 1282 (IIa) or (IIb) | —CH₂OH | —H | —CH₃ | —OCH₃ | —F | —C(H)— | —C(H)— |
| 1283 (IIa) or (IIb) | —CH₂OH | —H | —CH₃ | —OCH₃ | —F | —C(H)— | —N— |
| 1284 (IIa) or (IIb) | —CH₂OH | —H | —CH₃ | —OCH₃ | —F | —N— | —C(H)— |
| 1285 (IIa) or (IIb) | —CH₂OH | —H | —CH₃ | —NO₂ | —H | —C(H)— | —C(H)— |
| 1286 (IIa) or (IIb) | —CH₂OH | —H | —CH₃ | —NO₂ | —H | —C(H)— | —N— |
| 1287 (IIa) or (IIb) | —CH₂OH | —H | —CH₃ | —NO₂ | —H | —N— | —C(H)— |
| 1288 (IIa) or (IIb) | —CH₂OH | —H | —CH₃ | —NO₂ | —CH₃ | —C(H)— | —C(H)— |
| 1289 (IIa) or (IIb) | —CH₂OH | —H | —CH₃ | —NO₂ | —CH₃ | —C(H)— | —N— |
| 1290 (IIa) or (IIb) | —CH₂OH | —H | —CH₃ | —NO₂ | —CH₃ | —N— | —C(H)— |
| 1291 (IIa) or (IIb) | —CH₂OH | —H | —CH₃ | —NO₂ | —OCH₃ | —C(H)— | —C(H)— |
| 1292 (IIa) or (IIb) | —CH₂OH | —H | —CH₃ | —NO₂ | —OCH₃ | —C(H)— | —N— |
| 1293 (IIa) or (IIb) | —CH₂OH | —H | —CH₃ | —NO₂ | —OCH₃ | —N— | —C(H)— |
| 1294 (IIa) or (IIb) | —CH₂OH | —H | —CH₃ | —NO₂ | —OCF₃ | —C(H)— | —C(H)— |
| 1295 (IIa) or (IIb) | —CH₂OH | —H | —CH₃ | —NO₂ | —OCF₃ | —C(H)— | —N— |
| 1296 (IIa) or (IIb) | —CH₂OH | —H | —CH₃ | —NO₂ | —OCF₃ | —N— | —C(H)— |
| 1297 (IIa) or (IIb) | —CH₂OH | —H | —CH₃ | —NO₂ | —F | —C(H)— | —C(H)— |
| 1298 (IIa) or (IIb) | —CH₂OH | —H | —CH₃ | —NO₂ | —F | —C(H)— | —N— |
| 1299 (IIa) or (IIb) | —CH₂OH | —H | —CH₃ | —NO₂ | —F | —N— | —C(H)— |
| 1300 (IIa) or (IIb) | —CH₂OH | —H | —OCH₃ | —H | —H | —C(H)— | —C(H)— |
| 1301 (IIa) or (IIb) | —CH₂OH | —H | —OCH₃ | —H | —H | —C(H)— | —N— |
| 1302 (IIa) or (IIb) | —CH₂OH | —H | —OCH₃ | —H | —H | —N— | —C(H)— |
| 1303 (IIa) or (IIb) | —CH₂OH | —H | —OCH₃ | —H | —CH₃ | —C(H)— | —C(H)— |
| 1304 (IIa) or (IIb) | —CH₂OH | —H | —OCH₃ | —H | —CH₃ | —C(H)— | —N— |
| 1305 (IIa) or (IIb) | —CH₂OH | —H | —OCH₃ | —H | —CH₃ | —N— | —C(H)— |
| 1306 (IIa) or (IIb) | —CH₂OH | —H | —OCH₃ | —H | —OCH₃ | —C(H)— | —C(H)— |
| 1307 (IIa) or (IIb) | —CH₂OH | —H | —OCH₃ | —H | —OCH₃ | —C(H)— | —N— |
| 1308 (IIa) or (IIb) | —CH₂OH | —H | —OCH₃ | —H | —OCH₃ | —N— | —C(H)— |
| 1309 (IIa) or (IIb) | —CH₂OH | —H | —OCH₃ | —H | —OCF₃ | —C(H)— | —C(H)— |
| 1310 (IIa) or (IIb) | —CH₂OH | —H | —OCH₃ | —H | —OCF₃ | —C(H)— | —N— |
| 1311 (IIa) or (IIb) | —CH₂OH | —H | —OCH₃ | —H | —OCF₃ | —N— | —C(H)— |
| 1312 (IIa) or (IIb) | —CH₂OH | —H | —OCH₃ | —H | —F | —C(H)— | —C(H)— |
| 1313 (IIa) or (IIb) | —CH₂OH | —H | —OCH₃ | —H | —F | —C(H)— | —N— |
| 1314 (IIa) or (IIb) | —CH₂OH | —H | —OCH₃ | —H | —F | —N— | —C(H)— |
| 1315 (IIa) or (IIb) | —CH₂OH | —H | —OCH₃ | —CH₃ | —H | —C(H)— | —C(H)— |
| 1316 (IIa) or (IIb) | —CH₂OH | —H | —OCH₃ | —CH₃ | —H | —C(H)— | —N— |
| 1317 (IIa) or (IIb) | —CH₂OH | —H | —OCH₃ | —CH₃ | —H | —N— | —C(H)— |
| 1318 (IIa) or (IIb) | —CH₂OH | —H | —OCH₃ | —CH₃ | —CH₃ | —C(H)— | —C(H)— |
| 1319 (IIa) or (IIb) | —CH₂OH | —H | —OCH₃ | —CH₃ | —CH₃ | —C(H)— | —N— |
| 1320 (IIa) or (IIb) | —CH₂OH | —H | —OCH₃ | —CH₃ | —CH₃ | —N— | —C(H)— |
| 1321 (IIa) or (IIb) | —CH₂OH | —H | —OCH₃ | —CH₃ | —OCH₃ | —C(H)— | —C(H)— |
| 1322 (IIa) or (IIb) | —CH₂OH | —H | —OCH₃ | —CH₃ | —OCH₃ | —C(H)— | —N— |
| 1323 (IIa) or (IIb) | —CH₂OH | —H | —OCH₃ | —CH₃ | —OCH₃ | —N— | —C(H)— |
| 1324 (IIa) or (IIb) | —CH₂OH | —H | —OCH₃ | —CH₃ | —OCF₃ | —C(H)— | —C(H)— |
| 1325 (IIa) or (IIb) | —CH₂OH | —H | —OCH₃ | —CH₃ | —OCF₃ | —C(H)— | —N— |
| 1326 (IIa) or (IIb) | —CH₂OH | —H | —OCH₃ | —CH₃ | —OCF₃ | —N— | —C(H)— |
| 1327 (IIa) or (IIb) | —CH₂OH | —H | —OCH₃ | —CH₃ | —F | —C(H)— | —C(H)— |
| 1328 (IIa) or (IIb) | —CH₂OH | —H | —OCH₃ | —CH₃ | —F | —C(H)— | —N— |
| 1329 (IIa) or (IIb) | —CH₂OH | —H | —OCH₃ | —CH₃ | —F | —N— | —C(H)— |
| 1330 (IIa) or (IIb) | —CH₂OH | —H | —OCH₃ | —OCH₃ | —H | —C(H)— | —C(H)— |
| 1331 (IIa) or (IIb) | —CH₂OH | —H | —OCH₃ | —OCH₃ | —H | —C(H)— | —N— |
| 1332 (IIa) or (IIb) | —CH₂OH | —H | —OCH₃ | —OCH₃ | —H | —N— | —C(H)— |
| 1333 (IIa) or (IIb) | —CH₂OH | —H | —OCH₃ | —OCH₃ | —CH₃ | —C(H)— | —C(H)— |
| 1334 (IIa) or (IIb) | —CH₂OH | —H | —OCH₃ | —OCH₃ | —CH₃ | —C(H)— | —N— |
| 1335 (IIa) or (IIb) | —CH₂OH | —H | —OCH₃ | —OCH₃ | —CH₃ | —N— | —C(H)— |
| 1336 (IIa) or (IIb) | —CH₂OH | —H | —OCH₃ | —OCH₃ | —OCH₃ | —C(H)— | —C(H)— |
| 1337 (IIa) or (IIb) | —CH₂OH | —H | —OCH₃ | —OCH₃ | —OCH₃ | —C(H)— | —N— |
| 1338 (IIa) or (IIb) | —CH₂OH | —H | —OCH₃ | —OCH₃ | —OCH₃ | —N— | —C(H)— |
| 1339 (IIa) or (IIb) | —CH₂OH | —H | —OCH₃ | —OCH₃ | —OCF₃ | —C(H)— | —C(H)— |
| 1340 (IIa) or (IIb) | —CH₂OH | —H | —OCH₃ | —OCH₃ | —OCF₃ | —C(H)— | —N— |
| 1341 (IIa) or (IIb) | —CH₂OH | —H | —OCH₃ | —OCH₃ | —OCF₃ | —N— | —C(H)— |
| 1342 (IIa) or (IIb) | —CH₂OH | —H | —OCH₃ | —OCH₃ | —F | —C(H)— | —C(H)— |
| 1343 (IIa) or (IIb) | —CH₂OH | —H | —OCH₃ | —OCH₃ | —F | —C(H)— | —N— |
| 1344 (IIa) or (IIb) | —CH₂OH | —H | —OCH₃ | —OCH₃ | —F | —N— | —C(H)— |
| 1345 (IIa) or (IIb) | —CH₂OH | —H | —OCH₃ | —NO₂ | —H | —C(H)— | —C(H)— |
| 1346 (IIa) or (IIb) | —CH₂OH | —H | —OCH₃ | —NO₂ | —H | —C(H)— | —N— |
| 1347 (IIa) or (IIb) | —CH₂OH | —H | —OCH₃ | —NO₂ | —H | —N— | —C(H)— |
| 1348 (IIa) or (IIb) | —CH₂OH | —H | —OCH₃ | —NO₂ | —CH₃ | —C(H)— | —C(H)— |
| 1349 (IIa) or (IIb) | —CH₂OH | —H | —OCH₃ | —NO₂ | —CH₃ | —C(H)— | —N— |
| 1350 (IIa) or (IIb) | —CH₂OH | —H | —OCH₃ | —NO₂ | —CH₃ | —N— | —C(H)— |
| 1351 (IIa) or (IIb) | —CH₂OH | —H | —OCH₃ | —NO₂ | —OCH₃ | —C(H)— | —C(H)— |
| 1352 (IIa) or (IIb) | —CH₂OH | —H | —OCH₃ | —NO₂ | —OCH₃ | —C(H)— | —N— |
| 1353 (IIa) or (IIb) | —CH₂OH | —H | —OCH₃ | —NO₂ | —OCH₃ | —N— | —C(H)— |

| Compound | R₆ | R₁ | R₁' | R₁" | R₁'" | Y | Z |
|---|---|---|---|---|---|---|---|
| 1354 (IIa) or (IIb) | —CH₂OH | —H | —OCH₃ | —NO₂ | —OCF₃ | —C(H)— | —C(H)— |
| 1355 (IIa) or (IIb) | —CH₂OH | —H | —OCH₃ | —NO₂ | —OCF₃ | —C(H)— | —N— |
| 1356 (IIa) or (IIb) | —CH₂OH | —H | —OCH₃ | —NO₂ | —OCF₃ | —N— | —C(H)— |
| 1357 (IIa) or (IIb) | —CH₂OH | —H | —OCH₃ | —NO₂ | —F | —C(H)— | —C(H)— |
| 1358 (IIa) or (IIb) | —CH₂OH | —H | —OCH₃ | —NO₂ | —F | —C(H)— | —N— |
| 1359 (IIa) or (IIb) | —CH₂OH | —H | —OCH₃ | —NO₂ | —F | —N— | —C(H)— |
| 1360 (IIa) or (IIb) | —CH₂OH | —NO₂ | —H | —H | —H | —C(H)— | —C(H)— |
| 1361 (IIa) or (IIb) | —CH₂OH | —NO₂ | —H | —H | —H | —C(H)— | —N— |
| 1362 (IIa) or (IIb) | —CH₂OH | —NO₂ | —H | —H | —H | —N— | —C(H)— |
| 1363 (IIa) or (IIb) | —CH₂OH | —NO₂ | —H | —H | —CH₃ | —C(H)— | —C(H)— |
| 1364 (IIa) or (IIb) | —CH₂OH | —NO₂ | —H | —H | —CH₃ | —C(H)— | —N— |
| 1365 (IIa) or (IIb) | —CH₂OH | —NO₂ | —H | —H | —CH₃ | —N— | —C(H)— |
| 1366 (IIa) or (IIb) | —CH₂OH | —NO₂ | —H | —H | —OCH₃ | —C(H)— | —C(H)— |
| 1367 (IIa) or (IIb) | —CH₂OH | —NO₂ | —H | —H | —OCH₃ | —C(H)— | —N— |
| 1368 (IIa) or (IIb) | —CH₂OH | —NO₂ | —H | —H | —OCH₃ | —N— | —C(H)— |
| 1369 (IIa) or (IIb) | —CH₂OH | —NO₂ | —H | —H | —OCF₃ | —C(H)— | —C(H)— |
| 1370 (IIa) or (IIb) | —CH₂OH | —NO₂ | —H | —H | —OCF₃ | —C(H)— | —N— |
| 1371 (IIa) or (IIb) | —CH₂OH | —NO₂ | —H | —H | —OCF₃ | —N— | —C(H)— |
| 1372 (IIa) or (IIb) | —CH₂OH | —NO₂ | —H | —H | —F | —C(H)— | —C(H)— |
| 1373 (IIa) or (IIb) | —CH₂OH | —NO₂ | —H | —H | —F | —C(H)— | —N— |
| 1374 (IIa) or (IIb) | —CH₂OH | —NO₂ | —H | —H | —F | —N— | —C(H)— |
| 1375 (IIa) or (IIb) | —CH₂OH | —NO₂ | —H | —CH₃ | —H | —C(H)— | —C(H)— |
| 1376 (IIa) or (IIb) | —CH₂OH | —NO₂ | —H | —CH₃ | —H | —C(H)— | —N— |
| 1377 (IIa) or (IIb) | —CH₂OH | —NO₂ | —H | —CH₃ | —H | —N— | —C(H)— |
| 1378 (IIa) or (IIb) | —CH₂OH | —NO₂ | —H | —CH₃ | —CH₃ | —C(H)— | —C(H)— |
| 1379 (IIa) or (IIb) | —CH₂OH | —NO₂ | —H | —CH₃ | —CH₃ | —C(H)— | —N— |
| 1380 (IIa) or (IIb) | —CH₂OH | —NO₂ | —H | —CH₃ | —CH₃ | —N— | —C(H)— |
| 1381 (IIa) or (IIb) | —CH₂OH | —NO₂ | —H | —CH₃ | —OCH₃ | —C(H)— | —C(H)— |
| 1382 (IIa) or (IIb) | —CH₂OH | —NO₂ | —H | —CH₃ | —OCH₃ | —C(H)— | —N— |
| 1383 (IIa) or (IIb) | —CH₂OH | —NO₂ | —H | —CH₃ | —OCH₃ | —N— | —C(H)— |
| 1384 (IIa) or (IIb) | —CH₂OH | —NO₂ | —H | —CH₃ | —OCF₃ | —C(H)— | —C(H)— |
| 1385 (IIa) or (IIb) | —CH₂OH | —NO₂ | —H | —CH₃ | —OCF₃ | —C(H)— | —N— |
| 1386 (IIa) or (IIb) | —CH₂OH | —NO₂ | —H | —CH₃ | —OCF₃ | —N— | —C(H)— |
| 1387 (IIa) or (IIb) | —CH₂OH | —NO₂ | —H | —CH₃ | —F | —C(H)— | —C(H)— |
| 1388 (IIa) or (IIb) | —CH₂OH | —NO₂ | —H | —CH₃ | —F | —C(H)— | —N— |
| 1389 (IIa) or (IIb) | —CH₂OH | —NO₂ | —H | —CH₃ | —F | —N— | —C(H)— |
| 1390 (IIa) or (IIb) | —CH₂OH | —NO₂ | —H | —OCH₃ | —H | —C(H)— | —C(H)— |
| 1391 (IIa) or (IIb) | —CH₂OH | —NO₂ | —H | —OCH₃ | —H | —C(H)— | —N— |
| 1392 (IIa) or (IIb) | —CH₂OH | —NO₂ | —H | —OCH₃ | —H | —N— | —C(H)— |
| 1393 (IIa) or (IIb) | —CH₂OH | —NO₂ | —H | —OCH₃ | —CH₃ | —C(H)— | —C(H)— |
| 1394 (IIa) or (IIb) | —CH₂OH | —NO₂ | —H | —OCH₃ | —CH₃ | —C(H)— | —N— |
| 1395 (IIa) or (IIb) | —CH₂OH | —NO₂ | —H | —OCH₃ | —CH₃ | —N— | —C(H)— |
| 1396 (IIa) or (IIb) | —CH₂OH | —NO₂ | —H | —OCH₃ | —OCH₃ | —C(H)— | —C(H)— |
| 1397 (IIa) or (IIb) | —CH₂OH | —NO₂ | —H | —OCH₃ | —OCH₃ | —C(H)— | —N— |
| 1398 (IIa) or (IIb) | —CH₂OH | —NO₂ | —H | —OCH₃ | —OCH₃ | —N— | —C(H)— |
| 1399 (IIa) or (IIb) | —CH₂OH | —NO₂ | —H | —OCH₃ | —OCF₃ | —C(H)— | —C(H)— |
| 1400 (IIa) or (IIb) | —CH₂OH | —NO₂ | —H | —OCH₃ | —OCF₃ | —C(H)— | —N— |
| 1401 (IIa) or (IIb) | —CH₂OH | —NO₂ | —H | —OCH₃ | —OCF₃ | —N— | —C(H)— |
| 1402 (IIa) or (IIb) | —CH₂OH | —NO₂ | —H | —OCH₃ | —F | —C(H)— | —C(H)— |
| 1403 (IIa) or (IIb) | —CH₂OH | —NO₂ | —H | —OCH₃ | —F | —C(H)— | —N— |
| 1404 (IIa) or (IIb) | —CH₂OH | —NO₂ | —H | —OCH₃ | —F | —N— | —C(H)— |
| 1405 (IIa) or (IIb) | —CH₂OH | —NO₂ | —H | —NO₂ | —H | —C(H)— | —C(H)— |
| 1406 (IIa) or (IIb) | —CH₂OH | —NO₂ | —H | —NO₂ | —H | —C(H)— | —N— |
| 1407 (IIa) or (IIb) | —CH₂OH | —NO₂ | —H | —NO₂ | —H | —N— | —C(H)— |
| 1408 (IIa) or (IIb) | —CH₂OH | —NO₂ | —H | —NO₂ | —CH₃ | —C(H)— | —C(H)— |
| 1409 (IIa) or (IIb) | —CH₂OH | —NO₂ | —H | —NO₂ | —CH₃ | —C(H)— | —N— |
| 1410 (IIa) or (IIb) | —CH₂OH | —NO₂ | —H | —NO₂ | —CH₃ | —N— | —C(H)— |
| 1411 (IIa) or (IIb) | —CH₂OH | —NO₂ | —H | —NO₂ | —OCH₃ | —C(H)— | —C(H)— |
| 1412 (IIa) or (IIb) | —CH₂OH | —NO₂ | —H | —NO₂ | —OCH₃ | —C(H)— | —N— |
| 1413 (IIa) or (IIb) | —CH₂OH | —NO₂ | —H | —NO₂ | —OCH₃ | —N— | —C(H)— |
| 1414 (IIa) or (IIb) | —CH₂OH | —NO₂ | —H | —NO₂ | —OCF₃ | —C(H)— | —C(H)— |
| 1415 (IIa) or (IIb) | —CH₂OH | —NO₂ | —H | —NO₂ | —OCF₃ | —C(H)— | —N— |
| 1416 (IIa) or (IIb) | —CH₂OH | —NO₂ | —H | —NO₂ | —OCF₃ | —N— | —C(H)— |
| 1417 (IIa) or (IIb) | —CH₂OH | —NO₂ | —H | —NO₂ | —F | —C(H)— | —C(H)— |
| 1418 (IIa) or (IIb) | —CH₂OH | —NO₂ | —H | —NO₂ | —F | —C(H)— | —N— |
| 1419 (IIa) or (IIb) | —CH₂OH | —NO₂ | —H | —NO₂ | —F | —N— | —C(H)— |
| 1420 (IIa) or (IIb) | —CH₂OH | —NO₂ | —CH₃ | —H | —H | —C(H)— | —C(H)— |
| 1421 (IIa) or (IIb) | —CH₂OH | —NO₂ | —CH₃ | —H | —H | —C(H)— | —N— |
| 1422 (IIa) or (IIb) | —CH₂OH | —NO₂ | —CH₃ | —H | —H | —N— | —C(H)— |
| 1423 (IIa) or (IIb) | —CH₂OH | —NO₂ | —CH₃ | —H | —CH₃ | —C(H)— | —C(H)— |
| 1424 (IIa) or (IIb) | —CH₂OH | —NO₂ | —CH₃ | —H | —CH₃ | —C(H)— | —N— |
| 1425 (IIa) or (IIb) | —CH₂OH | —NO₂ | —CH₃ | —H | —CH₃ | —N— | —C(H)— |
| 1426 (IIa) or (IIb) | —CH₂OH | —NO₂ | —CH₃ | —H | —OCH₃ | —C(H)— | —C(H)— |
| 1427 (IIa) or (IIb) | —CH₂OH | —NO₂ | —CH₃ | —H | —OCH₃ | —C(H)— | —N— |
| 1428 (IIa) or (IIb) | —CH₂OH | —NO₂ | —CH₃ | —H | —OCH₃ | —N— | —C(H)— |
| 1429 (IIa) or (IIb) | —CH₂OH | —NO₂ | —CH₃ | —H | —OCF₃ | —C(H)— | —C(H)— |
| 1430 (IIa) or (IIb) | —CH₂OH | —NO₂ | —CH₃ | —H | —OCF₃ | —C(H)— | —N— |

| Compound | $R_6$ | $R_1$ | $R_1'$ | $R_1''$ | $R_1'''$ | Y | Z |
|---|---|---|---|---|---|---|---|
| 1431 (IIa) or (IIb) | —CH$_2$OH | —NO$_2$ | —CH$_3$ | —H | —OCF$_3$ | —N— | —C(H)— |
| 1432 (IIa) or (IIb) | —CH$_2$OH | —NO$_2$ | —CH$_3$ | —H | —F | —C(H)— | —C(H)— |
| 1433 (IIa) or (IIb) | —CH$_2$OH | —NO$_2$ | —CH$_3$ | —H | —F | —C(H)— | —N— |
| 1434 (IIa) or (IIb) | —CH$_2$OH | —NO$_2$ | —CH$_3$ | —H | —F | —N— | —C(H)— |
| 1435 (IIa) or (IIb) | —CH$_2$OH | —NO$_2$ | —CH$_3$ | —CH$_3$ | —H | —C(H)— | —C(H)— |
| 1436 (IIa) or (IIb) | —CH$_2$OH | —NO$_2$ | —CH$_3$ | —CH$_3$ | —H | —C(H)— | —N— |
| 1437 (IIa) or (IIb) | —CH$_2$OH | —NO$_2$ | —CH$_3$ | —CH$_3$ | —H | —N— | —C(H)— |
| 1438 (IIa) or (IIb) | —CH$_2$OH | —NO$_2$ | —CH$_3$ | —CH$_3$ | —CH$_3$ | —C(H)— | —C(H)— |
| 1439 (IIa) or (IIb) | —CH$_2$OH | —NO$_2$ | —CH$_3$ | —CH$_3$ | —CH$_3$ | —C(H)— | —N— |
| 1440 (IIa) or (IIb) | —CH$_2$OH | —NO$_2$ | —CH$_3$ | —CH$_3$ | —CH$_3$ | —N— | —C(H)— |
| 1441 (IIa) or (IIb) | —CH$_2$OH | —NO$_2$ | —CH$_3$ | —CH$_3$ | —OCH$_3$ | —C(H)— | —C(H)— |
| 1442 (IIa) or (IIb) | —CH$_2$OH | —NO$_2$ | —CH$_3$ | —CH$_3$ | —OCH$_3$ | —C(H)— | —N— |
| 1443 (IIa) or (IIb) | —CH$_2$OH | —NO$_2$ | —CH$_3$ | —CH$_3$ | —OCH$_3$ | —N— | —C(H)— |
| 1444 (IIa) or (IIb) | —CH$_2$OH | —NO$_2$ | —CH$_3$ | —CH$_3$ | —OCF$_3$ | —C(H)— | —C(H)— |
| 1445 (IIa) or (IIb) | —CH$_2$OH | —NO$_2$ | —CH$_3$ | —CH$_3$ | —OCF$_3$ | —C(H)— | —N— |
| 1446 (IIa) or (IIb) | —CH$_2$OH | —NO$_2$ | —CH$_3$ | —CH$_3$ | —OCF$_3$ | —N— | —C(H)— |
| 1447 (IIa) or (IIb) | —CH$_2$OH | —NO$_2$ | —CH$_3$ | —CH$_3$ | —F | —C(H)— | —C(H)— |
| 1448 (IIa) or (IIb) | —CH$_2$OH | —NO$_2$ | —CH$_3$ | —CH$_3$ | —F | —C(H)— | —N— |
| 1449 (IIa) or (IIb) | —CH$_2$OH | —NO$_2$ | —CH$_3$ | —CH$_3$ | —F | —N— | —C(H)— |
| 1450 (IIa) or (IIb) | —CH$_2$OH | —NO$_2$ | —CH$_3$ | —OCH$_3$ | —H | —C(H)— | —C(H)— |
| 1451 (IIa) or (IIb) | —CH$_2$OH | —NO$_2$ | —CH$_3$ | —OCH$_3$ | —H | —C(H)— | —N— |
| 1452 (IIa) or (IIb) | —CH$_2$OH | —NO$_2$ | —CH$_3$ | —OCH$_3$ | —H | —N— | —C(H)— |
| 1453 (IIa) or (IIb) | —CH$_2$OH | —NO$_2$ | —CH$_3$ | —OCH$_3$ | —CH$_3$ | —C(H)— | —C(H)— |
| 1454 (IIa) or (IIb) | —CH$_2$OH | —NO$_2$ | —CH$_3$ | —OCH$_3$ | —CH$_3$ | —C(H)— | —N— |
| 1455 (IIa) or (IIb) | —CH$_2$OH | —NO$_2$ | —CH$_3$ | —OCH$_3$ | —CH$_3$ | —N— | —C(H)— |
| 1456 (IIa) or (IIb) | —CH$_2$OH | —NO$_2$ | —CH$_3$ | —OCH$_3$ | —OCH$_3$ | —C(H)— | —C(H)— |
| 1457 (IIa) or (IIb) | —CH$_2$OH | —NO$_2$ | —CH$_3$ | —OCH$_3$ | —OCH$_3$ | —C(H)— | —N— |
| 1458 (IIa) or (IIb) | —CH$_2$OH | —NO$_2$ | —CH$_3$ | —OCH$_3$ | —OCH$_3$ | —N— | —C(H)— |
| 1459 (IIa) or (IIb) | —CH$_2$OH | —NO$_2$ | —CH$_3$ | —OCH$_3$ | —OCF$_3$ | —C(H)— | —C(H)— |
| 1460 (IIa) or (IIb) | —CH$_2$OH | —NO$_2$ | —CH$_3$ | —OCH$_3$ | —OCF$_3$ | —C(H)— | —N— |
| 1461 (IIa) or (IIb) | —CH$_2$OH | —NO$_2$ | —CH$_3$ | —OCH$_3$ | —OCF$_3$ | —N— | —C(H)— |
| 1462 (IIa) or (IIb) | —CH$_2$OH | —NO$_2$ | —CH$_3$ | —OCH$_3$ | —F | —C(H)— | —C(H)— |
| 1463 (IIa) or (IIb) | —CH$_2$OH | —NO$_2$ | —CH$_3$ | —OCH$_3$ | —F | —C(H)— | —N— |
| 1464 (IIa) or (IIb) | —CH$_2$OH | —NO$_2$ | —CH$_3$ | —OCH$_3$ | —F | —N— | —C(H)— |
| 1465 (IIa) or (IIb) | —CH$_2$OH | —NO$_2$ | —CH$_3$ | —NO$_2$ | —H | —C(H)— | —C(H)— |
| 1466 (IIa) or (IIb) | —CH$_2$OH | —NO$_2$ | —CH$_3$ | —NO$_2$ | —H | —C(H)— | —N— |
| 1467 (IIa) or (IIb) | —CH$_2$OH | —NO$_2$ | —CH$_3$ | —NO$_2$ | —H | —N— | —C(H)— |
| 1468 (IIa) or (IIb) | —CH$_2$OH | —NO$_2$ | —CH$_3$ | —NO$_2$ | —CH$_3$ | —C(H)— | —C(H)— |
| 1469 (IIa) or (IIb) | —CH$_2$OH | —NO$_2$ | —CH$_3$ | —NO$_2$ | —CH$_3$ | —C(H)— | —N— |
| 1470 (IIa) or (IIb) | —CH$_2$OH | —NO$_2$ | —CH$_3$ | —NO$_2$ | —CH$_3$ | —N— | —C(H)— |
| 1471 (IIa) or (IIb) | —CH$_2$OH | —NO$_2$ | —CH$_3$ | —NO$_2$ | —OCH$_3$ | —C(H)— | —C(H)— |
| 1472 (IIa) or (IIb) | —CH$_2$OH | —NO$_2$ | —CH$_3$ | —NO$_2$ | —OCH$_3$ | —C(H)— | —N— |
| 1473 (IIa) or (IIb) | —CH$_2$OH | —NO$_2$ | —CH$_3$ | —NO$_2$ | —OCH$_3$ | —N— | —C(H)— |
| 1474 (IIa) or (IIb) | —CH$_2$OH | —NO$_2$ | —CH$_3$ | —NO$_2$ | —OCF$_3$ | —C(H)— | —C(H)— |
| 1475 (IIa) or (IIb) | —CH$_2$OH | —NO$_2$ | —CH$_3$ | —NO$_2$ | —OCF$_3$ | —C(H)— | —N— |
| 1476 (IIa) or (IIb) | —CH$_2$OH | —NO$_2$ | —CH$_3$ | —NO$_2$ | —OCF$_3$ | —N— | —C(H)— |
| 1477 (IIa) or (IIb) | —CH$_2$OH | —NO$_2$ | —CH$_3$ | —NO$_2$ | —F | —C(H)— | —C(H)— |
| 1478 (IIa) or (IIb) | —CH$_2$OH | —NO$_2$ | —CH$_3$ | —NO$_2$ | —F | —C(H)— | —N— |
| 1479 (IIa) or (IIb) | —CH$_2$OH | —NO$_2$ | —CH$_3$ | —NO$_2$ | —F | —N— | —C(H)— |
| 1480 (IIa) or (IIb) | —CH$_2$OH | —NO$_2$ | —OCH$_3$ | —H | —H | —C(H)— | —C(H)— |
| 1481 (IIa) or (IIb) | —CH$_2$OH | —NO$_2$ | —OCH$_3$ | —H | —H | —C(H)— | —N— |
| 1482 (IIa) or (IIb) | —CH$_2$OH | —NO$_2$ | —OCH$_3$ | —H | —H | —N— | —C(H)— |
| 1483 (IIa) or (IIb) | —CH$_2$OH | —NO$_2$ | —OCH$_3$ | —H | —CH$_3$ | —C(H)— | —C(H)— |
| 1484 (IIa) or (IIb) | —CH$_2$OH | —NO$_2$ | —OCH$_3$ | —H | —CH$_3$ | —C(H)— | —N— |
| 1485 (IIa) or (IIb) | —CH$_2$OH | —NO$_2$ | —OCH$_3$ | —H | —CH$_3$ | —N— | —C(H)— |
| 1486 (IIa) or (IIb) | —CH$_2$OH | —NO$_2$ | —OCH$_3$ | —H | —OCH$_3$ | —C(H)— | —C(H)— |
| 1487 (IIa) or (IIb) | —CH$_2$OH | —NO$_2$ | —OCH$_3$ | —H | —OCH$_3$ | —C(H)— | —N— |
| 1488 (IIa) or (IIb) | —CH$_2$OH | —NO$_2$ | —OCH$_3$ | —H | —OCH$_3$ | —N— | —C(H)— |
| 1489 (IIa) or (IIb) | —CH$_2$OH | —NO$_2$ | —OCH$_3$ | —H | —OCF$_3$ | —C(H)— | —C(H)— |
| 1490 (IIa) or (IIb) | —CH$_2$OH | —NO$_2$ | —OCH$_3$ | —H | —OCF$_3$ | —C(H)— | —N— |
| 1491 (IIa) or (IIb) | —CH$_2$OH | —NO$_2$ | —OCH$_3$ | —H | —OCF$_3$ | —N— | —C(H)— |
| 1492 (IIa) or (IIb) | —CH$_2$OH | —NO$_2$ | —OCH$_3$ | —H | —F | —C(H)— | —C(H)— |
| 1493 (IIa) or (IIb) | —CH$_2$OH | —NO$_2$ | —OCH$_3$ | —H | —F | —C(H)— | —N— |
| 1494 (IIa) or (IIb) | —CH$_2$OH | —NO$_2$ | —OCH$_3$ | —H | —F | —N— | —C(H)— |
| 1495 (IIa) or (IIb) | —CH$_2$OH | —NO$_2$ | —OCH$_3$ | —CH$_3$ | —H | —C(H)— | —C(H)— |
| 1496 (IIa) or (IIb) | —CH$_2$OH | —NO$_2$ | —OCH$_3$ | —CH$_3$ | —H | —C(H)— | —N— |
| 1497 (IIa) or (IIb) | —CH$_2$OH | —NO$_2$ | —OCH$_3$ | —CH$_3$ | —H | —N— | —C(H)— |
| 1498 (IIa) or (IIb) | —CH$_2$OH | —NO$_2$ | —OCH$_3$ | —CH$_3$ | —CH$_3$ | —C(H)— | —C(H)— |
| 1499 (IIa) or (IIb) | —CH$_2$OH | —NO$_2$ | —OCH$_3$ | —CH$_3$ | —CH$_3$ | —C(H)— | —N— |
| 1500 (IIa) or (IIb) | —CH$_2$OH | —NO$_2$ | —OCH$_3$ | —CH$_3$ | —CH$_3$ | —N— | —C(H)— |
| 1501 (IIa) or (IIb) | —CH$_2$OH | —NO$_2$ | —OCH$_3$ | —CH$_3$ | —OCH$_3$ | —C(H)— | —C(H)— |
| 1502 (IIa) or (IIb) | —CH$_2$OH | —NO$_2$ | —OCH$_3$ | —CH$_3$ | —OCH$_3$ | —C(H)— | —N— |
| 1503 (IIa) or (IIb) | —CH$_2$OH | —NO$_2$ | —OCH$_3$ | —CH$_3$ | —OCH$_3$ | —N— | —C(H)— |
| 1504 (IIa) or (IIb) | —CH$_2$OH | —NO$_2$ | —OCH$_3$ | —CH$_3$ | —OCF$_3$ | —C(H)— | —C(H)— |
| 1505 (IIa) or (IIb) | —CH$_2$OH | —NO$_2$ | —OCH$_3$ | —CH$_3$ | —OCF$_3$ | —C(H)— | —N— |
| 1506 (IIa) or (IIb) | —CH$_2$OH | —NO$_2$ | —OCH$_3$ | —CH$_3$ | —OCF$_3$ | —N— | —C(H)— |
| 1507 (IIa) or (IIb) | —CH$_2$OH | —NO$_2$ | —OCH$_3$ | —CH$_3$ | —F | —C(H)— | —C(H)— |

-continued

| Compound | R$_6$ | R$_1$ | R$_1$' | R$_1$" | R$_1$'" | Y | Z |
|---|---|---|---|---|---|---|---|
| 1508 (IIa) or (IIb) | —CH$_2$OH | —NO$_2$ | —OCH$_3$ | —CH$_3$ | —F | —C(H)— | —N— |
| 1509 (IIa) or (IIb) | —CH$_2$OH | —NO$_2$ | —OCH$_3$ | —CH$_3$ | —F | —N— | —C(H)— |
| 1510 (IIa) or (IIb) | —CH$_2$OH | —NO$_2$ | —OCH$_3$ | —OCH$_3$ | —H | —C(H)— | —C(H)— |
| 1511 (IIa) or (IIb) | —CH$_2$OH | —NO$_2$ | —OCH$_3$ | —OCH$_3$ | —H | —C(H)— | —N— |
| 1512 (IIa) or (IIb) | —CH$_2$OH | —NO$_2$ | —OCH$_3$ | —OCH$_3$ | —H | —N— | —C(H)— |
| 1513 (IIa) or (IIb) | —CH$_2$OH | —NO$_2$ | —OCH$_3$ | —OCH$_3$ | —CH$_3$ | —C(H)— | —C(H)— |
| 1514 (IIa) or (IIb) | —CH$_2$OH | —NO$_2$ | —OCH$_3$ | —OCH$_3$ | —CH$_3$ | —C(H)— | —N— |
| 1515 (IIa) or (IIb) | —CH$_2$OH | —NO$_2$ | —OCH$_3$ | —OCH$_3$ | —CH$_3$ | —N— | —C(H)— |
| 1516 (IIa) or (IIb) | —CH$_2$OH | —NO$_2$ | —OCH$_3$ | —OCH$_3$ | —OCH$_3$ | —C(H)— | —C(H)— |
| 1517 (IIa) or (IIb) | —CH$_2$OH | —NO$_2$ | —OCH$_3$ | —OCH$_3$ | —OCH$_3$ | —C(H)— | —N— |
| 1518 (IIa) or (IIb) | —CH$_2$OH | —NO$_2$ | —OCH$_3$ | —OCH$_3$ | —OCH$_3$ | —N— | —C(H)— |
| 1519 (IIa) or (IIb) | —CH$_2$OH | —NO$_2$ | —OCH$_3$ | —OCH$_3$ | —OCF$_3$ | —C(H)— | —C(H)— |
| 1520 (IIa) or (IIb) | —CH$_2$OH | —NO$_2$ | —OCH$_3$ | —OCH$_3$ | —OCF$_3$ | —C(H)— | —N— |
| 1521 (IIa) or (IIb) | —CH$_2$OH | —NO$_2$ | —OCH$_3$ | —OCH$_3$ | —OCF$_3$ | —N— | —C(H)— |
| 1522 (IIa) or (IIb) | —CH$_2$OH | —NO$_2$ | —OCH$_3$ | —OCH$_3$ | —F | —C(H)— | —C(H)— |
| 1523 (IIa) or (IIb) | —CH$_2$OH | —NO$_2$ | —OCH$_3$ | —OCH$_3$ | —F | —C(H)— | —N— |
| 1524 (IIa) or (IIb) | —CH$_2$OH | —NO$_2$ | —OCH$_3$ | —OCH$_3$ | —F | —N— | —C(H)— |
| 1525 (IIa) or (IIb) | —CH$_2$OH | —NO$_2$ | —OCH$_3$ | —NO$_2$ | —H | —C(H)— | —C(H)— |
| 1526 (IIa) or (IIb) | —CH$_2$OH | —NO$_2$ | —OCH$_3$ | —NO$_2$ | —H | —C(H)— | —N— |
| 1527 (IIa) or (IIb) | —CH$_2$OH | —NO$_2$ | —OCH$_3$ | —NO$_2$ | —H | —N— | —C(H)— |
| 1528 (IIa) or (IIb) | —CH$_2$OH | —NO$_2$ | —OCH$_3$ | —NO$_2$ | —CH$_3$ | —C(H)— | —C(H)— |
| 1529 (IIa) or (IIb) | —CH$_2$OH | —NO$_2$ | —OCH$_3$ | —NO$_2$ | —CH$_3$ | —C(H)— | —N— |
| 1530 (IIa) or (IIb) | —CH$_2$OH | —NO$_2$ | —OCH$_3$ | —NO$_2$ | —CH$_3$ | —N— | —C(H)— |
| 1531 (IIa) or (IIb) | —CH$_2$OH | —NO$_2$ | —OCH$_3$ | —NO$_2$ | —OCH$_3$ | —C(H)— | —C(H)— |
| 1532 (IIa) or (IIb) | —CH$_2$OH | —NO$_2$ | —OCH$_3$ | —NO$_2$ | —OCH$_3$ | —C(H)— | —N— |
| 1533 (IIa) or (IIb) | —CH$_2$OH | —NO$_2$ | —OCH$_3$ | —NO$_2$ | —OCH$_3$ | —N— | —C(H)— |
| 1534 (IIa) or (IIb) | —CH$_2$OH | —NO$_2$ | —OCH$_3$ | —NO$_2$ | —OCF$_3$ | —C(H)— | —C(H)— |
| 1535 (IIa) or (IIb) | —CH$_2$OH | —NO$_2$ | —OCH$_3$ | —NO$_2$ | —OCF$_3$ | —C(H)— | —N— |
| 1536 (IIa) or (IIb) | —CH$_2$OH | —NO$_2$ | —OCH$_3$ | —NO$_2$ | —OCF$_3$ | —N— | —C(H)— |
| 1537 (IIa) or (IIb) | —CH$_2$OH | —NO$_2$ | —OCH$_3$ | —NO$_2$ | —F | —C(H)— | —C(H)— |
| 1538 (IIa) or (IIb) | —CH$_2$OH | —NO$_2$ | —OCH$_3$ | —NO$_2$ | —F | —C(H)— | —N— |
| 1539 (IIa) or (IIb) | —CH$_2$OH | —NO$_2$ | —OCH$_3$ | —NO$_2$ | —F | —N— | —C(H)— |
| 1540 (IIa) or (IIb) | —CH$_2$OH | —OCH$_3$ | —H | —H | —H | —C(H)— | —C(H)— |
| 1541 (IIa) or (IIb) | —CH$_2$OH | —OCH$_3$ | —H | —H | —H | —C(H)— | —N— |
| 1542 (IIa) or (IIb) | —CH$_2$OH | —OCH$_3$ | —H | —H | —H | —N— | —C(H)— |
| 1543 (IIa) or (IIb) | —CH$_2$OH | —OCH$_3$ | —H | —H | —CH$_3$ | —C(H)— | —C(H)— |
| 1544 (IIa) or (IIb) | —CH$_2$OH | —OCH$_3$ | —H | —H | —CH$_3$ | —C(H)— | —N— |
| 1545 (IIa) or (IIb) | —CH$_2$OH | —OCH$_3$ | —H | —H | —CH$_3$ | —N— | —C(H)— |
| 1546 (IIa) or (IIb) | —CH$_2$OH | —OCH$_3$ | —H | —H | —OCH$_3$ | —C(H)— | —C(H)— |
| 1547 (IIa) or (IIb) | —CH$_2$OH | —OCH$_3$ | —H | —H | —OCH$_3$ | —C(H)— | —N— |
| 1548 (IIa) or (IIb) | —CH$_2$OH | —OCH$_3$ | —H | —H | —OCH$_3$ | —N— | —C(H)— |
| 1549 (IIa) or (IIb) | —CH$_2$OH | —OCH$_3$ | —H | —H | —OCF$_3$ | —C(H)— | —C(H)— |
| 1550 (IIa) or (IIb) | —CH$_2$OH | —OCH$_3$ | —H | —H | —OCF$_3$ | —C(H)— | —N— |
| 1551 (IIa) or (IIb) | —CH$_2$OH | —OCH$_3$ | —H | —H | —OCF$_3$ | —N— | —C(H)— |
| 1552 (IIa) or (IIb) | —CH$_2$OH | —OCH$_3$ | —H | —H | —F | —C(H)— | —C(H)— |
| 1553 (IIa) or (IIb) | —CH$_2$OH | —OCH$_3$ | —H | —H | —F | —C(H)— | —N— |
| 1554 (IIa) or (IIb) | —CH$_2$OH | —OCH$_3$ | —H | —H | —F | —N— | —C(H)— |
| 1555 (IIa) or (IIb) | —CH$_2$OH | —OCH$_3$ | —H | —CH$_3$ | —H | —C(H)— | —C(H)— |
| 1556 (IIa) or (IIb) | —CH$_2$OH | —OCH$_3$ | —H | —CH$_3$ | —H | —C(H)— | —N— |
| 1557 (IIa) or (IIb) | —CH$_2$OH | —OCH$_3$ | —H | —CH$_3$ | —H | —N— | —C(H)— |
| 1558 (IIa) or (IIb) | —CH$_2$OH | —OCH$_3$ | —H | —CH$_3$ | —CH$_3$ | —C(H)— | —C(H)— |
| 1559 (IIa) or (IIb) | —CH$_2$OH | —OCH$_3$ | —H | —CH$_3$ | —CH$_3$ | —C(H)— | —N— |
| 1560 (IIa) or (IIb) | —CH$_2$OH | —OCH$_3$ | —H | —CH$_3$ | —CH$_3$ | —N— | —C(H)— |
| 1561 (IIa) or (IIb) | —CH$_2$OH | —OCH$_3$ | —H | —CH$_3$ | —OCH$_3$ | —C(H)— | —C(H)— |
| 1562 (IIa) or (IIb) | —CH$_2$OH | —OCH$_3$ | —H | —CH$_3$ | —OCH$_3$ | —C(H)— | —N— |
| 1563 (IIa) or (IIb) | —CH$_2$OH | —OCH$_3$ | —H | —CH$_3$ | —OCH$_3$ | —N— | —C(H)— |
| 1564 (IIa) or (IIb) | —CH$_2$OH | —OCH$_3$ | —H | —CH$_3$ | —OCF$_3$ | —C(H)— | —C(H)— |
| 1565 (IIa) or (IIb) | —CH$_2$OH | —OCH$_3$ | —H | —CH$_3$ | —OCF$_3$ | —C(H)— | —N— |
| 1566 (IIa) or (IIb) | —CH$_2$OH | —OCH$_3$ | —H | —CH$_3$ | —OCF$_3$ | —N— | —C(H)— |
| 1567 (IIa) or (IIb) | —CH$_2$OH | —OCH$_3$ | —H | —CH$_3$ | —F | —C(H)— | —C(H)— |
| 1568 (IIa) or (IIb) | —CH$_2$OH | —OCH$_3$ | —H | —CH$_3$ | —F | —C(H)— | —N— |
| 1569 (IIa) or (IIb) | —CH$_2$OH | —OCH$_3$ | —H | —CH$_3$ | —F | —N— | —C(H)— |
| 1570 (IIa) or (IIb) | —CH$_2$OH | —OCH$_3$ | —H | —OCH$_3$ | —H | —C(H)— | —C(H)— |
| 1571 (IIa) or (IIb) | —CH$_2$OH | —OCH$_3$ | —H | —OCH$_3$ | —H | —C(H)— | —N— |
| 1572 (IIa) or (IIb) | —CH$_2$OH | —OCH$_3$ | —H | —OCH$_3$ | —H | —N— | —C(H)— |
| 1573 (IIa) or (IIb) | —CH$_2$OH | —OCH$_3$ | —H | —OCH$_3$ | —CH$_3$ | —C(H)— | —C(H)— |
| 1574 (IIa) or (IIb) | —CH$_2$OH | —OCH$_3$ | —H | —OCH$_3$ | —CH$_3$ | —C(H)— | —N— |
| 1575 (IIa) or (IIb) | —CH$_2$OH | —OCH$_3$ | —H | —OCH$_3$ | —CH$_3$ | —N— | —C(H)— |
| 1576 (IIa) or (IIb) | —CH$_2$OH | —OCH$_3$ | —H | —OCH$_3$ | —OCH$_3$ | —C(H)— | —C(H)— |
| 1577 (IIa) or (IIb) | —CH$_2$OH | —OCH$_3$ | —H | —OCH$_3$ | —OCH$_3$ | —C(H)— | —N— |
| 1578 (IIa) or (IIb) | —CH$_2$OH | —OCH$_3$ | —H | —OCH$_3$ | —OCH$_3$ | —N— | —C(H)— |
| 1579 (IIa) or (IIb) | —CH$_2$OH | —OCH$_3$ | —H | —OCH$_3$ | —OCF$_3$ | —C(H)— | —C(H)— |
| 1580 (IIa) or (IIb) | —CH$_2$OH | —OCH$_3$ | —H | —OCH$_3$ | —OCF$_3$ | —C(H)— | —N— |
| 1581 (IIa) or (IIb) | —CH$_2$OH | —OCH$_3$ | —H | —OCH$_3$ | —OCF$_3$ | —N— | —C(H)— |
| 1582 (IIa) or (IIb) | —CH$_2$OH | —OCH$_3$ | —H | —OCH$_3$ | —F | —C(H)— | —C(H)— |
| 1583 (IIa) or (IIb) | —CH$_2$OH | —OCH$_3$ | —H | —OCH$_3$ | —F | —C(H)— | —N— |
| 1584 (IIa) or (IIb) | —CH$_2$OH | —OCH$_3$ | —H | —OCH$_3$ | —F | —N— | —C(H)— |

| Compound | R₆ | R₁ | R₁' | R₁" | R₁'" | Y | Z |
|---|---|---|---|---|---|---|---|
| 1585 (IIa) or (IIb) | —CH₂OH | —OCH₃ | —H | —NO₂ | —H | —C(H)— | —C(H)— |
| 1586 (IIa) or (IIb) | —CH₂OH | —OCH₃ | —H | —NO₂ | —H | —C(H)— | —N— |
| 1587 (IIa) or (IIb) | —CH₂OH | —OCH₃ | —H | —NO₂ | —H | —N— | —C(H)— |
| 1588 (IIa) or (IIb) | —CH₂OH | —OCH₃ | —H | —NO₂ | —CH₃ | —C(H)— | —C(H)— |
| 1589 (IIa) or (IIb) | —CH₂OH | —OCH₃ | —H | —NO₂ | —CH₃ | —C(H)— | —N— |
| 1590 (IIa) or (IIb) | —CH₂OH | —OCH₃ | —H | —NO₂ | —CH₃ | —N— | —C(H)— |
| 1591 (IIa) or (IIb) | —CH₂OH | —OCH₃ | —H | —NO₂ | —OCH₃ | —C(H)— | —C(H)— |
| 1592 (IIa) or (IIb) | —CH₂OH | —OCH₃ | —H | —NO₂ | —OCH₃ | —C(H)— | —N— |
| 1593 (IIa) or (IIb) | —CH₂OH | —OCH₃ | —H | —NO₂ | —OCH₃ | —N— | —C(H)— |
| 1594 (IIa) or (IIb) | —CH₂OH | —OCH₃ | —H | —NO₂ | —OCF₃ | —C(H)— | —C(H)— |
| 1595 (IIa) or (IIb) | —CH₂OH | —OCH₃ | —H | —NO₂ | —OCF₃ | —C(H)— | —N— |
| 1596 (IIa) or (IIb) | —CH₂OH | —OCH₃ | —H | —NO₂ | —OCF₃ | —N— | —C(H)— |
| 1597 (IIa) or (IIb) | —CH₂OH | —OCH₃ | —H | —NO₂ | —F | —C(H)— | —C(H)— |
| 1598 (IIa) or (IIb) | —CH₂OH | —OCH₃ | —H | —NO₂ | —F | —C(H)— | —N— |
| 1599 (IIa) or (IIb) | —CH₂OH | —OCH₃ | —H | —NO₂ | —F | —N— | —C(H)— |
| 1600 (IIa) or (IIb) | —CH₂OH | —OCH₃ | —CH₃ | —H | —H | —C(H)— | —C(H)— |
| 1601 (IIa) or (IIb) | —CH₂OH | —OCH₃ | —CH₃ | —H | —H | —C(H)— | —N— |
| 1602 (IIa) or (IIb) | —CH₂OH | —OCH₃ | —CH₃ | —H | —H | —N— | —C(H)— |
| 1603 (IIa) or (IIb) | —CH₂OH | —OCH₃ | —CH₃ | —H | —CH₃ | —C(H)— | —C(H)— |
| 1604 (IIa) or (IIb) | —CH₂OH | —OCH₃ | —CH₃ | —H | —CH₃ | —C(H)— | —N— |
| 1605 (IIa) or (IIb) | —CH₂OH | —OCH₃ | —CH₃ | —H | —CH₃ | —N— | —C(H)— |
| 1606 (IIa) or (IIb) | —CH₂OH | —OCH₃ | —CH₃ | —H | —OCH₃ | —C(H)— | —C(H)— |
| 1607 (IIa) or (IIb) | —CH₂OH | —OCH₃ | —CH₃ | —H | —OCH₃ | —C(H)— | —N— |
| 1608 (IIa) or (IIb) | —CH₂OH | —OCH₃ | —CH₃ | —H | —OCH₃ | —N— | —C(H)— |
| 1609 (IIa) or (IIb) | —CH₂OH | —OCH₃ | —CH₃ | —H | —OCF₃ | —C(H)— | —C(H)— |
| 1610 (IIa) or (IIb) | —CH₂OH | —OCH₃ | —CH₃ | —H | —OCF₃ | —C(H)— | —N— |
| 1611 (IIa) or (IIb) | —CH₂OH | —OCH₃ | —CH₃ | —H | —OCF₃ | —N— | —C(H)— |
| 1612 (IIa) or (IIb) | —CH₂OH | —OCH₃ | —CH₃ | —H | —F | —C(H)— | —C(H)— |
| 1613 (IIa) or (IIb) | —CH₂OH | —OCH₃ | —CH₃ | —H | —F | —C(H)— | —N— |
| 1614 (IIa) or (IIb) | —CH₂OH | —OCH₃ | —CH₃ | —H | —F | —N— | —C(H)— |
| 1615 (IIa) or (IIb) | —CH₂OH | —OCH₃ | —CH₃ | —CH₃ | —H | —C(H)— | —C(H)— |
| 1616 (IIa) or (IIb) | —CH₂OH | —OCH₃ | —CH₃ | —CH₃ | —H | —C(H)— | —N— |
| 1617 (IIa) or (IIb) | —CH₂OH | —OCH₃ | —CH₃ | —CH₃ | —H | —N— | —C(H)— |
| 1618 (IIa) or (IIb) | —CH₂OH | —OCH₃ | —CH₃ | —CH₃ | —CH₃ | —C(H)— | —C(H)— |
| 1619 (IIa) or (IIb) | —CH₂OH | —OCH₃ | —CH₃ | —CH₃ | —CH₃ | —C(H)— | —N— |
| 1620 (IIa) or (IIb) | —CH₂OH | —OCH₃ | —CH₃ | —CH₃ | —CH₃ | —N— | —C(H)— |
| 1621 (IIa) or (IIb) | —CH₂OH | —OCH₃ | —CH₃ | —CH₃ | —OCH₃ | —C(H)— | —C(H)— |
| 1622 (IIa) or (IIb) | —CH₂OH | —OCH₃ | —CH₃ | —CH₃ | —OCH₃ | —C(H)— | —N— |
| 1623 (IIa) or (IIb) | —CH₂OH | —OCH₃ | —CH₃ | —CH₃ | —OCH₃ | —N— | —C(H)— |
| 1624 (IIa) or (IIb) | —CH₂OH | —OCH₃ | —CH₃ | —CH₃ | —OCF₃ | —C(H)— | —C(H)— |
| 1625 (IIa) or (IIb) | —CH₂OH | —OCH₃ | —CH₃ | —CH₃ | —OCF₃ | —C(H)— | —N— |
| 1626 (IIa) or (IIb) | —CH₂OH | —OCH₃ | —CH₃ | —CH₃ | —OCF₃ | —N— | —C(H)— |
| 1627 (IIa) or (IIb) | —CH₂OH | —OCH₃ | —CH₃ | —CH₃ | —F | —C(H)— | —C(H)— |
| 1628 (IIa) or (IIb) | —CH₂OH | —OCH₃ | —CH₃ | —CH₃ | —F | —C(H)— | —N— |
| 1629 (IIa) or (IIb) | —CH₂OH | —OCH₃ | —CH₃ | —CH₃ | —F | —N— | —C(H)— |
| 1630 (IIa) or (IIb) | —CH₂OH | —OCH₃ | —CH₃ | —OCH₃ | —H | —C(H)— | —C(H)— |
| 1631 (IIa) or (IIb) | —CH₂OH | —OCH₃ | —CH₃ | —OCH₃ | —H | —C(H)— | —N— |
| 1632 (IIa) or (IIb) | —CH₂OH | —OCH₃ | —CH₃ | —OCH₃ | —H | —N— | —C(H)— |
| 1633 (IIa) or (IIb) | —CH₂OH | —OCH₃ | —CH₃ | —OCH₃ | —CH₃ | —C(H)— | —C(H)— |
| 1634 (IIa) or (IIb) | —CH₂OH | —OCH₃ | —CH₃ | —OCH₃ | —CH₃ | —C(H)— | —N— |
| 1635 (IIa) or (IIb) | —CH₂OH | —OCH₃ | —CH₃ | —OCH₃ | —CH₃ | —N— | —C(H)— |
| 1636 (IIa) or (IIb) | —CH₂OH | —OCH₃ | —CH₃ | —OCH₃ | —OCH₃ | —C(H)— | —C(H)— |
| 1637 (IIa) or (IIb) | —CH₂OH | —OCH₃ | —CH₃ | —OCH₃ | —OCH₃ | —C(H)— | —N— |
| 1638 (IIa) or (IIb) | —CH₂OH | —OCH₃ | —CH₃ | —OCH₃ | —OCH₃ | —N— | —C(H)— |
| 1639 (IIa) or (IIb) | —CH₂OH | —OCH₃ | —CH₃ | —OCH₃ | —OCF₃ | —C(H)— | —C(H)— |
| 1640 (IIa) or (IIb) | —CH₂OH | —OCH₃ | —CH₃ | —OCH₃ | —OCF₃ | —C(H)— | —N— |
| 1641 (IIa) or (IIb) | —CH₂OH | —OCH₃ | —CH₃ | —OCH₃ | —OCF₃ | —N— | —C(H)— |
| 1642 (IIa) or (IIb) | —CH₂OH | —OCH₃ | —CH₃ | —OCH₃ | —F3 | —C(H)— | —C(H)— |
| 1643 (IIa) or (IIb) | —CH₂OH | —OCH₃ | —CH₃ | —OCH₃ | —F | —C(H)— | —N— |
| 1644 (IIa) or (IIb) | —CH₂OH | —OCH₃ | —CH₃ | —OCH₃ | —F | —N— | —C(H)— |
| 1645 (IIa) or (IIb) | —CH₂OH | —OCH₃ | —CH₃ | —NO₂ | —H | —C(H)— | —C(H)— |
| 1646 (IIa) or (IIb) | —CH₂OH | —OCH₃ | —CH₃ | —NO₂ | —H | —C(H)— | —N— |
| 1647 (IIa) or (IIb) | —CH₂OH | —OCH₃ | —CH₃ | —NO₂ | —H | —N— | —C(H)— |
| 1648 (IIa) or (IIb) | —CH₂OH | —OCH₃ | —CH₃ | —NO₂ | —CH₃ | —C(H)— | —C(H)— |
| 1649 (IIa) or (IIb) | —CH₂OH | —OCH₃ | —CH₃ | —NO₂ | —CH₃ | —C(H)— | —N— |
| 1650 (IIa) or (IIb) | —CH₂OH | —OCH₃ | —CH₃ | —NO₂ | —CH₃ | —N— | —C(H)— |
| 1651 (IIa) or (IIb) | —CH₂OH | —OCH₃ | —CH₃ | —NO₂ | —OCH₃ | —C(H)— | —C(H)— |
| 1652 (IIa) or (IIb) | —CH₂OH | —OCH₃ | —CH₃ | —NO₂ | —OCH₃ | —C(H)— | —N— |
| 1653 (IIa) or (IIb) | —CH₂OH | —OCH₃ | —CH₃ | —NO₂ | —OCH₃ | —N— | —C(H)— |
| 1654 (IIa) or (IIb) | —CH₂OH | —OCH₃ | —CH₃ | —NO₂ | —OCF₃ | —C(H)— | —C(H)— |
| 1655 (IIa) or (IIb) | —CH₂OH | —OCH₃ | —CH₃ | —NO₂ | —OCF₃ | —C(H)— | —N— |
| 1656 (IIa) or (IIb) | —CH₂OH | —OCH₃ | —CH₃ | —NO₂ | —OCF₃ | —N— | —C(H)— |
| 1657 (IIa) or (IIb) | —CH₂OH | —OCH₃ | —CH₃ | —NO₂ | —F | —C(H)— | —C(H)— |
| 1658 (IIa) or (IIb) | —CH₂OH | —OCH₃ | —CH₃ | —NO₂ | —F | —C(H)— | —N— |
| 1659 (IIa) or (IIb) | —CH₂OH | —OCH₃ | —CH₃ | —NO₂ | —F | —N— | —C(H)— |
| 1660 (IIa) or (IIb) | —CH₂OH | —OCH₃ | —OCH₃ | —H | —H | —C(H)— | —C(H)— |
| 1661 (IIa) or (IIb) | —CH₂OH | —OCH₃ | —OCH₃ | —H | —H | —C(H)— | —N— |

-continued

| Compound | $R_6$ | $R_1$ | $R_1'$ | $R_1''$ | $R_1'''$ | Y | Z |
|---|---|---|---|---|---|---|---|
| 1662 (IIa) or (IIb) | —CH$_2$OH | —OCH$_3$ | —OCH$_3$ | —H | —H | —N— | —C(H)— |
| 1663 (IIa) or (IIb) | —CH$_2$OH | —OCH$_3$ | —OCH$_3$ | —H | —CH$_3$ | —C(H)— | —C(H)— |
| 1664 (IIa) or (IIb) | —CH$_2$OH | —OCH$_3$ | —OCH$_3$ | —H | —CH$_3$ | —C(H)— | —N— |
| 1665 (IIa) or (IIb) | —CH$_2$OH | —OCH$_3$ | —OCH$_3$ | —H | —CH$_3$ | —N— | —C(H)— |
| 1666 (IIa) or (IIb) | —CH$_2$OH | —OCH$_3$ | —OCH$_3$ | —H | —OCH$_3$ | —C(H)— | —C(H)— |
| 1667 (IIa) or (IIb) | —CH$_2$OH | —OCH$_3$ | —OCH$_3$ | —H | —OCH$_3$ | —C(H)— | —N— |
| 1668 (IIa) or (IIb) | —CH$_2$OH | —OCH$_3$ | —OCH$_3$ | —H | —OCH$_3$ | —N— | —C(H)— |
| 1669 (IIa) or (IIb) | —CH$_2$OH | —OCH$_3$ | —OCH$_3$ | —H | —OCF$_3$ | —C(H)— | —C(H)— |
| 1670 (IIa) or (IIb) | —CH$_2$OH | —OCH$_3$ | —OCH$_3$ | —H | —OCF$_3$ | —C(H)— | —N— |
| 1671 (IIa) or (IIb) | —CH$_2$OH | —OCH$_3$ | —OCH$_3$ | —H | —OCF$_3$ | —N— | —C(H)— |
| 1672 (IIa) or (IIb) | —CH$_2$OH | —OCH$_3$ | —OCH$_3$ | —H | —F | —C(H)— | —C(H)— |
| 1673 (IIa) or (IIb) | —CH$_2$OH | —OCH$_3$ | —OCH$_3$ | —H | —F | —C(H)— | —N— |
| 1674 (IIa) or (IIb) | —CH$_2$OH | —OCH$_3$ | —OCH$_3$ | —H | —F | —N— | —C(H)— |
| 1675 (IIa) or (IIb) | —CH$_2$OH | —OCH$_3$ | —OCH$_3$ | —CH$_3$ | —H | —C(H)— | —C(H)— |
| 1676 (IIa) or (IIb) | —CH$_2$OH | —OCH$_3$ | —OCH$_3$ | —CH$_3$ | —H | —C(H)— | —N— |
| 1677 (IIa) or (IIb) | —CH$_2$OH | —OCH$_3$ | —OCH$_3$ | —CH$_3$ | —H | —N— | —C(H)— |
| 1678 (IIa) or (IIb) | —CH$_2$OH | —OCH$_3$ | —OCH$_3$ | —CH$_3$ | —CH$_3$ | —C(H)— | —C(H)— |
| 1679 (IIa) or (IIb) | —CH$_2$OH | —OCH$_3$ | —OCH$_3$ | —CH$_3$ | —CH$_3$ | —C(H)— | —N— |
| 1680 (IIa) or (IIb) | —CH$_2$OH | —OCH$_3$ | —OCH$_3$ | —CH$_3$ | —CH$_3$ | —N— | —C(H)— |
| 1681 (IIa) or (IIb) | —CH$_2$OH | —OCH$_3$ | —OCH$_3$ | —CH$_3$ | —OCH$_3$ | —C(H)— | —C(H)— |
| 1682 (IIa) or (IIb) | —CH$_2$OH | —OCH$_3$ | —OCH$_3$ | —CH$_3$ | —OCH$_3$ | —C(H)— | —N— |
| 1683 (IIa) or (IIb) | —CH$_2$OH | —OCH$_3$ | —OCH$_3$ | —CH$_3$ | —OCH$_3$ | —N— | —C(H)— |
| 1684 (IIa) or (IIb) | —CH$_2$OH | —OCH$_3$ | —OCH$_3$ | —CH$_3$ | —OCF$_3$ | —C(H)— | —C(H)— |
| 1685 (IIa) or (IIb) | —CH$_2$OH | —OCH$_3$ | —OCH$_3$ | —CH$_3$ | —OCF$_3$ | —C(H)— | —N— |
| 1686 (IIa) or (IIb) | —CH$_2$OH | —OCH$_3$ | —OCH$_3$ | —CH$_3$ | —OCF$_3$ | —N— | —C(H)— |
| 1687 (IIa) or (IIb) | —CH$_2$OH | —OCH$_3$ | —OCH$_3$ | —CH$_3$ | —F | —C(H)— | —C(H)— |
| 1688 (IIa) or (IIb) | —CH$_2$OH | —OCH$_3$ | —OCH$_3$ | —CH$_3$ | —F | —C(H)— | —N— |
| 1689 (IIa) or (IIb) | —CH$_2$OH | —OCH$_3$ | —OCH$_3$ | —CH$_3$ | —F | —N— | —C(H)— |
| 1690 (IIa) or (IIb) | —CH$_2$OH | —OCH$_3$ | —OCH$_3$ | —OCH$_3$ | —H | —C(H)— | —C(H)— |
| 1691 (IIa) or (IIb) | —CH$_2$OH | —OCH$_3$ | —OCH$_3$ | —OCH$_3$ | —H | —C(H)— | —N— |
| 1692 (IIa) or (IIb) | —CH$_2$OH | —OCH$_3$ | —OCH$_3$ | —OCH$_3$ | —H | —N— | —C(H)— |
| 1693 (IIa) or (IIb) | —CH$_2$OH | —OCH$_3$ | —OCH$_3$ | —OCH$_3$ | —CH$_3$ | —C(H)— | —C(H)— |
| 1694 (IIa) or (IIb) | —CH$_2$OH | —OCH$_3$ | —OCH$_3$ | —OCH$_3$ | —CH$_3$ | —C(H)— | —N— |
| 1695 (IIa) or (IIb) | —CH$_2$OH | —OCH$_3$ | —OCH$_3$ | —OCH$_3$ | —CH$_3$ | —N— | —C(H)— |
| 1696 (IIa) or (IIb) | —CH$_2$OH | —OCH$_3$ | —OCH$_3$ | —OCH$_3$ | —OCH$_3$ | —C(H)— | —C(H)— |
| 1697 (IIa) or (IIb) | —CH$_2$OH | —OCH$_3$ | —OCH$_3$ | —OCH$_3$ | —OCH$_3$ | —C(H)— | —N— |
| 1698 (IIa) or (IIb) | —CH$_2$OH | —OCH$_3$ | —OCH$_3$ | —OCH$_3$ | —OCH$_3$ | —N— | —C(H)— |
| 1699 (IIa) or (IIb) | —CH$_2$OH | —OCH$_3$ | —OCH$_3$ | —OCH$_3$ | —OCF$_3$ | —C(H)— | —C(H)— |
| 1700 (IIa) or (IIb) | —CH$_2$OH | —OCH$_3$ | —OCH$_3$ | —OCH$_3$ | —OCF$_3$ | —C(H)— | —N— |
| 1701 (IIa) or (IIb) | —CH$_2$OH | —OCH$_3$ | —OCH$_3$ | —OCH$_3$ | —OCF$_3$ | —N— | —C(H)— |
| 1702 (IIa) or (IIb) | —CH$_2$OH | —OCH$_3$ | —OCH$_3$ | —OCH$_3$ | —F | —C(H)— | —C(H)— |
| 1703 (IIa) or (IIb) | —CH$_2$OH | —OCH$_3$ | —OCH$_3$ | —OCH$_3$ | —F | —C(H)— | —N— |
| 1704 (IIa) or (IIb) | —CH$_2$OH | —OCH$_3$ | —OCH$_3$ | —OCH$_3$ | —F | —N— | —C(H)— |
| 1705 (IIa) or (IIb) | —CH$_2$OH | —OCH$_3$ | —OCH$_3$ | —NO$_2$ | —H | —C(H)— | —C(H)— |
| 1706 (IIa) or (IIb) | —CH$_2$OH | —OCH$_3$ | —OCH$_3$ | —NO$_2$ | —H | —C(H)— | —N— |
| 1707 (IIa) or (IIb) | —CH$_2$OH | —OCH$_3$ | —OCH$_3$ | —NO$_2$ | —H | —N— | —C(H)— |
| 1708 (IIa) or (IIb) | —CH$_2$OH | —OCH$_3$ | —OCH$_3$ | —NO$_2$ | —CH$_3$ | —C(H)— | —C(H)— |
| 1709 (IIa) or (IIb) | —CH$_2$OH | —OCH$_3$ | —OCH$_3$ | —NO$_2$ | —CH$_3$ | —C(H)— | —N— |
| 1710 (IIa) or (IIb) | —CH$_2$OH | —OCH$_3$ | —OCH$_3$ | —NO$_2$ | —CH$_3$ | —N— | —C(H)— |
| 1711 (IIa) or (IIb) | —CH$_2$OH | —OCH$_3$ | —OCH$_3$ | —NO$_2$ | —OCH$_3$ | —C(H)— | —C(H)— |
| 1712 (IIa) or (IIb) | —CH$_2$OH | —OCH$_3$ | —OCH$_3$ | —NO$_2$ | —OCH$_3$ | —C(H)— | —N— |
| 1713 (IIa) or (IIb) | —CH$_2$OH | —OCH$_3$ | —OCH$_3$ | —NO$_2$ | —OCH$_3$ | —N— | —C(H)— |
| 1714 (IIa) or (IIb) | —CH$_2$OH | —OCH$_3$ | —OCH$_3$ | —NO$_2$ | —OCF$_3$ | —C(H)— | —C(H)— |
| 1715 (IIa) or (IIb) | —CH$_2$OH | —OCH$_3$ | —OCH$_3$ | —NO$_2$ | —OCF$_3$ | —C(H)— | —N— |
| 1716 (IIa) or (IIb) | —CH$_2$OH | —OCH$_3$ | —OCH$_3$ | —NO$_2$ | —OCF$_3$ | —N— | —C(H)— |
| 1717 (IIa) or (IIb) | —CH$_2$OH | —OCH$_3$ | —OCH$_3$ | —NO$_2$ | —F | —C(H)— | —C(H)— |
| 1718 (IIa) or (IIb) | —CH$_2$OH | —OCH$_3$ | —OCH$_3$ | —NO$_2$ | —F | —C(H)— | —N— |
| 1719 (IIa) or (IIb) | —CH$_2$OH | —OCH$_3$ | —OCH$_3$ | —NO$_2$ | —F | —N— | —C(H)— |

The following are additional embodiments in connection with each of the Compounds 100(IIa) through 1719(IIa) or 1719(IIb), above: the compound has a —CH$_3$ at a position para to the 6-membered ring's point of attachment to the triple bond; the compound has a —CF$_3$ at a position para to the 6-membered ring's point of attachment to the triple bond; the compound has a —F at a position para to the 6-membered ring's point of attachment to the triple bond; the compound has a —Cl at a position para to the 6-membered ring's point of attachment to the triple bond; the compound has a —NO$_2$ at a position para to the 6-membered ring's point of attachment to the triple bond; the compound has a —C(O)CH$_3$ at a position para to the 6-membered ring's point of attachment to the triple bond; the compound has a —C(CH$_3$)$_3$ at a position para to the 6-membered ring's point of attachment to the triple bond; the compound has a —CH(CH$_3$)$_2$ at a position para to the 6-membered ring's point of attachment to the triple bond; the compound has a —OC(O)CH$_3$ at a position para to the 6-membered ring's point of attachment to the triple bond; the compound has a —H at a position meta to the 6-membered ring's point of attachment to the triple bond; the compound has a —CH$_3$ at a position meta to the 6-membered ring's point of attachment to the triple bond; the compound has a —CF$_3$ at a position meta to the 6-membered ring's point of attachment to the triple bond; the compound has a —F at a position meta to the 6-membered ring's point of attachment to the triple bond;

the compound has a —Cl at a position meta to the 6-membered ring's point of attachment to the triple bond; the compound has a —NO$_2$ at a position meta to the 6-membered ring's point of attachment to the triple bond; the compound has a —C(O)CH$_3$ at a position meta to the 6-membered ring's point of attachment to the triple bond; the compound has a —C(CH$_3$)$_3$ at a position meta to the 6-membered ring's point of attachment to the triple bond; the compound has a —CH(CH$_3$)$_2$ at a position meta to the 6-membered ring's point of attachment to the triple bond; the compound has a —OC(O)CH$_3$ at a position meta to the 6-membered ring's point of attachment to the triple bond; the compound has a —H at a position ortho to the 6-membered ring's point of attachment to the triple bond; the compound has a —CH$_3$ at a position ortho to the 6-membered ring's point of attachment to the triple bond; the compound has a —CF$_3$ at a position ortho to the 6-membered ring's point of attachment to the triple bond; the compound has a —F at a position ortho to the 6-membered ring's point of attachment to the triple bond; the compound has a —Cl at a position ortho to the 6-membered ring's point of attachment to the triple bond; the compound has a —NO$_2$ at a position ortho to the 6-membered ring's point of attachment to the triple bond; the compound has a —C(O)CH$_3$ at a position ortho to the 6-membered ring's point of attachment to the triple bond; the compound has a —C(CH$_3$)$_3$ at a position ortho to the 6-membered ring's point of attachment to the triple bond; the compound has a —CH(CH$_3$)$_2$ at a position ortho to the 6-membered ring's point of attachment to the triple bond; and the compound has a —OC(O)CH$_3$ at a position ortho to the 6-membered ring's point of attachment to the triple bond.

5.3 Definitions

As used herein, the terms used above having following meaning:

"—(C$_1$–C$_{10}$)alkyl" means a saturated straight chain or branched non-cyclic hydrocarbon having from 1 to 10 carbon atoms. Representative saturated straight chain —(C$_1$–C$_{10}$)alkyls include -methyl, -ethyl, -n-propyl, -n-butyl, -n-pentyl, -n-hexyl, -n-heptyl, -n-octyl, -n-nonyl, and -n-decyl. Representative saturated branched —(C$_1$–C$_{10}$) alkyls include -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl, -2-methylhexyl, -3-methylhexyl, -4-methylhexyl, -5-methylhexyl, -2,3-dimethylbutyl, -2,3-dimethylpentyl, -2,4-dimethylpentyl, -2,3-dimethylhexyl, -2,4-dimethylhexyl, -2,5-dimethylhexyl, -2,2-dimethylpentyl, -2,2-dimethylhexyl, -3,3-dimethylpentyl, -3,3-dimethylhexyl, -4,4-dimethylhexyl, -2-ethylpentyl, -3-ethylpentyl, -2-ethylhexyl, -3-ethylhexyl, -4-ethylhexyl, -2-methyl-2-ethylpentyl, -2-methyl-3-ethylpentyl, -2-methyl-4-ethylpentyl, -2-methyl-2-ethylhexyl, -2-methyl-3-ethylhexyl, -2-methyl -4-ethylhexyl, -2,2-diethylpentyl, -3,3-diethylhexyl, -2,2-diethylhexyl, -3,3-diethylhexyl and the like.

"—(C$_1$–C$_6$)alkyl" means a saturated straight chain or branched non-cyclic hydrocarbon having from 1 to 6 carbon atoms. Representative saturated straight chain —(C$_1$–C$_6$) alkyls include -methyl, -ethyl, -n-propyl, -n-butyl, -n-pentyl, and -n-hexyl. Representative saturated branched —(C$_1$–C$_6$) alkyls include -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl and the like.

"—(C$_1$–C$_4$)alkyl" means a saturated straight chain or branched non-cyclic hydrocarbon having from 1 to 4 carbon atoms. Representative saturated straight chain —(C$_1$–C$_4$) alkyls include -methyl, -ethyl, -n-propyl, and -n-butyl. Representative saturated branched —(C$_1$–C$_4$)alkyls include -isopropyl, -sec-butyl, -isobutyl, and -tert-butyl.

"—(C$_1$–C$_3$)alkyl" means a saturated straight chain or branched non-cyclic hydrocarbon having from 1 to 3 carbon atoms. Representative saturated straight chain —(C$_1$–C$_3$) alkyls include -methyl, -ethyl, and -n-propyl. A representative saturated branched —(C$_1$–C$_3$)alkyl is -isopropyl.

"—(C$_2$–C$_{10}$)alkenyl" means a straight chain or branched nonfrom 2 to 10 carbon atoms and including at least one carbon-carbon double bond. Representative straight chain and branched (C$_2$–C$_{10}$)alkyl-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—(C$_2$–C$_6$)alkenyl" means a straight chain or branched non-cyclic hydrocarbon having from 2 to 6 carbon atoms and including at least one carbon-carbon double bond. Representative straight chain and branched (C$_2$–C$_6$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl and the like.

"—(C$_2$–C$_{10}$)alkynyl" means a straight chain or branched non-cyclic hydrocarbon having from 2 to 10 carbon atoms and including at lease one carbon-carbon triple bond. Representative straight chain and branched —(C$_2$–C$_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"—(C$_2$–C$_6$)alkynyl" means a straight chain or branched non-cyclic hydrocarbon having from 2 to 6 carbon atoms and including at lease one carbon-carbon triple bond. Representative straight chain and branched (C$_2$–C$_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—(C$_3$–C$_{10}$)cycloalkyl" means a saturated cyclic hydrocarbon having from 3 to 10 carbon atoms. Representative (C$_3$–C$_{10}$)cycloalkyls include -cyclopropyl, -cyclobutyl, -cyclopentyl, -cyclohexyl, -cycloheptyl, -cyclooctyl, -cyclononyl, and -cyclodecyl.

"—(C$_3$–C$_8$)cycloalkyl" means a saturated cyclic hydrocarbon having from 3 to 8 carbon atoms. Representative (C$_3$–C$_8$)cycloalkyls include -cyclopropyl, -cyclobutyl, -cyclopentyl, -cyclohexyl, -cycloheptyl, and -cyclooctyl.

"—(C$_8$–C$_{14}$)bicycloalkyl" means a bi-cyclic hydrocarbon ring system having from 8 to 14 carbon atoms and at least one saturated cyclic alkyl ring. Representative —(C$_8$–C$_{14}$) bicycloalkyls include -indanyl, -1,2,3,4-tetrahydronaphthyl, -5,6,7,8-tetrahydronaphthyl, -perhydronaphthyl and the like.

"—(C$_8$–C$_{14}$)tricycloalkyl" means a tri-cyclic hydrocarbon ring system having from 8 to 14 carbon atoms and at least one saturated ring. Representative —(C$_8$–C$_{14}$) tricycloalkyls include -pyrenyl, -1,2,3,4-tetrahydroanthracenyl, -perhydroanthracenyl, -aceanthreneyl, -1,2,3,4-tetrahydropenanthrenyl, -5,6,7,8-tetrahydrophenanthrenyl, -perhydrophenanthrenyl and the like.

"—($C_5$–$C_{10}$)cycloalkenyl" means a cyclic non-aromatic hydrocarbon having at least one carbon-carbon double bond in the cyclic system and from 5 to 10 carbon atoms. Representative ($C_5$–$C_{10}$)cycloalkenyls include -cyclopentenyl, -cyclopentadienyl, -cyclohexenyl, -cyclohexadienyl,-cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl and the like.

"—($C_5$–$C_8$)cycloalkenyl" means a cyclic non-aromatic hydrocarbon having at least one carbon-carbon double bond in the cyclic system and from 5 to 8 carbon atoms. Representative ($C_5$–$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl and the like.

"—($C_8$–$C_{14}$)bicycloalkenyl" means a bi-cyclic hydrocarbon ring system having at least one carbon-carbon double bond in each ring and from 8 to 14 carbon atoms. Representative —($C_8$–$C_{14}$)bicycloalkenyls include -indenyl, -pentalenyl, -naphthalenyl, -azulenyl, -heptalenyl, -1,2,7,8-tetrahydronaphthalenyl and the like.

"—($C_8$–$C_{14}$)tricycloalkenyl" means a tri-cyclic hydrocarbon ring system having at least one carbon-carbon double bond in each ring and from 8 to 14 carbon atoms. Representative —($C_8$–$C_{14}$)tricycloalkenyls include -anthracenyl, -phenanthrenyl, -phenalenyl, -acenaphthalenyl, -as-indacenyl, -s-indacenyl and the like.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur. One or both of the -(5- to 10-membered)heteroaryl's rings contain at least one carbon atom. Representative (5- to 10-membered)heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl and the like.

"-(3- to 7-membered)heterocycle" or "-(3- to 7-membered)heterocyclo" means a 3- to 7-membered monocyclic heterocyclic ring which is either saturated, unsaturated, non-aromatic or aromatic. A 3- or 4-membered -(3- to 7-membered)heterocycle can contain up to 3 heteroatoms, a 5-membered -(3- to 7-membered) heterocycle can contain up to 4 heteroatoms, a 6-membered -(3- to 7-membered)heterocycle can contain up to 6 heteroatoms, and a 7-membered -(3- to 7-membered) heterocycle can contain up to 7 heteroatoms. Each heteroatom is independently selected from nitrogen, which can be quaternized; oxygen; and sulfur, including sulfoxide and sulfone. The -(3- to 7-membered)heterocycle can be attached via any heteroatom or carbon atom. Representative -(3- to 7-membered)heterocycles include pyridyl, furyl, thiophenyl, pyrrolyl, oxazolyl, imidazolyl, thiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl and the like.

"-(3- to 5-membered)heterocycle" or "-(3- to 5-membered)heterocyclo" means a 3- to 5-membered monocyclic heterocyclic ring which is either saturated, unsaturated, non-aromatic or aromatic. A 3- or 4-membered -(3- to 5-membered)heterocycle can contain up to 3 heteroatoms and a 5-membered -(3- to 5-membered)heterocycle can contain up to 4 heteroatoms. Each heteroatom is independently selected from nitrogen, which can be quaternized; oxygen; and sulfur, including sulfoxide and sulfone. The -(3- to 5-membered)heterocycle can be attached via any heteroatom or carbon atom. Representative -(3- to 5-membered) heterocycles include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl and the like.

"-(7- to 10-membered)bicycloheterocycle" or "-(7- to 10-membered)bicycloheterocyclo" means a 7- to 10-membered bicyclic, heterocyclic ring having a saturated, unsaturated, non-aromatic or aromatic group. A -(7- to 10-membered)bicycloheterocycle contains from 1 to 4 heteroatoms independently selected from nitrogen, which can be quaternized; oxygen; and sulfur, including sulfoxide and sulfone. The (7- to 10-membered)bicycloheterocycle can be attached via any heteroatom or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, 1,3-benzodioxole and the like.

"—($C_{14}$)aryl" means a 14-membered aromatic carbocyclic moiety such as anthryl and phenanthryl.

"—$CH_2$(halo)" means a methyl group wherein one of the hydrogens of the methyl group has been replaced with a halogen. Representative —$CH_2$(halo) groups include —$CH_2F$, —$CH_2Cl$, —$CH_2Br$ and —$CH_2I$.

"—CH(halo)$_2$" means a methyl group wherein two of the hydrogens of the methyl group have been replaced with a halogen. Representative —CH(halo)$_2$ groups include —$CHF_2$, —$CHCl_2$, —$CHBr_2$, $CHBrCl$, $CHClI$ and —$CHI_2$.

"—C(halo)$_3$" means a methyl group wherein each of the hydrogens of the methyl group has been replaced with a halogen. Representative —C(halo)$_3$ groups include —$CF_3$, —$CF_2Cl$, —$CCl_3$, —$CBr_3$, —$CFBr_2$ and —$CI_3$.

"—Halogen" or "-halo" means —F, —Cl, —Br or —I.

The term "animal," includes, but is not limited to, a cow, monkey, horse, sheep, pig, chicken, turkey, quail, cat, dog, mouse, rat, rabbit, guinea pig and human.

The phrase "pharmaceutically acceptable salt," as used herein, is a salt formed from an acid and a basic nitrogen group of one of the Piperazine Compounds. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. The term "pharmaceutically acceptable salt" also refers to a salt prepared from a Piperazine Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia and organic amines, such as unsubstituted or hydroxy-substituted mono-, di- or trialkylamines; dicyclohexylamine; tributyl amine; pyridine; N-methyl-N-ethylamine; diethylamine-; triethylamine; mono-, bis- or tris-(2-hydroxy-lower alkyl amines), such as mono-, bis- or tris-(2-hydroxyethyl)amine, 2-hydroxy-tert-butylamine or tris-(hydroxymethyl)methylamine, N,N-di-lower alkyl-N-(hydroxy lower alkyl)-amines, such as N,N-dimethyl-N-(2-hydroxyethyl)amine or tri-(2-hydroxyethyl)amine; N-methyl-D-glucamine; and amino acids such as arginine, lysine and the like.

The phrase "effective amount" when used in connection with a Piperazine Compound means an amount effective for: (a) treating or preventing a Condition; or (b) inhibiting mGluR5 or mGluR1 function in a cell.

The phrase "effective amount" when used in connection with another therapeutic agent means an amount for providing the therapeutic effect of the therapeutic agent.

When a first group is "substituted with one or more" second groups, each of one or more of the first group's hydrogen atoms is replaced with a second group.

In one embodiment, a first group is substituted with up to three second groups.

In another embodiment, a first group is substituted with one or two second groups.

In another embodiment, a first group is substituted with only one second group.

The term "UI" means urinary incontinence.

The term "ALS" means amyotrophic lateral sclerosis.

The phrase "treatment of" and "treating" includes the amelioration or cessation a Condition or a symptom thereof.

The phrase "prevention of" and "preventing" includes the avoidance of the onset of a Condition or a symptom thereof.

5.4 Methods for Making the Piperazine Compounds

The Piperazine Compounds can be made using conventional organic syntheses and/or by the following illustrative methods.

Piperazine Compounds can be obtained by reacting a compound of formula A with an alkyl iodide, $R_2I$, at low temperature, e.g., about 0° C. to about −78° C., in the presence of lithium diisopropylamide ("LDA") in hexamethylphosphoramide ("HMPA") as shown below in Scheme A:

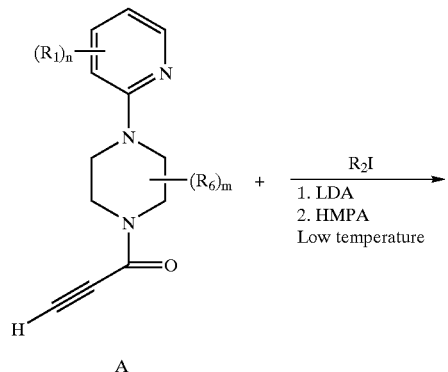

Scheme A

A

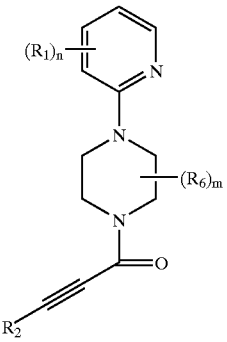

Formula (I)

A representative procedure for coupling a terminal acetylene with an alkyl iodide is provided in G. M. Strunz et al., Can. J. Chem. 419–432 (1996).

Piperazine Compounds can also be obtained by reacting a compound of formula A with an aryl iodide at room temperature in ethyl acetate in the presence of $Pd(Ph_3P)_2OAc_2$, CuI, and $Et_3N$, as shown below in Scheme B:

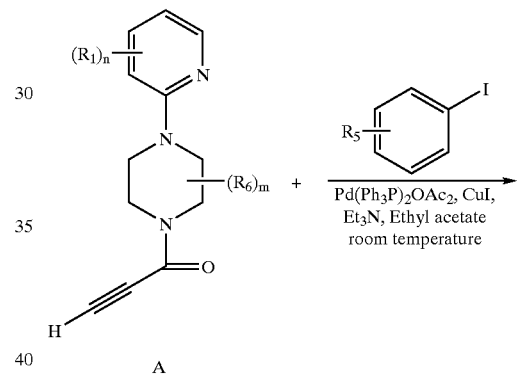

Scheme B

A

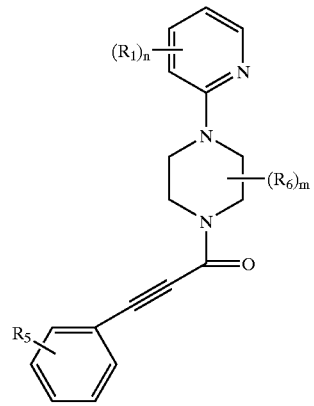

Formula (I)

A representative procedure for coupling a terminal acetylene with an aryl iodide is provided in L. A. Hay et al., J. Org. Chem. 5050–5058 (1998).

The compound of formula A can be prepared by reacting a compound of formula B with propynoic acid in the presence of 1-hydroxybenzotriazolehydrate ("HOBT") and 1,3-diisopropylcarbodiimide ("DIC") as shown below in Scheme C:

Scheme C

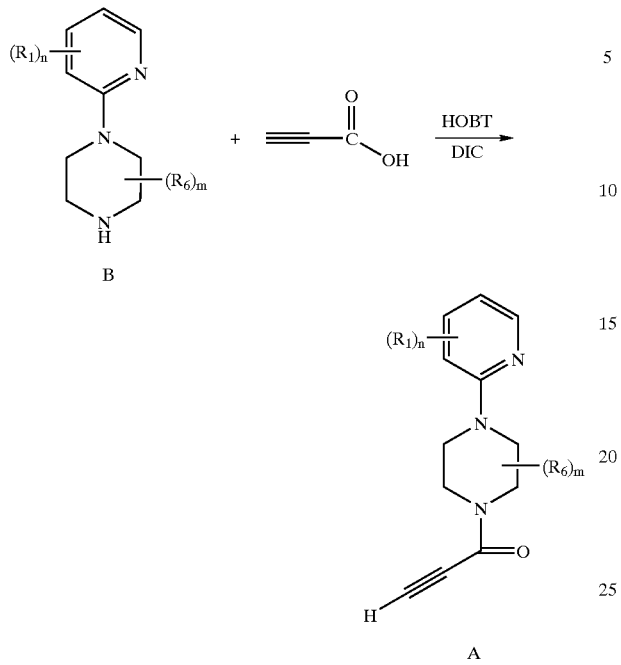

A representative procedure for coupling a carboxylic acid with an amine is provided in F. M. Martin et al., *Bioorg. Med. Chem. Lett.* 2887–2892 (1999).

The compound of formula A can also be prepared by reacting a compound of formula B with propynoyl chloride in the presence of tertiary amine, such as triethylamine, as shown below in Scheme D:

Scheme D

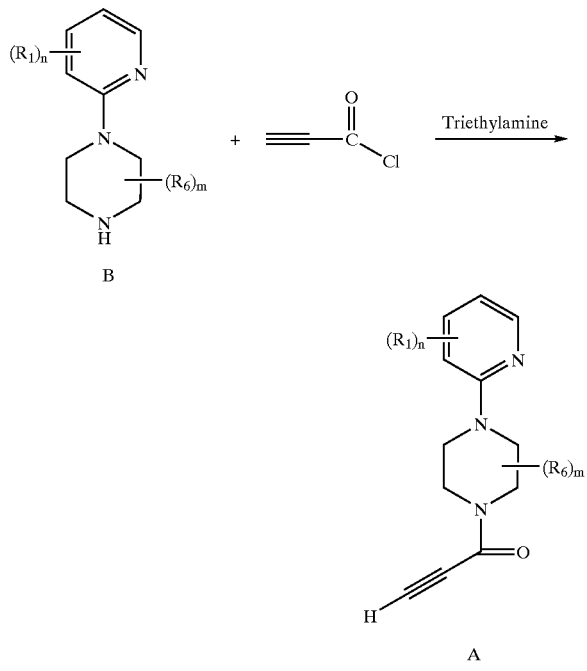

A representative procedure for coupling an acid chloride with an amine is provided in T. R. Herrin et al., *J. Med. Chem.* 1216–1223 (1975).

The compound of formula B can be prepared by reacting a 2-halo-substituted pyridine of formula C with piperazine D in chloroform, in the presence of triethylamine (TEA), at a temperature of 50° C. as shown below in Scheme E:

Scheme E

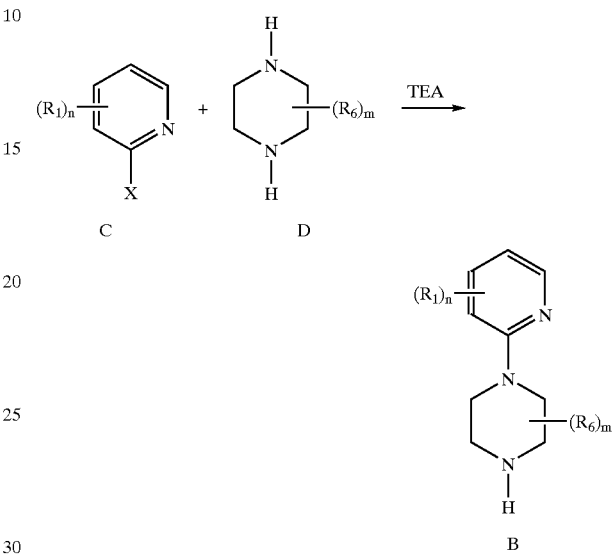

wherein X is I, Br, Cl, or F.

A representative procedure for reacting a 2-halo-piperidine with piperazine is provided in E. J. Jacobsen et al., *J. Med. Chem.* 1145–1151 (1990).

The substituted 2-halo-pyridines C are commercially available or can be prepared by methods well known to those skilled in the art.

Piperazine Compounds containing $R_2$ groups other than the $R_2$ groups exemplified in Schemes A through D can be prepared using analogous methods.

Certain Piperazine Compounds may have asymmetric centers and therefore exist in different enantiomeric and diastereomeric forms. A Piperazine Compound can be in the form of an optical isomer or a diastereomer. Accordingly, the invention encompasses Piperazine Compounds and their uses as described herein in the form of their optical isomers, diasteriomers and mixtures thereof, including a racemic mixture.

In addition, one or more hydrogen, carbon or other atoms of a Piperazine Compound can be replaced by an isotope of the hydrogen, carbon or other atoms. Such compounds, which are encompassed by the present invention, are useful as research and diagnostic tools in metabolism pharmacokinetic studies and in binding assays.

5.5 Therapeutic Uses of the Piperazine Compounds

In accordance with the invention, the Piperazine Compounds are administered to an animal in need of treatment or prevention of a Condition.

In one embodiment, an effective amount of a Piperazine Compound can be used to treat or prevent any condition treatable or preventable by inhibiting mGluR5. Examples of conditions that are treatable or preventable by inhibiting mGluR5 include, but are not limited to, pain, an addictive disorder, Parkinson's disease, parkinsonism, anxiety, a pruritic condition, and psychosis.

In another embodiment, an effective amount of a Piperazine Compound can be used to treat or prevent any condition treatable or preventable by inhibiting mGluR1. Examples of conditions that are treatable or preventable by inhibiting mGluR1 include, but are not limited to, pain, UI, an addictive disorder, Parkinson's disease, parkinsonism, anxiety, epilepsy, a seizure, stroke, a pruritic condition, psychosis, a cognitive disorder, a memory deficit, restricted brain function, Huntington's chorea, ALS, dementia, retinopathy, a muscle spasm, a migraine, vomiting, dyskinesia and depression.

The Piperazine Compounds can be used to treat or prevent acute or chronic pain. Examples of pain treatable or preventable using the Piperazine Compounds include, but are not limited to, cancer pain, central pain, labor pain, myocardial infarction pain, pancreatic pain, colic pain, postoperative pain, headache pain, muscle pain, pain associated with intensive care, arthritic pain, neuropathic pain, and pain associated with a periodontal disease, including gingivitis and periodontitis.

The Piperazine Compounds can also be used for inhibiting, preventing, or treating pain associated with inflammation or with an inflammatory disease in an animal. The pain to be inhibited, treated or prevented may be associated with inflammation associated with an inflammatory disease, which can arise where there is an inflammation of the body tissue, and which can be a local inflammatory response and/or a systemic inflammation. For example, the Piperazine Compounds can be used to inhibit, treat, or prevent pain associated with inflammatory diseases including, but not limited to: organ transplant rejection; reoxygenation injury resulting from organ transplantation (see Grupp et al., *J. Mol. Cell Cardiol.* 31:297–303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The Piperazine Compounds can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Piperazine Compounds can be used to treat or prevent UI. Examples of UI treatable or preventable using the Piperazine Compounds include, but are not limited to, urge incontinence, stress incontinence, overflow incontinence, neurogenic incontinence, and total incontinence.

The Piperazine Compounds can be used to treat or prevent an addictive disorder, including but not limited to, an eating disorder, an impulse-control disorder, an alcohol-related disorder, a nicotine-related disorder, an amphetamine-related disorder, a cannabis-related disorder, a cocaine-related disorder, an hallucinogen-related disorder, an inhalant-related disorders, and an opioid-related disorder, all of which are further sub-classified as listed below.

Eating disorders include, but are not limited to, Bulimia Nervosa, Nonpurging Type; Bulimia Nervosa, Purging Type; Anorexia; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder with delusions, Alcohol Abuse, Alcohol Intoxication, Alcohol Withdrawal, Alcohol Intoxication Delirium, Alcohol Withdrawal Delirium, Alcohol-Induced Persisting Dementia, Alcohol-Induced Persisting Amnestic Disorder, Alcohol Dependence, Alcohol-Induced Psychotic Disorder with hallucinations, Alcohol-Induced Mood Disorder, Alcohol-Induced Anxiety Disorder, Alcohol-Induced Sexual Dysfunction, Alcohol-Induced Sleep Disorder, Alcohol-Related Disorder not otherwise specified (NOS), Alcohol Intoxication, and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, and Amphetamine Related Disorder not otherwise specified (NOS).

Cannabis-related disorders include, but are not limited to, Cannabis Dependence, Cannabis Abuse, Cannabis Intoxication, Cannabis Intoxication Delirium, Cannabis-Induced Psychotic Disorder with delusions, Cannabis-Induced Psychotic Disorder with hallucinations, Cannabis-Induced Anxiety Disorder, and Cannabis Related Disorder not otherwise specified (NOS).

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, and Cocaine Related Disorder not otherwise specified (NOS).

Hallucinogen-related disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Persisting Perception Disorder (Flashbacks), and Hallucinogen Related Disorder not otherwise specified (NOS).

Inhalant-related disorders include, but are not limited to, Inhalant Dependence, Inhalant Abuse, Inhalant Intoxication, Inhalant Intoxication Delirium, Inhalant-Induced Psychotic Disorder with delusions, Inhalant-Induced Psychotic Disorder with hallucinations, Inhalant-Induced Anxiety Disorder, and Inhalant Related Disorder not otherwise specified (NOS).

Opioid-related disorders include, but are not limited to, Opioid Dependence, Opioid Abuse, Opioid Intoxication, Opioid Intoxication Delirium, Opioid-Induced Psychotic Disorder with delusions, Opioid-Induced Psychotic Disorder with hallucinations, Opioid-Induced Anxiety Disorder, Opioid Withdrawal, and Opioid Related Disorder not otherwise specified (NOS).

The Piperazine Compounds can be used to treat or prevent Parkinson's disease and parkinsonism and the symptoms associated with Parkinson's disease and parkinsonism, including but not limited to, bradykinesia, muscular rigidity, resting tremor, and impairment of postural balance.

The Piperazine Compounds can be used to treat or prevent generalized anxiety or severe anxiety and the symptoms associated with anxiety, including but not limited to, restlessness, tension, tachycardia, dyspnea, depression including chronic "neurotic" depression, panic disorder, agoraphobia and other specific phobias, eating disorders, and personality disorders.

The Piperazine Compounds can be used to treat or prevent epilepsy, including but not limited to, partial epilepsy, generalized epilepsy, and the symptoms associated with epilepsy, including but not limited to, simple partial seizures, jacksonian seizures, complex partial (psychomotor) seizures, convulsive seizures (grand mal or tonic-clonic seizures), petit mal (absence) seizures, and status epilepticus.

The Piperazine Compounds can be used to treat or prevent a seizure, including but not limited to, infantile spasms, febrile seizures, and epileptic seizures.

The Piperazine Compounds can be used to treat or prevent strokes, including but not limited to, ischemic strokes and hemorrhagic strokes.

The Piperazine Compounds can be used to treat or prevent a pruritic condition, including but not limited to, pruritus caused by dry skin, scabies, dermatitis, herpetiformis, atopic dermatitis, pruritus vulvae et ani, malaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, or fiberglass dermatitis.

The Piperazine Compounds can be used to treat or prevent psychosis, including but not limited to, schizophrenia, including paranoid schizophrenia, hebephrenic or disorganized schizophrenia, catatonic schizophrenia, undifferentiated schizophrenia, negative or deficit subtype schizophrenia, and non-deficit schizophrenia; a delusional disorder, including erotomanic subtype delusional disorder, grandiose subtype delusional disorder, jealous subtype delusional disorder, persecutory subtype delusional disorder, and somatic subtype delusional disorder; and brief psychosis.

The Piperazine Compounds can be used to treat or prevent a cognitive disorder, including but not limited to, delirium and dementia such as multi-infarct dementia, dementia pugilistica, dementia caused by AIDS, and dementia caused by Alzheimer's disease.

The Piperazine Compounds can be used to treat or prevent a memory deficiency, including but not limited to, dissociative amnesia and dissociative fugue.

The Piperazine Compounds can be used to treat or prevent restricted brain function, including but not limited to, that caused by surgery or an organ transplant, restricted blood supply to the brain, a spinal cord injury, a head injury, hypoxia, cardiac arrest, or hypoglycemia.

The Piperazine Compounds can be used to treat or prevent Huntington's chorea.

The Piperazine Compounds can be used to treat or prevent ALS.

The Piperazine Compounds can be used to treat or prevent retinopathy, including but not limited to, arteriosclerotic retinopathy, diabetic arteriosclerotic retinopathy, hypertensive retinopathy, non-proliferative retinopathy, and proliferative retinopathy.

The Piperazine Compounds can be used to treat or prevent a muscle spasm.

The Piperazine Compounds can be used to treat or prevent a migraine.

The Piperazine Compounds can be used to treat or prevent vomiting, including but not limited to, nausea vomiting, dry vomiting (retching), and regurgitation.

The Piperazine Compounds can be used to treat or prevent dyskinesia, including but not limited to, tardive dyskinesia and biliary dyskinesia.

The Piperazine Compounds can be used to treat or prevent depression, including but not limited to, major depression and bipolar disorder.

Without wishing to be bound by theory, Applicants believe that the Piperazine Compounds are antagonists for mGluR5.

The invention also relates to methods for inhibiting mGluR5 function in a cell comprising contacting a cell capable of expressing mGluR5 with an amount of a Piperazine Compound effective to inhibit mGluR5 function in the cell. This method can be used in vitro, for example, as an assay to select cells that express mGluR5 and, accordingly, are useful as part of an assay to select compounds useful for treating or preventing pain, an addictive disorder, Parkinson's disease, parkinsonism, anxiety, a pruritic condition or psychosis. The method is also useful for inhibiting mGluR5 function in a cell in vivo, in an animal, a human in one embodiment, by contacting a cell, in an animal, with an amount of a Piperazine Compound effective to inhibit mGluR5 function in the cell. In one embodiment, the method is useful for treating or preventing pain in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing a pruritic condition in an animal in need thereof. In another embodiment, the method is useful for treating or preventing psychosis in an animal in need thereof. Examples of cells capable of expressing mGluR5 are neuronal and glial cells of the central nervous system, particularly the brain, especially in the nucleus accumbens. Methods for assaying cells that express mGluR5 are well known in the art.

Without wishing to be bound by theory, Applicants believe that the Piperazine Compounds are antagonists for mGluR1.

The invention also relates to methods for inhibiting mGluR1 function in a cell comprising contacting a cell capable of expressing mGluR1 with an amount of a Piperazine Compound effective to inhibit mGluR1 function in the cell. This method can be used in vitro, for example, as an assay to select cells that express mGluR1 and, accordingly, are useful as part of an assay to select compounds useful for treating or preventing pain, UI, an addictive disorder, Parkinson's disease, parkinsonism, anxiety, epilepsy, a seizure, stroke, a pruritic condition, psychosis, a cognitive disorder, a memory deficit, restricted brain function, Huntington's chorea, ALS, dementia, retinopathy, a muscle spasm, a migraine, vomiting, dyskinesia or depression. The method is also useful for inhibiting mGluR1 function in a cell in vivo, in an animal, a human in one embodiment, by contacting a cell, in an animal, with an amount of a Piperazine Compound effective to inhibit mGluR1 function in the cell. In one embodiment, the method is useful for treating or preventing pain in an animal in need thereof. In another embodiment, the method is useful for treating or preventing UI in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing epilepsy in an animal in need thereof. In another embodiment, the method is useful for treating or preventing a seizure in an animal in need thereof. In another embodiment, the method is useful for treating or preventing stroke in an animal in need thereof. In another embodiment, the method is useful for treating or preventing a pruritic condition in an animal in need thereof. In another embodiment, the method is useful for treating or preventing psychosis in an animal in need thereof. In another embodiment, the method is useful for treating or preventing a cognitive disorder in an animal in need thereof. In another embodiment, the method is useful for treating or preventing a memory deficit in an animal in need thereof. In another embodiment, the method is useful for treating or preventing restricted brain function in an animal in need thereof. In another embodiment, the method is useful for treating or preventing Huntington's chorea in an animal in need thereof. In another embodiment, the method is useful for treating or preventing ALS in an animal in need thereof. In another embodiment, the method is useful for treating or preventing dementia in an animal in need thereof. In another embodiment, the method is useful for treating or preventing retinopathy in an animal in need thereof. In another embodiment, the method is useful for treating or preventing a muscle spasm in an animal in need thereof. In another embodiment, the method is useful for treating or preventing a migraine in an animal in need thereof. In another embodiment, the method is useful for treating or preventing vomiting in an animal in need thereof. In another embodiment, the method is useful for treating or preventing dyskinesia in an animal in need thereof. In another embodiment, the method is useful for treating or preventing depression in an animal in need thereof.

Examples of cells capable of expressing mGluR1 include, but are not limited to, cerebellar Purkinje neuron cells, Purkinje cell bodies (punctate), cells of spine(s) of the cerebellum; neurons and neurophil cells of olfactory-bulb glomeruli; cells of the superficial layer of the cerebral cortex; hippocampus cells; thalamus cells; superior colliculus cells; and spinal trigeminal nucleus cells. Methods for assaying cells that express mGluR1 are well known in the art.

5.6 Therapeutic/Prophylactic Administration and Compositions of the Invention Due to their activity, the Piperazine Compounds are advantageously useful in veterinary and human medicine. As described above, the Piperazine Compounds are useful for treating or preventing a Condition in an animal in need thereof.

When administered to an animal, the Piperazine Compounds are administered as a component of a composition that comprises a pharmaceutically acceptable carrier or excipient. The present compositions, which comprise a Piperazine Compound, can be administered orally. The Piperazine Compounds of the invention can also be administered by any other convenient route, for example, by infusion or bolus injection, by absorption through epithelial or mucocutaneous linings (e.g., oral, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer the Piperazine Compound.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the Piperazine Compounds into the bloodstream.

In specific embodiments, it can be desirable to administer the Piperazine Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Piperazine Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Piperazine Compounds can be formulated as a suppository, with traditional binders and excipients such as triglycerides.

In another embodiment, the Piperazine Compounds can be delivered in a vesicle, in particular a liposome (see Langer, *Science* 249:1527–1533 (1990) and Treat et al., *Liposomes in the Therapy of Infectious Disease and Cancer* 317–327 and 353–365 (1989).

In yet another embodiment, the Piperazine Compounds can be delivered in a controlled-release system or sustained-release system (see, e.g., Goodson, in Medical Applications of Controlled Release, supra, vol. 2, pp. 115–138 (1984)). Other controlled- or sustained-release systems discussed in the review by Langer, *Science* 249:1527–1533 (1990) can be used. In one embodiment, a pump can be used (Langer, *Science* 249:1527–1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the Piperazine Compounds, e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water, and in one embodiment physiological saline, is a particularly useful excipient when the Piperazine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447–1676 (Alfonso R. Gennaro ed., 19th ed. 1995), incorporated herein by reference.

In one embodiment, the Piperazine Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Piperazine Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the Piperazine Compounds are to be administered by infusion, they can be dispensed, for example, with an infusion bottle containing sterile pharmaceutical grade water or saline. Where the Piperazine Compounds are administered by injection, an ampule of sterile water for injection or saline can be provided so that the ingredients can be mixed prior to administration.

The Piperazine Compounds can be administered by controlled-release or sustained-release means or by delivery devices that are well known to those of ordinary skill in the art. Examples include, but are not limited to, those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained counterparts. In one embodiment, a controlled- or sustained-release composition comprises a minimal amount of a Piperazine Compound to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Piperazine Compound, and can thus reduce the occurrence of adverse side effects.

Controlled- or sustained-release compositions can initially release an amount of a Piperazine Compound that promptly produces the desired therapeutic or prophylactic effect, and gradually and continually release other amounts of the Piperazine Compound to maintain this level of therapeutic or prophylactic effect over an extended period of time. To maintain a constant level of the Piperazine Compound in the body, the Piperazine Compound can be released from the dosage form at a rate that will replace the amount of Piperazine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Piperazine Compound that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and should be decided according to the judgment of the practitioner and each patient's circumstances in view of published clinical studies. Suitable effective dosage amounts, however, range from about 10 micrograms to about 2500 milligrams about every 4 h, although they are typically about 100 mg or less. In one embodiment, the effective dosage amount ranges from about 0.01 milligrams to about 100 milligrams of a Piperazine Compound about every 4 h, in another embodiment, about 0.020 milligrams to about 50 milligrams about every 4 h, and in another embodiment, about 0.025 milligrams to about 20 milligrams about every 4 h. The effective dosage amounts described herein refer to total amounts administered; that is, if more than one Piperazine Compound is administered, the effective dosage amounts correspond to the total amount administered.

Where a cell capable of expressing mGluR5 or mGluR1 is contacted with a Piperazine Compound in vitro, the amount effective for inhibiting the receptor function in a cell will typically range from about 0.01 $\mu$g/L to about 5 mg/L, in one embodiment, from about 0.01 $\mu$g/L to about 2.5 mg/L, in another embodiment, from about 0.01 $\mu$g/L to about 0.5 mg/L, and in another embodiment, from about 0.01 $\mu$g/L to about 0.25 mg/L of a solution or suspension of a pharmaceutically acceptable carrier or excipient. In one embodiment, the volume of solution or suspension is from about 1 $\mu$L to about 1 mL. In another embodiment, the volume of solution or suspension is about 200 $\mu$L.

Where a cell capable of expressing mGluR5 or mGluR1 is contacted with a Piperazine Compound in vivo, the amount effective for inhibiting the receptor function in a cell will typically range from about 0.01 mg to about 100 mg/kg of body weight per day, in one embodiment, from about 0.1 mg to about 50 mg/kg body weight per day, and in another embodiment, from about 1 mg to about 20 mg/kg of body weight per day.

The Piperazine Compounds can be assayed in vitro or in vivo for the desired therapeutic or prophylactic activity prior to use in humans. Animal model systems can be used to demonstrate safety and efficacy.

The present methods for treating or preventing a Condition in an animal in need thereof can further comprise administering to the animal being administered a Piperazine Compound another therapeutic agent. In one embodiment, the other therapeutic agent is administered in an effective amount.

The present methods for inhibiting mGluR5 function in a cell capable of expressing mGluR5 can further comprise contacting the cell with an effective amount of another therapeutic agent.

The present methods for inhibiting mGluR1 function in a cell capable of expressing mGluR1 can further comprise contacting the cell with an effective amount of another therapeutic agent.

The other therapeutic agent includes, but is not limited to, an opioid agonist, a non-opioid analgesic, a non-steroidal anti-inflammatory agent, an antimigraine agent, a Cox-II inhibitor, an antiemetic, a $\beta$-adrenergic blocker, an anticonvulsant, an antidepressant, a Ca2+-channel blocker, an anticancer agent, an agent for treating or preventing one or more Conditions, and mixtures thereof.

Effective amounts of the other therapeutic agents are well known to those skilled in the art. However, it is well within the skilled artisan's purview to determine the other therapeutic agent's optimal effective-amount range. In one embodiment of the invention, where another therapeutic agent is administered to an animal, the effective amount of the Piperazine Compound is less than its effective amount would be where the other therapeutic agent is not administered. In this case, without being bound by theory, it is believed that the Piperazine Compounds and the other therapeutic agent act synergistically to treat or prevent a Condition.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in Goodman & Gilman's The Pharmacological Basis of Therapeutics 617–57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196–1221 (A. R. Gennaro ed. 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpipride, dihydroergotamine, dolasetron, ergocomine, ergocominine, ergocryptine, ergot, ergotamine, flumedroxone acetate, fonazine, lisuride, lomerizine, methysergide oxetorone, pizotyline, and mixtures thereof.

The other therapeutic agent can also be an agent useful for reducing any potential side effects of a Piperazine Compounds. For example, the other therapeutic agent can be an antiemetic agent. Examples of useful antiemetic agents include, but are not limited to, metoclopromide, domperidone, prochlorperazine, promethazine, chlorpromazine, trimethobenzamide, odansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthrryl)hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimelidine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, gabapentin, lamotrigine, γ-vinyl GABA, acetazolamide, and felbamate.

Examples of useful therapeutic agents for treating or preventing a seizure include, but are not limited to, carbamazepine, ethosuximide, gabapentin, lamotrigine, phenobarbital, phenytoin, primidone, valproic acid, trimethadione, benzodiazepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT$_3$ receptor antagonists such as odansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A Piperazine Compound and the other therapeutic agent can act additively or, in one embodiment, synergistically. In one embodiment, a Piperazine Compound is administered concurrently with another therapeutic agent. In one embodiment, a composition comprising an effective amount of a Piperazine Compound and an effective amount of another therapeutic agent can be administered. Alternatively, a composition comprising an effective amount of a Piperazine Compound and a different composition comprising an effective amount of another therapeutic agent can be concurrently administered. In another embodiment, an effective amount of a Piperazine Compound is administered prior or subsequent to administration of an effective amount of another therapeutic agent. In this embodiment, the Piperazine Compound is administered while the other therapeutic agent exerts its therapeutic effect, or the other therapeutic agent is administered while the Piperazine Compound exerts its preventative or therapeutic effect for treating or preventing a Condition.

In another embodiment a composition of the invention is prepared by a method comprising admixing a Piperazine Compound and pharmaceutically acceptable salt and a pharmaceutically acceptable carrier or excipient. Admixing can be accomplished using methods well known for admixing a compound (or salt) and a pharmaceutically acceptable carrier or excipient. In one embodiment the Piperazine Compound or the pharmaceutically acceptable salt of the Compound is present in the composition in an effective amount.

5.7 Kits

The invention encompasses kits that can simplify the administration of a Piperazine Compound to an animal.

A typical kit of the invention comprises a unit dosage form of a Piperazine Compound. In one embodiment, the unit dosage form is a container, which can be sterile, containing an effective amount of a Piperazine Compound and a pharmaceutically acceptable carrier or excipient. The kit can further comprise a label or printed instructions instructing the use of the Piperazine Compound to treat a Condition. The kit can also further comprise a unit dosage form of another therapeutic agent, for example, a container containing an effective amount of the other therapeutic agent. In one embodiment, the kit comprises a container containing an effective amount of a Piperazine Compound and an effective amount of another therapeutic agent. Examples of other therapeutic agents include, but are not limited to, those listed above.

Kits of the invention can further comprise a device that is useful for administering the unit dosage forms. Examples of such a device includes, but are not limited to, a syringe, a drip bag, a patch, an inhaler, and an enema bag.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

6. EXAMPLES

Examples 1–68 relate to the synthesis of illustrative Piperazine Compounds.

6.1 Example 1

Synthesis of Compound AA

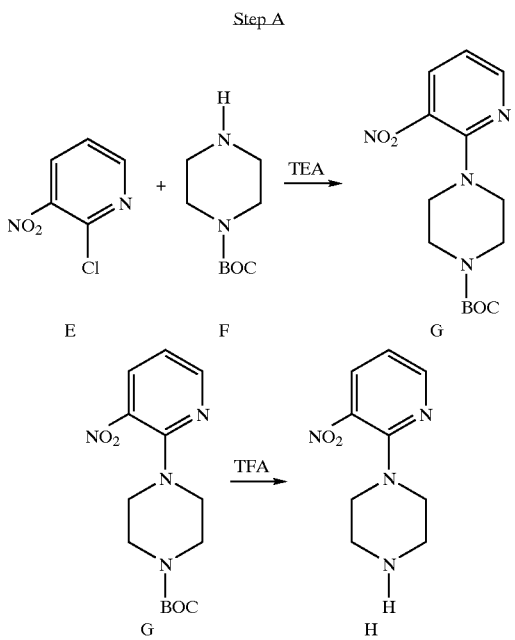

A solution of 2-chloro-3-nitropyridine E (4.2 g, 27 mmol) (commercially available from Aldrich Chemical Co., Milwaukee, Wis.), t-butyl 1-piperazinecarboxylate F (5.0 g, 27 mmol), and triethylamine ("TEA") (10 mL) in CH$_2$Cl$_2$ (200 mL) was stirred at room temperature for 4 h. The solution was then extracted with water, the organic layer separated and dried (Na$_2$SO$_4$), and the organic solvent removed under reduced pressure to provide compound G. Liquid chromatography—mass spectral ("LCMS") analysis showed 100% conversion to compound G. Compound G was redissolved in CH$_2$Cl$_2$ (150 mL) and the resulting solution cooled to 0° C. Trifluoroacetic acid ("TFA") (60 mL) was then slowly added to the solution and the resulting mixture allowed to stir overnight at room temperature. The solution was then evaporated to dryness to afford 1-(3-nitro-pyridin-2-yl)-piperazine, compound H, as yellow powder. Compound H was used in final step C without further purification.

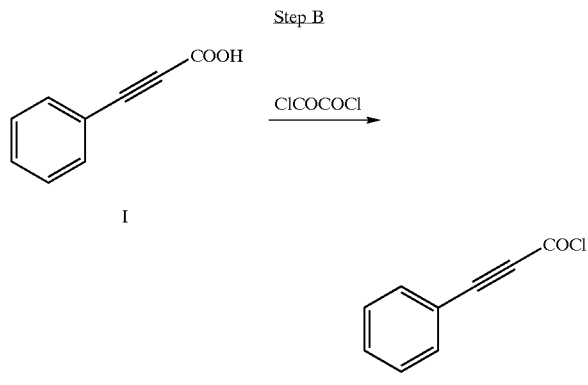

Phenylpropynoic acid I (1.9 g, 13 mmol) was dissolved in 75 mL anhydrous CH$_2$Cl$_2$ and oxalyl chloride (3.8 mL, 43 mmol) was added followed by 2 drops of dimethylformamide. The resulting mixture was protected from exposure to moisture with a drying tube and stirred at room temperature for 2 hours. The solution was then evaporated to dryness to afford compound J. Compound J was used in final step C without further purification.

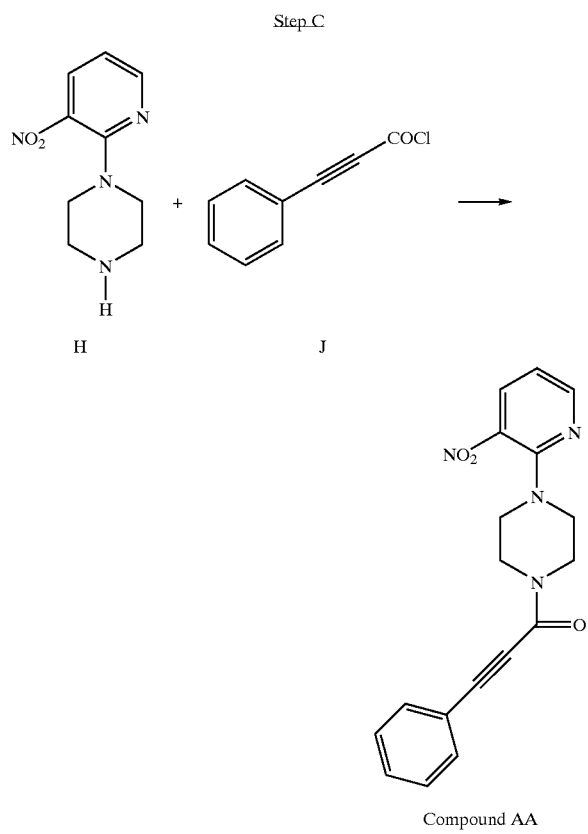

Compound J, prepared in step B, was dissolved in anhydrous tetrahydrofuran (15 mL) and the resulting solution was added dropwise to a solution of compound H (3.0 g) in anhydrous tetrahydrofuran (150 mL) with stirring and the resulting mixture stirred overnight at room temperature. The reaction mixture was then washed 3 times with brine, dried (Na$_2$SO$_4$), and the solvent removed under reduced pressure to provide a residue that was purified by chromatography on a silica column using 1:1 ethyl acetate/hexane as the eluent to provide compound AA as a light yellow solid (70% yield). The structure of Compound AA was confirmed by $^1$H NMR and mass spectral (MS) analysis.

Compound AA: $^1$H NMR (CDCl$_3$) d 8.40 (dd, J=4.4 and 1.6 Hz, 1H), 8.21 (dd, J=8.0 and 1.6 Hz, 1H), 7.57 (m, 2H), 7.42 (m, 3H), 6.88 (dd, J=8.0 and 4.4 Hz, 1H), 4.01 (t, J=5.2 Hz, 2H), 3.87 (t, J=5.2 Hz, 2H), 3.54 (m, 4H); MS (EI): m/z 359 (M+Na$^+$).

6.2 Example 2

Synthesis of Compound AB

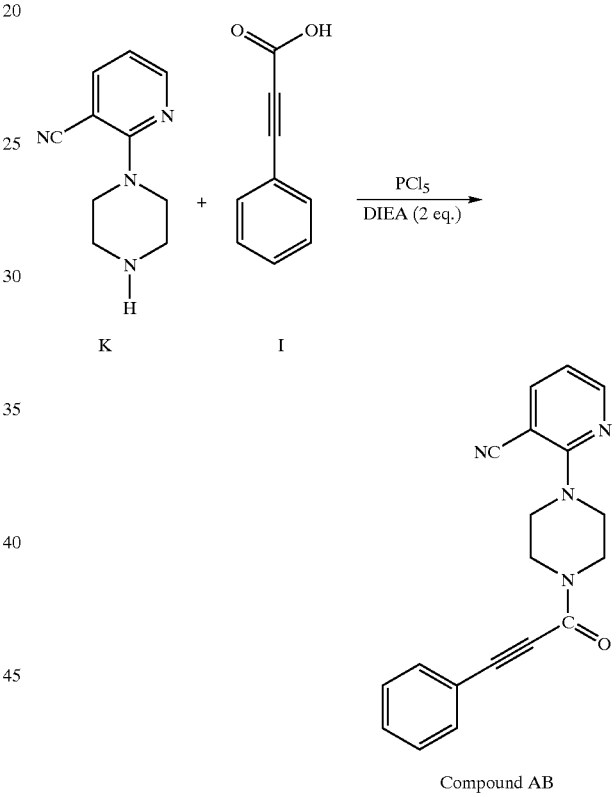

To a mixture of compound K (1.2 mmol) (made from the reaction of 2-chloro-3-cyanopyridine and t-butyl 1-piperazinecarboxylate, compound F, according to the method of Step A in Example 1) and PCl$_5$ (1.2 mmol) in 5 mL of dichloroethane was added, in one portion, 1 mmol (1 eq.) of compound I and 2 eq. of diisopropylethylamine ("DIEA") and the resulting reaction mixture was allowed to stir at 40° C. for 2 h. Thin-layer chromatography demonstrated the complete disappearance of compound K. 5 mL of aqueous NaOH (1 N) was added to the reaction mixture and the organic layer separated. The aqueous layer was then extracted with ethyl acetate (3 mL, 2 times) and the organic layers combined, dried (potassium carbonate), and the solvent removed under reduced pressure to provide a brown oil. The resulting brown oil was dissolved in 1 mL of dichloromethane ("DCM") and purified by column chromatography on a silica column (5 g silica). The column was eluted by gradient elution starting with 100% hexane and gradually increasing the polarity of the solvent to 20% ethyl acetate/hexane and then eluting with 5% triethylamine/40% ethyl acetate/55% hexane to provide Compound AB as an oil. High pressure liquid chromatography ("HPLC") analysis showed that the purity of Compound AB was greater than 97%. The structure of Compound AB was confirmed by $^1$H NMR and mass spectral ("MS") analysis.

Compound AB: $^1$H NMR (CDCl$_3$) d 3.65 (m, 2H), 3.80 (m, 2H), 3.87 (m, 2H), 4.05 (m, 2H), 6.75 (dd, 1H), 7.30–7.50 (m, 2H), 7.60 (m, 2H), 7.80 (d, 1H), 8.35 (d, 1H). MS: m/z 317.1 (M+1).

6.3 Example 3

Synthesis of Compounds AE, AX and AY

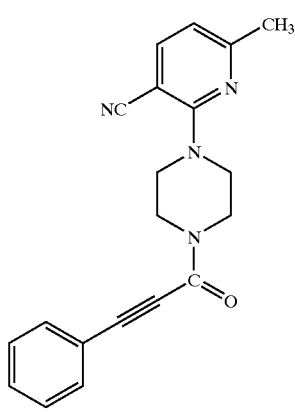

Compound AX

Compound AX was prepared by reacting 1-(6-methyl-3-nitro-pyridin-2-yl)-piperazine with compound I using a procedure analogous to that used to make Compound AB (Example 6.2). HPLC analysis showed that the purity of Compound AX was greater than 97%. The structure of Compound AX, was confirmed by $^1$H NMR and MS analysis.

Compound AX: $^1$H NMR (CDCl$_3$) d 2.40 (s, 1H), 3.65 (m, 2H), 3.80 (m, 2H), 3.87 (m, 2H), 4.05 (m, 2H), 6.60 (d, 1H), 7.30–7.50 (m, 2H), 7.60 (m, 2H), 7.65 (d, 1H). MS: m/z 331.2.

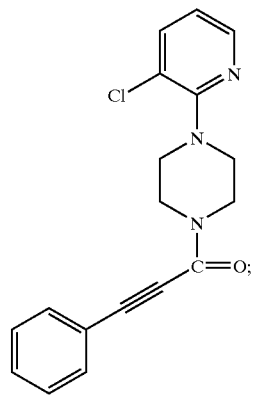

Compound AE

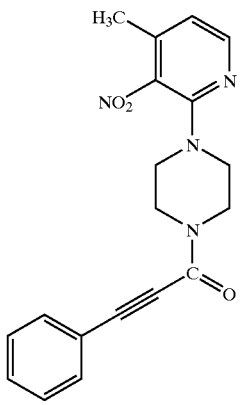

Compound AY

Compounds AE and AY can be prepared by reacting 1-(3-chloro-pyridin-2-yl)-piperazine (for Compound AE) or 1-(4-methyl-3-nitro-pyridin-2-yl)-piperazine (for Compound AY) with compound I using a procedure analogous to that used to make Compound AB (Example 6.2).

6.4 Example 4

Synthesis of Compound AO

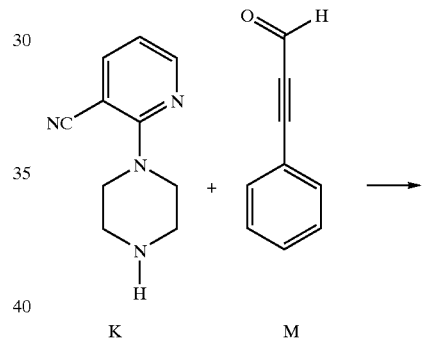

K        M

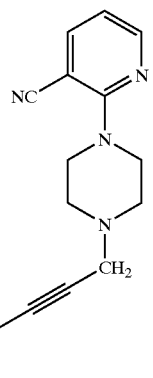

Compound AO

To a mixture of compound K (1 mmol) (made from the reaction of 2-chloro-3-cyanopyridine and t-butyl 1-piperazinecarboxylate, compound F, according to the method of Step A in Example 1) and propargyl aldehyde, compound M (1 mmol) in 5 mL of dichloroethane was added, in one portion, 310 mg of sodium triacetoxyborohydride (1.4 mmol, 1.4 eq.) and the resulting reaction mixture was allowed to stir overnight. Thin-layer chromatography demonstrated the complete disappearance of compound K. 5 mL of 1 N NaOH was then added to the reaction mixture and the organic layer separated. The aqueous layer was then extracted with ethyl acetate (3 mL, 2 times) and the organic layers combined, dried (potassium carbonate), and the solvent removed under reduced pressure to provide a brown oil. The resulting brown oil was dissolved in 1 mL of DCM and purified by column chromatography on a silica column (5 g silica). The column was eluted by gradient elution starting with 100% hexane and gradually increasing the polarity of the solvent to 20% ethyl acetate/hexane and then eluting with 5% triethylamine/40% ethyl acetate/55% hexane to provide Compound AO as an oil. HPLC analysis showed that the purity of Compound AO was greater than 97%. The structure of Compound AO was confirmed by $^1$H NMR and MS analysis.

Compound AO: $^1$H NMR (CDCl$_3$) d 2.80–2.90 (m, 4H), 3.60 (m, 2H), 3.80–3.90 (m, 4H), 6.75 (dd, 1H), 7.30–7.60 (m, 5H), 7.80 (d, 1H), 8.35 (d, 1H). MS: m/z 303.1 (M+1).

6.5 Example 5

Synthesis of Compounds AQ, AW, AZ, BA and BB

Compound AQ

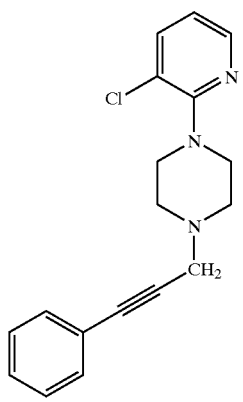

Compound AW

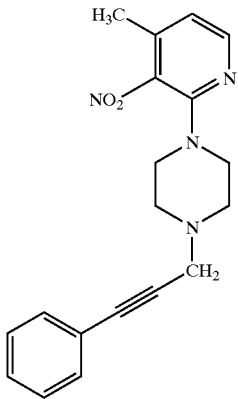

Compound BB

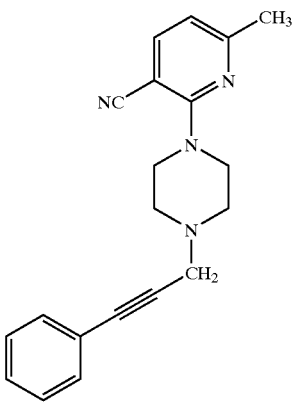

Compounds AQ, AW and BB were prepared by reacting compound M with 1-(3-chloro-pyridin-2-yl)-piperazine (for Compound AQ), 1-(4-methyl-3-nitro-pyridin-2-yl)-piperazine (for Compound AW), or 1-(6-methyl-3-cyano-pyridin-2-yl)-piperazine (for Compound BB) using a procedure analogous to that used to make Compound AO (Example 4). The structure of Compounds AQ, AW and BB were confirmed by $^1$H NMR and MS analysis.

Compound AQ: $^1$H NMR (CDCl$_3$) d 2.75–2.85 (m, 4H), 3.40–3.50 (bs, 4H), 3.60 (s, 2H), 6.80 (dd, 1H), 7.30–7.60 (m, 5H), 7.60 (d, 1H), 8.20 (d, 1H). MS: m/z 312.1.

Compound AW: $^1$H NMR (CDCl$_3$) d 2.30 (s, 3H), 2.70–2.80 (m, 4H), 3.40–3.60 (m, 4H), 3.65 (s, 2H), 6.65 (d, 1H), 7.30–7.60 (m, 5H), 8.15 (d, 1H). MS: m/z 337.2.

Compound BB: $^1$H NMR (CDCl$_3$) d 2.40 (s, 3H), 2.75–2.85 (m, 4H), 3.60 (s, 2H), 3.80–3.90 (m, 4H), 6.60 (d, 1H), 7.30–7.50 (m, 5H), 7.65 (d, 1H). MS: m/z 317.1.

Compounds AZ and BA can be prepared by reacting 4-phenyl-3-butyn-2-one and 1-(3-nitro-pyridin-2-yl)-piperazine (for Compound AZ) or 1-(3-cyano-pyridin-2-yl)-piperazine (for Compound BA) using a procedure analogous to that used to make Compound AO (Example 4) as depicted below.

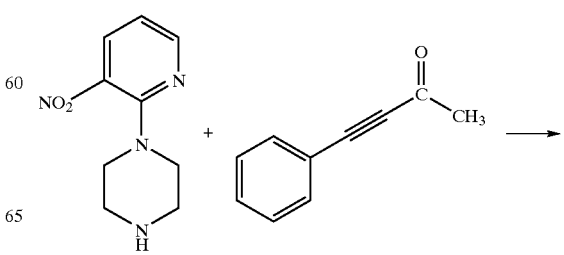

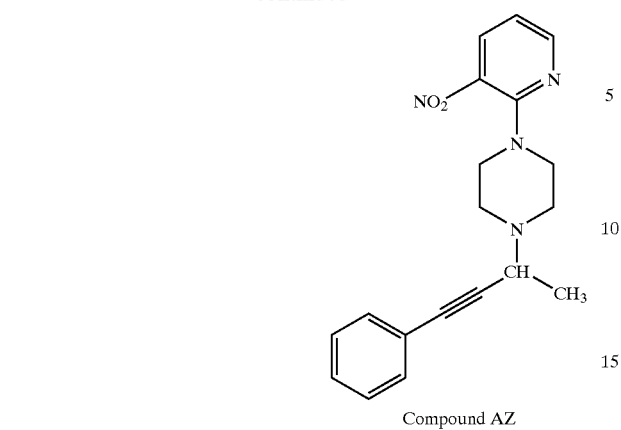

Compound AZ

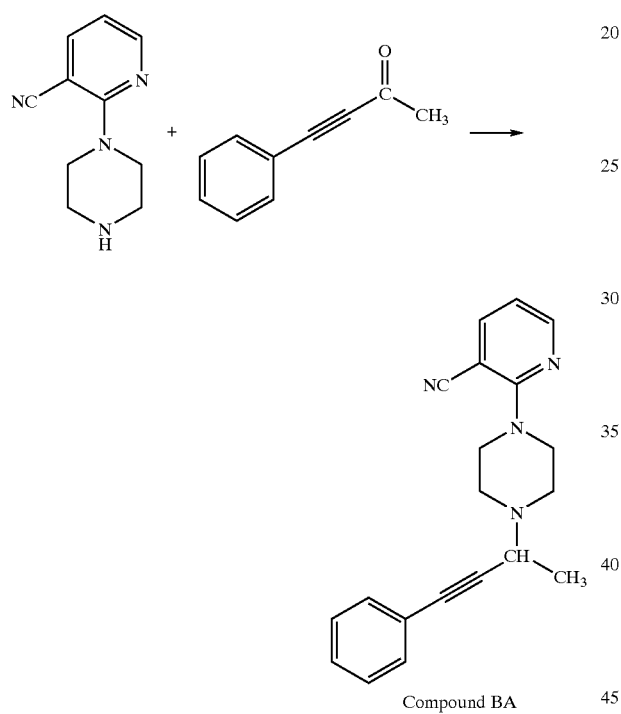

Compound BA

6.6 Example 6

Synthesis of Compounds BC and BD

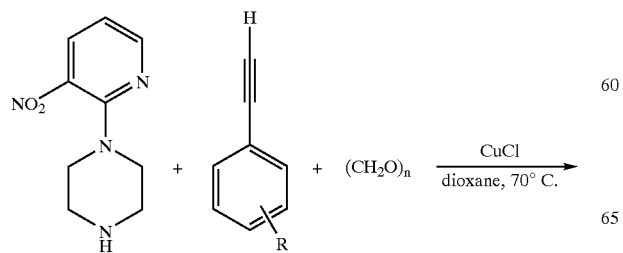

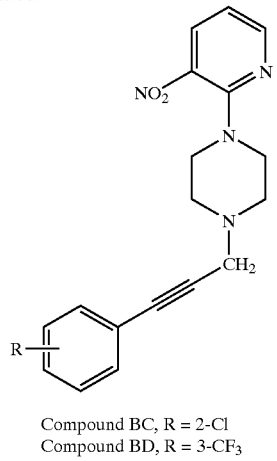

Compound BC, R = 2-Cl
Compound BD, R = 3-CF$_3$

Compounds BC and BD were prepared by reacting compound H (prepared according to the method described in Step A of Example 1) with the appropriately substituted phenylacetylene and paraformaldehyde in dioxane at 70° C. in the presence of CuCl. The structure of Compounds BC and BD was confirmed by $^1$H NMR.

Compound BC: $^1$H NMR (CDCl$_3$) d 8.34 (dd, 1H, J=4.5, 1.75), 8.13 (dd, 1H, J=8.05, 1.75), 7.46 (dd, 1H, J=7.37, 1.94), 7.38 (dd, 1H, J=7.89, 1.34), 7.27–7.17 (m, 2H), 6.75 (dd, 1H, J=8.04, 4.52), 3.66 (s, 2H), 3.55 (t, 1H, J=4.94), 2.79 (t, 1H, J=4.95).

Compound BD: $^1$H NMR (CDCl$_3$) d 8.35 (dd, 1H, J=4.53, 1.74), 8.15 (dd, 1H, J=8.03, 1.73), 7.56 (m, 4H), 6.78 (dd, 1H, J=8.05, 4.54), 3.61 (s, 2H), 3.56 (t, 1H, J=4.92), 2.77 (t, 1H, J=4.94).

6.7 Example 7

Synthesis of Compound BE

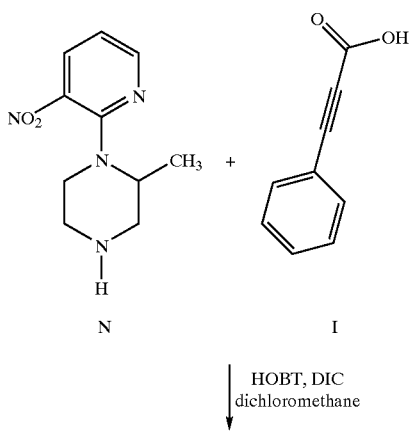

HOBT, DIC
dichloromethane

Compound BE was prepared by reacting compound N (prepared according to the method described in Step A of Example 1) with compound I in the presence of HOBT and DIC in methylene chloride at 70° C. The structure of Compound BE was confirmed by $^1$H NMR.

Compound BE: $^1$H NMR (CDCl$_3$) δ 8.39 (m, 1H), 8.17 (m, 1H), 7.55 (m, 1H), 7.43 (m, 3H), 6.85 (dd, J=4.5, 8.03 Hz, 1H), 4.55 (m, 1H), 4.42 (m, 1.5H), 4.26 (dt, J=3.0, 13.3 Hz, 0.5H), 3.66 (dd, J=3.54, 13.3 Hz, 0.5H), 3.52 (m, 1H), 3.40 (m, 1H), 3.25 (dd, J=3.54, 13.3 Hz, 0.5H), 3.10 (m, 0.5H), 1.35 (d, J=6.72 Hz, 1.5H), 1.30 (d, J=6.72 Hz, 1.5H).

6.8 Example 8

Synthesis of Compound BF

Compound BF was prepared by reacting compound O (prepared according to the method described in Step A of Example 1) with compound I in the presence of HOBT and DIC in methylene chloride at 70° C. The structure of Compound BF was confirmed by $^1$H NMR.

Compound BF: $^1$H NMR (CDCl$_3$) δ 8.39 (d, J=4.3 Hz, 1H), 8.20 (dd, J=1.69, 8.04 Hz, 1H), 7.55 (m, 2H), 7.43 (m, 3H), 6.85 (dd, J=4.5, 8.04 Hz, 1H), 4.90 (m, 0.5H), 4.75 (m, 0.5H), 4.42 (dt, J=3.0, 10.5 Hz, 0.5H), 4.30 (t, J=3.0, 10.5 Hz, 0.5H), 3.80 (m, 2.5H), 3.45 (m, 1.5H), 3.12 (m, 1H), 1.43 (d, J =6.78 Hz, 1.5H), 1.32 (d, J=6.78 Hz, 1.5H).

6.9 Example 9

Synthesis of Compound AP

A mixture of compound H (145 mg, 0.7 mmol) (prepared according to the method described in Step A of Example 1), 4 Å molecular sieves (0.6 g), and phenylpropargyl aldehyde, compound M, (85 μL, 0.7 mmol) in 4 mL of anhydrous methanol was stirred at room temperature for 10 min. Sodium triacetoxyborohydride (177 mg, 0.8 mmol) was then added to the mixture and the mixture allowed to stir at room temperature for 30 min. 5 mL of aqueous NaOH (3 N) was then added to the reaction mixture and the reaction mixture was extracted with ethyl acetate. The organic layer was separated, dried, and the solvent removed under reduced pressure to provide a residue that was purified by column chromatography using a silica gel column to provide Compound AP as a yellow oil (76% yield). The identity of Compound AP was confirmed by $^1$H NMR and MS analysis.

Compound AP: $^1$H NMR (CDCl$_3$) δ 8.35 (dd, J=4.8 and 2.0 Hz, 1H), 8.14 (dd, J=8.0 and 2.0 Hz, 1H), 7.45 (m, 2H), 7.32 (m, 3H), 6.76 (dd, J=8.0 and 4.8 Hz, 1H), 3.60 (s, 2H), 3.57 (t, J=4.8 Hz, 4H), 2.77 (t, J=4.8 Hz, 4H). MS (EI): m/z 323 (M+H)$^+$.

6.10 Example 10

Synthesis of Compound AV

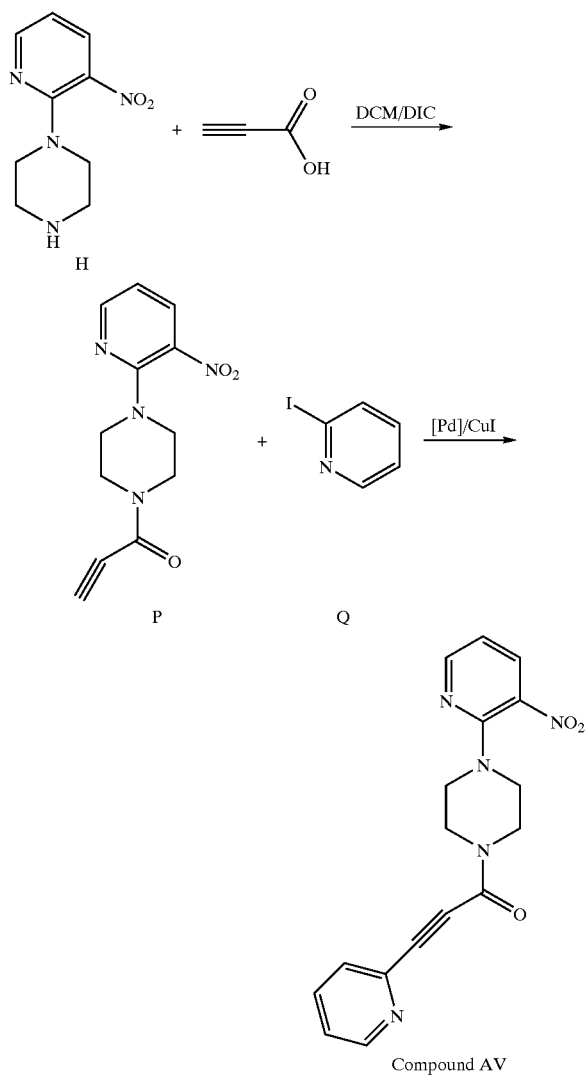

Compound AV

A solution of compound H (5 g, 24 mmol) in 250 mL of DCM was cooled to 0° C. and HOBT (1.0 g, 8 mmol), propynoic acid (2 g, 28 mmol) and 4-(dimethylamino)pyridine (100 mg) were added 0° C. Then, DIC (4 mL) was added slowly over a 30 minute period. The resulting mixture was warmed to 25° C. over about a 14 hour period, then cooled to 0° C. The precipitate was removed by filtration. The supernatant was washed with 30 mL of aqueous NaOH (2 N) followed by washing with 50 mL of brine. The solvent was removed under reduced pressure to provide a residue that was purified by chromatography on a silica column using 3:7 ethyl acetate/hexane as the eluent to provide 5 g of compound P as yellow solid (80% yield).

A mixture of compound P (1.0 g), 2-iodopyridine (compound Q; 1.0 g), TEA (1 mL) and ethyl acetate (20 mL) was degassed and flushed with nitrogen. Pd[(phenyl)$_3$P]$_2$Cl$_2$ (100 mg) and CuI (50 mg) were added. The resulting mixture was heated to 50° C. and maintained at that temperature for 5 hours. Then, the solvent was removed under reduced pressure to provide a residue that was purified by chromatography on a silica column using 1:1 ethyl acetate/hexane as the eluent to provide 1.1 g of Compound AV as a yellow solid (84% yield).

Compound AV: $^1$H NMR (CDCl$_3$) 8.67 (dd, 0.5H, J=1.7 and 4.8 Hz), 8.65 (dd, 0.5H, J=1.7 and 4.8 Hz), 8.39 (dd, 1H, J=1.7 and 4.6 Hz), 8.19 (dd, 1H, J=1.7 and 8.2 Hz), 7.75 (ddd, 1H, J=1.7, 6.0 and 7.7 Hz), 7.64 (dd, 0.5H, J=1.1 and 7.8 Hz), 7.62 (dd, 0.5H, J=1.0 and 7.7 Hz), 7.37 (dd, 0.5H, J=4.8 and 7.6 Hz), 7.35 (dd, 0.5H, J=4.8 and 7.6 Hz), 6.87 (dd, 1H, J=4.8 and 8.2 Hz), 4.02–4.05 (m, 2H), 3.83–3.87 (m, 2H), 3.49–3.55 (m, 4H). MS (EI): m/z 360 (M+23).

6.11 Example 11

Synthesis of Compound BG

Compound BG was prepared according to Example 10, except that 3-iodopyridine was used in place of compound Q.

6.12 Example 12

Synthesis of Compound BG

Compound BG was prepared from compound P according to Example 10, except that 3-bromopyridine was used in place of compound Q.

Compound BG: $^1$H NMR (CDCl$_3$) 8.40 (dd, 1H, J=1.7 and 4.6 Hz), 8.22 (dd, 1H, J=1.7 and 8.2 Hz), 7.65 (dd, 1H, J=1.5 and 7.8 Hz), 7.46 (dd, 1H, J=1.5 and 8.1 Hz), 7.39 (ddd, 1H, J=1.5, 5.8 and 7.9 Hz), 7.31 (ddd, 1H, J=1.3, 6.1 and 7.6 Hz), 6.87 (dd, 1H, J=4.6 and 7.9 Hz), 4.09–4.13 (m, 2H), 3.85–3.89 (m, 2H), 3.51–3.58 (m, 4H). MS (EI): m/z 370 (M+23).

6.13 Example 13

Synthesis of Compound BH

Compound BH was prepared according to Example 10, except that 2-iodopyrazine was used in place of compound Q.

6.14 Example 14

Synthesis of Compound BI

Compound BI was prepared according to Example 10, except that 2-bromo-6-methoxypyridine was used in place of compound Q.

6.15 Example 15

Synthesis of Compound BJ

Compound BJ was prepared according to Example 10, except that 2-bromo-3-methylpyridine was used in place of compound Q.

6.16 Example 16

Synthesis of Compound BK

Compound BK was prepared according to Example 10, except that 2-iodo-6-methylpyridine was used in place of compound Q.

6.17 Example 17

Synthesis of Compound BL

Compound BL was prepared according to Example 10, except that 2-bromo-5-methylpyridine was used in place of compound Q.

6.18 Example 18

Synthesis of Compound BM

Compound BM was prepared according to Example 10, except that 2-bromo-4-methylpyridine was used in place of compound Q.

6.19 Example 19

Synthesis of Compound BN

Compound BN was prepared according to Example 10, except that 4-iodopyridine was used in place of compound Q.

6.20 Example 20

Synthesis of Compound BO

Compound BO was prepared according to Example 10, except that 5-iodo-2-methoxypyridine was used in place of compound Q.

6.21 Example 21

Synthesis of Compound BP

Compound BP was prepared according to Example 10, except that 2-fluoro-5-iodopyridine was used in place of compound Q.

6.22 Example 22

Synthesis of Compound CK

Compound CK was prepared from compound P according to Example 10, except that 4-bromoanisole was used in place of compound Q.

Compound CK: $^1$H NMR (CDCl$_3$) 8.45 (d, 1H), 8.25 (d, 1H), 7.50–7.60 (m, 2H), 6.90–6.70 (m, 3H), 4.05 (dd, 2H), 3.70–3.80 (m, 5H), 3.45–3.55 (m, 4H). MS (EI): m/z 367 (M+1).

6.23 Example 23

Synthesis of Compound 100

Compound 100 was prepared according to Example 1, except that 2-chloropyridine was used in place of compound E.

Compound 100: $^1$H NMR (CDCl$_3$) 8.25 (d, 1H), 7.55–7.65 (m, 3H), 7.40–7.46 (m, 3H), 6.70–6.80 (m, 2H), 4,10 (dd, 2H), 3.90 (dd, 2H), 3.80 (dd, 2H), 3.75 (dd, 2H). MS (EI): m/z 292 (M+1).

6.24 Example 24

Synthesis of Compound BW

Compound BW was prepared from compound P according to Example 10, except that 3-bromo-4-fluorotoluene was used in place of compound Q.

Compound BW: $^1$H NMR (CDCl$_3$) 8.40 (dd, 1H, J=1.3 and 4.6 Hz), 8.21 (dd, 1H, J=1.7 and 8.1 Hz), 7.38 (dd, 1H, J=1.9 and 6.6 Hz), 7.21–7.24 (m, 1H), 7.02 (dd, 1H, J=8.6 and 8.7 Hz), 6.88 (dd, 1H, J=4.6 and 8.1 Hz), 4.01–4.04 (m, 2H), 3.85–3.88 (m, 2H), 3.52–3.56 (m, 4H), 2.34 (s, 3H). MS (EI): m/z 370 (M+1).

6.25 Example 25

Synthesis of Compound BQ

Compound BQ was prepared from compound P according to Example 10, except that 4-bromo-1,2-(methylenedioxy) benzene was used in place of compound Q.

Compound BQ: $^1$H NMR (CDCl$_3$) 8.40 (d, 1H), 8.23 (d, 1H), 7.20 (d, 1H), 7.00 (s, 1H), 6.80–6.90 (m, 1H), 6.75 (d, 1H), 6.05 (s, 2H), 4.05 (dd, 2H), 3.80 (dd, 2H), 3.70–3.80 (m, 4H). MS (EI): m/z 381 (M+1).

6.26 Example 26

Synthesis of Compound BV

Compound BV was prepared according to Example 7, except that compound H was used in place of compound N and 2-hexynoic acid was used in place of compound I.

Compound BV: $^1$H NMR (CDCl$_3$) 8.45 (d, 1H), 8.20 (d, 1H), 6.90 (dd, 1H), 4.05 (dd, 2H), 3.80 (dd, 2H), 3.70–3.80 (m, 4H), 2.50 (t, 2H), 1.75–1.85 (m, 2H), 1.10 (t, 3H). MS (EI): m/z 303 (M+1).

6.27 Example 27

Synthesis of Compound 286

Compound 286 was prepared according to Example 1, except that 2-chloro-6-methoxy-3-nitropyridine was used in place of compound E.

6.28 Example 28

Synthesis of Compound CH

Compound CH was prepared according to Example 1, except that 2-chloro-3-trifluoromethylpyridine was used in place of compound E.

6.29 Example 29

Synthesis of Compound 283

Compound 283 was prepared according to Example 1, except that 2-chloro-6-methyl-3-nitropyridine was used in place of compound E.

6.30 Example 30

Synthesis of Compound 145

Compound 145 was prepared according to Example 1, except that 2-chloro-5-nitropyridine was used in place of compound E.

6.31 Example 31

Synthesis of Compound 103

Compound 103 was prepared according to Example 1, except that 2-chloro-6-methylpyridine was used in place of compound E.

6.32 Example 32

Synthesis of Compound 160

Compound 160 was prepared according to Example 1, except that 2-chloro-4-methylpyridine was used in place of compound E.

6.33 Example 33

Synthesis of Compound 115

Compound 115 was prepared according to Example 1, except that 2-chloro-5-methylpyridine was used in place of compound E.

6.34 Example 34

Synthesis of Compound CZ

Compound CZ was prepared according to Example 1, except that 2,6-dichloro-3-nitropyridine was used in place of compound E.

6.35 Example 35

Synthesis of Compound DA

Compound DA was prepared according to Example 1, except that 2-chloro-3-carbomethoxypyridine was used in place of compound E.

6.36 Example 36

Synthesis of Compound DB

Compound DB was prepared according to Example 1, except that 2-chloro-6-nitropyridine was used in place of compound E.

6.37 Example 37

Synthesis of Compound 163

Compound 163 was prepared according to Example 1, except that 2,4-dimethyl-6-chloropyridine was used in place of compound E.

6.38 Example 38

Synthesis of Compound DE

Compound DE was prepared according to Example 7, except that compound H was used in place of compound N and 2-butynoic acid was used in place of compound I.

6.39 Example 39

Synthesis of Compound BT

Compound BT was prepared according to Example 7, except that compound H was used in place of compound N and 2-octynoic acid was used in place of compound I.

6.40 Example 40

Synthesis of Compound BU

Compound BU was prepared according to Example 7, except that compound H was used in place of compound N and 2-heptynoic acid was used in place of compound I.

6.41 Example 41

Synthesis of Compound BS

Compound BS was prepared according to Example 7, except that compound H was used in place of compound N and 2-nonynoic acid was used in place of compound I.

6.42 Example 42

Synthesis of Compound BX

Compound BX was prepared according to Example 10, except that 3,5-difluoroiodobenzene was used in place of compound Q.

6.43 Example 43

Synthesis of Compound BY

Compound BY was prepared according to Example 10, except that 2,4-dimethoxyiodobenzene was used in place of compound Q.

6.44 Example 44

Synthesis of Compound DF

Compound DF was prepared according to Example 10, except that 3-fluoroiodobenzene was used in place of compound Q.

6.45 Example 45

Synthesis of Compound DG

Compound DG was prepared according to Example 10, except that 2-fluoroiodobenzene was used in place of compound Q.

6.46 Example 46

Synthesis of Compound BZ

Compound BZ was prepared according to Example 10, except that 2-chloro-5-iodotoluene was used in place of compound Q.

6.47 Example 47

Synthesis of Compound CA

Compound CA was prepared according to Example 10, except that 4-chloro-2-fluoroiodobenzene was used in place of compound Q.

6.48 Example 48

Synthesis of Compound DH

Compound DH was prepared according to Example 10, except that 2-chloroiodobenzene was used in place of compound Q.

6.49 Example 49

Synthesis of Compound DI

Compound DI was prepared according to Example 10, except that 3-trifluoromethoxyiodobenzene was used in place of compound Q.

6.50 Example 50

Synthesis of Compound CB

Compound CB was prepared according to Example 10, except that 5-chloro-2-methoxyiodobenzene was used in place of compound Q.

6.51 Example 51

Synthesis of Compound CC

Compound CC was prepared according to Example 10, except that 2-fluoro-5-iodotoluene was used in place of compound Q.

6.52 Example 52

Synthesis of Compound DJ

Compound DJ was prepared according to Example 10, except that 4-chloroiodobenzene was used in place of compound Q.

6.53 Example 53

Synthesis of Compound DK

Compound DK was prepared according to Example 10, except that 4-fluoroiodobenzene was used in place of compound Q.

6.54 Example 54

Synthesis of Compound CD

Compound CD was prepared according to Example 10, except that 2,5-difluoroiodobenzene was used in place of compound Q.

6.55 Example 55

Synthesis of Compound DL

Compound DL was prepared according to Example 10, except that 3-nitroiodobenzene was used in place of compound Q.

6.56 Example 56

Synthesis of Compound DN

Compound DN was prepared according to Example 10, except that 4-tert-butyliodobenzene was used in place of compound Q.

6.57 Example 57

Synthesis of Compound CE

Compound CE was prepared according to Example 10, except that 3-chloro-2-fluoroiodobenzene was used in place of compound Q.

6.58 Example 58

Synthesis of Compound CI

Compound CI was prepared from compound P according to Example 10, except that 2-iodoanisole was used in place of compound Q.

6.59 Example 59

Synthesis of Compound CJ

Compound CJ was prepared from compound P according to Example 10, except that 3-iodoanisole was used in place of compound Q.

6.60 Example 60

Synthesis of Compound CL

Compound CL was prepared from compound P according to Example 10, except that 2-iodotoluene was used in place of compound Q.

6.61 Example 61

Synthesis of Compound CM

Compound CM was prepared from compound P according to Example 10, except that 4-iodotoluene was used in place of compound Q.

6.62 Example 62

Synthesis of Compound CP

Compound CP was prepared from compound P according to Example 10, except that 3-iodotoluene was used in place of compound Q.

6.63 Example 63

Synthesis of Compound DO

Compound DO was prepared according to Example 10, except that 5-iodo-2-methoxypyridine was used in place of compound Q.

6.64 Example 64

Synthesis of Compound DQ

Compound DQ was prepared according to Example 10, except that 2-fluoro-4-iodopyridine was used in place of compound Q.

6.65 Example 65

Synthesis of Compound DR

Compound DR was prepared according to Example 10, except that 4-iodopyridine was used in place of compound Q.

6.66 Example 66

Synthesis of Compound DS

Compound DS was prepared according to Example 10, except that 2-iodopyridine was used in place of compound Q.

6.67 Example 67

Synthesis of Compound DT

Compound DT was prepared according to Example 10, except that 3-iodopyridine was used in place of compound Q.

6.68 Example 68

Synthesis of Compound DU

Compound DU was prepared according to Example 10, except that 2-fluoro-5-iodopyridine was used in place of compound Q.

6.69 Example 69

Binding of an Illustrative Piperazine Compound to mGluR5

The following assay demonstrates that Compound AA, an illustrative Piperazine Compound, binds to mGluR5.

Cell cultures: Primary glial cultures were prepared from cortices of Sprague-Dawley 18 days old embryos. The cortices were dissected and then dissociated by trituration. The resulting cell homogenate was plated onto poly-D-lysine precoated T175 flasks (BIOCOAT, commercially available from Becton Dickinson and Company Inc. of Franklin Lakes, N.J.) in Dulbecco's Modified Eagle's Medium ("DMEM," pH 7.4), buffered with 25 mM HEPES, and supplemented with 15% fetal calf serum ("FCS," commercially available from Hyclone Laboratories Inc. of Omaha, Nebr.), and incubated at 37° C. and 5% $CO_2$. After 24 hours, FCS supplementation was reduced to 10%. On day six, oligodendrocytes and microglia were removed by strongly lapping the sides of the flasks. One day following this purification step, secondary astrocytes cultures were established by subplating onto 96 poly-D-lysine precoated T175 flasks (BIOCOAT) at a density of 65,000 cells/well in DMEM and 10% FCS. After 24 hours, the astrocytes were washed with serum free medium and then cultured in DMEM, without glutamate, supplemented with 0.5% FCS, 20 mM HEPES, 10 ng/mL epidermal growth factor ("EGF"), 1 mM sodium pyruvate, and 1× penicillin/streptomycin at pH 7.5 for 3 to 5 days at 37° C. and 5% $CO_2$. The procedure allows the expression of the mGluR5 receptor by astrocytes, as demonstrated by S. Miller et al., *J. Neuroscience* 15(9):6103–6109 (1995).

Assay Protocol: After 3–5 days incubation with EGF, the astrocytes were washed with 127 mM NaCl, 5 mM KCl, 2 mM $MgCl_2$, 700 mM $NaH_2PO_4$, 2 mM $CaCl_2$, 5 mM $NaHCO_3$, 8 mM HEPES, 10 mM Glucose at pH 7.4 ("Assay Buffer") and loaded with the dye Fluo-4 (commercially available from Molecular Probes Inc. of Eugene, Oreg.) using 0.1 mL of Assay Buffer containing Fluo-4 (3 mM final). After 90 minutes of dye loading, the cells were then washed twice with 0.2 mL Assay Buffer and resuspended in 0.1 mL of Assay Buffer. The plates containing the astrocytes were then transferred to a Fluorometric Imaging Plate reader (commercially available from Molecular Devices Corporation of Sunnyvale, Calif.) for the assessment of calcium mobilization flux in the presence of glutamate and in the presence or absence of antagonist. After monitoring fluorescence for 15 seconds to establish a baseline, DMSO solutions containing various concentrations of the Piperazine Compounds diluted in Assay Buffer (0.05 mL of 4× dilutions for competition curves) were added to the cell plate and fluorescence was monitored for 2 minutes. 0.05 mL of a 4× glutamate solution (agonist) was then added to each well to provide a final glutamate concentration in each well of 10 mM. Plate fluorescence was then monitored for an additional 60 seconds after agonist addition. The final DMSO concentration in the assay was 1.0%. In each experiment, fluorescence was monitored as a function of time and the data analyzed using Microsoft Excel and GraphPad Prism. Dose-response curves were fit using a non-linear regression to determine $IC_{50}$ value. Compound AA (see Example 6.1) showed an $IC_{50}$ value of 8.9±4.8 nM (mean of 3 experiments). FIG. 1 represents a typical dose response curve, i.e., a single experiment, for Compound AA. In each experiment each data point was determined two times. These results show that Compound AA, an illustrative Piperazine Compound, binds to the mGluR5 receptor.

6.70 Example 70

Binding of a Piperazine Compound to mGluR5

Alternatively, the following assay can be used to demonstrate that Piperazine Compounds bind to and modulate the activity of mGluR5 and, accordingly, are useful for treating or preventing, e.g., pain.

40,000 CHO-rat mGluR5 cells/well are plated into 96 well plate (Costar 3409, Black, clear bottom, 96 well, tissue culture treated) for an overnight incubation in Dulbecco's Modified Eagle's Medium (DMEM, pH 7.4) and supplemented with glutamine, 10% FBS, 1% Pen/Strep, and 500 ug/mL Gencticin. CHO-rat mGluR5 cells are washed and treated with Optimem medium and incubated for 1–4 hours prior to loading cells. Cell plates are then washed with loading buffer (127 mM NaCl, 5 mM KCl, 2 mM $MgCl_2$, 700 $\mu$M Na $H_2PO_4$, 2 mM $CaCl_2$, 5 mM $NaHCO_3$, 8 mM Hepes, and 10 mM glucose, pH 7.4) and then incubated with 3 $\mu$M Fluo 4 (commercially available from Molecular probes Inc. of Eugene, Oreg.) in 0.1 mL of loading buffer. After 90 minutes of dye loading, the cells are then washed twice with 0.2 mL loading buffer and resuspended in 0.1 mL loading buffer.

The plates containing the CHO-rat mGluR5 cells are then transferred to a Fluorometric Imaging Plate Reader (FLIPR) (commercially available from Molecular Devices Corporation of Sunnyvale, Calif.) for the assessment of calcium mobilization flux in the presence of glutamate and in the presence or absence of test compounds. After monitoring fluorescence for 15 seconds to establish a baseline, DMSO solutions containing various concentrations of the test compound diluted in loading buffer (0.05 mL of 4× dilutions for the competition curves) are added to the cell plate and fluorescence is monitored for 2 minutes. 0.05 mL of 4× glutamate solution (agonist) is then added to each well to provide a final glutamate concentration in each well of 10 uM. Plate fluorescence is then monitored for an additional 60 seconds after agonist addition. The final DMSO concentration in the assay is 1.0%. In each experiment, fluorescence is monitored as a function of time and the data analyzed using Microsoft Excel and GraphPad Prism. Dose-response curves are fit using a non-linear regression to determine the IC50 value. In each experiment, each data point is determined two times.

6.71 Example 71

In Vivo Assays for Treatment or Prevention of Pain

The following assays can be used to demonstrate that Piperazine Compounds are useful for treating or preventing pain.

Test Animals: Each experiment uses rats weighing between 200–260 g at the start of the experiment. The rats are group-housed and have free access to food and water at all times, except prior to oral administration of a Piperazine Compound when food is removed for 16 hours before dosing. A control group acts as a comparison to rats treated with a Piperazine Compound. The control group is administered the carrier for the Piperazine Compound. The volume of carrier administered to the control group is the same as the volume of carrier and Piperazine Compound administered to the test group.

Acute Pain: To assess the actions of the Piperazine Compounds for the treatment or prevention of acute pain the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Piperazine Compound. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20 \text{ s pre-administration latency})} \times 100$$

The rat tail flick test is described in F. E. D'Amour et al., "A Method for Determining Loss of Pain Sensation," *J. Pharmacol. Exp. Ther.* 72:74–79 (1941). The results show that Piperazine Compounds are useful for treating or preventing acute pain.

Acute pain can also be assessed by measuring the animal's response to noxious mechanical stimuli by determining the paw withdrawal threshold (PWT), as described below.

Inflammatory Pain: To assess the actions of the Piperazine Compounds for the treatment or prevention of inflammatory pain the Freund's complete adjuvant (FCA) model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," Naunyn-Schmiedeberg's Archives of Pharmacology 342:666–670 (1990)). The left hind paw of each animal is administered a 50 µL intraplantar injection of 50% FCA. 24 hour post injection, the animal is assessed for response to noxious mechanical stimuli by determining the PWT, as described below. Rats are then administered a single injection of 1, 3, 10 or 30 mg/Kg of either a Piperazine Compound, 30 mg/Kg indomethacin or carrier. Responses to noxious mechanical stimuli are then determined 1, 3, 5 and 24 hours post administration. Percentage reversal of hyperalgesia for each animal is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of the Piperazine Compounds for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," Pain 43:205–218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3 and 5 hours after drug administration for the left rear paw of the animal. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$–$S_2$ levels. The $L_6$ transverse process is carefully removed with a pair of small rongeurs to identify visually the $L_4$–$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, immediately prior to and 1, 3 and 5 hours after being administered a Piperazine Compound for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," Pain 50(3):355–363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," Pharmacology Biochemistry and Behavior 31:451–455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," Pain 32(1):77–88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodvnia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4–8 seconds or until a nociceptive withdrawal behavior is observed. Flinching, paw withdrawal or licking of the paw are considered nociceptive behavioral responses.

6.72 Example 72

In Vivo Assays for Treatment or Prevention of Anxiety

The following assays can be used to demonstrate that Piperazine Compounds are useful for treating or preventing anxiety. The elevated plus maze test or the shock-probe burying test can be used to assess the anxiolytic activity of Piperazine Compounds in rats or mice.

The Elevated Plus Maze Test: The elevated plus maze consists of a platform with 4 arms, two open and two closed (50×10×50 cm enclosed with an open roof). Rats (or mice) are placed in the center of the platform, at the crossroad of the 4 arms, facing one of the closed arms. Time spent in the open arms vs the closed arms and number of open arm entries during the testing period are recorded. This test is conducted prior to drug administration and again after drug administration. Test results are expressed as the mean time spent in open arms and the mean number of entries into open arms. Known anxiolytic drugs increase both the time spent in open arms and number of open arm entries. The elevated plus maze test is described in D. Treit, "Animal Models for the Study of Anti-anxiety Agents: A Review," Neuroscience & Biobehavioral Reviews 9(2):203–222 (1985).

The Shock-Probe Burying Test: For the shock-probe burying test the testing apparatus consists of a plexiglass box measuring 40×30×40 cm, evenly covered with approximately 5 cm of bedding material (odor absorbent kitty litter) with a small hole in one end through which a shock probe (6.5 cm long and 0.5 cm in diameter) is inserted. The plexiglass shock probe is helically wrapped with two copper wires through which an electric current is administered. The current is set at 2 mA. Rats are habituated to the testing apparatus for 30 min on 4 consecutive days without the shock probe in the box. On test day, rats are placed in one corner of the test chamber following drug administration. The probe is not electrified until the rat touches it with its snout or fore paws, at which point the rat receives a brief 2 mA shock. The 15 min testing period begins once the rat receives its first shock and the probe remains electrified for the remainder of the testing period. The shock elicits burying behavior by the rat. Following the first shock, the duration of time the rat spends spraying bedding material toward or over the probe with its snout or fore paws (burying behavior) is measured as well as the number of contact-induced shocks the rat receives from the probe. Known anxiolytic drugs reduce the amount of burying behavior. In addition, an index of the rat's reactivity to each shock is scored on a 4 point scale. The total time spent immobile during the 15 min testing period is used as an index of general activity. The shock-probe burying test is described in D. Treit, 1985, supra. The results show that Piperazine Compounds are useful for treating or preventing anxiety.

6.73 Example 73

In Vivo Assays for Treatment or Prevention of an Addictive Disorder

The following assays can be used to demonstrate that Piperazine Compounds are useful for treating or preventing an addictive disorder. The condition place preference test or drug self-administration test can be used to assess the ability of Piperazine Compounds to attenuate the rewarding properties of known drugs of abuse.

The Condition Place Preference Test: The apparatus for the conditioned place preference test consists of two large compartments (45×45×30 cm) made of wood with a plexiglass front wall. These two large compartments are distinctly different. Doors at the back of each large compartment lead to a smaller box (36×18×20 cm) box made of wood, painted grey, with a ceiling of wire mesh. The two large compartments differ in terms of shading (white vs black), level of illumination (the plexiglass door of the white compartment is covered with aluminum foil except for a window of 7×7 cm), texture (the white compartment has a 3 cm thick floor board (40×40 cm) with nine equally spaced 5 cm diameter holes and the black has a wire mesh floor), and olfactory cues (saline in the white compartment and 1 mL of 10% acetic acid in the black compartment). On habituation and testing days, the doors to the small box remain open, giving the rat free access to both large compartments.

The first session that a rat is placed in the apparatus is a habituation session and entrances to the smaller grey compartment remain open giving the rat free access to both large compartments. During habituation, rats generally show no preference for either compartment. Following habituation, rats are given 6 conditioning sessions. Rats are divided into 4 groups: carrier pre-treatment+carrier (control group), Piperazine Compound pre-treatment+carrier, carrier pre-treatment+morphine, Piperazine Compound pre-treatment+morphine. During each conditioning session the rat is injected with one of the drug combinations and confined to one compartment for 30 min. On the following day, the rat receives a carrier +carrier treatment and is confined to the other large compartment. Each rat receives three conditioning sessions consisting of 3 drug combination-compartment and 3 carrier-compartment pairings. The order of injections and the drug/compartment pairings are counterbalanced within groups. On the test day, rats are injected prior to testing (30 min to 1 hour) with either morphine or carrier and the rat is placed in the apparatus, the doors to the grey compartment remain open and the rat is allowed to explore the entire apparatus for 20 min. The time spent in each compartment is recorded. Known drugs of abuse increase the time spent in the drug-paired compartment during the testing session. If the Piperazine Compound blocks the acquisition of morphine conditioned place preference (reward), there will be no difference in time spent in each side in rats pre-treated with a Piperazine Compound and the group will not be different from the group of rats that was given carrier+carrier in both compartments. Data will be analyzed as time spent in each compartment (drug combination-paired vs carrier-paired). Generally, the experiment is repeated with a minimum of 3 doses of a Piperazine Compound.

The Drug Self-Administration Test: The apparatus for the drug self-administration test is a standard commercially available operant conditioning chamber. Before drug trials begin rats are trained to press a lever for a food reward. After stable lever pressing behavior is acquired, rats are tested for acquisition of lever pressing for drug reward. Rats are implanted with chronically indwelling jugular catheters for i.v. administration of compounds and are allowed to recover for 7 days before training begins. Experimental sessions are conducted daily for 5 days in 3 hour sessions. Rats are trained to self-administer a known drug of abuse, such as morphine. Rats are then presented with two levers, an "active" lever and an "inactive" lever. Pressing of the active lever results in drug infusion on a fixed ratio 1 (FR1) schedule (i.e., one lever press gives an infusion) followed by a 20 second time out period (signaled by illumination of a light above the levers). Pressing of the inactive lever results in infusion of excipient. Training continues until the total number of morphine infusions stabilizes to within ±10% per session. Trained rats are then used to evaluate the effect of Piperazine Compounds pre-treatment on drug self-administration. On test day, rats are pre-treated with a Piperazine Compound or excipient and then are allowed to self-administer drug as usual. If the Piperazine Compound blocks the rewarding effects of morphine, rats pre-treated with the Piperazine Compound will show a lower rate of responding compared to their previous rate of responding and compared to excipient pre-treated rats. Data is analyzed as the change in number of drug infusions per testing session (number of infusions during test session—number of infusions during training session).

6.74 Example 74

Functional Assay for Characterizing mGluR1 Antagonistic Properties

The following assay can be used to demonstrate that Piperazine Compounds bind to and modulate the activity of mGluR5 and, accordingly, are useful for treating or preventing, e.g., pain. Functional assays for the characterization of mGluR1 antagonistic properties are well known in the art. For example, the following procedure can be used.

cDNA encoding rat mGluR1 a receptor is obtained from, e.g., Prof. S. Nakanishi (Kyoto, Japan). It is transiently transfected into HEK-EBNA cells using a procedure described by Schlaeger et al., *New Dev. New Appl. Anim. Cell Techn.*, Proc. ESACT Meet., $15^{th}$a (1998), 105–112 and 117–120. $[Ca^{2+}]$ measurements are performed on mGluR1a transfected HEK-EBNA cells after incubation of the cells with Fluo-3 AM (0.5 μM final concentration) for 1 hour at 37° C. followed by 4 washes with assay buffer (DMEM supplemented with Hank's salt and 20 mM HEPES. $[Ca^{2+}]$ measurements are done using a flurometric imaging plate reader, e.g., FLIPR. 10 μM glutamate as agonist is used to evaluate the potency of the antagonists.

Increasing concentrations of antagonists are applied to the cells 5 minutes prior to application of the agonist. The inhibition (antagonists) curves are fitted with appropriate software, for example, the four-parameter logistic equation giving $IC_{50}$ and Hill coefficient using the iterative nonlinear curve fitting software Origin from Microcal Software Inc., Northampton, Mass.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A compound of formula:

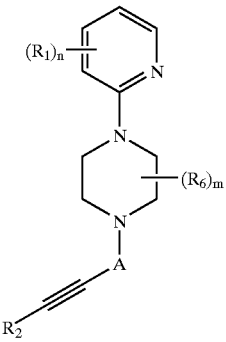

or a pharmaceutically acceptable salt thereof, wherein:

A is —C(O)—, —C(S)—, —CH($C_1$-$C_4$ alkyl)-, —C($C_1$-$C_4$ alkyl)($C_1$-$C_4$ alkyl)-, —CH(phenyl)- or —C(phenyl)$_2$-, each phenyl independently being unsubstituted or substituted with one or more $R_7$ groups;

each $R_1$ is independently —H, —($C_1$-$C_3$)alkyl, —O($C_1$-$C_3$ alkyl), -halo, —$OCF_3$, —$NO_2$, —OH, —CN, —S(O)$_2R_4$, —C(O)$OR_4$, —OC(O)$R_4$, —$NH_2$ or —$NHR_4$;

$R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle or -(7- to 10-membered)bicycloheterocycle, each of which is unsubstituted or substituted with one or more $R_3$ groups, or $R_2$ is -phenyl, -naphthyl or —($C_{14}$)aryl, each of which is unsubstituted or substituted with one or more $R_5$ groups, or $R_2$ is -(5- to 10-membered)heteroaryl, which is unsubstituted or substituted with one or more $R_5'$ groups;

each $R_3$ is independently —CN, —OH, -halo, —$N_3$, —$NO_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$ or —CH(halo)$_2$;

each $R_5$ is independently —($C_1$-$C_6$)alkyl, —O($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_3$-$C_5$)heterocycle, —C(halo)$_3$, —OC(halo)$_3$, —CH(halo)$_2$, —OCH(halo)$_2$, —CN, —OH, -halo, —$N_3$, —$NO_2$, —N($R_4$)$_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_5'$ is independently —($C_1$-$C_6$)alkyl, —O($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_3$-$C_5$)heterocycle, —C(halo)$_3$, —OC(halo)$_3$, —CH(halo)$_2$, —OCH(halo)$_2$, —CN, —OH, -halo, —$N_3$, —$NO_2$, —N($R_4$)$_2$, —CH=$NR_4$, —$NR_4$OH, —$COR_4$, —C(O)$OR_4$, —OC(O)$R_4$, —OC(O)$OR_4$, —$SR_4$, —S(O)$R_4$ or —S(O)$_2R_4$;

each $R_6$ is independently —($C_1$-$C_3$ alkyl), —$CH_2$OH, —OH, -halo, —$NO_2$, —CN or —$NH_2$;

each $R_7$ is independently —($C_1$-$C_6$)alkyl, —O($C_1$-$C_6$) alkyl, halo, —C(halo)$_3$ or —OC(halo)$_3$;

m is 0, 1 or 2; and n is an integer from 1–4.

2. The compound or a pharmaceutically acceptable salt of the compound of claim 1, wherein A is —C(O)—.

3. The compound or a pharmaceutically acceptable salt of the compound of claim 2, wherein:

n is 1;

$R_1$ is substituted at the 3-position of the pyridyl ring and is —$CH_3$, -halo, —$NO_2$,—OH or —CN; and $R_2$ is -phenyl, -naphthyl or —($C_{14}$)aryl, each which is unsubstituted or substituted with one or more $R_5$ groups.

4. The compound or a pharmaceutically acceptable salt of the compound of claim 2, wherein:

n is 1;

$R_1$ is substituted at the 3-position of the pyridyl ring and is —$CH_3$, -halo, —$NO_2$, —OH or —CN; and $R_2$ is -(5- to 10-membered)heteroaryl, which is unsubstituted or substituted with one or more $R_5'$ groups.

5. The compound or a pharmaceutically acceptable salt of the compound of claim 2, wherein:

n is 1;

$R_1$ is substituted at the 3-position of the pyridyl ring and is —$CH_3$, -halo, —$NO_2$, —OH or —CN; and $R_2$ is —($C_1$-$C_{10}$)alkyl, which is unsubstituted or substituted with one or more $R_3$ groups.

6. The compound or a pharmaceutically acceptable salt of the compound of claim 1, wherein m is 1 and $R_6$ is attached to a carbon atom adjacent to the nitrogen atom attached to the A group.

7. The compound or a pharmaceutically acceptable salt of the compound of claim 6, wherein $R_6$ is —$CH_3$.

8. A compound of formula:

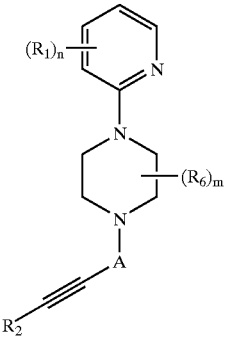

or a pharmaceutically acceptable salt thereof, wherein:

A is —C(O)—, —C(S)—, —$CH_2$—, —CH($C_1$-$C_4$ alkyl)-, —C($C_1$-$C_4$ alkyl)($C_1$-$C_4$ alkyl)-, —CH(phenyl)- or —C(phenyl)$_2$-, each phenyl independently being unsubstituted or substituted with one or more $R_7$ groups;

each $R_1$ is independently —H, —($C_1$-$C_3$)alkyl, —O($C_1$-$C_3$ alkyl), -halo, —$OCF_3$, —$NO_2$, —OH, —CN, —S(O)$_2$$R_4$, —C(O)O$R_4$, —OC(O)$R_4$, —$NH_2$ or —NH$R_4$;

$R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl or —($C_8$-$C_{14}$)tricycloalkenyl, each of which is unsubstituted or substituted with one or more $R_3$ groups, or $R_2$ is -phenyl, -naphthyl or —($C_{14}$)aryl, each of which is unsubstituted or substituted with one or more $R_5$ groups;

each $R_3$ is independently —CN, —OH, -halo, —$N_3$, —$NO_2$, =N$R_4$, —CH=N$R_4$, —N$R_4$OH, —O$R_4$, —CO$R_4$, —C(O)O$R_4$, —OC(O)$R_4$, —OC(O)O$R_4$, —S$R_4$, —S(O)$R_4$ or —S(O)$_2$$R_4$;

each $R_4$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle —C(halo)$_3$ or —CH(halo)$_2$;

each $R_5$ is independently —($C_1$-$C_6$)alkyl, —O($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_3$-$C_5$)heterocycle —C(halo)$_3$, —OC(halo)$_3$, —CH(halo)$_2$, —OCH(halo)$_2$, —CN, —OH, -halo, —$N_3$, —$NO_2$, —N($R_4$)$_2$, —CH=N$R_4$, —N$R_4$OH, —O$R_4$, —CO$R_4$, —C(O)O$R_4$, —OC(O)$R_4$, —OC(O)O$R_4$, —S$R_4$, —S(O)$R_4$ or —S(O)$_2$$R_4$;

each $R_6$ is independently —($C_1$-$C_3$ alkyl), —$CH_2$OH, —OH, -halo, —$NO_2$, —CN or —$NH_2$;

each $R_7$ is independently —($C_1$-$C_6$)alkyl, —O($C_1$-$C_6$) alkyl, halo, —C(halo)$_3$ or —OC(halo)$_3$;

m is 0, 1 or 2; and n is an integer from 1–4.

9. The compound or a pharmaceutically acceptable salt of the compound of claim 8, wherein A is —C(O)—.

10. The compound or a pharmaceutically acceptable salt of the compound of claim 9, wherein:

n is 1;

$R_1$ is substituted at the 3-position of the pyridyl ring and is —$CH_3$, -halo, —$NO_2$, —OH or —CN; and $R_2$ is -phenyl, -naphthyl or —($C_{14}$)aryl, each which is unsubstituted or substituted with one or more $R_5$ groups.

11. The compound or a pharmaceutically acceptable salt of the compound of claim 9, wherein:

n is 1;

$R_1$ is substituted at the 3-position of the pyridyl ring and is —$CH_3$, -halo, —$NO_2$, —OH or —CN; and $R_2$ is -(5- to 10-membered)heteroaryl, which is unsubstituted or substituted with one or more $R_5$' groups.

12. The compound or a pharmaceutically acceptable salt of the compound of claim 9, wherein:

n is 1;

$R_1$ is substituted at the 3-position of the pyridyl ring and is —$CH_3$, -halo, —$NO_2$, —OH or —CN; and $R_2$ is —($C_1$-$C_{10}$)alkyl, which is unsubstituted or substituted with one or more $R_3$ groups.

13. The compound or a pharmaceutically acceptable salt of the compound of claim 8, wherein m is 1 and $R_6$ is attached to a carbon atom adjacent to the nitrogen atom attached to the A group.

14. The compound or a pharmaceutically acceptable salt of the compound of claim 13, wherein $R_6$ is —$CH_3$.

15. A compound of formula:

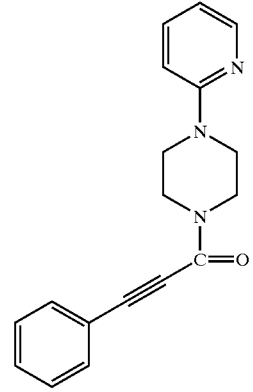

or a pharmaceutically acceptable salt thereof.

16. A compound of formula:

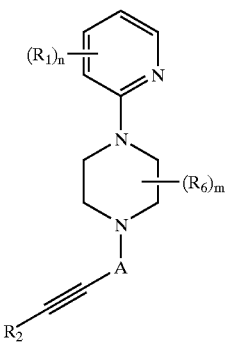

or a pharmaceutically acceptable salt thereof, wherein:

A is —C(O)—, —C(S)—, —CH($C_1$-$C_4$ alkyl)- or —C($C_1$-$C_4$ alkyl)($C_1$-$C_4$ alkyl)-;

each $R_1$ is independently —$(C_1$–$C_3)$alkyl, -halo, —$NO_2$, —OH, or —CN;

m is 0 or 1;

n is an integer from 1–4;

$R_2$ is —$(C_1$–$C_{10})$alkyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_8$–$C_{14})$tricycloalkyl, —$(C_5$–$C_{10})$cycloalkenyl, —$(C_8$–$C_{14})$bicycloalkenyl, —$(C_8$–$C_{14})$tricycloalkenyl, -(3- to 7-membered)heterocycle, or -(7- to 10-membered)bicycloheterocycle, each of which is unsubstituted or substituted with one or more $R_3$ groups, or $R_2$ is -phenyl, -naphthyl or —$(C_{14})$aryl, each of which is unsubstituted or substituted with one or more $R_5$ groups, or $R_2$ is -(5- to 10-membered)heteroaryl which is unsubstituted or substituted with one or more $R_5'$ groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —$(C_1$–$C_6)$alkyl, —$(C_2$–$C_6)$alkenyl, —$(C_2$–$C_6)$alkynyl, —$(C_3$–$C_8)$cycloalkyl, —$(C_5$–$C_8)$cycloalkenyl, -phenyl, -(3- to 5-membered)heterocycle, —C(halo)$_3$ or —CH(halo)$_2$;

each $R_5$ is independently —$(C_1$–$C_6)$alkyl, —$(C_2$–$C_6)$alkenyl, —$(C_2$–$C_6)$alkynyl, —$(C_3$–$C_8)$cycloalkyl, —$(C_5$–$C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$, or —S(O)$_2R_4$;

each $R_5'$ is independently —$(C_1$–$C_6)$alkyl, —$(C_2$–$C_6)$alkenyl, —$(C_2$–$C_6)$alkynyl, —$(C_3$–$C_8)$cycloalkyl, —$(C_5$–$C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$COR_4$, —C(O)$OR_4$, —OC(O)$R_4$, —OC(O)$OR_4$, —$SR_4$, —S(O)$R_4$, or —S(O)$_2R_4$; and each $R_6$ is —$(C_1$–$C_3)$alkyl.

17. The compound or a pharmaceutically acceptable salt of the compound of claim 16, wherein A is —C(O)—.

18. The compound or a pharmaceutically acceptable salt of the compound of claim 17, wherein:

n is 1;

$R_1$ is substituted at the 3-position of the pyridyl ring and is —$CH_3$, -halo, —$NO_2$, —OH or —CN; and $R_2$ is -phenyl, -naphthyl or —$(C_{14})$aryl, each which is unsubstituted or substituted with one or more $R_5$ groups.

19. The compound or a pharmaceutically acceptable salt of the compound of claim 18, wherein:

n is 1;

$R_1$ is substituted at the 3-position of the pyridyl ring and is —$NO_2$; and $R_2$ is -phenyl, which is unsubstituted or substituted with one or more $R_5$ groups selected from —$(C_1$–$C_6)$alkyl, —$(C_2$–$C_6)$alkenyl, —$(C_2$–$C_6)$alkynyl, —$(C_3$–$C_8)$cycloalkyl, —$(C_5$–$C_8)$cycloalkenyl, -phenyl, -(3- to 5-membered)heterocycle, —C(halo)$_3$ or —CH(halo)$_2$.

20. The compound or a pharmaceutically acceptable salt of the compound of claim 19, wherein $R_2$ is unsubstituted phenyl.

21. The compound or a pharmaceutically acceptable salt of the compound of claim 16, wherein:

A is —C(O)—;

n is 1;

$R_1$ is —$CH_3$; and $R_2$ is unsubstituted phenyl.

22. The compound or a pharmaceutically acceptable salt of the compound of claim 16, wherein:

A is —C(O)—;

n is 1;

$R_1$ is substituted at the 3-position of the pyridyl ring and is —$NO_2$, -halo or —CN; and $R_2$ is unsubstituted phenyl.

23. The compound or a pharmaceutically acceptable salt of the compound of claim 16, wherein m is 1 and $R_6$ is attached to a carbon atom adjacent to the nitrogen atom attached to the A group.

24. The compound or a pharmaceutically acceptable salt of the compound of claim 23, wherein $R_6$ is —$CH_3$.

25. A compound of formula:

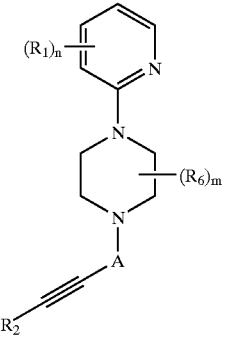

or a pharmaceutically acceptable salt thereof, wherein:

A is —C(O)—, —C(S)—, —$CH_2$—, —CH($C_1$–$C_4$ alkyl)- or —C($C_1$–$C_4$ alkyl)($C_1$–$C_4$ alkyl)-;

each $R_1$ is independently —$(C_1$–$C_3)$alkyl, -halo, —$NO_2$, —OH or —CN;

m is 0 or 1;

n is an integer from 1–4;

$R_2$ is —$(C_1$–$C_{10})$alkyl, —$(C_2$–$C_{10})$alkenyl, —$(C_2$–$C_{10})$alkynyl, —$(C_3$–$C_{10})$cycloalkyl, —$(C_8$–$C_{14})$bicycloalkyl, —$(C_8$–$C_{14})$tricycloalkyl, —$(C_5$–$C_{10})$cycloalkenyl, —$(C_8$–$C_{14})$bicycloalkenyl or —$(C_8$–$C_{14})$tricycloalkenyl, each of which is unsubstituted or substituted with one or more $R_3$ groups, or $R_2$ is -phenyl, -naphthyl or —$(C_{14})$aryl, each of which is unsubstituted or substituted with one or more $R_5$ groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$, or —S(O)$_2R_4$;

each $R_4$ is independently —H, —$(C_1$–$C_6)$alkyl, —$(C_2$–$C_6)$alkenyl, —$(C_2$–$C_6)$alkynyl, —$(C_3$–$C_8)$cycloalkyl, —$(C_5$–$C_8)$cycloalkenyl, -phenyl, -(3- to 5-membered)heterocycle, —C(halo)$_3$ or —CH(halo)$_2$;

each $R_5$ is independently —$(C_1$–$C_6)$alkyl, —$(C_2$–$C_6)$alkenyl, —$(C_2$–$C_6)$alkynyl, —$(C_3$–$C_8)$cycloalkyl, —$(C_5$–$C_8)$cycloalkenyl, -phenyl, -(3- to 5-membered)heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$, or —S(O)$_2R_4$; and each $R_6$ is —$(C_1$–$C_3)$alkyl.

26. The compound or a pharmaceutically acceptable salt of the compound of claim 25, wherein m is 1 and $R_6$ is attached to a carbon atom adjacent to the nitrogen atom attached to the A group.

27. The compound or a pharmaceutically acceptable salt of the compound of claim 26, wherein $R_6$ is —$CH_3$.

28. A compound of formula:

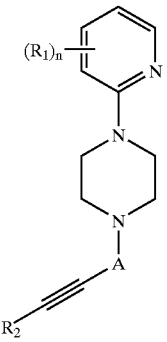

or a pharmaceutically acceptable salt thereof, wherein:

A is —C(O)—, —C(S)—, —CH($C_1$-$C_4$ alkyl)- or —C($C_1$-$C_4$ alkyl)($C_1$-$C_4$ alkyl)-;

each $R_1$ is independently —($C_1$-$C_3$)alkyl, -halo, —$NO_2$, —OH or —CN;

n is an integer from 1–4;

$R_2$ is —($C_1$-$C_{10}$)alkyl, —($C_2$-$C_{10}$)alkenyl, —($C_2$-$C_{10}$) alkynyl, —($C_3$-$C_{10}$)cycloalkyl, —($C_8$-$C_{14}$) bicycloalkyl, —($C_8$-$C_{14}$)tricycloalkyl, —($C_5$-$C_{10}$) cycloalkenyl, —($C_8$-$C_{14}$)bicycloalkenyl, —($C_8$-$C_{14}$) tricycloalkenyl, -(3- to 7-membered)heterocycle or -(7- to 10-membered)bicycloheterocycle, each of which is unsubstituted or substituted with one or more $R_3$ groups, or $R_2$ is -phenyl, -naphthyl or —($C_{14}$)aryl, each of which is unsubstituted or substituted with one or more $R_5$ groups, or $R_2$ is -(5- to 10-membered)heteroaryl which is unsubstituted or substituted with one or more $R_5$' groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O)$OR_4$, —$SR_4$, —S(O)$R_4$ or —S(O)$_2R_4$;

each $R_4$ is independently —H, —($C_1$-$C_6$)alkyl, —($C_2$-$C_6$)alkenyl, —($C_2$-$C_6$)alkynyl, —($C_3$-$C_8$) cycloalkyl, —($C_5$-$C_8$)cycloalkenyl, -phenyl, -(3- to 5-membered)heterocycle, —C(halo)$_3$ or —CH(halo)$_2$;

each $R_5$ is independently —($C_1$-$C_6$)alkyl, —($C_2$-$C_6$) alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$OR_4$, —$COR_4$, —C(O)$OR_4$, —OC(O) $R_4$, —OC(O)$OR_4$, —$SR_4$, —S(O)$R_4$ or —S(O)$_2R_4$; and each $R_5$' is independently —($C_1$-$C_6$)alkyl, —($C_2$-$C_6$) alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —CN, —OH, -halo, —$N_3$, —$NO_2$, —$N(R_4)_2$, —CH=$NR_4$, —$NR_4$OH, —$COR_4$, —C(O)$OR_4$, —OC(O)$R_4$, —OC (O)$OR_4$, —$SR_4$, —S(O)$R_4$ or —S(O)$_2R_4$.

29. The compound or a pharmaceutically acceptable salt of the compound of claim 28, wherein A is —C(O)—.

30. The compound or a pharmaceutically acceptable salt of the compound of claim 29, wherein:

n is 1;

$R_1$ is substituted at the 3-position of the pyridyl ring and is —$CH_3$, -halo, —$NO_2$, —OH or —CN; and $R_2$ is -phenyl, -naphthyl or —($C_{14}$)aryl, each which is unsubstituted or substituted with one or more $R_5$ groups.

31. The compound or a pharmaceutically acceptable salt of the compound of claim 30, wherein:

n is 1;

$R_1$ is substituted at the 3-position of the pyridyl ring and is —$NO_2$; and $R_2$ is -phenyl, which is unsubstituted or substituted with one or more $R_5$ groups selected from —($C_1$-$C_6$)alkyl, —($C_2$-$C_6$)alkenyl, —($C_2$-$C_6$)alkynyl, —($C_3$-$C_8$) cycloalkyl, —($C_5$-$C_8$)cycloalkenyl, -phenyl, -(3- to 5-membered)heterocycle, —C(halo)$_3$ or —CH(halo)$_2$.

32. The compound or a pharmaceutically acceptable salt of the compound of claim 31, wherein $R_2$ is unsubstituted phenyl.

33. The compound or a pharmaceutically acceptable salt of the compound of claim 28, wherein:

A is —C(O)—;

n is 1;

$R_1$ is —$CH_3$; and $R_2$ is unsubstituted phenyl.

34. The compound or a pharmaceutically acceptable salt of the compound of claim 28, wherein:

A is —C(O)—;

n is 1;

$R_1$ is substituted at the 3-position of the pyridyl ring and is —$NO_2$, -halo or —CN; and $R_2$ is unsubstituted phenyl.

35. A compound of formula:

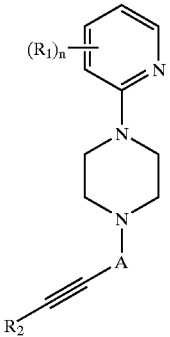

or a pharmaceutically acceptable salt thereof, wherein:

A is —C(O)—, —C(S)—, —$CH_2$—, —CH($C_1$-$C_4$ alkyl)- or —C($C_1$-$C_4$ alkyl)($C_1$-$C_4$ alkyl)-;

each $R_1$ is independently —($C_1$-$C_3$)alkyl, -halo, —$NO_2$, —OH or —CN;

n is an integer from 1–4;

$R_2$ is —($C_1$-$C_{10}$)alkyl, —($C_2$-$C_{10}$)alkenyl, —($C_2$-$C_{10}$) alkynyl, —($C_3$-$C_{10}$)cycloalkyl, —($C_8$-$C_{14}$) bicycloalkyl, —($C_8$-$C_{14}$)tricycloalkyl, —($C_5$-$C_{10}$) cycloalkenyl, —($C_8$-$C_{14}$)bicycloalkenyl or —($C_8$-$C_{14}$)tricycloalkenyl, each of which is unsubstituted or substituted with one or more $R_3$ groups, or $R_2$ is -phenyl, -naphthyl or —($C_{14}$)aryl, each of which is unsubstituted or substituted with one or more $R_5$ groups;

each $R_3$ is independently —CN, —OH, -halo, —$N_3$, —$NO_2$, —$N(R_4)_2$, =$NR_4$, —CH=$NR_4$, —$NR_4$OH, —$OR_4$, —$COR_4$, —C(O)$OR_4$, —OC(O)$R_4$, —OC(O) $OR_4$, —$SR_4$, —S(O)$R_4$ or —S(O)$_2R_4$;

each $R_4$ is independently —H, —($C_1$-$C_6$)alkyl, —($C_2$-$C_6$)alkenyl, —($C_2$-$C_6$)alkynyl, —($C_3$-$C_8$)

cycloalkyl, —(C$_5$–C$_8$)cycloalkenyl, -phenyl, -(3- to 5-membered)heterocycle, —C(halo)$_3$ or —CH(halo)$_2$; and each R$_5$ is independently —(C$_1$–C$_6$)alkyl, —(C$_2$–C$_6$)alkenyl, —(C$_2$–C$_6$)alkynyl, —(C$_3$–C$_8$)cycloalkyl, —(C$_5$–C$_8$)cycloalkenyl, -phenyl, -(3- to 5-membered) heterocycle, —C(halo)$_3$, —CH(halo)$_2$, —CN, —OH, -halo, —N$_3$, —NO$_2$, —N(R$_4$)$_2$, —CH=NR$_4$, —NR$_4$OH, —OR$_4$, —COR$_4$, —C(O)OR$_4$, —OC(O)R$_4$, —OC(O)OR$_4$, —SR$_4$, —S(O)R$_4$ or —S(O)$_2$R$_4$.

36. A composition comprising an effective amount of a compound or a pharmaceutically acceptable salt of the compound of claim 1 and a pharmaceutically acceptable carrier or excipient.

37. A composition comprising an effective amount of a compound or a pharmaceutically acceptable salt of the compound of claim 8 and a pharmaceutically acceptable carrier or excipient.

38. A composition comprising an effective amount of a compound or a pharmaceutically acceptable salt of the compound of claim 15 and a pharmaceutically acceptable carrier or excipient.

39. A composition comprising an effective amount of a compound or a pharmaceutically acceptable salt of the compound of claim 16 and a pharmaceutically acceptable carrier or excipient.

40. A composition comprising an effective amount of a compound or a pharmaceutically acceptable salt of the compound of claim 25 and a pharmaceutically acceptable carrier or excipient.

41. A composition comprising an effective amount of a compound or a pharmaceutically acceptable salt of the compound of claim 28 and a pharmaceutically acceptable carrier or excipient.

42. A composition comprising an effective amount of a compound or a pharmaceutically acceptable salt of the compound of claim 35 and a pharmaceutically acceptable carrier or excipient.

43. A method for treating pain in an animal, comprising administering to an animal in need thereof an effective amount of a compound or a pharmaceutically acceptable salt of the compound of claim 1.

44. A method for treating pain in an animal, comprising administering to an animal in need thereof an effective amount of a compound or a pharmaceutically acceptable salt of the compound of claim 8.

45. A method for treating pain in an animal, comprising administering to an animal in need thereof an effective amount of a compound or a pharmaceutically acceptable salt of the compound of claim 15.

46. A method for treating pain in an animal, comprising administering to an animal in need thereof an effective amount of a compound or a pharmaceutically acceptable salt of the compound of claim 16.

47. A method for treating pain in an animal, comprising administering to an animal in need thereof an effective amount of a compound or a pharmaceutically acceptable salt of the compound of claim 25.

48. A method for treating pain in an animal, comprising administering to an animal in need thereof an effective amount of a compound or a pharmaceutically acceptable salt of the compound of claim 28.

49. A method for treating pain in an animal, comprising administering to an animal in need thereof an effective amount of a compound or a pharmaceutically acceptable salt of the compound of claim 35.

50. A method for treating anxiety in an animal, comprising administering to an animal in need thereof an effective amount of a compound or a pharmaceutically acceptable salt of the compound of claim 1.

51. A method for treating anxiety in an animal, comprising administering to an animal in need thereof an effective amount of a compound or a pharmaceutically acceptable salt of the compound of claim 8.

52. A method for treating anxiety in an animal, comprising administering to an animal in need thereof an effective amount of a compound or a pharmaceutically acceptable salt of the compound of claim 15.

53. A method for treating anxiety in an animal, comprising administering to an animal in need thereof an effective amount of a compound or a pharmaceutically acceptable salt of the compound of claim 16.

54. A method for treating anxiety in an animal, comprising administering to an animal in need thereof an effective amount of a compound or a pharmaceutically acceptable salt of the compound of claim 25.

55. A method for treating anxiety in an animal, comprising administering to an animal in need thereof an effective amount of a compound or a pharmaceutically acceptable salt of the compound of claim 28.

56. A method for treating anxiety in an animal, comprising administering to an animal in need thereof an effective amount of a compound or a pharmaceutically acceptable salt of the compound of claim 35.

57. A method for treating Parkinson's disease in an animal, comprising administering to an animal in need thereof an effective amount of a compound or a pharmaceutically acceptable salt of the compound of claim 1.

58. A method for treating Parkinson's disease in an animal, comprising administering to an animal in need thereof an effective amount of a compound or a pharmaceutically acceptable salt of the compound of claim 8.

59. A method for treating Parkinson's disease in an animal, comprising administering to an animal in need thereof an effective amount of a compound or a pharmaceutically acceptable salt of the compound of claim 15.

60. A method for treating Parkinson's disease in an animal, comprising administering to an animal in need thereof an effective amount of a compound or a pharmaceutically acceptable salt of the compound of claim 16.

61. A method for treating Parkinson's disease in an animal, comprising administering to an animal in need thereof an effective amount of a compound or a pharmaceutically acceptable salt of the compound of claim 25.

62. A method for treating Parkinson's disease in an animal, comprising administering to an animal in need thereof an effective amount of a compound or a pharmaceutically acceptable salt of the compound of claim 28.

63. A method for treating Parkinson's disease in an animal, comprising administering to an animal in need thereof an effective amount of a compound or a pharmaceutically acceptable salt of the compound of claim 35.

64. A method for treating depression in an animal, comprising administering to an animal in need thereof an effective amount of a compound or a pharmaceutically acceptable salt of the compound of claim 1.

65. A method for treating depression in an animal, comprising administering to an animal in need thereof an effective amount of a compound or a pharmaceutically acceptable salt of the compound of claim 8.

66. A method for treating depression in an animal, comprising administering to an animal in need thereof an effective amount of a compound or a pharmaceutically acceptable salt of the compound of claim 15.

67. A method for treating depression in an animal, comprising administering to an animal in need thereof an effective amount of a compound or a pharmaceutically acceptable salt of the compound of claim 16.

68. A method for treating depression in an animal, comprising administering to an animal in need thereof an effective amount of a compound or a pharmaceutically acceptable salt of the compound of claim 25.

69. A method for treating depression in an animal, comprising administering to an animal in need thereof an effective amount of a compound or a pharmaceutically acceptable salt of the compound of claim 28.

70. A method for treating depression in an animal, comprising administering to an animal in need thereof an effective amount of a compound or a pharmaceutically acceptable salt of the compound of claim 35.

71. A method for preparing a composition, the method comprising admixing a compound or a pharmaceutically acceptable salt of the compound of claim 1 and a pharmaceutically acceptable carrier or excipient.

72. A method for preparing a composition, the method comprising admixing a compound or a pharmaceutically acceptable salt of the compound of claim 8 and a pharmaceutically acceptable carrier or excipient.

73. A method for preparing a composition, the method comprising admixing a compound or a pharmaceutically acceptable salt of the compound of claim 15 and a pharmaceutically acceptable carrier or excipient.

74. A method for preparing a composition, the method comprising admixing a compound or a pharmaceutically acceptable salt of the compound of claim 16 and a pharmaceutically acceptable carrier or excipient.

75. A method for preparing a composition, the method comprising admixing a compound or a pharmaceutically acceptable salt of the compound of claim 25 and a pharmaceutically acceptable carrier or excipient.

76. A method for preparing a composition, the method comprising admixing a compound or a pharmaceutically acceptable salt of the compound of claim 28 and a pharmaceutically acceptable carrier or excipient.

77. A method for preparing a composition, the method comprising admixing a compound or a pharmaceutically acceptable salt of the compound of claim 35 and a pharmaceutically acceptable carrier or excipient.

\* \* \* \* \*